(12) United States Patent
Kishore et al.

(10) Patent No.: US 12,428,628 B2
(45) Date of Patent: *Sep. 30, 2025

(54) RECOMBINANT PRODUCTION OF STEVIOL GLYCOSIDES

(71) Applicant: Danstar Ferment AG, Schweiz (CH)

(72) Inventors: Ganesh M. Kishore, Saint Louis, MO (US); Michael Motion, San Francisco, CA (US); Paula M. Hicks, Bend, OR (US); Jorgen Hansen, Frederiksberg (DK); Jens Houghton Larsen, Birkerod (DK); Esben Halkjaer Hansen, Frederiksberg (DK); Michael Dalgaard Mikkelsen, Vaerlose (DK); Sabina Tavares, San Francisco, CA (US); Charlotte Blom, San Francisco, CA (US)

(73) Assignee: Danstar Ferment AG, Schweiz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/756,786

(22) Filed: Jun. 27, 2024

(65) Prior Publication Data
US 2025/0027131 A1 Jan. 23, 2025

Related U.S. Application Data

(60) Continuation of application No. 18/470,785, filed on Sep. 20, 2023, now abandoned, which is a continuation of application No. 17/373,612, filed on Jul. 12, 2021, now abandoned, which is a continuation of application No. 16/460,320, filed on Jul. 2, 2019, now abandoned, which is a continuation of application No. 15/382,354, filed on Dec. 16, 2016, now Pat. No. 10,392,644, which is a division of application No. 13/701,406, filed as application No. PCT/US2011/038967 on Jun. 2, 2011, now Pat. No. 9,562,251.

(60) Provisional application No. 61/471,622, filed on Apr. 4, 2011, provisional application No. 61/434,582, filed on Jan. 20, 2011, provisional application No. 61/350,553, filed on Jun. 2, 2010.

(51) Int. Cl.
| | |
|---|---|
| *C12N 9/10* | (2006.01) |
| *A23L 2/60* | (2006.01) |
| *A23L 27/30* | (2016.01) |
| *C07H 15/256* | (2006.01) |
| *C12N 9/02* | (2006.01) |
| *C12N 9/04* | (2006.01) |
| *C12N 9/88* | (2006.01) |
| *C12N 9/90* | (2006.01) |
| *C12N 15/52* | (2006.01) |
| *C12N 15/81* | (2006.01) |
| *C12N 15/82* | (2006.01) |
| *C12P 7/42* | (2006.01) |
| *C12P 15/00* | (2006.01) |
| *C12P 19/56* | (2006.01) |

(52) U.S. Cl.
CPC ............ *C12N 9/1051* (2013.01); *A23L 2/60* (2013.01); *A23L 27/36* (2016.08); *C07H 15/256* (2013.01); *C12N 9/0006* (2013.01); *C12N 9/0042* (2013.01); *C12N 9/0073* (2013.01); *C12N 9/1077* (2013.01); *C12N 9/1085* (2013.01); *C12N 9/88* (2013.01); *C12N 9/90* (2013.01); *C12N 15/52* (2013.01); *C12N 15/8243* (2013.01); *C12N 15/8245* (2013.01); *C12P 7/42* (2013.01); *C12P 15/00* (2013.01); *C12P 19/56* (2013.01); *C12Y 101/01088* (2013.01); *C12Y 106/02004* (2013.01); *C12Y 114/13078* (2013.01); *C12Y 114/13079* (2013.01); *C12Y 204/01126* (2013.01); *C12Y 205/01029* (2013.01); *C12Y 402/03019* (2013.01); *C12Y 505/01012* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,590,160 A | 5/1986 | Nishihashi et al. |
| 5,198,360 A | 3/1993 | Ballou |
| 5,204,253 A | 4/1993 | Sanford et al. |
| 5,306,862 A | 4/1994 | Chappell et al. |
| 5,460,949 A | 10/1995 | Saunders et al. |

(Continued)

FOREIGN PATENT DOCUMENTS

| | | |
|---|---|---|
| CN | 101314776 | 12/2008 |
| CN | 101720910 | 6/2010 |

(Continued)

OTHER PUBLICATIONS

Morita, Yasumasa, et al.; The Plant Journal; 42.3 (2005): 353-363. (Year: 2005).*

(Continued)

*Primary Examiner* — Weihua Fan
(74) *Attorney, Agent, or Firm* — McDonnell Boehnen Hulbert & Berghoff LLP

(57) ABSTRACT

Recombinant microorganisms, plants, and plant cells are disclosed that have been engineered to express novel recombinant genes encoding steviol biosynthetic enzymes and UDP-glycosyltransferases (UGTs). Such microorganisms, plants, or plant cells can produce steviol or steviol glycosides, e.g., rubusoside or Rebaudioside A, which can be used as natural sweeteners in food products and dietary supplements.

24 Claims, 14 Drawing Sheets
Specification includes a Sequence Listing.

(56) References Cited

U.S. PATENT DOCUMENTS

| | | | |
|---|---|---|---|
| 5,538,880 | A | 7/1996 | Lundquist et al. |
| 6,013,863 | A | 1/2000 | Lundquist et al. |
| 6,215,051 | B1 | 4/2001 | Yu et al. |
| 6,255,557 | B1 | 7/2001 | Brandle |
| 6,284,493 | B1 | 9/2001 | Roth |
| 6,284,506 | B1 | 9/2001 | Hoshino et al. |
| 6,329,571 | B1 | 12/2001 | Hiei |
| 6,586,202 | B2 | 7/2003 | Hoshino et al. |
| 6,660,507 | B2 | 12/2003 | Cheng et al. |
| 6,806,076 | B1 | 10/2004 | Miyake et al. |
| 6,969,595 | B2 | 11/2005 | Brzostowicz et al. |
| 7,034,140 | B2 | 4/2006 | Bramucci et al. |
| 7,056,717 | B2 | 6/2006 | Cheng et al. |
| 7,098,000 | B2 | 8/2006 | Cheng et al. |
| 7,129,392 | B2 | 10/2006 | Hahn et al. |
| 7,132,268 | B2 | 11/2006 | Miyake et al. |
| 7,172,886 | B2 | 2/2007 | Keasling et al. |
| 7,183,089 | B2 | 2/2007 | Keasling et al. |
| 7,186,891 | B1 | 3/2007 | Chappell et al. |
| 7,208,298 | B2 | 4/2007 | Miyake et al. |
| 7,335,815 | B2 | 2/2008 | Boronat et al. |
| 7,364,885 | B2 | 4/2008 | Miyake et al. |
| 7,422,884 | B2 | 9/2008 | Bai et al. |
| 7,514,597 | B2 | 4/2009 | Nakamura et al. |
| 7,569,389 | B2 | 8/2009 | Feldmann et al. |
| 7,692,065 | B2 | 4/2010 | Harper et al. |
| 7,838,287 | B2 | 11/2010 | Goldsmith et al. |
| 7,923,541 | B2 | 4/2011 | Yang et al. |
| 7,927,851 | B2 | 4/2011 | Brandle et al. |
| 7,981,647 | B2 | 7/2011 | Berry et al. |
| 9,441,233 | B2 | 9/2016 | Apuya et al. |
| 9,562,251 | B2 | 2/2017 | Kishore et al. |
| 9,957,539 | B2 | 5/2018 | Ono et al. |
| 10,947,515 | B2 | 3/2021 | Boer et al. |
| 2002/0142408 | A1 | 10/2002 | DiCosimo et al. |
| 2003/0033626 | A1 | 2/2003 | Hahn et al. |
| 2003/0148416 | A1 | 8/2003 | Berry et al. |
| 2003/0148479 | A1 | 8/2003 | Keasling et al. |
| 2003/0190734 | A1 | 10/2003 | Hoshino et al. |
| 2003/0219798 | A1 | 11/2003 | Gokarn et al. |
| 2004/0010815 | A1 | 1/2004 | Lange et al. |
| 2004/0072311 | A1 | 4/2004 | DiCosimo et al. |
| 2004/0078846 | A1 | 4/2004 | Desouza et al. |
| 2004/0176570 | A1 | 9/2004 | Bacher et al. |
| 2004/0194162 | A1 | 9/2004 | Hahn et al. |
| 2005/0003474 | A1 | 1/2005 | Desouza et al. |
| 2005/0032169 | A1 | 2/2005 | Miyake et al. |
| 2006/0014264 | A1 | 1/2006 | Sauer et al. |
| 2006/0079476 | A1 | 4/2006 | Keasling et al. |
| 2006/0083838 | A1 | 4/2006 | Jackson et al. |
| 2007/0004000 | A1 | 1/2007 | Miyake et al. |
| 2007/0077616 | A1 | 4/2007 | Keasling et al. |
| 2007/0099261 | A1 | 5/2007 | Keasling et al. |
| 2007/0118916 | A1 | 5/2007 | Puzio et al. |
| 2007/0128311 | A1 | 6/2007 | Prakash et al. |
| 2007/0166782 | A1 | 7/2007 | Keasling et al. |
| 2007/0202579 | A1 | 8/2007 | Berry et al. |
| 2007/0238157 | A1 | 10/2007 | Millis et al. |
| 2007/0238159 | A1 | 10/2007 | Millis et al. |
| 2007/0238160 | A1 | 10/2007 | Millis et al. |
| 2007/0254354 | A1 | 11/2007 | Millis et al. |
| 2007/0269857 | A1 | 11/2007 | Miyake et al. |
| 2007/0286850 | A1 | 12/2007 | Bai et al. |
| 2008/0064063 | A1 | 3/2008 | Brandle et al. |
| 2008/0081358 | A1 | 4/2008 | Vittanen et al. |
| 2008/0131926 | A1 | 6/2008 | Miyake et al. |
| 2008/0216397 | A1 | 9/2008 | Busby et al. |
| 2008/0261280 | A1 | 10/2008 | Hahn et al. |
| 2008/0271205 | A1 | 10/2008 | Yamaguchi et al. |
| 2008/0286870 | A1 | 11/2008 | Vittanen et al. |
| 2008/0292775 | A1 | 11/2008 | Prakash et al. |
| 2008/0318227 | A1 | 12/2008 | Bacher et al. |
| 2009/0004724 | A1 | 1/2009 | Keasling et al. |
| 2009/0047718 | A1 | 2/2009 | Blaschek et al. |
| 2009/0055974 | A1 | 2/2009 | Tanksley et al. |
| 2009/0074935 | A1 | 3/2009 | Lee |
| 2009/0143308 | A1 | 6/2009 | Monk et al. |
| 2009/0286262 | A1 | 11/2009 | Slack |
| 2009/0298706 | A1 | 12/2009 | Lee et al. |
| 2010/0112156 | A1 | 5/2010 | Abelyan et al. |
| 2010/0120096 | A1 | 5/2010 | Kitaoka et al. |
| 2010/0221801 | A1 | 9/2010 | Van Dyk |
| 2010/0297722 | A1 | 11/2010 | Anterola et al. |
| 2010/0316782 | A1 | 12/2010 | Shi et al. |
| 2011/0087011 | A1 | 4/2011 | Chiang et al. |
| 2011/0092684 | A1 | 4/2011 | Abelyan et al. |
| 2011/0126318 | A1 | 5/2011 | Allen et al. |
| 2011/0160311 | A1 | 6/2011 | Prakash et al. |
| 2012/0021111 | A1 | 1/2012 | Pfister et al. |
| 2012/0083593 | A1 | 4/2012 | Liu et al. |
| 2012/0164678 | A1 | 6/2012 | Stephanopoulos et al. |
| 2012/0178169 | A1 | 7/2012 | Voytas et al. |
| 2013/0137138 | A1 | 5/2013 | Hansen |
| 2013/0171328 | A1 | 7/2013 | Kishore et al. |
| 2014/0329281 | A1 | 11/2014 | Houghton-Larsen et al. |
| 2015/0159188 | A1 | 6/2015 | Ono et al. |
| 2015/0342234 | A1 | 12/2015 | Hicks et al. |
| 2021/0147815 | A1 | 5/2021 | Boer et al. |

FOREIGN PATENT DOCUMENTS

| | | |
|---|---|---|
| CN | 102216313 | 10/2011 |
| CN | 102559528 | 7/2012 |
| CN | 103397064 | 11/2013 |
| CN | 104845990 | 8/2015 |
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2575432 | 4/2013 |
| EP | 2902410 | 8/2015 |
| JP | 59101408 | 6/1984 |
| JP | 3-277275 | 12/1991 |
| JP | 05-115298 | 5/1993 |
| JP | 2005185101 | 7/2005 |
| JP | 2009034080 | 2/2009 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006069610 | 7/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2008/091547 | 7/2008 |
| WO | WO 2009/005704 | 1/2009 |
| WO | WO 2009/037329 | 3/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | WO 2009/11513 | 9/2009 |
| WO | 2009/140394 | 11/2009 |

(56) References Cited

FOREIGN PATENT DOCUMENTS

| WO | WO 2010/021001 | 2/2010 |
|---|---|---|
| WO | WO 2010/038911 | 4/2010 |
| WO | WO 2010/044960 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | WO 2011/060057 | 5/2011 |
| WO | 2011/140329 | 11/2011 |
| WO | 2011/151326 | 12/2011 |
| WO | 2011/153378 | 12/2011 |
| WO | WO 2011/153144 | 12/2011 |
| WO | WO 2012/075030 | 6/2012 |
| WO | WO 2013/019050 | 2/2013 |
| WO | WO 2013/022989 | 2/2013 |
| WO | WO 2013/021261 | 5/2013 |
| WO | WO 2013/076577 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |
| WO | WO 2014/086890 | 6/2014 |
| WO | WO 2014/122227 | 8/2014 |
| WO | WO 2014/122328 | 8/2014 |
| WO | 2014/191581 | 12/2014 |
| WO | WO2014/191580 | 12/2014 |
| WO | 2015/011209 | 1/2015 |
| WO | WO 2015/007748 | 1/2015 |
| WO | 2015/014959 | 2/2015 |
| WO | 2015/016393 | 2/2015 |
| WO | WO 2015/014969 | 2/2015 |
| WO | WO 2015/028324 | 3/2015 |
| WO | WO 2015051454 | 4/2015 |
| WO | WO 2015/132411 | 9/2015 |
| WO | 2016/023844 | 2/2016 |
| WO | WO 2016/038095 | 3/2016 |
| WO | WO 2016/120486 | 8/2016 |
| WO | WO 2017/025362 | 2/2017 |

OTHER PUBLICATIONS

Gloster, Tracey M. "Advances in understanding glycosyltransferases from a structural perspective." Current opinion in structural biology 28 (2014): 131-141. (Year: 2014).*
Ünligil, Uluğ M., and James M. Rini. "Glycosyltransferase structure and mechanism." Current opinion in structural biology 10.5 (2000): 510-517. (Year: 2000).*
Brandle, J. E., and P. G. Telmer. "Steviol glycoside biosynthesis." Phytochemistry 68.14 (2007): 1855-1863 (Year: 2007).*
Liu et al., "Functional and Biochemical Characterization of *Escherichia coli* Sugar Efflux Transporters," JBC, 274 (33):22977-22984 (Aug. 1999).
Sun et al., "Regulation and Function of *Escherichia coli* Sugar Efflux Transporter A (Set A) during Glucose-Phosphate Stress," J of Bacteriology, 193(1):143-153 (Jan. 2011).
Shao et al., "Crystal structures of a multifunctional triterpene/flavonoid glycosyltransferase from Medicago truncatula," Plant Cell 17(11):3141-54 (2005).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast *Kluyveromyces lactis*," FEMS Yeast Res. 6 (3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73 (13):4342-50 (2007).
Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583 (20):3303-9 (2009).
Xu et al., "Generation of hepatitis B virus PreS2-S antigen in Hansenula polymorpha," Virol Sin. 29(6):403-9 (Dec. 2014).
Yadav et al., "A review on the improvement of stevia [Stevia rebaudiana (Bertoni)]," Can J Plant Sci. 91:1-27 (2011).
Yao et al., "A genetic linkage map for Stevia rebaudiana," Genome 42:657-61 (1999).
Yazaki, "Abc transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14): e115 (Aug. 2004).
Zhu et al., "A multi-omic map of the lipid-producing yeast *Rhodosporidium toruloides*," Nature Commun. 3:1112 (Oct. 2012).
GenBank Accession No. AAF61439.1, dated Sep. 25, 2000 (2 pages).
GenBank Accession No. AAM53963.1, dated Jun. 17, 2002 (2 pages).
GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454.4, dated May 28, 2008 (2 pages).
GenBank Accession No. EU722415.1, dated Jun. 10, 2008 (2 pages).
GenBank Accession No. EU751291.1, dated Jun. 24, 2008 (2 pages).

(56) References Cited

OTHER PUBLICATIONS

EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide SEQ ID No. 4723" (1 page), dated Jun. 2, 2005.
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
GenBank Accession No. AAS07253.1, dated Jan. 31, 2004 (3 pages).
Guo et al., "Protein tolerance to random amino acid change", Proceedings of the National Academy of Sciences USA, vol. 101, No. 25, pp. 9205-9210 (2004).
Liu et al., "Biosynthesis of Rebaudioside A by Whole Cell of Recombinant *Saccharomyces cerevisiae*," Food and Fermentation Industries, 38(7) : 6-10 (2012) (Abstract translation).
Ni et al., "Outer membrane mutation effects on UDP-glucose permeability and whole-cell catalysis rate," Appl Microbiol Biotechnol. 73(2):384-93 (2006).
Prisic et al, "Synergistic substrate inhibition of ent-copalyl diphosphate synthase: a potential feed-forward inhibition mechanism limiting gibberellin metabolism," Plant Physiol. 144(1):445-54 (2007).
Unligil et al., "Glycosyltransferase structure and mechanism," Curr Opin Struct Biol. 10(5):510-7 (2000).
Wanchao et al., "Advances on the Stevoil Glycoside Biosynthesis and Its Key Enzymes," Biotechnology Bulletin, Feb. 2008 (English Abstract translation).
International Search Report by the International Searching Authority for International Application No. PCT/EP2015/070620; mailed Mar. 29, 2016, pp. 1-10.
Written Opinion of the International Searching Authority for International Application No. PCT/EP2015/070620; mailed Mar. 29, 2016, pp. 1-24.
Garber et al., "Computational methods for transcriptome annotation and quantification using RNA-seq," Nat Methods 8(6):469-77 (2011).
Kawai et al., "Transformation of *Saccharomyces cerevisiae* and other fungi: methods and possible underlying mechanism," Bioeng Bugs. 1(6):395-403 (2010).
Lin et al., "Arrestin-related ubiquitin-ligase adaptors regulate endocytosis and protein turnover at the cell surface," Cell 135(4):714-25 (2008).
Nagalakshmi et al., "The transcriptional landscape of the yeast genome defined by RNA sequencing," Science 320 (5881 ): 1344-9 (2008).
Nikko & Pelham, "Arrestin-mediated endocytosis of yeast plasma membrane transporters," Traffic 10(12): 1856-67 (2009).
Nikko et al. "Arrestin-like proteins mediate ubiquitination and endocytosis of the yeast metal transporter Smf1," EMBO Rep. 9(12):1216-21 (2008).
Olsson et al., "Microbial production of next-generation stevia sweeteners," Microbial Cell Factories, 15:11-14 (2016).
Partow et al., "Characterization of different promoters for designing a new expression vector in *Saccharomyces cerevisiae*," Yeast 27:955-64 (2010).
Robinson & Oshlack et al., "A scaling normalization method for differential expression analysis of RNA-seq data," Genome Bioi. 11(3):R25 (2010).
Saier Jr. et al., "The transporter classification database," Nucl. Acids Res., 42(1):D251-258 (2014).
Wang et al., "RNA-Seq: a revolutionary tool for transcriptomics," Nat Rev Genet. 10(1):57-63 (2009).
Wilhelm et al., "Defining transcribed regions using RNA-seq," Nature Protocols 5:255-66 (2010).
YANG Quanhua et.al., "Analysis of the Chemical constituents of Stevia rebaudiana and its sweetness," Journal of Beijing University of Chemical Technology, vol. 39, No. 2., p. 28-32 (2012) (English Abstract).
International Search Report issued by the International Searching Authority for International Application No. PCT/US2011/038967, dated Sep. 1, 2011 (10 pages).

Written Opinion of the International Searching Authority for International Application No. PCT/US2011/038967, dated Sep. 1, 2011 (12 pages).
International Preliminary Report on Patentability issued by the International Bureau for International Application No. PCT/US2011/038967, dated Dec. 4, 2012 (13 pages).
Third-Party Submission under 37 CFR 1.290 for U.S. Appl. No. 13/701,406, dated Mar. 7, 2014 (238 pages).
Extended European Search Report and Opinion issued by the European Patent Office for European Application No. 11790428.4, dated Dec. 20, 2013.
Non-Final Office Action for U.S. Appl. No. 14/237,540, mailed Dec. 30, 2015 (pp. 1-19).
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
International Preliminary Report on Patentability issued by the International Bureau for International Application No. PCT/US2012/050021, dated Feb. 11, 2014.
Extended European Search Report issued in EP 15193074.0; dated Feb. 12, 2016, pp. 1-9.
International Search Report from the International Searching Authority for International Application No. PCT/EP2014/052363, mailed Sep. 22, 2014 (12 pages).
Written Opinion of the International Searching Authority for International Application No. PCT/EP2014/052363, mailed Sep. 22, 2014 (10 pages).
International Preliminary Report on Patentability issued by the International Bureau for International Application No. PCT/EP2014/052363, dated Aug. 11, 2015 (11 pages).
International Preliminary Report on Patentability issued by the International Bureau for International Application No. PCT/EP2014/052675, dated Aug. 11, 2015 (8 pages).
International Search Report of the International Searching Authority for International Application No. PCT/EP2013/075587, mailed Feb. 20, 2014 (pp. 1-5).
Written Opinion of the International Searching Authority for International Application No. PCT/EP2013/075587, mailed Feb. 20, 2014 (pp. 1-9).
International Preliminary Report on Patentability from the International Bureau for International Application No. PCT/EP2013/075587, dated Jun. 9, 2015 (pp. 1-10).
Invitation to Pay Additional Fees and, Where Applicable, Protest Fee by the International Searching Authority for International Application No. PCT/EP2015/070620, mailed Nov. 27, 2015 (pp. 1-14).
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).
Chen et al., "Sugar transporters for intercellular exchange and nutrition of pathogens," Nature 468(7323):527-32 (2010).
Chen et al., "Fusion protein linkers: Property, design, and functionality", Advanced Drug Delivery reviews, 65 (0):1257-69 (2013).
Daran et al., "Genetic and biochemical characterization of the UGP1 gene encoding the UDP-glucose pyrophosphorylase from *Saccharomyces cerevisiae*," Eur J Biochem. 233(2):520-30 (Jul. 1995).
Husar et al., "Overexpression of the UGT73C6 alters brassinosteriod glucoside formation in *Arabidopsis thaliana*", BMC Plant Biology, 11:1-14 (2011).
Khan et al., "Physical and chemical mutagenesis in Stevia rebaudiana: variant generation with higher UGT expression and glycosidic profile but with low photosynthetic capabilities," Acta Physiologiae Plantarum 38(1) (2016).
Malonek et al., "The NADPH-cytochrome P450 Reductase Gene from Gibberalla fujikuroi is Essential for Gibberellin Biosynthesis", J Bio Chem. 279(24):25075-84 (Jun. 2004).

(56) References Cited

OTHER PUBLICATIONS

Mao et al., "Produce steviol glycosides in engineered yeast", 2015 Synthetic Biology: Engineering, Evolution & Design (SEED), Poster Abstract (Jun. 2015).
Nagatoshi et al., "UGT75L6 and UGT94E5 mediate sequential glucosylation of crocetin to crocin in Gardenia jasminoides", FEBS Letters, 586:1055-1061 (2012).
Wang et al., "Pathway mining-based integration of critical enzyme parts for de novo biosynthesis of steviol glycoside sweetener in *Escherichia coli*", Cell Research, 26:258-261 (Sep. 2015).
Wang et al., "Efficient enzymatic production of rebaudioside A from stevioside", Bioscience, Biotechnology, and Biochemistry, 80:67-73 (Aug. 2015).
Wang et al., "Design and construction of artificial biological systems for complex natural products biosynthesis", Chinese Journal of Biotechnology, 29:1146-1160 (2013).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside: In-house validation and application to wheat," Journal of Chromatography A, 1423, pp. 183-189 (2015).
Yang et al., "Base substitution mutations in uridinediphosphate-dependent glycosyltransferase 76G1 gene of Stevia rebaudioside A; Mustation in UGT76G1, a key gene of steviol glycoside synthesis", Plant Physiology and Biochemistry, 80:220-225 (2014).
Examination Report issued by the European Patent Office for European Application No. 12750513.9, dated Nov. 26, 2014.
Arnold, F. H. "Combinatorial and computational challenges for biocatalyst design," Nature 409(6817):253-257 (2001).
Duetz, "Microtiter plates as mini-bioreactors: miniaturization of fermentation methods," Trends Microbiol 15 (10):469-75 (2007).
François et al., "Reserve carbohydrates metabolism in the yeast *Saccharomyces cerevisiae*," FEMS Microbiol Rev., 25(1):125-45 (2001).
Jones et al., "UGT73C6 and UGT78D1, Glycosyltransferases Involved in Flavonol Glycoside Biosynthesis in *Arabidopsis thaliana*\*," J. Biol. Chem., vol. 278, No. 45, pp. 43910-43918 (2003).
Popenberger et al., Heterologous Expression of *Arabidopsis* UDP-Glucosyltransferases in *Saccharomyces cerevisiae* for Production ofZearalenone-4-0-Glucoside, Appl. Environ. Microbial., vol. 72, pp. 4404-4410 (2006).
Wang et al., "Glycosylation and Glycosyltransferase of Small Molecular Compounds of Plant," China Academic Journal, vol. 44-5, 997-1003 (2008).
Non-Final Office Action for U.S. Appl. No. 15/382,354, mailed Oct. 12, 2018, pp. 1-22.
Non-Final Office Action for U.S. Appl. No. 16/460,320, mailed Jan. 14, 2021, pp. 1-26.
Broun, et al., Catalytic placiticity of fatty acid modification enzymes underlying chemical diversity of plant lipids, Science, VOl 272: 1315-1317 (1998).
Cheng, "Food Biotechnology", Inner Mongolia Science and Technology Press (2008).
Devos, et al., "Practical limits of function prediction," Proteins: Structure, Function and Genectics, vol. 41: 98-107 (2000).
Pearson & Lipman, "Improved tools for biological sequence comparison", Proc Natl. Acad. Sci. 85:(8):244-8 (1988).
Seffernick, et al., "Melamine deaminase and Altrazine chlorohydrolase: 98 percent identical but functionally different", J. Bacterial, vol. 183 (8):2405-2410 (2001).
Whisstock, et al., "Prediction of protein function from protein sequence", Q. Rev. Biophysicis, vol. 36 (3): 307-340 (2003).
Witkowski, et al., "Conversion of b-ketoacyl synthase to a Malonyl Decarboxylase by replacement of the active cysteine with glutamine", Biochemistry, vol. 38: 11643-11650 (1999).
Morita, et al., The Plant Journal; 42(3) 353-363 (2005).
Gloster, Tracey, et al,, Advances in understanding glycosyltransferases from a structural perspective & nbsp. Current opinion in structural biology & nbsp, 28:131-141 (2014).
Unligil, et al., Glycosyltransferase structure and mechanism & nbsp.,Current opinion in structural biology & nbsp, 10.5: 510-517 (2000).
Brandle, et al, "Steviol glycoside biosynthesis & nbsp" Phytochemistry & nbsp, 68.14 (1855-1863 (2007).
Mikayama et al., "Molecular cloning and functional expression of a cDNA encoding glycosylation-inhibiting factor," Proc Natl Acad Sci U S A. 90(21):10056-60 (1993).
Rudinger et al., "Characteristics of the amino acids as components of a peptide hormone sequence," Peptide Hormones. Bioi. Council. pp. 5-7 (1976).
Saier, "Families of transmembrane sugar transport proteins," Mol Microbiol., 35(4):699-710 (2000).
Mahe et al., "The ATP Binding Cassette Transporters Pdr5 and Snq2 of *Saccharomyces cerevisiae* Can Mediate Transport of Steriods via in Vivo", JBC, 271(41):25167-25172. (Oct. 1996).
Starratt et al., "Rebaudioside F, a diterpene glycoside from Stevia redaudiana", Phytochemistry, 59(4):367-370. (Feb. 2002). Abstract.
Uniprot Accession No. Q75183, dated Jul. 5, 2004 (pp. 1-2).
Uniprot Accession No. Q75183, dated Jul. 22, 2008 (pp. 1-4).
Abraham & Bhat, "Permeabilization of baker's yeast with N-lauroyl sarcosine," J Ind Microbial Biotechnol. 35 (8):799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31 (10):3307-30 (1992).
Ajikumar et al., "Terpenoids: opportunities for biosynthsis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42 (4):2827-37 (2010).
Bankar et al., "Environmental and industrial applications of Yarrowia lipolytica," Appl Microbiol Biotechnol. 84 (5):847-65 (Oct. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis," Plant Mol Biol. 50(4-5):613-22 (2002).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Carretero-Paulet et al., "Expression and Molecular Analysis of the *Arabidopsis* DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Chemler et al., "Biosynthesis of isoprenoids, polyunsaturated fatty acids and flavonoids in *Saccharomyces cerevisiae*," Microb Cell Fact. 5:20 (2006).
Chen, "Summary on Study of Stevioside," China Pharmacist, 10(6):598-599 (2007).
Chen et al., "MolProbity: all-atom structure validation for macromolecular crystallography," Acta Crystallogr D Biol Crystallogr 66(Pt 1):12-21 (Jan. 2010).
Chica et al., "Semi-rational approaches to engineering enzyme activity: combining the benefits of directed evolution and rational design," Curr Opin Biotechnol.16(4):378-84 (2005).
Chow & Palecek, "Enzyme encapsulation in permeabilized *Saccharomyces cerevisiae* cells," Biotechnol Prog. 20 (2):449-56 (2004).
Correa et al., "Genetic mapping of 1,3-beta-glucanase-encoding genes in *Saccharomyces cerevisiae*," Current Genet. 22(4):283-8 (1992).

(56) References Cited

OTHER PUBLICATIONS

Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Del Sorbo et al., "Fungal transporters involved in efflux of natural toxic compounds and fungicides," Fungal. Genet. Biol. 30(1):1-15 (Jun. 2000).
Diener et al., "*Arabidopsis* ALF5, a multidrug efflux transporter gene family member, confers resistance to toxins," Plant Cell 13(7):1625-38 (Jul. 2001).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28 (5):637-46 (2003).
Dubois & Stephenson, "Diterpenoid sweeteners. Synthesis and sensory evaluation of stevioside analogues with improved organoleptic properties," J. Med. Chem. 28(1):93-8 (Jan. 1985).
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
EMBOSS Needle results for Pairwise Sequence Alignment of UGT91D1 and UGT91D2; dated Apr. 4, 2016, 2 pages.
Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).
Estrada De Martin et al., "Ice2p is important for the distribution and structure of the cortical ER network in *Saccharomyces cerevisiae*," J Cell Sci. 118(Pt 1):65-77 (Oct. 2006).
Fernandez et al., "Activation of chitin synthetase in permeabilized cells of a *Saccharomyces cerevisiae* mutant lacking proteinase B," J Bacteriol. 152(3):1255-64 (1982).
Flores et al., "Permeabilization of yeast cells (*Kluyveromyces lactis*) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).
Giaever & Nislow, "The yeast deletion collection: a decade of functional genomics," Genetics 197(2):451-65 (Jun. 2014).
Gietz & Schiestl, "High-efficiency yeast transformation using the LiAc/SS carrier DNA/PEG method," Nat Protoc. 2 (1):31-4 (2007).
Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast *Schizosaccharomyces pombe*," Biotechnol. & Biotechnol. Eq. 20(3):76-82 (2006).
Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Iandolino et al., " High-Quality RNA, cDNA, and Derived EST Libraries From Grapevine (*Vitis vinifera* L.)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosythesis: baxane 13 alpha-hydroxylase is a cytochrome P450-dependent monooxygenase," Proc Natl Acad Sci U S A 98(24):13595-600 (2001).
Bateman et al., "Pfam 3.1: 1313 multiple alignments and profile HMMs match the majority of proteins," Nucleic Acids Res. 27(1):260-2 (Jan. 1999).
Bay & Turner, "Diversity and evolution of the small multidrug resistance protein family," BMC Evol. Biol. 9:140 (Jun. 2009).
Brachmann et al., "Designer deletion strains derived from *Saccharomyces cerevisiae* S288C: a useful set of strains and plasmids for PCR-mediated gene disruption and other applications," Yeast 14:115-32 (1998).
Chen et al., "Transferring a biosynthetic cycle into a productive *Escherichia coli* strain: large-scale synthesis of galactosides," J. Am. Chem. Soc. 123(36):8866-7 (Sep. 2001).
Chenna et al., "Multiple sequence alignment with the Clustal series of programs," Nucleic Acids Res. 31 (13):3497-500 (Jul. 2003).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAH69913, dated Jul. 15, 2006 (2 pages).
GenBank Accession No. AEE36246, dated Oct. 6, 2014 (3 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06920.1, dated Dec. 28, 2004 (2 pages).
GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. AF034774, dated Apr. 17, 1998 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. CAG41604, dated Feb. 6, 2015 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).

(56) References Cited

OTHER PUBLICATIONS

GenBank Accession No. NM_116512, dated Jan. 22, 2014 (3 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. NP_194183, dated Jan. 22, 2014 (4 pages).
GenBank Accession No. NP_195399, dated Jan. 22, 2014 (3 pages).
GenBank Accession No. NP_197872.1, dated Jan. 22, 2014 (2 pages).
GenBank Accession No. Q9UVY5.1, dated Apr. 1, 2015 (3 pages).
Boer, "Strain and process development for fermentative production of Rebaudiosides" Abstract of Offered Oral from 33rd International Specialised Symposium on Yeasts; Jun. 26-29, 2017 University of College Cork, Ireland; pp. 1-2.
Patent Examination Report No. 1 issued by IP Australia for Australian Application No. 2011261394, dated Jan. 15, 2015.
Response to Patent Examination Report No. 1 issued by IP Australia for Australian Application No. 2011261394, dated Feb. 5, 2015.
Patent Examination Report No. 2 issued by IP Australia for Australian Application No. 2011261394, dated Feb. 23, 2015.
Notice of Acceptance issued by IP Australia for Australian Application No. 2011261394, dated Aug. 13, 2015 (pp. 1-3).
Office Action for Canadian Patent Application No. 2,802,627, mailed Dec. 15, 2015 (pp. 1-5).
English Translation of First Office Action issued by the State Intellectual Property Office of People's Republic of China for CN Application No. 201180038475.4, dated Nov. 21, 2013.
English Translation on Response to First Office Action issued by the State Intellectual Property Office of People's Republic of China for CN Application No. 201180038475.4, dated Apr. 8, 2014.
English Translation of Second Office Action issued by the State Intellectual Property Office of People's Republic of China for Chinese Application No. 201180038475.4, dated Aug. 13, 2014.
English Translation of Response to Second Office Action issued by the State Intellectual Property Office of People's Republic of China for CN Application No. 201180038475.4, dated Oct. 28, 2014.
English Translation of Third Office Action issued by the State Intellectual Property Office of People's Republic of China for Chinese Application No. 201180038475.4, dated Mar. 3, 2015.
Notification of Grant of Patent Application issued by the State Intellectual Property Office of People's Republic of China for Chinese Application No. 201180038475.4, dated Dec. 1, 2015 (pp. 1-5). English translation included.
Response to Extended Search Report and Opinion issued by the European Patent Office for European Application No. 11790428.4, dated Jul. 16, 2014.
Communication pursuant to Rule 114(2) EPC for European Application No. 11790428.4, dated Nov. 28, 2014.
Examination Report issued by the European Patent Office for European Application No. 11790428.4, dated Dec. 1, 2014.
Response to Examination Report issued by the European Patent Office for European Application No. 11790428.4, dated Jun. 1, 2015 (16 pages).
Communication pursuant to Rule 114(2) EPC for European Application No. 11790428.4, dated Apr. 25, 2016 (19 pages).
Examination Report issued by the European Patent Office for European Application No. 11790428.4, dated May 13, 2016 (12 pages).
English Translation of Notification of Reasons for Refusal of Japanese Application No. 2013-513355, dated Aug. 4, 2015 (pp. 1-10).
Decision of Refusal in Japanese Patent Application No. 2013-513355; dispatch No. 304859, dispatch date Jul. 6, 2016, pp. 1-3. English translation submitted.
First Examination Report issued by the Intellectual Property Office of New Zealand for New Zealand Application No. 604915, dated Sep. 2, 2013.
Response to First Examination Report issued by the Intellectual Property Office of New Zealand for New Zealand Application No. 604915, dated Jan. 17, 2014.
Further Examination Report issued by the Intellectual Property Office of New Zealand for New Zealand Application No. 604915, dated Feb. 3, 2014.
Response to Further Examination Report issued by the Intellectual Property Office of New Zealand for New Zealand Application No. 604915, dated May 27, 2014.
Further Examination Report issued by the Intellectual Property Office of New Zealand for New Zealand Application No. 604915, dated Jun. 18, 2014.
Response to Further Examination Report issued by the Intellectual Property Office of New Zealand for New Zealand Application No. 604915, dated Sep. 15, 2014.
Notice of Acceptance issued by the Intellectual Property Office of New Zealand for New Zealand Application No. 604915, dated Oct. 7, 2014 (1 page).
First Examination Report issued by the Intellectual Property Office of New Zealand for New Zealand Application No. 700097, dated Oct. 6, 2014 (pp. 1-2).
Notice of Acceptance issued by the Intellectual Property Office of New Zealand for New Zealand Application No. 700097, dated Oct. 7, 2015 (1 page).
First Examination Report issued by the Intellectual Property Office of New Zealand for New Zealand Application No. 708078, dated May 28, 2015 (pp. 1-3).
Search Report issued by the Intellectual Property Office of Singapore for Singaporean Application No. 201208854-8, dated Nov. 3, 2014.
Written Opinion issued by the Intellectual Property Office of Singapore for Singaporean Application No. 201208854-8, dated Nov. 3, 2014.
Second Written Opinion in Singapore Patent Application No. 201208854-8; dated Apr. 18, 2016, pp. 1-12.
Final Office Action issued in U.S. Appl. No. 14/237,540; mailed Jul. 8, 2016, pp. 1-19.
English Translation of First Office Action and Search Report issued by the State Intellectual Property Office of People's Republic of China for Chinese Application No. 201280038853.3, dated Feb. 16, 2015.
English Translation of Second Office Action and Search Report issued by the State Intellectual Property Office of People's Republic of China for Chinese Application No. 201280038853.3, dated Jan. 11, 2016.
Communication pursuant to Rules 161(1) and 162 (EPC) issued by the European Patent Office for European Application No. 12750513.9, dated Mar. 14, 2014.
Response to Communication pursuant to Rules 161(1) and 162 (EPC) issued by the European Patent Office for European Application No. 12750513.9, dated Aug. 4, 2014.
Response to Examination Report issued by the European Patent Office for European Application No. 12750513.9, dated Mar. 25, 2015.
Statement of Facts and Arguments In Support Of Opposition for EP Application No. 12750513.9; mailed Feb. 28, 2017. pp. 1-24.
Communication of Notice of Opposition against EP Application No. 12750513.9; mailed Mar. 6, 2017. pp. 1-8.
Sequence alignment between the sequence of Uniprot database entry Q75183 version 31, updated Jul. 22, 2008 and SEQ ID No. 152 (from European Patent No. 2742142) as cited in Notice of Opposition against EP Application No. 12750513.9; mailed Mar. 6, 2017; pp. 1-2.
Non-Final Office Action for U.S. Appl. No. 14/761,629, mailed Mar. 21, 2017 (pp. 1-19).
Final Office Action for U.S. Appl. No. 14/761,629, mailed Aug. 11, 2017 (pp. 1-16).
Communication pursuant to Rules 161(1) and 162 EPC for European Application No. 14704558.7, dated Sep. 18, 2015 (2 pages).
Response to Communication pursuant to Rules 161(1) and 162 EPC for European Application No. 14704558.7, dated Mar. 17, 2016 (pp. 1-24).

(56) References Cited

OTHER PUBLICATIONS

Non-Final Office Action for U.S. Appl. No. 14/764,898, mailed Mar. 30, 2017 (pp. 1-17).
GenBank Accession No. AZF53544, dated Apr. 14, 2011 (2 pages).
UniProt Accession No. B5MEX6, Nov. 4, 2008 (1 page).
UniProt Accession No. E4MVV7, Feb. 8, 2011 (1 page).
Chen et al., "Progress in the Application of Affinity Tags for the Expression and Purification of Recombinant Proteins," China Biotechnology, vol. 32, No. 12, pp. 93-103, Dec. 15, 2012 (English Abstract).
Ohta et al., MassBank Accession No. FU000299 (May 2016).
Ohta et al., MassBank Accession No. FU000332 (May 2016).
Tiwari et al., "Plant secondary metabolism linked glycosyltransferases: An update on expaning knowledge and scopes", Biotechnology Advances, 34:714-739 (May 2016).
Third Party Submission in U.S. Appl. No. 14/648,747; dated Mar. 28, 2016, pp. 1-231.
International Search Report of the International Searching Authority for International Application No. PCT/EP2017/061774; mailed Aug. 30, 2017, pp. 1-20.
Written Opinion of the International Searching Authority for International Application No. PCT/EP2017/061774; mailed Aug. 30, 2017, pp. 1-13.
Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathwayin Stevia rebaudiana (Bertoni)" Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast Rhodosporidium toruloides Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-6 (2000).
Ma et al., "Molecular cloning and characterization of Stevia Rebaudiana UDP-glucosyltransferase," Acta Biologiae Experimentalis Sinica 36(2):123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).

Madan et al., "Stevia rebaudiana (Bert.) Bertoni—A Review," Indian Journal of Natural Products and Resources 1 (3):267-86 (2010).
Madhav et al., "Functional and structural variation of uridine diphosphate glycosyltransferase (UGT) gene of Stevia rebaudiana-UGTSr involved in the synthesis of rebaudioside A," Plant Physiol. Biochem. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of ent-copalyl diphosphate synthase from *Scoparia dulcis* L.," Plant Sci. 169:760-7 (2005).
Nelson et al., "P450 superfamily: update on new sequences, gene mapping, accession Nos. and nomenclature," Pharmacogenetics 6:1-42 (1996).
Newman et al., "High-level production of amorpha-4, 11-diene in a two-phase partitioning bioreactor of metabolically engineered *Escherichia coli*," Biotechnol Bioeng 95(4):684-91 (2006).
Nicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Nour-Eldin et al., "USER cloning and USER fusion: the ideal cloning techniques for small and big laboratories," Methods Mol Biol. 643:185-200 (2010).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31 (6):532-7 (Dec. 2014).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).

(56) References Cited

OTHER PUBLICATIONS

Presecki & Vasic-Racki, "Production of L-malic acid by permeabilized cells of commercial *Saccharomyces* sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast Rhodotorula glutinis for the bioconversion of crude glycerol from biodiesel plant to lipids and carotenoids," Process Biochemistry 46(1):210-8 (Jan. 2011).
Schwab et al., Poster, "Watchmaker®—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol. 143 (3):212-23 (2007).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).
Hallstrom & Moye-Rowley, "Divergent transcriptional control of multidrug resistance genes in *Saccharomyces cerevisiae*," J. Biol. Chem. 273(4):2098-104 (Jan. 1998).
Katzmann et al., "Expression of an ATP-binding cassette transporter-encoding gene (YOR1) is required for oligomycin resistance in *Saccharomyces cerevisiae*," Mol. Cell Biol. 15(12):6875-83 (Dec. 1995).
Li et al., "Phylogenetic analysis of the UDP-glycosyltransferase multigene family of *Arabidopsis thaliana*," J. Biol. Chem. 276(6):4338-43 (Oct. 2000).
Masada et al., "An efficient chemoenzymatic production of small molecule glucosides with in situ UDP-glucose recycling," FEBS Lett. 581(13):2562-6 (May 2007).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2″-O-glucosyltransferase, due to 4-bp insertions in the gene," Plant J. 42(3):353-63 (May 2005).
Nagy et al., "Role of the yeast ABC transporter Yor1p in cadmium detoxification," Biochimie 88(11):1665-71 (Jun. 2006).
Nikaido & Takatsuk, "Mechanisms of RND multidrug efflux pumps," Biochim. Biophys. Acta. 1794(5):769-81 (May 2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).
Osmani et al., "Substrate specificity of plant UDP-dependent glycosyltransferases predicted from crystal structures and homology modeling," Phytochemistry 70(3):325-47 (Feb. 2009).
Richman et al., "Functional genomics uncovers three glucosyltransferases involved in the synthesis of the major sweet glucosides of Stevia rebaudiana," Plant J. 41(1):56-67 (Jan. 2005).

Riesmeier et al., "Isolation and characterization of a sucrose carrier cDNA from spinach by functional expression in yeast," EMBO J. 11(13):4705-13 (Dec. 1992).
Rodríguez-Concepción & Boronat, "Elucidation of the methylerythritol phosphate pathway for isoprenoid biosynthesis in bacteria and plastids. A metabolic milestone achieved through genomics," Plant Physiol. 130 (3):1079-89 (Nov. 2002).
Saier Jr et al., "The major facilitator superfamily," J. Mol. Microbiol. Biotechnol. 1(2):257-79 (Nov. 1999).
Saier Jr et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coli*," J. Biol. Chem. 279(8):6613-9 (Dec. 2003).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J. Biol. Chem. 280(2):899-906 (Jan. 2005).
Shao et al., "Enhanced production of alpha-galactosyl epitopes by metabolically engineered Pichia pastoris," Appl. Environ. Microbiol. 69(9):5238-42 (Sep. 2003).
Son et al., "Production of flavonoid O-glucoside using sucrose synthase and flavonoid O-glucosyltransferase fusion protein," J. Microbiol. Biotechnol. 19(7):709-12 (Jul. 2009).
Sonnhammer et al., "Pfam: a comprehensive database of protein domain families based on seed alignments," Proteins 28(3):405-20 (Jul. 1997).
Sonnhammer et al., "Pfam: multiple sequence alignments and HMM-profiles of protein domains," Nucleic Acids Res. 26(1):320-2 (Jan. 1998).
Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).
International Search Report by the International Searching Authority for International Application No. PCT/EP2014/052675, mailed Apr. 23, 2014 (5 pages).
Written Opinion of the International Searching Authority for International Application No. PCT/EP2014/052675, mailed Apr. 23, 2014 (7 pages).
Ceunen & Geuns, "Steviol glycosides: chemical diversity, metabolism, and function," J. Nat. Prod. 76(6):1201-28 (Jun. 2013).
Olsson et al., "Microbial production of next-generation stevia sweeteners," Microbial Cell Factories, 15:1-14 (2016).
Song et al., "The Aspergillus fumigatus 1-29 damage resistance protein family coordinately regulates ergosterol biosynthesis and azole susceptibility," MBIO, 7:1-13 (2016).
Non-Final Office Action for U.S. Appl. No. 14/648,747, mailed Mar. 23, 2017, pp. 1-20.
Third Party Observation in EP Application No. 13801569.8; mailed Apr. 26, 2017. pp. 1-5.
Final Office Action for U.S. Appl. No. 14/648,747, mailed Sep. 6, 2017 (pp. 1-19).
Third Party Observation in EP Application No. 13801569.8; mailed Oct. 23, 2017. pp. 1-6.
International Preliminary Report on Patentability from the International Bureau for International Application PCT/EP2015/070620; mailed Mar. 14, 2017 (pp. 1-25).
Third Party Submission in U.S. Appl. No. 15/506,196; dated Mar. 9, 2018 pp. 1-68.
International Preliminary Report on Patentability from the International Bureau for International Application PCTEP2015/068314; mailed Feb. 14, 2017 (pp. 1-10).
International Search Report and Written Opinion of the International Searching Authority for International Application No. PCT/EP2015/052007; mailed Jul. 4, 2016, pp. 1-24.
International Preliminary Report on Patentability from the International Bureau for International Application PCT/EP2015/052007; mailed Aug. 1, 2017 (pp. 1-16).
International Search Report and Written Opinion of the International Searching Authority for International Application No. PCT/EP2016/068259; mailed Jan. 24, 2017, pp. 1-18.

(56) References Cited

OTHER PUBLICATIONS

International Preliminary Report on Patentability from the International Bureau for International Application PCT/EP2016/068259; mailed Feb. 13, 2018 (pp. 1-11).
International Search Report and Written Opinion of International Search Authority for International Application No. PCTEP2016/080516; mailed Mar. 15, 2017, pp. 1-22.
International Search Report and Written Opinion of the International Searching Authority for International Application No. PCT/EP2017/061775; mailed Sep. 6, 2017, pp. 1-17.
International Search Report and Written Opinion of International Search Authority for International Application No. PCTEP2017/059028; mailed Jun. 27, 2017, pp. 1-15.
International Search Report and Written Opinion of International Search Authority for International Application No. PCT/EP2017/055589; mailed May 12, 2017, pp. 1-18.
International Search Report and Written Opinion of the International Searching Authority for International Application No. PCT/EP2017/078473; mailed Jan. 25, 2018, pp. 1-16.

* cited by examiner

Rubusoside
NMR-Data in d5-Pyridine

| No | Literature | | | Analyte | | HSQC |
|---|---|---|---|---|---|---|
| | 1H | | 13C | 1H | | |
| | δ [ppm] | M J[Hz] | | δ [ppm] | M J[Hz] | |
| 1 | | | 40.8 | | | 40.7 |
| 2 | | | 19.4 | | | 19.4 |
| 3 | | | 38.3 | | | 38.0 |
| 4 | | | 44.0 | | | - |
| 5 | | | 57.3 | | | 57.1 |
| 6 | | | 22.1 | | | 22.0 |
| 7 | | | 41.1 | | | 41.5 |
| 8 | | | 42.4 | | | - |
| 9 | | | 53.9 | | | 53.7 |
| 10 | | | 39.8 | | | - |
| 11 | | | 20.7 | | | 20.5 |
| 12 | | | 37.2 | | | 36.8 |
| 13 | | | 85.9 | | | - |
| 14 | | | 44.5 | | | 44.5 |
| 15 | | | 47.7 | | | 47.6 |
| 16 | | | 154.5 | | | - |
| 17 | 4.99 / 5.33 | br s / br s | 104.4 | 4.99 / 5.46 | br s / br s | 104.2 |
| 18 | 1.25 | s | 28.3 | 1.25 | s | 28.3 |
| 19 | | | 176.9 | | | - |
| 20 | 1.26 | s | 15.6 | 1.21 | s | 15.6 |
| 13-O-Glc | | | | | | |
| 1 | 5.13 | d 7.7 | 99.7 | 5.00 | d 8.4 | 99.0 |
| 2 | 4.07 | dd 7.7/9.0 | 75.2 | | | 74.8 |
| 3 | 4.22 | dd 9.0/8.9 | 78.8 | | | 78.2 |
| 4 | 4.32 | dd 8.9/8.8 | 72.3 | | | 71.8 |
| 5 | 4.00 | ddd 8.8/2.4/4.4 | 78.0 | | | 77.2 |
| 6 | 4.45 / 4.26 | dd 2.4/12.0 / dd 2.4/12.0 | 63.0 | 4.42 | dd 2.3/12.5 | 62.6 |
| 19-O-Glc | | | | | | |
| 1 | 6.14 | d 7.9 | 95.9 | 5.99 | d 8.1 | 95.2 |
| 2 | 4.20 | dd 7.9/9.0 | 74.0 | | | 73.5 |
| 3 | 4.22 | dd 9.0/9.0 | 79.1 | | | 78.4 |
| 4 | 4.09 | dd 9.0/8.8 | 71.1 | | | 70.7 |
| 5 | 3.98 | ddd 8.8/2.2/4.6 | 79.3 | | | 78.4 |
| 6 | 4.61 / 4.26 | dd 2.2/11.7 / dd 4.6/11.7 | 62.1 | 4.31 / 4.22 | dd 2.5/12.3 / dd 4.0/11.7 | 61.8 |

Multiple Sequence Alignment

```
SEQ ID NO:14   MYNVTYEQNSKAMATSQSTVDDRKQLRVATFPWLAFGHILPFLQLSKLIA
SEQ ID NO:16   ----------------MATSDSIVDDRKQLRVATFPWLAFGHILPFLQLSKLIA
SEQ ID NO:12   ----------------MATSDSIVDDRKQLRVATFPWLAFGHILPFLQLSKLIA
SEQ ID NO: 5   ----------------MATSDSIVDDRKQLRVATFPWLAFGHILPYLQLSKLIA
SEQ ID NO:10   ----------------MATSDSIVDDRKQLRVATFPWLAFGHILPYLQLSKLIA
                                ************************:******

SEQ ID NO:14   EKGHKVSFLSTTRNIQRLSSHISPLINVVQLTLPRVQELPEDAEATTDVH
SEQ ID NO:16   EKGHKVSFLSTTRNIQRLSSHISPLINVVQLTLPRVQELPEDAEATTDVH
SEQ ID NO:12   EKGHKVSFLSTTRNIQRLSSHISPLINVVQLTLPRVQELPEDAEATTDVH
SEQ ID NO: 5   EKGHKVSFLSTTRNIQRLSSHISPLINVVQLTLPRVQELPEDAEATTDVH
SEQ ID NO:10   EKGHKVSFLSTTRNIQRLSSHISPLINVVQLTLPRVQELPEDAEATTDVH
               **************************************************

SEQ ID NO:14   PEDIQYLKKAVDGLQPEVTRFLEQHSPDWIIYDFTHYWLPSIAASLGTSR
SEQ ID NO:16   PEDIQYLKKAVDGLQPEVTRFLEQHSPDWIIYDFTHYWLPSTAASLGISR
SEQ ID NO:12   PEDIQYLKKAVDGLQPEVTRFLEQHSPDWIIYDFTHYWLPSTAASLGISR
SEQ ID NO: 5   PEDIPYLKKASDGLQPEVTRFLEQHSPDWIYDYTHYWLPSTAASLGISR
SEQ ID NO:10   PEDIPYLKKASDGLQPEVTRFLEQHSPDWIYDYTHYWLPSTAASLGISR
               ****.****:******************* **:*******:******:**

SEQ ID NO:14   AYFCVITPWTIAYLAPSSDAMINDSDGKTTVEDLTTPPKWFPFPTKVCWR
SEQ ID NO:16   AYFCVITPWTIAYLAPSSDAMINDSDGRTTVEDLTTPPKWFPFPTKVCWR
SEQ ID NO:12   AYFCVITPWTIAYLAPSSDAMINDSDGRTTVEDLTTPPKWFPFPTKVCWR
SEQ ID NO: 5   AHFSVTTPWAIAYMGPSADAMINGSEGRTTVEDLTTPPKWFPFPTKVCWR
SEQ ID NO:10   AHFSVTTPNAIAYMGPSADAMINGSDGRTTVEDLTTPPKWFPFPTKVCWR
               *:*.* ***:***:.**:****** *:*:*******************

SEQ ID NO:14   KHDLARMEFYEAPGISDSYRMGMVFKGSDCLLFKCYINEFGTQWLPLLETL
SEQ ID NO:16   KHDLARMEPYEAPGISDSYRMGMVFKGSDCLLFKCYINEFGTQWLPLLETL
SEQ ID NO:12   KHDLARMEPYEAPGISDSYRMGMVFKGSDCLLFKCYHEFGTQWLPLLETL
SEQ ID NO: 5   KHDLARLVEYKAPGISDGYRMGLVLKGSECLLSKCYEEFGTQWLPLLETL
SEQ ID NO:10   KHEMARLVPYKAPGISDGYRMGLVIKGSDCLLSKCYHEFGTQWLPLLETL
               **::**: ::*****.****:*:***:*** ***  **********

SEQ ID NO:14   HQVPVVPGLLPPEIPGDEKDETWVSIKKWLDGKQKGSVVYVALGSSEALV
```

FIG. 8

```
SEQ ID NO:14   HQVPVVPVGLLPEIPGDEKDETWVSIKKWLDGEKQKGSVVYVALGSEALV
SEQ ID NO:16   HQVPVVPVGLLPEIPGDEKDETWVSIKKWLDGKQKGSVVYVALGSEALV
SEQ ID NO:12   HQVPVVPVGLLPPETPGDEKDETWVSIKKWLDGKQKGSVVYVALGSEVLV
SEQ ID NO: 5   HQVPVVPVGLLPPEVRGDEKDETWVSIKKWLDGKQKGSVVYVALGSEVLV
SEQ ID NO:10   HQVPVVPVGLLPPEIPGDEKDETWVSIKKWLDGKQKGSVVYVALGSEVLV
               ************ * * .*****************.********** **

SEQ ID NO:14   SQTEVVELALGLELSGLPFVWAYRKPKGPAKSDSVELPDGFVERTRDRGL
SEQ ID NO:16   SQTEVVELALGLELSGLPFVWAYRKPKGPAKSDSVELPDGFVERTRDRGL
SEQ ID NO:12   SQTEVVELALGLELSGLPFVWAYRRKGPAKSDSVELPDGFVERTRDRGL
SEQ ID NO: 5   SQTEVVELALGLELSGLPFVWAYEKPKGPAKSDSVELPDGFVERTRDRGL
SEQ ID NO:10   SQTEVVELALGLELSGLPFVWAYRKPKGPAKSDSVELPDGFVERTRDRGL
               *********************  ***********************

SEQ ID NO:14   VWTSWAPQLRILSHESVCGFLTHCGSGSIVEGLMFGHPLIMLPIFCDQPL
SEQ ID NO:16   VWTSWAPQLRILSHESVCGFLTHCGSGSIVEGLMFGHPLIMLPIFCDQPL
SEQ ID NO:12   VWTSWAPQLRILSHESVCGFLTHCGSGSIVEGLMFGHPLIMLPIFCDQPL
SEQ ID NO: 5   VWTSWAPQLRILSHESVCGFLTHCGSGSIVEGLMFGHPLIMLPLFGDQPL
SEQ ID NO:10   VWTSWAPQLRILSHESVCGFLTHCGSGSIVEGLMFGBELIMLPIFCDQPL
               ****************************************  *  ***

SEQ ID NO:14   NARLLEDKQVGIEIPRNEEDGCLTKESVARSLRSVVVENEGEIYKANARA
SEQ ID NO:16   NARLLEDKQVGIEIPRNEEDGCLTKESVARGLRSVVVENEGEIYKANARA
SEQ ID NO:12   NARLLEDKQVGIEIPRNEEDGCLTKESVARSLRSVVVENEGEIYKANARE
SEQ ID NO: 5   NARLLEDKQVGIEIPRNEEDGCLTKESVARSLRSVVVEKEGEIYKANARE
SEQ ID NO:10   NARLLEDKQVGIEIPRNEEDGCLTKESVARSLRSVVVEKEGEIYKANARE
               ******************************.****** ********* *

SEQ ID NO:14   LSKIYNDTKVEKEYVSQFVDYLEKMARAVAIDHES
SEQ ID NO:16   LSKIYNDTKVEKEYVSQFVDYLEKMARAVAIDHES
SEQ ID NO:12   LSKIYNDTKVEKEYVSQFVDYLEKMARAVAIDHES
SEQ ID NO: 5   LSKIYNDTKVEKEYVSQFVDYLEKNARAVAIDHES
SEQ ID NO:10   LSKIYNDTKVEKEYVSQFVDYLEKNTRAVAIDHES
               ************************ *********

CLUSTAL W (1.82) multiple sequence alignment
```

FIG. 8, CONTINUED

RECOMBINANT PRODUCTION OF STEVIOL GLYCOSIDES

CROSS-REFERENCE TO RELATED APPLICATIONS

This application is a continuation of U.S. application Ser. No. 18/470,785, filed on Sep. 20, 2023, which is a continuation of U.S. application Ser. No. 17/373,612, filed on Jul. 12, 2021, now abandoned, which is a continuation of U.S. application Ser. No. 16/460,320, filed on Jul. 2, 2019, now abandoned, which is a continuation of U.S. application Ser. No. 15/382,354 filed on Dec. 16, 2016, now U.S. Pat. No. 10,392,644, granted on Aug. 27, 2019, which is a divisional of U.S. application Ser. No. 13/701,406, filed on Mar. 22, 2013, now U.S. Pat. No. 9,562,251, granted on Feb. 7, 2017, which is a U.S. national phase of International Application No. PCT/US2011/038967 filed on Jan. 2, 2011, which claims the benefit of U.S. Provisional Application No. 61/350,553, filed on Jun. 2, 2010, U.S. Provisional Application No. 61/434,582, filed on Jan. 20, 2011, and U.S. Provisional Application No. 61/471,622, filed on Apr. 4, 2011. The entire disclosure contents of these applications are herewith incorporated by reference in their entirety into the present application.

SEQUENCE LISTING

The instant application contains a Sequence Listing which has been submitted electronically and is hereby incorporated by reference in its entirety. The Sequence Listing was created on Jun. 27, 2024, is named "13-1229-US CON3_SequenceListing.xml", and is 336,570 bytes in size.

TECHNICAL FIELD

This disclosure relates to the recombinant production of steviol and steviol glycosides. In particular, this disclosure relates to the production of steviol and steviol glycosides such as rubusoside and/or rebaudioside A by recombinant hosts such as recombinant microorganisms, plants, or plant cells. This disclosure also provides compositions containing steviol glycosides.

BACKGROUND

Sweeteners are well known as ingredients used most commonly in the food, beverage, or confectionary industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine and sucralose. *Stevia* extract is a natural sweetener that can be isolated and extracted from a perennial shrub, *Stevia rebaudiana*. *Stevia* is commonly grown in South America and Asia for commercial production of *stevia* extract. *Stevia* extract, purified to various degrees, is used commercially as a high intensity sweetener in foods and in blends or alone as a tabletop sweetener.

Extracts of the *Stevia* plant contain rebaudiosides and other steviol glycosides that contribute to the sweet flavor, although the amount of each glycoside often varies among different production batches. Existing commercial products are predominantly rebaudioside A with lesser amounts of other glycosides such as rebaudioside C, D, and F. *Stevia* extracts may also contain contaminants such as plant-derived compounds that contribute to off-flavors. These off-flavors can be more or less problematic depending on the food system or application of choice. Potential contaminants include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α- and β-amyrin, lupeol, β-amryin acetate, pentacyclic triterpene, centauredin, quercitin, epi-alpha-cadinol, carophyllenes and derivatives, beta-pinene, beta-sitosterol, and gibberellin.

SUMMARY

Provided herein is a recombinant host, such as a microorganism, comprising one or more biosynthesis genes whose expression results in production of steviol. Such genes include a gene encoding a copalyl diphosphate synthase, a gene encoding a kaurene synthase, a gene encoding a kaurene oxidase; and a gene encoding a steviol synthetase. The recombinant host can include a gene encoding a bifunctional copalyl diphosphate synthase and kaurene synthase, in place of the genes encoding copalyl diphosphate synthase and kaurene synthase. At least one of the genes is a recombinant gene. In some embodiments the recombinant host further comprises a gene encoding a geranylgeranyl diphosphate synthase. The recombinant host can further comprise a gene encoding a truncated HMG-COA reductase and/or a gene encoding a CPR. The expression of one or more of the genes can be inducible.

In one aspect, this document features a recombinant host that includes a recombinant gene encoding a UGT91D2 polypeptide (e.g., a UGT91D2e or UGT91D2m polypeptide). The UGT91D2 polypeptide can have at least 90% identity (e.g., at least 95% or 99% identity) to the amino acid sequence set forth in SEQ ID NO:5. The UGT91D2 polypeptide can include at least one amino acid substitution at residues 1-19, 27-38, 44-87, 96-120, 125-141, 159-184, 199-202, 215-380, or 387-473 of SEQ ID NO:5. For example, the UGT91D2 polypeptide can include an amino acid substitution at one or more residues selected from the group consisting of residues 30, 93, 99, 122, 140, 142, 148, 153, 156, 195, 196, 199, 206, 207, 211, 221, 286, 343, 427, and 438 of SEQ ID NO: 5. In one embodiment, the UGT91D2 polypeptide includes an arginine at residue 206, a cysteine at residue 207, and an arginine at residue 343 relative to SEQ ID NO:5. In one embodiment, the UGT91D2 polypeptide includes a phenylalanine at residue 30, a glutamine at residue 93, a valine at residue 99, a phenylalanine at residue 122, a tyrosine at residue 140, a cysteine at residue 142, a threonine at residue 148, an alanine at residue 153, a serine at residue 156, a methionine at residue 195, a glutamic acid at residue 196, a glutamic acid at residue 199, a methionine at residue 211, a phenylalanine at residue 221, an alanine at residue 286, an asparagine at residue 427, or an alanine at residue 438 relative to SEQ ID NO:5. The polypeptide can have the amino acid sequence of SEQ ID NO: 5 or SEQ ID NO:95.

A host described herein further can include a recombinant gene encoding a UGT85C polypeptide having at least 90% identity to the amino acid sequence set forth in SEQ ID NO:3. For example, the UGT85C polypeptide can include one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471 of SEQ ID NO: 3.

A host described herein further can include a recombinant gene encoding a UGT76G polypeptide having at least 90% identity to the amino acid sequence set forth in SEQ ID NO:7. For example, the UGT76G polypeptide can have one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 of SEQ ID NO:7.

This document also features a recombinant host that includes a recombinant gene encoding a UGT85C polypeptide having at least 90% identity to the amino acid sequence set forth in SEQ ID NO:3, and having one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471 of SEQ ID NO:3. For example, the UGT85C polypeptide can include substitutions at residues 13, 15, 60, 270, 289, and 418 of SEQ ID NO: 3. For example, the UGT85C polypeptide can include a) substitutions at residues 13, 60, and 270 of SEQ ID NO:3; b) substitutions at residues 60 and 87 of SEQ ID NO:3; c) substitutions at residues 65, 71, 220, 243, and 270 of SEQ ID NO:3; d) substitutions at residues 65, 71, 220, 243, 270, and 441 of SEQ ID NO:3; e) substitutions at residues 65, 71, 220, 389, and 394 of SEQ ID NO:3; f) substitutions at residues 65, 71, 270, and 289 of SEQ ID NO:3; g) substitutions at residues 15 and 65 of SEQ ID NO:3; h) substitutions at residues 65 and 270 of SEQ ID NO:3; i) substitutions at residues 65 and 440 of SEQ ID NO: 3; j) substitutions at residues 65 and 441 of SEQ ID NO:3; k) substitutions at residues 65 and 418 of SEQ ID NO:3; l) substitutions at residues 220, 243, 270, and 334 of SEQ ID NO:3; or m) substitutions at residues 270 and 289 of SEQ ID NO:3.

In another aspect, this document features a recombinant host that includes a recombinant gene encoding a UGT76G polypeptide having at least 90% identity to the amino acid sequence set forth in SEQ ID NO:7, and having one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346. For example, the UGT76G polypeptide can have a) substitutions at amino acid residues 74, 87, 91, 116, 123, 125, 126, 130, 145, 192, 193, 194, 196, 198, 199, 200, 203, 204, 205, 206, 207, 208, and 291; b) substitutions at residues 74, 87, 91, 116, 123, 125, 126, 130, 145, 192, 193, 194, 196, 198, 199, 200, 203, 204, 205, 206, 207, 208, 266, 273, 274, 284, 285, and 291; or c) substitutions at residues 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346.

Any of the hosts described herein further can include a gene encoding a UGT74G1 polypeptide (e.g., a recombinant gene encoding a UGT74G1 polypeptide).

Any of the hosts described herein further can include one or more of: (i) a gene encoding a geranylgeranyl diphosphate synthase; (ii) a gene encoding a bifunctional copalyl diphosphate synthase and kaurene synthase, or a gene encoding a copalyl diphosphate synthase and a gene encoding a kaurene synthase; (iii) a gene encoding a kaurene oxidase; (iv) a gene encoding a steviol synthetase; (v) a gene encoding a truncated HMG-COA; (vi) a gene encoding a CPR; (vii) a gene encoding a rhamnose synthetase; (viii) a gene encoding a UDP-glucose dehydrogenase; and (ix) a gene encoding a UDP-glucuronic acid decarboxylase. At least one of the genes of (i), (ii), (iii), (iv), (v), (vi), (vii), (viii), or (ix) can be a recombinant gene. In some embodiments, each of the genes of (i), (ii), (iii), and (iv) is a recombinant gene.

This document also features an isolated nucleic acid encoding a polypeptide having at least 90% sequence identity (e.g., at least 95% or 99% sequence identity) to the amino acid sequence set forth in SEQ ID NO:5. The polypeptide can include at least one amino acid substitution at residues 1-19, 27-38, 44-87, 96-120, 125-141, 159-184, 199-202, 215-380, or 387-473 of SEQ ID NO:5. The polypeptide can include an amino acid substitution at one or more residues selected from the group consisting of residues 30, 93, 99, 122, 140, 142, 148, 153, 156, 195, 196, 199, 206, 207, 211, 221, 286, 343, 427, and 438 of SEQ ID NO:5. The polypeptide can include an arginine at residue 206, a cysteine at residue 207, and an arginine at residue 343 of SEQ ID NO:5. In some embodiments, the polypeptide includes a phenylalanine at residue 30, a glutamine at residue 93, a valine at residue 99, a phenylalanine at residue 122, a tyrosine at residue 140, a cysteine at residue 142, a threonine at residue 148, an alanine at residue 153, a serine at residue 156, a methionine at residue 195, a glutamic acid at residue 196, a glutamic acid at residue 199, a methionine at residue 211, a phenylalanine at residue 221, an alanine at residue 286, an asparagine at residue 427, or an alanine at residue 438 of SEQ ID NO:5.

In another aspect, this document features an isolated polypeptide having an amino acid sequence with at least 90% identity to the amino acid sequence of SEQ ID NO:5.

This document also features a recombinant host that includes (i) a gene encoding a geranylgeranyl diphosphate synthase; (ii) a gene encoding a bifunctional copalyl diphosphate synthase and kaurene synthase, or a gene encoding a copalyl diphosphate synthase and a gene encoding a kaurene synthase; (iii) a gene encoding a kaurene oxidase; and (iv) a gene encoding a steviol synthetase; wherein at least one of said genes. The host can produce steviol when cultured under conditions in which each of the genes is expressed, and can accumulate to at least 1 mg/L in the culture medium. The geranylgeranyl diphosphate synthase can have greater than 90% sequence identity to one of the amino acid sequences set forth in SEQ ID NOs: 121-128. The copalyl diphosphate synthase can have greater than 90% sequence identity to one of the amino acid sequences set forth in SEQ ID NOs: 129-131. The kaurene synthase can have greater than 90% sequence identity to one of the amino acid sequences set forth in 132-135. The kaurene oxidase can have greater than 90% sequence identity to one of the amino acid sequences set forth in 138-141. The steviol synthetase can have greater than 90% sequence identity to one of the amino acid sequences set forth in SEQ ID NOs: 142-146. The host further can include a gene encoding a truncated HMG-COA and/or a gene encoding a CPR.

Any of the recombinant hosts further can include one or more of a gene encoding a UGT74G1 polypeptide, a UGT85C2 polypeptide, a UGT76G1 polypeptide, or a UGT91D2 polypeptide.

Any of the recombinant hosts can produce at least one steviol glycoside when cultured under conditions in which each of the genes is expressed. The steviol glycoside can be selected from the group consisting of steviol-13-O-glucoside, steviol-19-O-glucoside, rubusoside, rebaudioside A, rebaudioside B, rebaudioside C, rebaudioside D, rebaudioside E, rebaudioside F, and dulcoside A. The steviol glycoside can accumulate to at least 1 mg/liter (e.g., at least 10 mg/liter or 20 mg/liter) of culture medium when cultured under said conditions.

Any of the recombinant hosts further can include one or more of i) a gene encoding a deoxyxylulose 5-phosphate synthase (DXS); ii) a gene encoding a D-1-deoxyxylulose 5-phosphate reductoisomerase (DXR); iii) a gene encoding a 4-diphosphocytidyl-2-C-methyl-D-erythritol synthase (CMS); iv) a gene encoding a 4-diphosphocytidyl-2-C-methyl-D-erythritol kinase (CMK); v) a gene encoding a 4-diphosphocytidyl-2-C-methyl-D-erythritol 2,4-cyclodiphosphate synthase (MCS); vi) a gene encoding a 1-hydroxy-2-methyl-2 (E)-butenyl 4-diphosphate synthase (HDS); or vii) a gene encoding a 1-hydroxy-2-methyl-2 (E)-butenyl 4-diphosphate reductase (HDR).

Any of the recombinant hosts further can include one or more of ix) a gene encoding a acetoacetyl-CoA thiolase; x) a gene encoding a truncated HMG-COA reductase; xi) a gene encoding a mevalonate kinase; xii) a gene encoding a phosphomevalonate kinase; or xiii) a gene encoding a mevalonate pyrophosphate decarboxylase.

In any of the hosts described herein, expression of one or more of the genes can be inducible.

Any of the hosts described herein can be a microorganism (e.g., a Saccharomycete such as *Saccharomyces cerevisiae*, or *Escherichia coli*), or a plant or plant cell (e.g., a *Stevia* such as a *Stevia rebaudiana, Physcomitrella*, or tobacco plant or plant cell).

In another aspect, this document features a method of producing steviol or a steviol glycoside. The method includes growing a host described herein in a culture medium, under conditions in which the genes are expressed; and recovering the steviol or steviol glycoside produced by the host. The growing step can include inducing expression of one or more of the genes. The steviol or steviol glycoside is selected from the group consisting of steviol-13-O-glucoside, steviol-19-O-glucoside, rubusoside, rebaudioside A, rebaudioside B, rebaudioside C, rebaudioside D, rebaudioside E, rebaudioside F, and dulcoside A.

Also provided herein is a method of producing steviol or a steviol glycoside. The method includes growing a microorganism in a culture medium, under conditions in which a geranylgeranyl diphosphate synthase, copalyl diphosphate synthase, kaurene synthase, kaurene oxidase, kaurenoic acid 13-hydroxylase gene and optionally a UGT74G1 and/or a UGT85C2 gene are expressed, and recovering the steviol or steviol glycoside produced by the microorganism. The microorganism can be a *Saccharomyces* spp. In some embodiments, the growing step comprises inducing expression of one or more of the geranylgeranyl diphosphate synthase, copalyl diphosphate synthase, kaurene synthase, kaurene oxidase, kaurenoic acid 13-hydroxylase, UGT74G1 and UGT85C2 genes. In some embodiments, the recovering step comprises purifying the steviol or steviol glycoside from the culture medium by HPLC. The steviol or steviol glycoside can be steviol, rubusoside, rebaudioside C, rebaudioside F, or dulcoside A.

Also provided herein is a recombinant *Saccharomyces* strain, comprising one or more biosynthesis genes whose expression results in production of ent-kaurene. The biosynthesis genes include a gene encoding a bifunctional copalyl diphosphate synthase and kaurene synthase, or a gene encoding a copalyl diphosphate synthase and a gene encoding a kaurene synthase. The strain produces ent-kaurene upon expression of the copalyl diphosphate synthase and the kaurene synthase.

In another aspect, this document features an isolated nucleic acid having greater than 90% sequence identity (e.g., greater than 95% or 99% sequence identity) to one of the nucleotide sequences set forth in SEQ ID NOs: 18-25, 34-36, 4-43, 48, 49, 52-55, 60-64, 70-72, 77, or 79.

This document also features a recombinant host that includes (i) a gene encoding a UGT74G1; (ii) a gene encoding a UGT85C2; (iii) a gene encoding a UGT76G1; and (iv) a gene encoding a UGT91D2, wherein at least one of said genes is a recombinant gene. In some embodiments, each of the genes is a recombinant gene. The host can produce at least one steviol glycoside when cultured under conditions in which each of the genes is expressed. The host further can include (a) a gene encoding a bifunctional copalyl diphosphate synthase and kaurene synthase, or a gene encoding a copalyl diphosphate synthase and a gene encoding a kaurene synthase; (b) a gene encoding a kaurene oxidase; (c) a gene encoding a steviol synthetase; and (d) a gene encoding a geranylgeranyl diphosphate synthase. The steviol glycoside can be rebaudioside A, rebaudioside D or rebaudioside E. This document also features a steviol glycoside composition produced by such a host. The composition can have greater than 4% rebaudioside D by weight of total steviol glycosides and a reduced level of *stevia* plant-derived contaminants relative to a *stevia* extract. The composition can have greater than 4% rebaudioside E by weight of total steviol glycosides and a reduced level of *stevia* plant-derived contaminants relative to a *stevia* extract.

Also featured herein is an isolated nucleic acid encoding a polypeptide having greater than 90% sequence identity to the amino acid sequences of UGT91D2e and UGT91D2m, excluding the amino acid sequence of UGT91D2m, as well as the isolated polypeptides having greater than 90% sequence identity to the amino acid sequence of UGT91D2e or UGT91D2m, excluding the amino acid sequence of UGT91D2m.

This document also features steviol glycoside composition produced by the host described herein. The composition having reduced levels of *stevia* plant-derived contaminants relative to a *stevia* extract.

In another aspect, this document features a recombinant host. The host includes (i) a recombinant gene encoding a UGT91D2; (ii) a recombinant gene encoding a UGT74G1; (iii) a recombinant gene encoding a UGT85C2; (iv) a recombinant gene encoding a UGT76G1; and (v) a gene encoding a rhamnose synthetase, wherein the host produces at least one steviol glycoside when cultured under conditions in which each of the genes is expressed. The host further can include (a) a gene encoding a bifunctional copalyl diphosphate synthase and kaurene synthase, or a gene encoding a copalyl diphosphate synthase and a gene encoding a kaurene synthase; (b) a gene encoding a kaurene oxidase; (c) a gene encoding a steviol synthetase; and (d) a gene encoding a geranylgeranyl diphosphate synthase. The steviol glycoside can be rebaudioside C or dulcoside A. This document also features a steviol glycoside composition produced by such a host. The composition has greater than 15% rebaudioside C by weight of total steviol glycosides and a reduced level of *stevia* plant-derived contaminants relative to a *stevia* extract. A steviol glycoside composition produced by such a host also is featured. The composition can have greater than 15% dulcoside A by weight of total steviol glycosides and a reduced level of *stevia* plant-derived contaminants relative to a *stevia* extract.

This document also features a recombinant host. The host includes (i) a recombinant gene encoding a UGT91D2; (ii) a recombinant gene encoding a UGT74G1; (iii) a recombinant gene encoding a UGT85C2; (iv) a recombinant gene encoding a UGT76G1; (v) a gene encoding a UDP-glucose dehydrogenase; and (vi) a gene encoding a UDP-glucuronic acid decarboxylase, wherein the host produces at least one steviol glycoside when cultured under conditions in which each of the genes is expressed. The host further can include (a) a gene encoding a bifunctional copalyl diphosphate synthase and kaurene synthase, or a gene encoding a copalyl diphosphate synthase and a gene encoding a kaurene synthase; (b) a gene encoding a kaurene oxidase; (c) a gene encoding a steviol synthetase; and (d) a gene encoding a geranylgeranyl diphosphate synthase. The steviol glycoside can be rebaudioside F. This document also features a steviol glycoside composition produced by such hosts. The composition can have greater than 4% rebaudioside F by weight of total steviol glycosides and a reduced level of *stevia* plant-derived contaminants relative to a *stevia* extract.

In another aspect, this document features a method of producing a steviol glycoside composition. The method includes growing a host described herein in a culture medium, under conditions in which each of the genes is expressed; and recovering the steviol glycoside composition produced by the host, wherein the recovered composition is enriched for rebaudioside A, rebaudioside C, rebaudioside D, rebaudioside E, rebaudioside F or dulcoside A relative to the steviol glycoside composition of a wild-type *Stevia* plant. The steviol glycoside composition produced by the host (e.g., microorganism) can have a reduced level of *stevia* plant-derived contaminants relative to a *stevia* extract.

This document also features a food product that includes a steviol glycoside composition enriched for rebaudioside A, rebaudioside C, rebaudioside D, rebaudioside E, rebaudioside F or dulcoside A relative to the steviol glycoside composition of a wild-type *Stevia* plant.

In another aspect, this document features a method of identifying whether a polymorphism is associated with variation in a trait. The method includes determining whether one or more genetic polymorphisms in a population of plants is associated with the locus for a polypeptide set forth in SEQ ID NO:5 and functional homologs thereof; and measuring the correlation between variation in the trait in plants of the population and the presence of the one or more genetic polymorphisms in plants of the population, thereby identifying whether or not the one or more genetic polymorphisms are associated with variation in the trait.

In yet another aspect, this document features a method of making a plant line. The method includes determining whether one or more genetic polymorphisms in a population of plants is associated with the locus for a polypeptide set forth in SEQ ID NO: 5 and functional homologs thereof; identifying one or more plants in the population in which the presence of at least one of the genetic polymorphisms is associated with variation in a trait; crossing one or more of the identified plants with itself or a different plant to produce seed; crossing at least one progeny plant grown from the seed with itself or a different plant; and repeating the crossing steps for an additional 0-5 generations to make said plant line, wherein at least one of the genetic polymorphisms is present in the plant line.

This document also features a method for transferring a second sugar moiety to the C-2' of a glucose in a steviol glycoside. The method includes contacting the steviol glycoside with a UGT91D2 polypeptide and a UDP-sugar under suitable reaction conditions for the transfer of the second sugar moiety to the steviol glycoside. The UGT91D2 polypeptide can have at least 90% sequence identity (e.g., at least 95% or 99%) to the amino acid sequence set forth in SEQ ID NO:5. The UGT91D2 polypeptide can include at least one amino acid substitution at residues 1-19, 27-38, 44-87, 96-120, 125-141, 159-184, 199-202, 215-380, or 387-473 of SEQ ID NO:5. The UGT91D2 polypeptide can include an amino acid substitution at one or more residues selected from the group consisting of residues 30, 93, 99, 122, 140, 142, 148, 153, 156, 195, 196, 199, 206, 207, 211, 221, 286, 343, 427, and 438 of SEQ ID NO:5. The steviol glycoside can be selected from the group consisting of steviol-13-O-glucoside, rubusoside, stevioside, and Rebaudioside A. The steviol glycoside can be rubusoside and the second sugar moiety is glucose, and stevioside is produced upon transfer of the second glucose moiety. The steviol glycoside can be stevioside and the second sugar moiety can be glucose, and Rebaudioside E is produced upon transfer of the second glucose moiety. The steviol glycoside can be stevioside, wherein stevioside is contacted with the UGT91D2 polypeptide and a UGT76G1 polypeptide under suitable reaction conditions to produce Rebaudioside D. The steviol glycoside can be steviol-13-O-glucoside and steviol-1,2 bioside is produced upon transfer of said second glucose moiety. The steviol glycoside can be steviol-13-O-glucoside and steviol-1,2-xylobioside is produced upon transfer of the second sugar moiety. The steviol glycoside can be steviol-13-O-glucoside and steviol-1,2-rhamnobioside can be produced upon transfer of the second sugar moiety. The steviol glycoside can be Rebaudioside A, and Rebaudioside D is produced upon transfer of a second glucose moiety.

In another aspect, this document features a method of determining the presence of a polynucleotide in a *Stevia* plant. The method includes contacting at least one probe or primer pair with nucleic acid from the *Stevia* plant, wherein the probe or primer pair is specific for a polynucleotide that encodes a UGT polypeptide, wherein the UGT polypeptide has at least 90% sequence identity to SEQ ID NO: 5, SEQ ID NO: 1, SEQ ID NO: 3 or SEQ ID NO:7 and determining whether or not the polynucleotide is present in said *Stevia* plant.

This document also features a kit for genotyping a *Stevia* biological sample. The kit includes a primer pair that specifically amplifies, or a probe that specifically hybridizes to, a polynucleotide that encodes a UGT polypeptide having at least 90% sequence identity to SEQ ID NO: 5, SEQ ID NO: 1, SEQ ID NO: 3 or SEQ ID NO:7.

Also provided herein is a recombinant microorganism, comprising one or more biosynthesis genes whose expression results in production of one or more steviol glycosides. The biosynthesis genes include a gene encoding a geranylgeranyl diphosphate synthase, a gene encoding a copalyl diphosphate synthase and a gene encoding a kaurene synthase, a gene encoding a kaurene oxidase, a gene encoding a steviol synthetase, and a gene encoding a UGT74G1 and/or a UGT85C2. At least one of the genes is a recombinant gene. The microorganism can comprise a gene encoding a bifunctional copalyl diphosphate synthase and kaurene synthase in place of the genes encoding copalyl diphosphate synthase and kaurene synthase.

The recombinant microorganism produces at least one steviol glycoside when cultured under conditions in which each of the genes is expressed. The steviol glycoside can be rubusoside, rebaudioside C, rebaudioside F, dulcoside B, or dulcoside A.

The recombinant microorganism can be a Saccharomycete, e.g., *Saccharomyces cerevisiae*, and can have one or more genetic modifications that reduce EXG1 and EXG2 glycoside hydrolase activity relative to a control microorganism that lacks such genetic modifications, and can have one or more genetic modifications that reduce ergosterol biosynthesis relative to a control microorganism that lacks such genetic modifications. The *Saccharomyces* produces rubusoside when cultured under conditions in which each of the genes is expressed. The rubusoside can accumulate to at least 10 mg/liter of culture medium. The Saccharomycete can be a *Saccharomyces cerevisiae* strain designated CEY171, CEY191, or CEY213.

The recombinant microorganism can further comprise a gene encoding an SM12UGT and a gene encoding a UGT76G1, and produce a steviol glycoside when cultured under conditions in which each of the genes is expressed. The steviol glycoside can be rebaudioside A.

Also provided herein is a recombinant microorganism, comprising one or more biosynthesis genes whose expression results in production of at least one steviol glycoside. The biosynthesis genes include a gene encoding an SM12UGT, a gene encoding a UGT74G1, a gene encoding a UGT76G1 and a gene encoding a UGT85C2. The recombinant microorganism produces rebaudioside A or rebaudioside B when cultured under conditions in which each of the genes is expressed. The rebaudioside A or rebaudioside B can accumulate to at least 1 mg/L in the culture medium.

Also featured herein is a recombinant microorganism, comprising a gene encoding a UGT91D2 polypeptide, e.g., a recombinant UGT91D2 gene.

Also featured herein is a recombinant microorganism, comprising a gene encoding a geranylgeranyl diphosphate synthase, a gene encoding a bifunctional copalyl diphosphate synthase and kaurene synthase (or a gene encoding a copalyl diphosphate synthase and a gene encoding a kaurene synthase), a gene encoding a kaurene oxidase, a gene encoding a steviol synthetase, a gene encoding a UGT74G1, a gene encoding a UGT85C2, a gene encoding a UGT76G1, and a gene encoding a UGT91D2. At least one of the genes is a recombinant gene. The recombinant microorganism can produce at least one steviol glycoside, e.g., rebaudioside A, rebaudioside B, and/or rebaudioside F, when cultured under conditions in which each of the genes is expressed. The recombinant microorganism can accumulate at least 20 mg of steviol glycoside per liter of culture medium when cultured under such conditions. The recombinant microorganism can be a Saccharomycete, e.g., *Saccharomyces cerevisiae*, and can have one or more genetic modifications that reduce EXG1 and EXG2 glycoside hydrolase activity relative to a control microorganism that lacks such genetic modifications, and can have one or more genetic modifications that reduce ergosterol biosynthesis relative to a control microorganism that lacks such genetic modifications.

Also featured herein is a recombinant microorganism, comprising a gene encoding a UGT74G1, a gene encoding a UGT85C2, a gene encoding a UGT76G1, and a gene encoding a UGT91D2. At least one of the genes is a recombinant gene. The recombinant microorganism can produce a steviol glycoside, e.g., rebaudioside A or rebaudioside B, when cultured under conditions in which each of the genes is expressed. The rebaudioside A or rebaudioside B can accumulate to at least 15 mg/L in the culture medium.

The recombinant microorganisms described above can further comprise a gene encoding a deoxyxylulose 5-phosphate synthase (DXS), and/or a gene encoding a D-1-deoxyxylulose 5-phosphate reductoisomerase (DXR), and/or a gene encoding a 4-diphosphocytidyl-2-C-methyl-D-erythritol synthase (CMS), and/or a gene encoding a 4-diphosphocytidyl-2-C-methyl-D-erythritol kinase (CMK), and/or a gene encoding a 4-diphosphocytidyl-2-C-methyl-D-erythritol 2,4-cyclodiphosphate synthase (MCS), and/or a gene encoding a 1-hydroxy-2-methyl-2 (E)-butenyl 4-diphosphate synthase (HDS), and/or a gene encoding a 1-hydroxy-2-methyl-2 (E)-butenyl 4-diphosphate reductase (HDR).

The recombinant microorganisms described above can further comprise a gene encoding a acetoacetyl-CoA thiolase, and/or a gene encoding a truncated HMG-COA reductase, and/or a gene encoding a mevalonate kinase, and/or a gene encoding a phosphomevalonate kinase, and/or a gene encoding a mevalonate pyrophosphate decarboxylase.

Unless otherwise defined, all technical and scientific terms used herein have the same meaning as commonly understood by one of ordinary skill in the art to which the invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting. Other features and advantages of the invention will be apparent from the following detailed description. Applicants reserve the right to alternatively claim any disclosed invention using the transitional phrase "comprising," "consisting essentially of," or "consisting of," according to standard practice in patent law.

DESCRIPTION OF DRAWINGS

FIG. 8 is an alignment of UGT91D1 and UGT91D2 amino acid sequences (SEQ ID NOs: 14, 16, 12, 5, and 10, respectively).

Like reference symbols in the various drawings indicate like elements.

DETAILED DESCRIPTION

Figure 1:
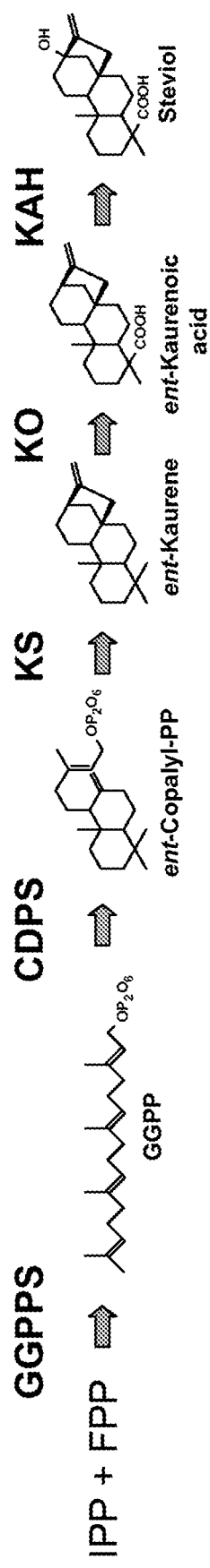
FIG. 1 is a scheme illustrating the biosynthesis of steviol from geranylgeranyl diphosphate.

Two glycosides, stevioside and rebaudioside A, are the primary compounds in commercially-produced *stevia* extracts. Stevioside is reported to have a more bitter and less sweet taste than rebaudioside A and, therefore, a higher proportion of rebaudioside A in an extract preparation is preferred. However, the composition of *stevia* extract can vary from lot to lot depending on the soil and climate in which the plants are grown. Depending upon the sourced plant, the climate conditions, and the extraction process, the amount of rebaudioside A in commercial preparations is reported to vary from 20 to 97% of the total steviol glycoside content, typically >50-80% and sometimes as high as >95-97% of the total steviol glycosides. Moreover, other steviol glycosides are present in varying amounts in *stevia* extracts, which further complicates the ability to produce a sweetener with a consistent taste profile by extraction and purification from *Stevia* plants. For example, Rebaudioside B is typically present at less than 1-2%, whereas Rebaudioside C can be present at levels as high as 7-15%. Rebaudioside D is typically present in levels of 2% or less, and Rebaudioside F is typically present in compositions at 3.5% or less of the total steviol glycosides. Even trace amounts of the minor steviol glycosides are reported to affect the flavor profile of a *Stevia* extract. Additionally, it is thought that some of the contaminants from the *Stevia* plant, even at very low concentrations, may also provide off-flavors to some of the commercially available plant extracts.

This document is based on the discovery that recombinant hosts such as plant cells, plants, or microorganisms can be developed that express polypeptides useful for the biosynthesis of steviol. Further, such hosts can express Uridine 5'-diphospho (UDP) glycosyl transferases suitable for producing steviol glycosides such as rubusoside and rebaudioside A. Recombinant microorganisms are particularly useful hosts. Expression of these biosynthetic polypeptides in various microbial chassis allows steviol and its glycosides to be produced in a consistent, reproducible manner from energy and carbon sources such as sugars, glycerol, $CO_2$, $H_2$, and sunlight. The proportion of each steviol glycoside produced by a recombinant host can be tailored by incorporating preselected biosynthetic enzymes into the hosts and expressing them at appropriate levels, to produce a sweetener composition with a consistent taste profile. Furthermore, the concentrations of steviol glycosides produced by recombinant hosts are expected to be higher than the levels of steviol glycosides produced in the *Stevia* plant, which improves the efficiency of the downstream purification. Such sweetener compositions contain little or no plant based contaminants, relative to the amount of contaminants present in *Stevia* extracts.

At least one of the genes is a recombinant gene, the particular recombinant gene(s) depending on the species or strain selected for use. Additional genes or biosynthetic modules can be included in order to increase steviol and glycoside yield, improve efficiency with which energy and carbon sources are converted to steviol and its glycosides, and/or to enhance productivity from the cell culture or plant. Such additional biosynthetic modules include genes involved in the synthesis of the terpenoid precursors, isopentenyl diphosphate and dimethylallyl diphosphate. Additional biosynthetic modules include terpene synthase and terpene cyclase genes, such as genes encoding geranylgeranyl diphosphate synthase and copalyl diphosphate synthase; these genes may be endogenous genes or recombinant genes.

I. STEVIOL AND STEVIOL GLYCOSIDE BIOSYNTHESIS POLYPEPTIDES

A. Steviol Biosynthesis Polypeptides

Figure 3:
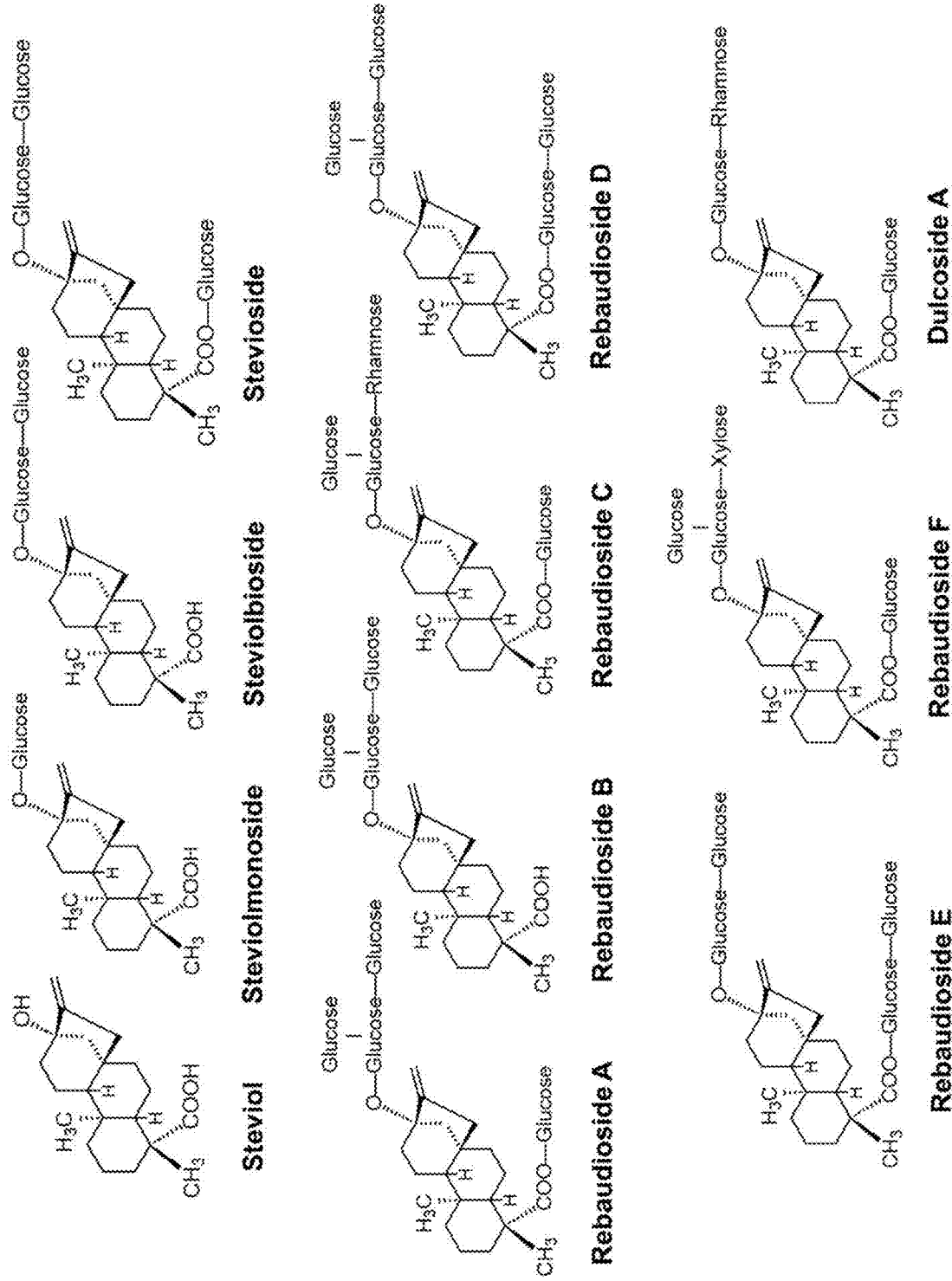
FIG. 3 shows chemical structures for various steviol glycosides.
Figure 4:
FIG. 4 is a schematic representation of rebA production in *Saccharomyces cerevisiae*.

Chemical structures for several of the compounds found in *Stevia* extracts are shown in FIG. 3, including the diterpene steviol and various steviol glycosides. CAS numbers are shown in Table A below. See also, *Steviol Glycosides Chemical and Technical Assessment 69th JECFA*, prepared by Harriet Wallin, Food Agric. Org. (2007).

TABLE A

| COMPOUND | CAS# |
| --- | --- |
| Steviol | 471-80-7 |
| Rebaudioside A | 58543-16-1 |
| Steviolbioside | 41093-60-1 |
| Stevioside | 57817-89-7 |
| Rebaudioside B | 58543-17-2 |
| Rebaudioside C | 63550-99-2 |
| Rebaudioside D | 63279-13-0 |
| Rebaudioside E | 63279-14-1 |
| Rebaudioside F | 438045-89-7 |
| Rubusoside | 63849-39-4 |
| Dulcoside A | 64432-06-0 |

It has been discovered that expression of certain genes in a host such as a microorganism confers the ability to synthesize steviol upon that host. As discussed in more detail below, one or more of such genes may be present naturally in a host. Typically, however, one or more of such genes are recombinant genes that have been transformed into a host that does not naturally possess them.

The biochemical pathway to produce steviol involves formation of geranylgeranyl diphosphate, cyclization to (−) copalyl diphosphate, followed by oxidation and hydroxylation to form steviol. See FIG. 1. Thus, conversion of geranylgeranyl diphosphate to steviol in a recombinant microorganism involves the expression of a gene encoding a kaurene synthase (KS), a gene encoding a kaurene oxidase (KO), and a gene encoding a steviol synthetase (KAH). Steviol synthetase also is known as kaurenoic acid 13-hydroxylase.

Suitable KS polypeptides are known. For example, suitable KS enzymes include those made by *Stevia rebaudiana, Zea mays* and *Populus trichocarpa*. See, SEQ ID NOs: 132-135. Nucleotide sequences encoding these polypeptides are described in more detail below. See, for example, Table 3 and SEQ ID NOs: 40-47.

Suitable KO polypeptides are known. For example, suitable KO enzymes include those made by *Stevia rebaudiana, Arabidopsis thaliana, Gibberella fujikuroi* and *Trametes versicolor*. See, SEQ ID NOs: 138-141. Nucleotide sequences encoding these polypeptides are described in more detail below. See, for example, Table 5 and SEQ ID NOs: 52-59.

Suitable KAH polypeptides are known. For example, suitable KAH enzymes include those made by *Stevia rebaudiana, Arabidopsis thaliana, Vitis vinifera* and *Medicago truncatula*. See, e.g., SEQ ID NOs: 142-146; U.S. Patent Publication No. 2008-0271205; U.S. Patent Publication No. 2008-0064063 and Genbank Accession No. gi 189098312. The steviol synthetase from *Arabidopsis thaliana* is classified as a CYP714A2. Nucleotide sequences encoding these polypeptides are described in more detail below. See, for example, Table 6 and SEQ ID NOs: 60-69.

In some embodiments, a recombinant microorganism contains a recombinant gene encoding a KO and/or a KAH polypeptide. Such microorganisms also typically contain a recombinant gene encoding a cytochrome P450 reductase (CPR) polypeptide, since certain combinations of KO and/or KAH polypeptides require expression of an exogenous CPR polypeptide. In particular, the activity of a KO and/or a KAH polypeptide of plant origin can be significantly increased by the inclusion of a recombinant gene encoding an exogenous CPR polypeptide. Suitable CPR polypeptides are known. For example, suitable CPR enzymes include those made by *Stevia rebaudiana, Arabidopsis thaliana*, and *Giberella fujikuroi*. See, e.g., SEQ ID NOs: 147-149. Nucleotide sequences encoding these polypeptides are described in more detail below. See, for example, Table 7 and SEQ ID NOs: 70-75.

Expression in a recombinant microorganism of these genes results in the conversion of geranylgeranyl diphosphate to steviol.

B. Steviol Glycoside Biosynthesis Polypeptides

In some embodiments, a recombinant host described herein can convert steviol to a steviol glycoside. Such a host (e.g., microorganism) contains genes encoding one or more UDP Glycosyl Transferases, also known as UGTs. UGTs transfer a monosaccharide unit from an activated nucleotide sugar to an acceptor moiety, in this case, an —OH or —COOH moiety on steviol or steviol derivative. UGTs have been classified into families and subfamilies based on sequence homology. Li et al. *J. Biol. Chem.* 276:4338-4343 (2001).

B. 1 Rubusoside Biosynthesis Polypeptides

Figure 2A:
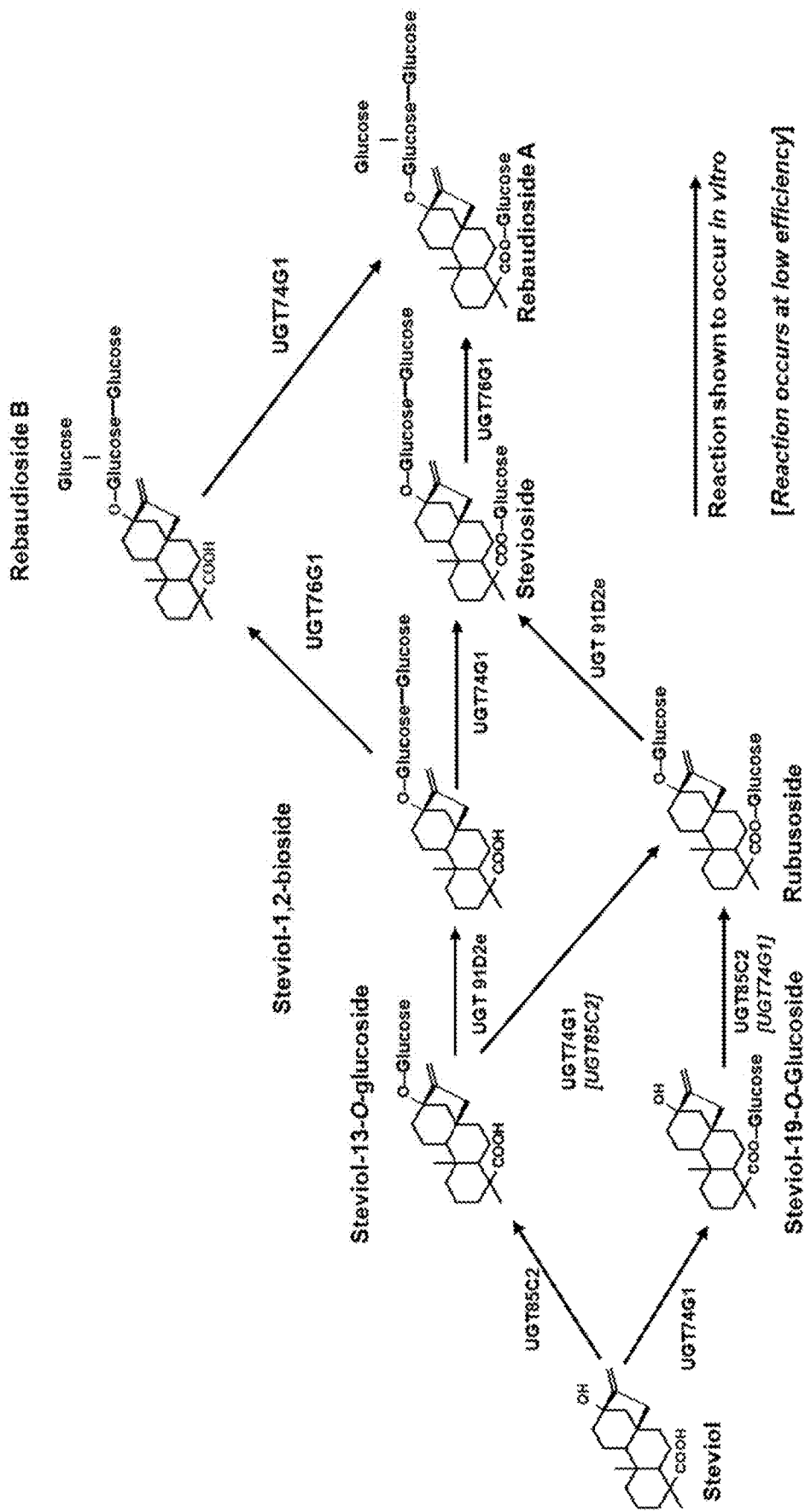
FIGS. 2A-D show representative pathways for the biosynthesis of steviol glycosides from steviol.
Figure 2B:
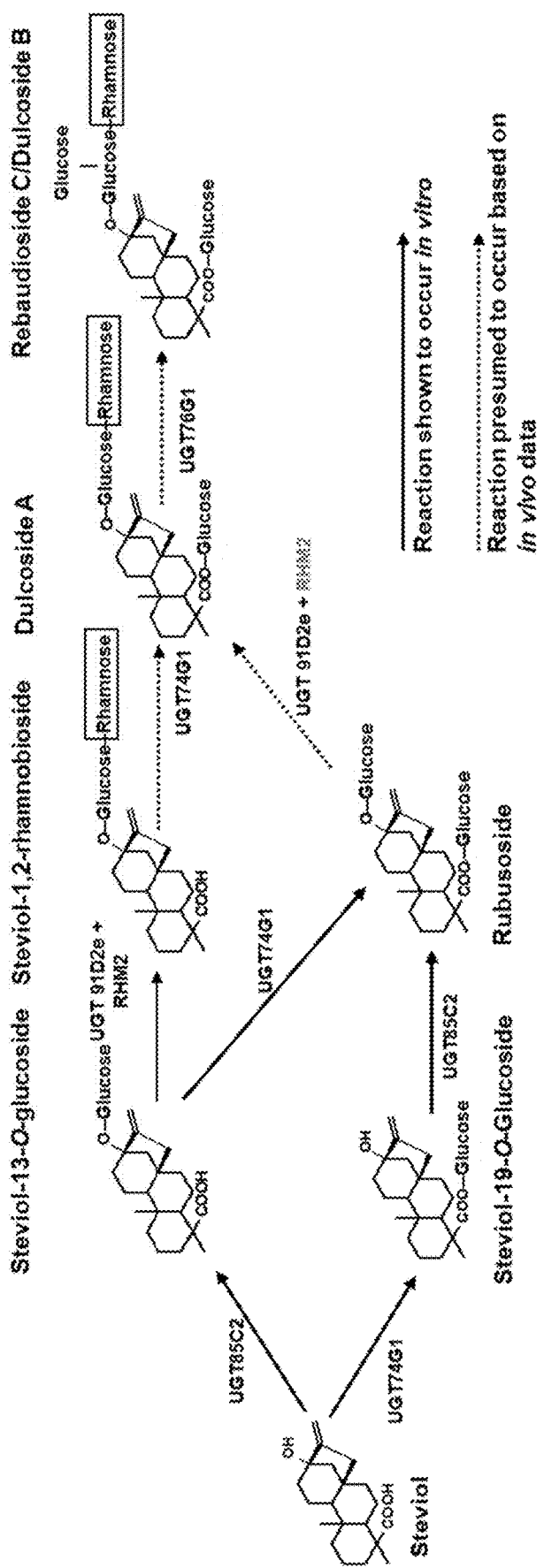
Figure 2C:
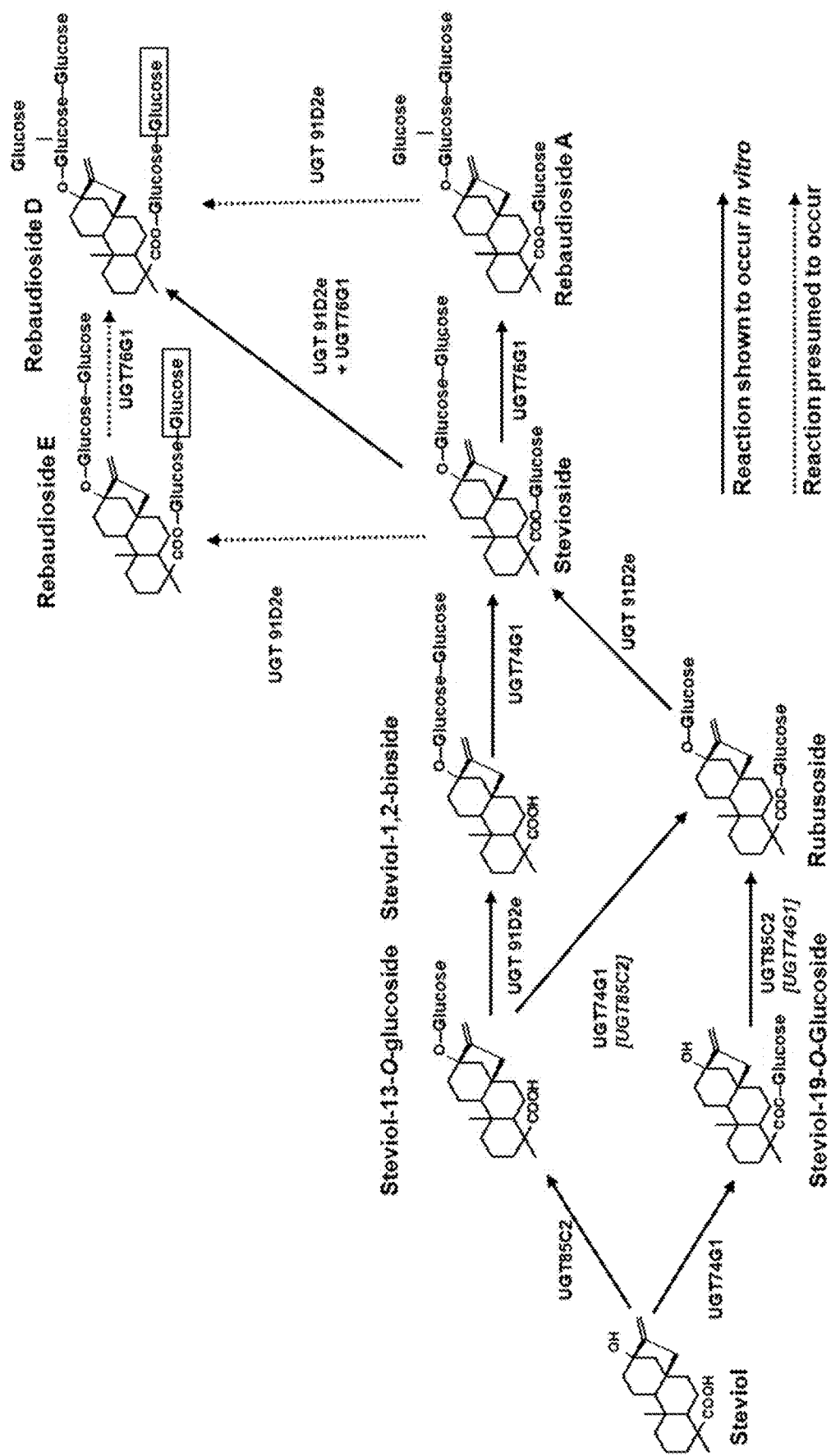
Figure 2D:
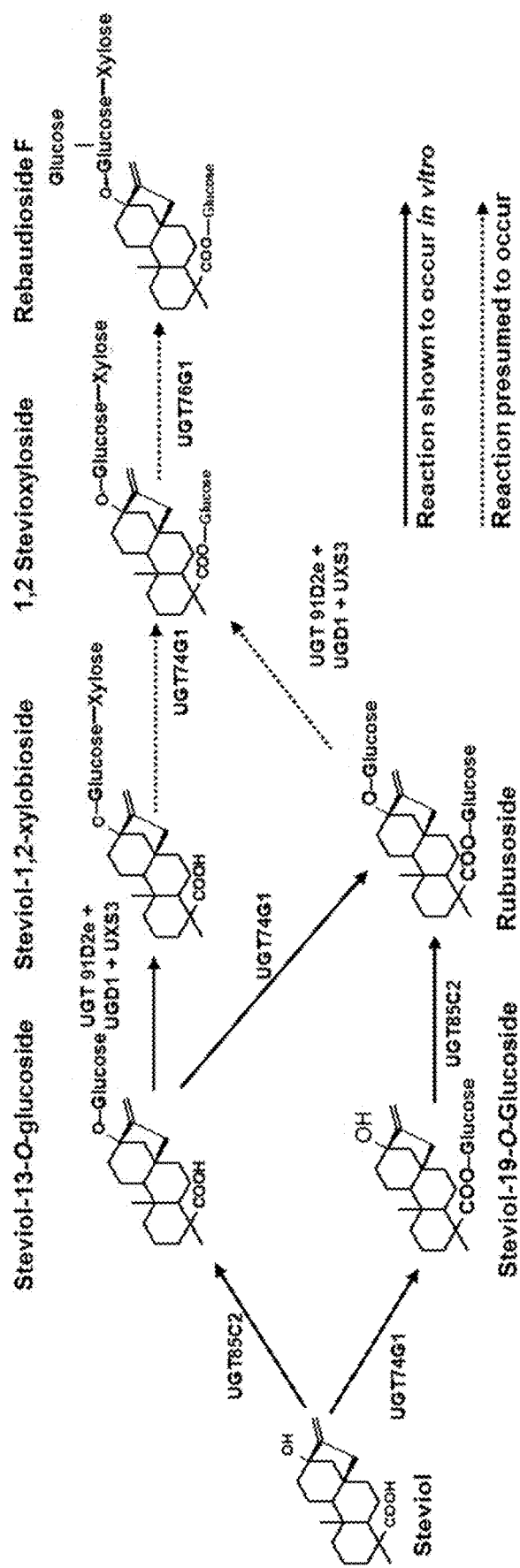

The biosynthesis of rubusoside involves glycosylation of the 13-OH and the 19-COOH of steviol. See FIG. 2A. It has been discovered that conversion of steviol to rubusoside in a recombinant host such as a microorganism can be accomplished by the expression of gene(s) encoding UGTs 85C2 and 74G1, which transfer a glucose unit to the 13-OH or the 19-COOH, respectively, of steviol.

Thus, a suitable UGT85C2 functions as a uridine 5'-diphospho glucosyl: steviol 13-OH transferase, and a uridine 5'-diphospho glucosyl: steviol-19-O-glucoside 13-OH transferase. Functional UGT85C2 polypeptides also may catalyze glucosyl transferase reactions that utilize steviol glycoside substrates other than steviol and steviol-19-O-glucoside.

A suitable UGT74G1 polypeptide functions as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose.

A recombinant microorganism expressing a functional UGT74G1 and a functional UGT85C2 can make rubusoside and both steviol monosides (i.e., Steviol 13-O-monoglucoside and Steviol 19-O-monoglucoside) when fed steviol in the medium. One or more of such genes may be present naturally in the host. Typically, however, such genes are recombinant genes that have been transformed into a host (e.g., microorganism) that does not naturally possess them.

As used herein, the term recombinant host is intended to refer to a host, the genome of which has been augmented by at least one incorporated DNA sequence. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. Generally, the introduced DNA is not originally resident in the host that is the recipient of the DNA, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a host by genetic engineering methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA.

Suitable UGT74G1 and UGT85C2 polypeptides include those made by *Stevia rebaudiana*. Genes encoding functional UGT74G1 and UGT85C2 polypeptides from *Stevia* are reported in Richman, et al. *Plant J.* 41:56-67 (2005). Amino acid sequences of *S. rebaudiana* UGT74G1 and UGT85C2 polypeptides are set forth in SEQ ID NOs: 1 and 3, respectively. Nucleotide sequences encoding UGT74G1 and UGT85C2 that have been optimized for expression in yeast are set forth in SEQ ID NOs: 2 and 4, respectively. See also the UGT85C2 and UGT74G1 variants described in Examples 17 and 18, respectively.

In some embodiments, the recombinant host is a microorganism. The recombinant microorganism can be grown on media containing steviol in order to produce rubusoside. In other embodiments, however, the recombinant microorganism expresses one or more recombinant genes involved in steviol biosynthesis, e.g., a CDPS gene, a KS gene, a KO gene and/or a KAH gene. Thus, a microorganism containing a CDPS gene, a KS gene, a KO gene and a KAH gene in addition to a UGT74G1 and a UGT85C2 gene is capable of producing both steviol monosides and rubusoside without the necessity for including steviol in the culture media.

In some embodiments, the recombinant microorganism further expresses a recombinant gene encoding a geranylgeranyl diphosphate synthase (GGPPS). Suitable GGPPS polypeptides are known. For example, suitable GGPPS enzymes include those made by *Stevia rebaudiana, Gibberella fujikuroi, Mus musculus, Thalassiosira pseudonana, Streptomyces clavuligerus, Sulfulobus acidocaldarius, Synechococcus* sp. and *Arabidopsis thaliana*. See, SEQ ID NOs: 121-128. Nucleotide sequences encoding these polypeptides are described in more detail below. See Table 1 and SEQ ID NOs: 18-33. In some embodiments, the recombinant microorganism further expresses recombinant genes involved in diterpene biosynthesis or production of terpenoid precursors, e.g., genes in the methylerythritol 4-phosphate (MEP) pathway or genes in the mevalonate (MEV) pathway discussed below.

B. 2 Rebaudioside A Biosynthesis Polypeptides

The biosynthesis of rebaudioside A involves glucosylation of the aglycone steviol. Specifically, rebaudioside A can be formed by glucosylation of the 13-OH of steviol which forms the 13-O-steviolmonoside, glucosylation of the C-2' of the 13-O-glucose of steviolmonoside which forms steviol-1,2-bioside, glucosylation of the C-19 carboxyl of steviol-1,2-bioside which forms stevioside, and glucosylation of the C-3' of the C-13-O-glucose of stevioside. The order in which each glucosylation reaction occurs can vary. See FIG. 2A.

It has been discovered that conversion of steviol to rebaudioside A in a recombinant host can be accomplished by the expression of gene(s) encoding the following functional UGTs: 74G1, 85C2, 76G1 and 91D2. Thus, a recombinant microorganism expressing these four UGTs can make rebaudioside A when fed steviol in the medium. Typically, one or more of these genes are recombinant genes that have been transformed into a microorganism that does not naturally possess them. It has also been discovered that UGTs designated herein as SM12UGT can be substituted for UGT91D2.

Suitable UGT74G1 and UGT85C2 polypeptides include those discussed above. A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. See, FIGS. 2A, 2B, 2C and 2D. Suitable UGT76G1 polypeptides include those made by *S. rebaudiana* and reported in Richman, et al. *Plant J.* 41:56-67 (2005). The amino acid sequence of a *S. rebaudiana* UGT76G1 polypeptide is set forth in SEQ ID NO:7. The nucleotide sequence encoding the UGT76G1 polypeptide of SEQ ID NO:7 has been optimized for expression in yeast and is set forth in SEQ ID NO:8. See also the UGT76G1 variants set forth in Example 18.

A suitable UGT91D2 polypeptide functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT91D2 polypeptide also functions as a uridine 5'-diphospho glucosyl: rubusoside transferase transferring a glucose moiety to the C-2' of the 13-O-glucose of the acceptor molecule, rubusoside.

Functional UGT91D2 polypeptides may also catalyze reactions that utilize steviol glycoside substrates other than steviol-13-O-glucoside and rubusoside, e.g., functional UGT91D2 polypeptides may utilize stevioside as a substrate, transferring a glucose moiety to the C-2' of the 19-O-glucose residue to produce Rebaudioside E. Functional UGT91D2 polypeptides may also utilize Rebaudioside A as a substrate, transferring a glucose moiety to the C-2' of the 19-O-glucose residue to produce Rebaudioside D. However, a functional UGT91D2 polypeptide typically does not transfer a glucose moiety to steviol compounds having a 1,3-bound glucose at the C-13 position, i.e., transfer of a glucose moiety to steviol 1,3-bioside and 1,3-stevioside does not occur.

Functional UGT91D2 polypeptides can transfer sugar moieties from donors other than uridine diphosphate glucose. For example, a functional UGT91D2 polypeptide can act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a functional UGT91D2 polypeptide can act as a uridine 5'-diphospho L-rhamnosyl: steviol-13-O-glucoside transferase, transferring a rhamnose moiety to the C-2' of the 13-O-glucose of the acceptor molecule, steviol-13-O-glucoside Suitable functional UGT91D2 polypeptides include those disclosed herein, e.g., the polypeptides designated UGT91D2e and UGT91D2m. The amino acid sequence of an exemplary UGT91D2e polypeptide from *Stevia rebaudiana* is set forth in SEQ ID NO: 5. SEQ ID NO:6 is a nucleotide sequence encoding the polypeptide of SEQ ID NO:5 that has been codon optimized for expression in yeast. The *S. rebaudiana* nucleotide sequence encoding the polypeptide of SEQ ID NO:5 is set forth in SEQ ID NO:9. The amino acid sequences of exemplary UGT91D2m polypeptides from *S. rebaudiana* are set forth in SEQ ID NOs: 10 and 12, and are encoded by the nucleic acid sequences set forth in SEQ ID NOs: 11 and 13, respectively. See also the UGT91D2 variants of Example 16, e.g., a variant containing a substitution at amino acid residues 206, 207, and 343.

As indicated above, UGTs designated herein as SM12UGT can be substituted for UGT91D2. Suitable functional SM12UGT polypeptides include those made by *Ipomoea purpurea* (Japanese morning glory) and described in Morita et al. *Plant J.* 42, 353-363 (2005). The amino acid sequence encoding the *I. purpurea* IP3GGT polypeptide is set forth in SEQ ID NO:76. SEQ ID NO:77 is a nucleotide sequence encoding the polypeptide of SEQ ID NO:76 that has been codon optimized for expression in yeast. Another suitable SM12UGT polypeptide is a Bp94B1 polypeptide having an R25S mutation. See Osmani et al. *Plant Phys.* 148:1295-1308 (2008) and Sawada et al. *J. Biol. Chem.* 280:899-906 (2005). The amino acid sequence encoding the *Bellis perennis* (red daisy) UGT94B1 polypeptide is set forth in SEQ ID NO:78. SEQ ID NO:79 is the nucleotide sequence encoding the polypeptide of SEQ ID NO:78 that has been codon optimized for expression in yeast.

In some embodiments, the recombinant microorganism is grown on media containing steviol-13-O-glucoside or steviol-19-O-glucoside in order to produce rebaudioside A. In such embodiments, the microorganism contains and expresses genes encoding a functional UGT91D2, a functional UGT74G1 and a functional UGT76G1, and is capable of producing rebaudioside A when it is fed steviol, one or both of the steviolmonosides, or rubusoside in the culture media.

In other embodiments, the recombinant microorganism is grown on media containing rubusoside in order to produce rebaudioside A. In such embodiments, the microorganism contains and expresses genes encoding a functional UGT91D2 and a functional UGT76G1, and is capable of producing rebaudioside A when it is fed rubusoside in the culture media.

In other embodiments the recombinant microorganism expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a UGT74G1, a UGT85C2, a UGT91D2 gene and a UGT76G1 gene, is capable of producing rebaudioside A without the necessity for including steviol in the culture media.

In some embodiments, the recombinant microorganism further contains and expresses a recombinant GGPPS gene in order to provide increased levels of the diterpene precursor geranylgeranyl diphosphate, for increased flux through the rebaudioside A biosynthetic pathway. In some embodiments, the recombinant microorganism further contains and expresses recombinant genes involved in diterpene biosynthesis or production of terpenoid precursors, e.g., genes in the MEP or MEV pathway discussed below.

B. 3 Dulcoside a and Rebaudioside C Biosynthesis Polypeptides

The biosynthesis of rebaudioside C and/or dulcoside A involves glucosylation and rhamnosylation of the aglycone steviol. Specifically, dulcoside A can be formed by glucosylation of the 13-OH of steviol which forms steviol-13-O-glucoside, rhamnosylation of the C-2' of the 13-O-glucose of steviol-13-O-glucoside which forms the 1,2 rhamnobioside, and glucosylation of the C-19 carboxyl of the 1,2 rhamnobioside. Rebaudioside C can be formed by glucosylation of the C-3' of the C-13-O-glucose of dulcoside A. The order in which each glycosylation reaction occurs can vary. See FIG. 2B.

It has been discovered that conversion of steviol to dulcoside A in a recombinant host can be accomplished by the expression of gene(s) encoding the following functional UGTs: 85C2, 91D2, and 74G1. Thus, a recombinant microorganism expressing these three UGTs and a rhamnose synthetase can make dulcoside A when fed steviol in the medium. Alternatively, a recombinant microorganism expressing two UGTs, 91D2 and 74G1, and rhamnose synthetase can make dulcoside A when fed the monoside, steviol-13-O-glucoside or steviol-19-O-glucoside, in the medium. Similarly, conversion of steviol to rebaudioside C in a recombinant microorganism can be accomplished by the expression of gene(s) encoding UGTs 85C2, 91D2, 74G1, and 76G1 and rhamnose synthetase when fed steviol, by the expression of genes encoding UGTs 91D2, 74G1 and 76G1, and rhamnose synthetase when fed steviol-13-O-glucoside, by the expression of genes encoding UGTs 85C2, 91D2 and 76G1, and rhamnose synthetase when fed steviol-19-O-glucoside, or by the expression of genes encoding UGTs 91D2 and 76G1 and rhamnose synthetase when fed rubusoside. Typically, one or more of these genes are recombinant genes that have been transformed into a microorganism that does not naturally possess them.

Suitable UGT91D2, UGT74G1, UGT76G1 and UGT85C2 polypeptides include the functional UGT polypeptides discussed herein. Rhamnose synthetase provides increased amounts of the UDP-rhamnose donor for rhamnosylation of the steviol compound acceptor. Suitable rhamnose synthetases include those made by *Arabidopsis thaliana*, such as the product of the *A. thaliana* RHM2 gene.

In some embodiments, a UGT79B3 polypeptide is substituted for a UGT91D2 polypeptide. Suitable UGT79B3 polypeptides include those made by *Arabidopsis thaliana*, which are capable of rhamnosylation of steviol 13-O-monoside in vitro. *A. thaliana* UGT79B3 can rhamnosylate glucosylated compounds to form 1,2-rhamnosides. The amino acid sequence of an *Arabidopsis thaliana* UGT79B3 is set forth in SEQ ID NO: 150. The nucleotide sequence encoding the amino acid sequence of SEQ ID NO:150 is set forth in SEQ ID NO:151.

In some embodiments rebaudioside C can be produced using in vitro methods while supplying the appropriate UDP-sugar or a cell-free system for regeneration of UDP-sugars. See, for example, "An integrated cell-free metabolic platform for protein production and synthetic biology" by Jewett M C, Calhoun K A, Voloshin A, Wuu J J and Swartz J R in Molecular Systems Biology, 4, article 220 (2008). Reactions may be carried out together, or stepwise. For instance, rebaudioside C may be produced from rubusoside with the addition of stoichiometric amounts of UDP-rhamnose and UGT91d2e, followed by addition of UGT76G1 and an excess or stoichiometric supply of UDP-glucose. In some embodiments phosphatases are used to remove secondary products and improve the reaction yields.

In other embodiments, the recombinant host expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a UGT85C2, a UGT74G1, a UGT91D2 gene and a UGT76G1 gene, is capable of producing rebaudioside C without the necessity for including steviol in the culture media. In addition, the recombinant host typically expresses an endogenous or a recombinant gene encoding a rhamnose synthetase. Such a gene is useful in order to provide increased amounts of the UDP-rhamnose donor for rhamnosylation of the steviol compound acceptor. Suitable rhamnose synthetases include those made by *Arabidopsis thaliana*, such as the product of the *A. thaliana* RHM2 gene.

One with skill in the art will recognize that by modulating relative expression levels of different UGT genes as well as modulating the availability of UDP-rhamnose, a recombinant host can be tailored to specifically produce steviol and steviol glycoside products in a desired proportion. Transcriptional regulation of steviol biosynthesis genes, and steviol glycoside biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycoside.

In some embodiments, the recombinant host further contains and expresses a recombinant GGPPS gene in order to provide increased levels of the diterpene precursor geranylgeranyl diphosphate, for increased flux through the rebaudioside A biosynthetic pathway. In some embodiments, the recombinant host further contains a genetic construct to silence or reduce the expression of non-steviol pathways consuming geranylgeranyl diphosphate, ent-Kaurenoic acid or farnesyl pyrophosphate, thereby providing increased flux through the steviol and steviol glycosides biosynthetic pathways. For example, flux to sterol production pathways such as ergosterol may be reduced by downregulation of the ERG9 gene. In cells that produce gibberellins, gibberellin synthesis may be downregulated to increase flux of ent-kaurenoic acid to steviol. In carotenoid-producing organisms, flux to steviol may be increased by downregulation of one or more carotenoid biosynthetic genes.

In some embodiments, the recombinant host further contains and expresses recombinant genes involved in diterpene biosynthesis or production of terpenoid precursors, e.g., genes in the MEP or MEV pathway discussed below.

In some embodiments, a recombinant host such as a microorganism produces steviol glycoside compositions that have greater than at least 15% rebaudioside C of the total steviol glycosides, e.g., at least 20% rebaudioside C, 30-40% rebaudioside C, 40-50% rebaudioside C, 50-60% rebaudioside C, 60-70% rebaudioside C, 70-80% rebaudioside C, 80-90% rebaudioside C. In some embodiments, a recombinant host such as a microorganism produces steviol glycoside compositions that have at least 90% rebaudioside C, e.g., 90-99% rebaudioside C. Other steviol glycosides present may include those depicted in FIGS. 2A and B such as steviol monosides, steviol glucobiosides, steviol rhamnobiosides, rebaudioside A, and Dulcoside A. In some embodiments, the rebaudioside C-enriched composition produced by the host can be further purified and the rebaudioside C or Dulcoside A so purified may then be mixed with other steviol glycosides, flavors, or sweeteners to obtain a desired flavor system or sweetening composition. For instance, a rebaudioside C-enriched composition produced by a recombinant microorganism can be combined with a rebaudioside A, F, or D-enriched composition produced by a different recombinant microorganism, with rebaudioside A, F, or D purified from a *Stevia* extract, or with rebaudioside A, F, or D produced in vitro.

B. 4 Rebaudioside E and Rebaudioside D Biosynthesis Polypeptides

The biosynthesis of rebaudioside E and/or rebaudioside D involves glucosylation of the aglycone steviol. Specifically, rebaudioside E can be formed by glucosylation of the 13-OH of steviol which forms steviol-13-O-glucoside, glucosylation of the C-2' of the 13-O-glucose of steviol-13-O-glucoside which forms the steviol-1,2-bioside, glucosylation of the C-19 carboxyl of the 1,2-bioside to form 1,2-stevioside, and glucosylation of the C-2' of the 19-O-glucose of the 1,2-stevioside to form rebaudioside E. Rebaudioside D can be formed by glucosylation of the C-3' of the C-13-O-glucose of rebaudioside E. The order in which each glycosylation reaction occurs can vary. For example, the glucosylation of the C-2' of the 19-O-glucose may be the last step in the pathway, wherein Rebaudioside A is an intermediate in the pathway. See FIG. 2C.

It has been discovered that conversion of steviol to rebaudioside D in a recombinant host can be accomplished by the expression of gene(s) encoding the following functional UGTs: 85C2, 91D2, 74G1 and 76G1. Thus, a recombinant microorganism expressing these four UGTs can make rebaudioside D when fed steviol in the medium. Alternatively, a recombinant microorganism expressing two functional UGTs, 91D2 and 76G1, can make rebaudioside D when fed rubusoside or 1,2-stevioside in the medium. As another alternative, a recombinant microorganism expressing three functional UGTs, 74G1, 91D2 and 76G1, can make rebaudioside D when fed the monoside, steviol-13-O-glucoside, in the medium. Similarly, conversion of steviol-19-O-glucoside to rebaudioside D in a recombinant microorganism can be accomplished by the expression of genes encoding UGTs 85C2, 91D2 and 76G1 when fed steviol-19-O-glucoside. Typically, one or more of these genes are recombinant genes that have been transformed into a host that does not naturally possess them.

Suitable UGT91D2, UGT74G1, UGT76G1 and UGT85C2 polypeptides include the functional UGT polypeptides discussed herein. In some embodiments, a UGT79B3 polypeptide is substituted for a UGT91, as discussed above.

In some embodiments, rebaudioside D or rebaudioside E can be produced using in vitro methods while supplying the appropriate UDP-sugar or a cell-free system for regeneration of UDP-sugars. See, for example, Jewett M C, et al. *Molecular Systems Biology*, Vol. 4, article 220 (2008). Conversions requiring multiple reactions may be carried out together, or stepwise. Rebaudioside D may be produced from Rebaudioside A that is commercially available enriched extract or produced via biosynthesis, with the addition of stoichiometric or excess amounts of UDP-glucose and UGT91D2e. In some embodiments phosphatases are used to remove secondary products and improve the reaction yields.

One with skill in the art will recognize that by modulating relative expression levels of different UGT genes, a recombinant host can be tailored to specifically produce steviol and steviol glycoside products in a desired proportion. Transcriptional regulation of steviol biosynthesis genes and steviol glycoside biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycoside. One with skill in the art will recognize that a higher proportion of rebaudioside D or E or more efficient conversion to rebaudioside D or E can be obtained with a diglycosylation enzyme that has a higher activity for the 19-O-glucoside reaction as compared to the 13-O-glucoside reaction (substrates rebaudioside A and stevioside).

In other embodiments, the recombinant host expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a UGT85C2, a UGT74G1, a UGT91D2 gene and a UGT76G1 gene, is capable of producing rebaudiosides E and D without the necessity for including steviol in the culture media.

In some embodiments, the recombinant host further contains and expresses a recombinant GGPPS gene in order to provide increased levels of the diterpene precursor geranylgeranyl diphosphate, for increased flux through the steviol biosynthetic pathway. In some embodiments, the recombinant host further contains a genetic construct to silence the expression of non-steviol pathways consuming geranylgeranyl diphosphate, ent-Kaurenoic acid or farnesyl pyrophosphate, thereby providing increased flux through the steviol and steviol glycosides biosynthetic pathways. For example, flux to sterol production pathways such as ergosterol may be reduced by downregulation of the ERG9 gene. In cells that produce gibberellins, gibberellin synthesis may be downregulated to increase flux of ent-kaurenoic acid to steviol. In carotenoid-producing organisms, flux to steviol may be increased by downregulation of one or more carotenoid biosynthetic genes. In some embodiments, the recombinant host further contains and expresses recombinant genes involved in diterpene biosynthesis or production of terpenoid precursors, e.g., genes in the MEP or MEV pathways discussed below.

In some embodiments, a recombinant host such as a microorganism produces rebaudioside D-enriched steviol glycoside compositions that have greater than at least 3% rebaudioside D by weight total steviol glycosides, e.g., at least 4% rebaudioside D at least 5% rebaudioside D, 10-20% rebaudioside D, 20-30% rebaudioside D, 30-40% rebaudioside D, 40-50% rebaudioside D, 50-60% rebaudioside D, 60-70% rebaudioside D, 70-80% rebaudioside D. In some embodiments, a recombinant host such as a microorganism produces steviol glycoside compositions that have at least 90% rebaudioside D, e.g., 90-99% rebaudioside D. Other steviol glycosides present may include those depicted in FIG. 2C such as steviol monosides, steviol glucobiosides, rebaudioside A, rebaudioside E, and stevioside. In some embodiments, the rebaudioside D-enriched composition produced by the host (e.g., microorganism) can be further purified and the rebaudioside D or rebaudioside E so purified can then be mixed with other steviol glycosides, flavors, or sweeteners to obtain a desired flavor system or sweetening composition. For instance, a rebaudioside D-enriched composition produced by a recombinant host can be combined with a rebaudioside A, C, or F-enriched composition produced by a different recombinant host, with rebaudioside A, F, or C purified from a *Stevia* extract, or with rebaudioside A, F, or C produced in vitro.

B. 5 Rebaudioside F Biosynthesis Polypeptides

The biosynthesis of rebaudioside F involves glucosylation and xylosylation of the aglycone steviol. Specifically, rebaudioside F can be formed by glucosylation of the 13-OH of steviol which forms steviol-13-O-glucoside, xylosylation of the C-2' of the 13-O-glucose of steviol-13-O-glucoside which forms steviol-1,2-xylobioside, glucosylation of the C-19 carboxyl of the 1,2-xylobioside to form 1,2-stevioxyloside, and glucosylation of the C-3' of the C-13-O-glucose of 1,2-stevioxyloside to form rebaudioside F. The order in which each glycosylation reaction occurs can vary. See FIG. 2D.

It has been discovered that conversion of steviol to rebaudioside F in a recombinant host can be accomplished by the expression of genes encoding the following functional UGTs: 85C2, 91D2, 74G1 and 76G1, along with endogenous or recombinantly expressed UDP-glucose dehydrogenase and UDP-glucuronic acid decarboxylase. Thus, a recombinant microorganism expressing these four UGTs along with endogenous or recombinant UDP-glucose dehydrogenase and UDP-glucuronic acid decarboxylase can make rebaudioside F when fed steviol in the medium. Alternatively, a recombinant microorganism expressing two functional UGTs, 91D2 and 76G1, can make rebaudioside F when fed rubusoside in the medium. As another alternative, a recombinant microorganism expressing a functional UGT 76G1 can make rebaudioside F when fed 1,2 steviorhamnoside. As another alternative, a recombinant microorganism expressing three functional UGTs, 74G1, 91D2 and 76G1, can make rebaudioside F when fed the monoside, steviol-13-O-glucoside, in the medium. Similarly, conversion of steviol-19-O-glucoside to rebaudioside F in a recombinant microorganism can be accomplished by the expression of genes encoding UGTs 85C2, 91D2 and 76G1 when fed steviol-19-O-glucoside. Typically, one or more of these genes are recombinant genes that have been transformed into a host that does not naturally possess them.

Suitable UGT91D2, UGT74G1, UGT76G1 and UGT85C2 polypeptides include the functional UGT polypeptides discussed herein. In some embodiments, a UGT79B3 polypeptide is substituted for a UGT91, as discussed above. UDP-glucose dehydrogenase and UDP-glucuronic acid decarboxylase provide increased amounts of the UDP-xylose donor for xylosylation of the steviol compound acceptor. Suitable UDP-glucose dehydrogenases and UDP-glucuronic acid decarboxylases include those made by *Arabidopsis thaliana* or *Cryptococcus neoformans*. For example, suitable UDP-glucose dehydrogenase and UDP-glucuronic acid decarboxylases polypeptides can be encoded by the *A. thaliana* UGD1 gene and UXS3 gene, respectively. See, Oka and Jigami, FEBS J. 273:2645-2657 (2006).

In some embodiments rebaudioside F can be produced using in vitro methods while supplying the appropriate UDP-sugar or a cell-free system for regeneration of UDP-sugars. See, for example, Jewett M C, et al. *Molecular Systems Biology*, Vol. 4, article 220 (2008). Reactions may be carried out together, or stepwise. For instance, rebaudioside F may be produced from rubusoside with the addition of stoichiometric amounts of UDP-xylose and UGT91D2e, followed by addition of UGT76G1 and an excess or stoichiometric supply of UDP-glucose. In some embodiments phosphatases are used to remove secondary products and improve the reaction yields.

In other embodiments, the recombinant host expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a UGT85C2, a UGT74G1, a UGT91D2 gene and a UGT76G1 gene, is capable of producing rebaudioside F without the necessity for including steviol in the culture media. In addition, the recombinant host typically expresses an endogenous or a recombinant gene encoding a UDP-glucose dehydrogenase and a UDP-glucuronic acid decarboxylase. Such genes are useful in order to provide increased amounts of the UDP-xylose donor for xylosylation of the steviol compound acceptor. Suitable UDP-glucose dehydrogenases and UDP-glucuronic acid decarboxylases include those made by *Arabidopsis thaliana* or *Cryptococcus neoformans*. For example, suitable UDP-glucose dehydrogenase and UDP-glucuronic acid decarboxylases polypeptides can be encoded by the *A. thaliana* UGD1 gene and UXS3 gene, respectively. See, Oka and Jigami, FEBS J. 273:2645-2657 (2006).

One with skill in the art will recognize that by modulating relative expression levels of different UGT genes as well as modulating the availability of UDP-xylose, a recombinant microorganism can be tailored to specifically produce steviol and steviol glycoside products in a desired proportion. Transcriptional regulation of steviol biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycosides.

In some embodiments, the recombinant host further contains and expresses a recombinant GGPPS gene in order to provide increased levels of the diterpene precursor geranylgeranyl diphosphate, for increased flux through the steviol biosynthetic pathway. In some embodiments, the recombinant host further contains a genetic construct to silence the expression of non-steviol pathways consuming geranylgeranyl diphosphate, ent-Kaurenoic acid or farnesyl pyrophosphate, thereby providing increased flux through the steviol and steviol glycosides biosynthetic pathways. For example, flux to sterol production pathways such as ergosterol may be reduced by downregulation of the ERG9 gene. In cells that produce gibberellins, gibberellin synthesis may be downregulated to increase flux of ent-kaurenoic acid to steviol. In carotenoid-producing organisms, flux to steviol may be increased by downregulation of one or more carotenoid biosynthetic genes. In some embodiments, the recombinant host further contains and expresses recombinant genes involved in diterpene biosynthesis, e.g., genes in the MEP pathway discussed below.

In some embodiments, a recombinant host such as a microorganism produces rebaudioside F-enriched steviol glycoside compositions that have greater than at least 4% rebaudioside F by weight total steviol glycosides, e.g., at least 5% rebaudioside F, at least 6% of rebaudioside F, 10-20% rebaudioside F, 20-30% rebaudioside F, 30-40% rebaudioside F, 40-50% rebaudioside F, 50-60% rebaudioside F, 60-70% rebaudioside F, 70-80% rebaudioside F. In some embodiments, a recombinant host such as a microorganism produces steviol glycoside compositions that have at least 90% rebaudioside F, e.g., 90-99% rebaudioside F. Other steviol glycosides present may include those depicted in FIGS. 2A and D such as steviol monosides, steviol glucobiosides, steviol xylobiosides, rebaudioside A, stevioxyloside, rubusoside and stevioside. In some embodiments, the rebaudioside F-enriched composition produced by the host can be mixed with other steviol glycosides, flavors, or sweeteners to obtain a desired flavor system or sweetening composition. For instance, a rebaudioside F-enriched composition produced by a recombinant microorganism can be combined with a rebaudioside A, C, or D-enriched composition produced by a different recombinant microorganism, with rebaudioside A, C, or D purified from a *Stevia* extract, or with rebaudioside A, C, or D produced in vitro.

C. Other Polypeptides

Genes for additional polypeptides whose expression facilitates more efficient or larger scale production of steviol or a steviol glycoside can also be introduced into a recombinant host. For example, a recombinant microorganism, plant, or plant cell can also contain one or more genes encoding a geranylgeranyl diphosphate synthase (GGPPS, also referred to as GGDPS). As another example, the recombinant host can contain one or more genes encoding a rhamnose synthetase, or one or more genes encoding a UDP-glucose dehydrogenase and/or a UDP-glucuronic acid decarboxylase. As another example, a recombinant host can also contain one or more genes encoding a cytochrome P450 reductase (CPR). Expression of a recombinant CPR facilitates the cycling of NADP+ to regenerate NADPH, which is utilized as a cofactor for terpenoid biosynthesis. Other methods can be used to regenerate NADHP levels as well. In circumstances where NADPH becomes limiting; strains can be further modified to include exogenous transhydrogenase genes. See, e.g., Sauer et al., *J. Biol. Chem.* 279: 6613-6619 (2004). Other methods are known to those with skill in the art to reduce or otherwise modify the ratio of NADH/NADPH such that the desired cofactor level is increased.

As another example, the recombinant host can contain one or more genes encoding one or more enzymes in the MEP pathway or the mevalonate pathway. Such genes are useful because they can increase the flux of carbon into the diterpene biosynthesis pathway, producing geranylgeranyl diphosphate from isopentenyl diphosphate and dimethylallyl diphosphate generated by the pathway. The geranylgeranyl diphosphate so produced can be directed towards steviol and steviol glycoside biosynthesis due to expression of steviol biosynthesis polypeptides and steviol glycoside biosynthesis polypeptides.

C. 1 MEP Biosynthesis Polypeptides

In some embodiments, a recombinant host contains one or more genes encoding enzymes involved in the methylerythritol 4-phosphate (MEP) pathway for isoprenoid biosynthesis. Enzymes in the MEP pathway include deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2 (E)-butenyl 4-diphosphate synthase (HDS) and 1-hydroxy-2-methyl-2 (E)-butenyl 4-diphosphate reductase (HDR). One or more DXS genes, DXR genes, CMS genes, CMK genes, MCS genes, HDS genes and/or HDR genes can be incorporated into a recombinant microorganism. See, Rodríguez-Concepción and Boronat, *Plant Phys.* 130:1079-1089 (2002).

Suitable genes encoding DXS, DXR, CMS, CMK, MCS, HDS and/or HDR polypeptides include those made by *E. coli, Arabidopsis thaliana* and *Synechococcus* leopoliensis. Nucleotide sequences encoding DXR polypeptides are described, for example, in U.S. Pat. No. 7,335,815.

C. 2 Mevalonate Biosynthesis Polypeptides

In some embodiments, a recombinant host contains one or more genes encoding enzymes involved in the mevalonate pathway for isoprenoid biosynthesis. Genes suitable for transformation into a host encode enzymes in the mevalonate pathway such as a truncated 3-hydroxy-3-methylglutaryl (HMG)-CoA reductase (tHMG), and/or a gene encoding a mevalonate kinase (MK), and/or a gene encoding a phosphomevalonate kinase (PMK), and/or a gene encoding a mevalonate pyrophosphate decarboxylase (MPPD). Thus, one or more HMG-COA reductase genes, MK genes, PMK genes, and/or MPPD genes can be incorporated into a recombinant host such as a microorganism.

Suitable genes encoding mevalonate pathway polypeptides are known. For example, suitable polypeptides include those made by *E. coli, Paracoccus denitrificans, Saccharomyces cerevisiae, Arabidopsis thaliana, Kitasatospora griseola, Homo sapiens, Drosophila melanogaster, Gallus gallus, Streptomyces* sp. KO-3988, *Nicotiana attenuata, Kitasatospora griseola, Hevea brasiliensis, Enterococcus faecium* and Haematococcus pluvialis. See, e.g., U.S. Pat. Nos. 7,183,089, 5,460,949, and 5,306,862.

D. Functional Homologs

Functional homologs of the polypeptides described above are also suitable for use in producing steviol or steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional UGT polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide: polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol or steviol glycoside biosynthesis polypeptides. Sequence analysis can involve BLAST, Reciprocal BLAST, or PSI-BLAST analysis of nonredundant databases using a GGPPS, a CDPS, a KS, a KO or a KAH amino acid sequence as the reference sequence. Amino acid sequence is, in some instances, deduced from the nucleotide sequence. Those polypeptides in the database that have greater than 40% sequence identity are candidates for further evaluation for suitability as a steviol or steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol biosynthesis polypeptides, e.g., conserved functional domains.

Conserved regions can be identified by locating a region within the primary amino acid sequence of a steviol or a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. The information included at the Pfam database is described in Sonnhammer et al., *Nucl. Acids Res.,* 26:320-322 (1998); Sonnhammer et al., *Proteins,* 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol glycosides in a recombinant host include functional homologs of UGT91D2e, UGT91D2m, UGT85C, and UGT76G. Such homologs have greater than 90% (e.g., at least 95% or 99%) sequence identity to the amino acid sequence of UGT91D2e (SEQ ID NO:5), UGT91D2m (SEQ ID NO:10), UGT85C (SEQ ID NO:3), or UGT76G (SEQ ID NO:7). Variants of UGT91D2, UGT85C, and UGT76G polypeptides typically have 10 or fewer amino acid substitutions within the primary amino acid sequence, e.g., 7 or fewer amino acid substitutions, 5 or conservative amino acid substitutions, or between 1 and 5 substitutions. However, in some embodiments, variants of UGT91D2, UGT85C, and UGT76G polypeptides can have 10 or more amino acid substitutions (e.g., 10, 15, 20, 25, 30, 35, 10-20, 10-35, 20-30, or 25-35 amino acid substitutions). The substitutions may be conservative, or in some embodiments, non-conservative. Non-limiting examples of non-conservative changes in UGT91D2e polypeptides include glycine to arginine and tryptophan to arginine. Non-limiting examples of non-conservative substitutions in UGT76G polypeptides include valine to glutamic acid, glycine to glutamic acid, glutamine to alanine, and serine to proline. Non-limiting examples of changes to UGT85C polypeptides include histidine to aspartic acid, proline to serine, lysine to threonine, and threonine to arginine.

In some embodiments, a useful UGT91D2 homolog can have amino acid substitutions (e.g., conservative amino acid substitutions) in regions of the polypeptide that are outside of predicted loops, e.g., residues 20-26, 39-43, 88-95, 121-124, 142-158, 185-198, and 203-214 are predicted loops in the N-terminal domain and residues 381-386 are predicted loops in the C-terminal domain of SEQ ID NO:5. For example, a useful UGT91D2 homolog can include at least one amino acid substitution at residues 1-19, 27-38, 44-87, 96-120, 125-141, 159-184, 199-202, 215-380, or 387-473 of SEQ ID NO:5. In some embodiments, a UGT91D2 homolog can have an amino acid substitution at one or more residues selected from the group consisting of residues 30, 93, 99, 122, 140, 142, 148, 153, 156, 195, 196, 199, 206, 207, 211, 221, 286, 343, 427, and 438 of SEQ ID NO: 5. For example, a UGT91D2 functional homolog can have an amino acid substitution at one or more of residues 206, 207, and 343, such as an arginine at residue 206, a cysteine at residue 207, and an arginine at residue 343 of SEQ ID NO:5. See, SEQ ID NO: 95. Other functional homologs of UGT91D2 can have one or more of the following: a tyrosine or phenylalanine at residue 30, a proline or glutamine at residue 93, a serine or valine at residue 99, a tyrosine or a phenylalanine at residue 122, a histidine or tyrosine at residue 140, a serine or cysteine at residue 142, an alanine or threonine at residue 148, a methionine at residue 152, an alanine at residue 153, an alanine or serine at residue 156, a glycine at residue 162, a leucine or methionine at residue 195, a glutamic acid at residue 196, a lysine or glutamic acid at residue 199, a leucine or methionine at residue 211, a leucine at residue 213, a serine or phenylalanine at residue 221, a valine or isoleucine at residue 253, a valine or alanine at residue 286, a lysine or asparagine at residue 427, an alanine at residue 438, and either an alanine or threonine at residue 462 of SEQ ID NO:5. See, Examples 11 and 16, and Tables 12 and 14. A useful variant UGT91D2 polypeptide also can be constructed based on the alignment set forth in FIG. 8.

In some embodiments, a useful UGT85C homolog can have one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471 of SEQ ID NO: 3. Non-limiting examples of useful UGT85C homologs include polypeptides having substitutions (with respect to SEQ ID NO:3) at residue 65; at residue 65 in combination with residue 15, 270, 418, 440, or 441; residues 13, 15, 60, 270, 289, and 418; substitutions at residues 13, 60, and 270; substitutions at residues 60 and 87; substitutions at residues 65, 71, 220, 243, and 270; substitutions at residues 65, 71, 220, 243, 270, and 441; substitutions at residues 65, 71, 220, 389, and 394; substitutions at residues 65, 71, 270, and 289; substitutions at residues 220, 243, 270, and 334; or substitutions at residues 270 and 289. See, Example 17 and Table 15.

In some embodiments, a useful UGT76G homolog can have one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 of SEQ ID NO:7. Non-limiting examples of useful UGT76G homologs include polypeptides having substitutions (with respect to SEQ ID NO:7) at residues 74, 87, 91, 116, 123, 125, 126, 130, 145, 192, 193, 194, 196, 198, 199, 200, 203, 204, 205, 206, 207, 208, and 291; residues 74, 87, 91, 116, 123, 125, 126, 130, 145, 192, 193, 194, 196, 198, 199, 200, 203, 204, 205, 206, 207, 208, 266, 273, 274, 284, 285, and 291; or residues 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346. See, Example 18 and Table 16.

Methods to modify the substrate specificity of, for example UGT91D2e, are known to those skilled in the art, and include without limitation site-directed/rational mutagenesis approaches, random directed evolution approaches and combinations in which random mutagenesis/saturation techniques are performed near the active site of the enzyme. For example see Sarah A. Osmani, et al. *Phytochemistry* 70 (2009) 325-347.

A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.*, 31 (13): 3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that a functional UGT91D2 polypeptide can include additional amino acids that are not involved in glucosylation or other enzymatic activities carried out by UGT91D2, and thus such a polypeptide can be longer than would otherwise be the case. For example, a UGT91D2 polypeptide can include a purification tag, a chloroplast transit peptide, a mitochondrial transit peptide, an amyloplast peptide, signal peptide, or a secretion tag added to the amino or carboxy terminus. In some embodiments, a UGT91D2 polypeptide includes an amino acid sequence that functions as a reporter, e.g., a green fluorescent protein or yellow fluorescent protein.

II. STEVIOL AND STEVIOL GLYCOSIDE BIOSYNTHESIS NUCLEIC ACIDS

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). SEQ ID NOs: 18-25, 34-36, 40-43, 48-49, 52-55, 60-64, and 70-72 set forth nucleotide sequences encoding certain enzymes for steviol and steviol glycoside biosynthesis, modified for increased expression in yeast. As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a yeast strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites. As another example, expression of membrane transporters involved in transport of steviol glycosides can be inhibited, such that secretion of glycosylated steviosides is inhibited. Such regulation can be beneficial in that secretion of steviol glycosides can be inhibited for a desired period of time during culture of the microorganism, thereby increasing the yield of glycoside product(s) at harvest. In such cases, a nucleic acid that inhibits expression of the polypeptide or gene product may be included in a recombinant construct that is transformed into the strain. Alternatively, mutagenesis can be used to generate mutants in genes for which it is desired to inhibit function.

III. HOSTS

A. Microorganisms

A number of prokaryotes and eukaryotes are suitable for use in constructing the recombinant microorganisms described herein, e.g., gram-negative bacteria, yeast and fungi. A species and strain selected for use as a steviol or steviol glycoside production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species may be suitable. For example, suitable species may be in a genus selected from the group consisting of *Agaricus, Aspergillus, Bacillus, Candida, Corynebacterium, Escherichia, Fusarium/Gibberella, Kluyveromyces*, Laetiporus, Lentimuis, Phaffia, *Phanerochaete, Pichia, Physcomitrella, Rhodoturula, Saccharomyces, Schizosaccharomyces, Sphaceloma, Xanthophyllomyces* and *Yarrowia*. Exemplary species from such genera include Lentinus tigrimis, Laetiporus *sulphureus, Phanerochaete chrysosporium, Pichia pastoris, Physcomitrella patens, Rhodoturula glutinis* 32, *Rhodoturula mucilaginosa*, Phaffia rhodozyma UBV-AX, *Xanthophyllomyces dendrorhous, Fusarium fujikuroi/Gibberella fujikuroi, Candida utilis* and *Yarrowia lipolytica*. In some embodiments, a microorganism can be an Ascomycete such as *Gibberella fujikuroi, Kluyveromyces lactis, Schizosaccharomyces pombe, Aspergillus niger*, or *Saccharomyces cerevisiae*. In some embodiments, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of steviol glycosides.

*Saccharomyces cerevisiae*

*Saccharomyces cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms.

A steviol biosynthesis gene cluster can be expressed in yeast using any of a number of known promoters. Strains that overproduce terpenes are known and can be used to increase the amount of geranylgeranyl diphosphate available for steviol and steviol glycoside production.

*Aspergillus* spp.

*Aspergillus* species such as *A. oryzae, A. niger* and *A. sojae* are widely used microorganisms in food production, and can also be used as the recombinant microorganism platform. Nucleotide sequences are available for genomes of

*A. nidulans, A. fumigatus, A. oryzae, A. clavatus, A. flavus, A. niger,* and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for the production of food ingredients such as steviol and steviol glycosides. Example 23 describes cloning methodology for production of steviol glycosides in *Aspergillus nidulans*.

*Escherichia coli*

*Escherichia coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella,* and *Phanerochaete* spp.

*Agaricus, Gibberella,* and *Phanerochaete* spp. can be useful because they are known to produce large amounts of gibberellin in culture. Thus, the terpene precursors for producing large amounts of steviol and steviol glycosides are already produced by endogenous genes. Thus, modules containing recombinant genes for steviol or steviol glycoside biosynthesis polypeptides can be introduced into species from such genera without the necessity of introducing mevalonate or MEP pathway genes.

*Rhodobacter* spp.

*Rhodobacter* can be use as the recombinant microorganism platform. Similar to *E. coli*, there are libraries of mutants available as well as suitable plasmid vectors, allowing for rational design of various modules to enhance product yield. Isoprenoid pathways have been engineered in membraneous bacterial species of *Rhodobacter* for increased production of carotenoid and CoQ10. See, U.S. Patent Publication Nos. 20050003474 and 20040078846. Methods similar to those described above for *E. coli* can be used to make recombinant *Rhodobacter* microorganisms.

*Physcomitrella* spp.

*Physcomitrella* mosses, when grown in suspension culture, have characteristics similar to yeast or other fungal cultures. This genera is becoming an important type of cell for production of plant secondary metabolites, which can be difficult to produce in other types of cells. Example 22 describes production of active UGT enzymes in the steviol glycoside pathway in *P. patens*.

B. Plant Cells or Plants

In some embodiments, the nucleic acids and polypeptides described herein are introduced into plants or plant cells to increase overall steviol glycoside production or enrich for the production of specific steviol glycosides in proportion to others. Thus, a host can be a plant or a plant cell that includes at least one recombinant gene described herein. A plant or plant cell can be transformed by having a recombinant gene integrated into its genome, i.e., can be stably transformed. Stably transformed cells typically retain the introduced nucleic acid with each cell division. A plant or plant cell can also be transiently transformed such that the recombinant gene is not integrated into its genome. Transiently transformed cells typically lose all or some portion of the introduced nucleic acid with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, U.S. Pat. Nos. 5,538,880; 5,204,253; 6,329,571; and 6,013,863. If a cell or cultured tissue is used as the recipient tissue for transformation, plants can be regenerated from transformed cultures if desired, by techniques known to those skilled in the art.

A population of transgenic plants can be screened and/or selected for those members of the population that have a trait or phenotype conferred by expression of the transgene. For example, a population of progeny of a single transformation event can be screened for those plants having a desired level of expression of a steviol or steviol glycoside biosynthesis polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or nucleic acids. Methods for performing all of the referenced techniques are known. As an alternative, a population of plants comprising independent transformation events can be screened for those plants having a desired trait, such as production of a steviol glycoside or modulated biosynthesis of a steviol glycoside. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a steviol glycoside level relative to a control plant that lacks the transgene.

The nucleic acids, recombinant genes, and constructs described herein can be used to transform a number of monocotyledonous and dicotyledonous plants and plant cell systems. Non-limiting examples of suitable monocots include, for example, cereal crops such as rice, rye, sorghum, millet, wheat, maize, and barley. The plant may be a non-cereal monocot such as asparagus, banana, or onion. The plant also may be a dicot such as stevia (*Stevia rebaudiana*), soybean, cotton, sunflower, pea, geranium, spinach, or tobacco. In some cases, the plant may contain the precursor pathways for phenyl phosphate production such as the mevalonate pathway, typically found in the cytoplasm and mitochondria. The non-mevalonate pathway is more often found in plant plastids [Dubey, et al., 2003 *J. Biosci.* 28 637-646]. One with skill in the art may target expression of steviol glycoside biosynthesis polypeptides to the appropriate organelle through the use of leader sequences, such that steviol glycoside biosynthesis occurs in the desired location of the plant cell. One with skill in the art will use appropriate promoters to direct synthesis, e.g., to the leaf of a plant, if so desired. Expression may also occur in tissue cultures such as callus culture or hairy root culture, if so desired.

In one embodiment, one or more nucleic acid or polypeptides described herein are introduced into *Stevia* (e.g., *Stevia rebaudiana*) such that overall steviol glycoside biosynthesis is increased or that the overall steviol glycoside composition is selectively enriched for one or more specific steviol glycosides. For example, one or more recombinant genes can be introduced into *Stevia* such that one or more of the following are expressed: a UGT91D enzyme such as UGT91D2e (e.g., SEQ ID NO:5 or a functional homolog thereof), UGT91D2m (e.g., SEQ ID NO:10); a UGT85C enzyme such as a variant set forth in Table 15, or a UGT76G1 enzyme such as a variant set forth in Example 18. Nucleic acid constructs typically include a suitable promoter (e.g., 35S, e35S, or ssRUBISCO promoters) operably linked to a nucleic acid encoding the UGT polypeptide. Nucleic acids can be introduced into *Stevia* by *Agrobacterium*-mediated transformation; electroporation-mediated gene transfer to protoplasts; or by particle bombardment. See, e.g., Singh, et al., Compendium of Transgenic Crop Plants: Transgenic Sugar, Tuber and Fiber, Edited by Chittaranjan Kole and Timothy C. Hall, Blackwell Publishing Ltd. (2008), pp. 97-115. For particle bombardment of *stevia* leaf derived callus, the parameters can be as follows: 6 cm distance, 1100 psi He pressure, gold particles, and one bombardment.

*Stevia* plants can be regenerated by somatic embryogenesis as described by Singh et al., 2008, supra. In particular, leaf segments (approximately 1-2 cm long) can be removed from 5 to 6-week-old in vitro raised plants and incubated (adaxial side down) on MS medium supplemented with B5 vitamins, 30 g sucrose and 3 g Gelrite. 2,4-dichlorophenoxyacetic acid (2,4-D) can be used in combination with 6-benzyl adenine (BA), kinetin (KN), or zeatin. Proembryogenic masses appear after 8 weeks of subculture. Within 2-3 weeks of subcultures, somatic embryos will appear on the surface of cultures. Embryos can be matured in medium containing BA in combination with 2,4-D, a-naphthaleneacetic acid (NAA), or indolbutyric acid (IBA). Mature somatic embryos that germinate and form plantlets can be excised from calli. After plantlets reach 3-4 weeks, the plantlets can be transferred to pots with vermiculite and grown for 6-8 weeks in growth chambers for acclimatization and transferred to greenhouses.

In one embodiment, steviol glycosides are produced in rice. Rice and maize are readily transformable using techniques such as *Agrobacterium*-mediated transformation. Binary vector systems are commonly utilized for *Agrobacterium* exogenous gene introduction to monocots. See, for example, U.S. Pat. Nos. 6,215,051 and 6,329,571. In a binary vector system, one vector contains the T-DNA region, which includes a gene of interest (e.g., a UGT described herein) and the other vector is a disarmed Ti plasmid containing the vir region. Co-integrated vectors and mobilizable vectors also can be used. The types and pretreatment of tissues to be transformed, the strain of *Agrobacterium* used, the duration of the inoculation, the prevention of overgrowth and necrosis by the *Agrobacterium*, can be readily adjusted by one of skill in the art. Immature embryo cells of rice can be prepared for transformation with *Agrobacterium* using binary vectors. The culture medium used is supplemented with phenolic compounds. Alternatively, the transformation can be done in planta using vacuum infiltration. See, for example, WO 2000037663, WO 2000063400, and WO 2001012828.

IV. METHODS OF PRODUCING STEVIOL AND STEVIOL GLYCOSIDES

Recombinant hosts described herein can be used in methods to produce steviol or steviol glycosides. For example, if the recombinant host is a microorganism, the method can include growing the recombinant microorganism in a culture medium under conditions in which steviol and/or steviol glycoside biosynthesis genes are expressed. The recombinant microorganism may be grown in a fed batch or continuous process. Typically, the recombinant microorganism is grown in a fermentor at a defined temperature(s) for a desired period of time. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, geranylgeranyl diphosphate, kaurene and kaurenoic acid, can be determined by extracting samples from culture media for analysis according to published methods.

After the recombinant microorganism has been grown in culture for the desired period of time, steviol and/or one or more steviol glycosides can then be recovered from the culture using various techniques known in the art. If the recombinant host is a plant or plant cells, steviol or steviol glycosides can be extracted from the plant tissue using various techniques known in the art. For example, a crude lysate of the cultured microorganism or plant tissue can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound(s) can then be further purified by preparative HPLC. See also WO 2009/140394.

The amount of steviol or steviol glycoside produced can be from about 1 mg/l to about 1,500 mg/l, e.g., about 1 to about 10 mg/l, about 3 to about 10 mg/l, about 5 to about 20 mg/l, about 10 to about 50 mg/l, about 10 to about 100 mg/l, about 25 to about 500 mg/l, about 100 to about 1,500 mg/l, or about 200 to about 1,000 mg/l. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing steviol while a second microorganism comprises steviol glycoside biosynthesis genes. Alternatively, the two or more microorganisms each can be grown in a separate culture medium and the product of the first culture medium, e.g., steviol, can be introduced into second culture medium to be converted into a subsequent intermediate, or into an end product such as rebaudioside A. The product produced by the second, or final microorganism is then recovered. It will also be appreciated that in some embodiments, a recombinant microorganism is grown using nutrient sources other than a culture medium and utilizing a system other than a fermentor.

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides and have a consistent taste profile. Thus, the recombinant microorganisms, plants, and plant cells described herein can facilitate the production of compositions that are tailored to meet the sweetening profile desired for a given food product and that have a proportion of each steviol glycoside that is consistent from batch to batch. Microorganisms described herein do not produce the undesired plant byproducts found in *Stevia* extracts. Thus, steviol glycoside compositions produced by the recombinant microorganisms described herein are distinguishable from compositions derived from *Stevia* plants.

V. FOOD PRODUCTS

The steviol and steviol glycosides obtained by the methods disclosed herein can be used to make food products, dietary supplements and sweetener compositions. For example, substantially pure steviol or steviol glycoside such as rebaudioside A can be included in food products such as ice cream, carbonated beverages, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately or growing different plants/plant cells, each producing a specific steviol or steviol glycoside, recovering the steviol or steviol glycoside in substantially pure form from each microorganism or plant/plant cells and then combining the compounds to obtain a mixture containing each compound in the desired proportion. The recombinant microorganisms, plants, and plant cells described herein permit more precise and consistent mixtures to be obtained compared to current *Stevia* products. In another alternative, a substantially pure steviol or steviol glycoside can be incorporated into a food product along with other sweeteners, e.g. saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. Patent Publication No. 2007/0128311. In some embodiments, the steviol or steviol glycoside may be provided with a flavor (e.g., citrus) as a flavor modulator. For example, Rebaudioside C can be used as a sweetness enhancer or sweetness modulator, in particular for carbohydrate based sweeteners, such that the amount of sugar can be reduced in the food product.

Compositions produced by a recombinant microorganism, plant, or plant cell described herein can be incorporated into food products. For example, a steviol glycoside composition produced by a recombinant microorganism, plant, or plant cell can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism, plant, or plant cell can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism, plant, or plant cell can be incorporated into a baked good (e.g., a biscuit) such that the food product has a maximum of 300 mg steviol glycoside/kg food on a dry weight basis. A steviol glycoside composition produced by a recombinant microorganism, plant, or plant cell can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism, plant, or plant cell can be incorporated into a bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis.

For example, such a steviol glycoside composition can have from 90-99% rebaudioside A and an undetectable amount of *stevia* plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a rebaudioside B-enriched composition having greater than 3% rebaudioside B and be incorporated into the food product such that the amount of rebaudioside B in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the rebaudioside B-enriched composition has an undetectable amount of stevia plant-derived contaminants.

Such a steviol glycoside composition can be a rebaudioside C-enriched composition having greater than 15% rebaudioside C and be incorporated into the food product such that the amount of rebaudioside C in the product is from 20-600 mg/kg, e.g., 100-600 mg/kg, 20-100 mg/kg, 20-95 mg/kg, 20-250 mg/kg, 50-75 mg/kg or 50-95 mg/kg on a dry weight basis. Typically, the rebaudioside C-enriched composition has an undetectable amount of stevia plant-derived contaminants.

Such a steviol glycoside composition can be a rebaudioside D-enriched composition having greater than 3% rebaudioside D and be incorporated into the food product such that the amount of rebaudioside D in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the rebaudioside D-enriched composition has an undetectable amount of stevia plant-derived contaminants.

Such a steviol glycoside composition can be a rebaudioside E-enriched composition having greater than 3% rebaudioside E and be incorporated into the food product such that the amount of rebaudioside E in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the rebaudioside E-enriched composition has an undetectable amount of stevia plant-derived contaminants.

Such a steviol glycoside composition can be a rebaudioside F-enriched composition having greater than 4% rebaudioside F and be incorporated into the food product such that the amount of rebaudioside F in the product is from 25-1000 mg/kg, e.g., 100-600 mg/kg, 25-100 mg/kg, 25-95 mg/kg, 50-75 mg/kg or 50-95 mg/kg on a dry weight basis. Typically, the rebaudioside F-enriched composition has an undetectable amount of stevia plant-derived contaminants.

Such a steviol glycoside composition can be a dulcoside A-enriched composition having greater than 4% dulcoside A and be incorporated into the food product such that the amount of dulcoside A in the product is from 25-1000 mg/kg, e.g., 100-600 mg/kg, 25-100 mg/kg, 25-95 mg/kg, 50-75 mg/kg or 50-95 mg/kg on a dry weight basis. Typically, the dulcoside A-enriched composition has an undetectable amount of stevia plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for rebaudioside A, rebaudioside C, rebaudioside D, rebaudioside E, rebaudioside F, or dulcoside A can be package in a sachet, for example, at from 10,000 to 30,000 mg steviol glycoside/kg product on a dry weight basis, for tabletop use.

VI. PLANT BREEDING

A. Polymorphisms

Polymorphisms among the nucleic acids described herein (e.g., UGT91D2 nucleic acids) can be used as markers in plant genetic mapping and plant breeding programs in Stevia. See, e.g., Yao et al., Genome, 1999, 42:657-661. Thus, the polymorphisms described herein can be used in a method of identifying whether that polymorphism is associated with variation in a trait. The method involves measuring the correlation between variation in the trait in plants of a Stevia line or population and the presence of one or more genetic polymorphisms in those plants, thereby identifying whether or not the genetic polymorphisms are associated with variation in the trait. Typically, the trait is the total amount of steviol glycosides present in leaves of the plant, although the trait also can be the amount of a particular steviol glycoside, e.g., rebaudioside A, rebaudioside B, rebaudioside C, rebaudioside D, rebaudioside E, rebaudioside F, or dulcoside A. In some embodiments, the trait is the amount of steviol, or the amount of an isoprenoid precursor. A statistically significant correlation between the trait and the presence of the polymorphic marker is determined using an appropriate parametric or non-parametric statistic, e.g., Chi-square test, Student's t-test, Mann-Whitney test, or F-test. A statistically significant correlation between, for example, the amount of rebaudioside A in a plant and presence of a polymorphic marker indicates that the marker may be useful in a marker-assisted breeding program for selection of altered rebaudioside A levels.

Polymorphisms may be detected by means known in the art, including without limitation, restriction fragment length polymorphism (RFLP), random amplified polymorphic DNA detection (RAPD), amplified fragment length polymorphism (AFLP), simple sequence repeat (SSR) or microsatellites. Discovery, detection, and genotyping of polymorphisms have been described in the literature. See, e.g., Henry, ed. (2001) Plant Genotyping. The DNA Fingerprinting of Plants Wallingford: CABI Publishing; and Phillips and Vasil, eds. (2001) DNA-based Markers in Plants Dordrecht: Kluwer Academic Publishers. For example, a primer or probe derived from the nucleic acid sequences set forth in SEQ ID NO:6, SEQ ID NO:9, or SEQ ID NO:96, or the complements thereof, can be used to identify one or more individual plants that possess the polymorphic allele that is correlated with a desired steviol glycoside composition. Those plants then can be used in a breeding program to combine the polymorphic allele with a plurality of other alleles at other loci that are correlated with the desired steviol glycoside composition. As will be evident to one of skill, the number and type of markers required can differ, depending on the trait(s) to be selected for and the degree of correlation for each marker. The methods, therefore, involve detecting a plurality of polymorphisms in the genome of the plant in certain embodiments. It will be appreciated that the method may further comprise storing the results of the step of detecting the plurality of polymorphisms on a computer readable medium.

Thus, in some embodiments, a method for identifying Stevia plant lines or populations comprises supplying a nucleic acid sample for a Stevia plant, providing amplification primers for amplifying a region of a Stevia plant corresponding to a UGT gene having 90% or greater sequence identity to a nucleic acid encoding the polypeptides set forth in SEQ ID NOs: 1, 3, 5, or 7, present in the sample, applying the amplification primers to the nucleic acid sample such that amplification of the region occurs, and identifying plants having a desired trait based on the presence of one or more polymorphisms in the amplified nucleic acid sample that correlate with the trait.

In some embodiments, a method of determining the presence of a polynucleotide in a *Stevia* plant involves contacting at least one probe or primer pair with nucleic acid from the plant. The probe or primer pair is specific for a polynucleotide that encodes a UGT polypeptide having at least 90% sequence identity to SEQ ID NOs: 1, 3, 5, or 7. The presence or absence of the polynucleotide is then determined.

In addition to methods for detecting polymorphisms and determining the genotype of a *Stevia* plant, kits suitable for carrying out the methods are also described, as well as a computer readable medium produced by such methods that contains data generated by the methods. A kit for genotyping a *Stevia* biological sample includes a primer pair that specifically amplifies, or a probe that specifically hybridizes to, a polynucleotide that encodes a UGT polypeptide having at least 90% sequence identity to SEQ ID NOs: 1, 3, 5, or 7. Such kits typically have the primer or probe contained within suitable packaging material.

In some embodiments of the methods and kits described herein, one or more sets of oligonucleotides, each capable of recognizing the presence or absence of a specific and defined genomic position, is used. For polyploid *Stevia* lines or populations, more oligonucleotides are desirable. The lower limit is one oligonucleotide pair and the upper limit is set by the desired resolution capacity of the method and the test kit. Hybridization of the oligonucleotides to DNA from the *Stevia* plant is preferably recorded in situ by any conventional labelling system, applying for instance terminal transferase and conventional recordable labels. As an alternative to in situ labelling the hybridized sample DNA may be released from the solid support and subsequently hybridized with labelled polynucleotide sequences corresponding to each of the original oligonucleotide sequences attached to the solid support. Hybridization is optionally reversible and the solid support can be returned to its original state for reuse. A labelled dideoxynucleotide can be incorporated at the end of the oligonucleotide provided that the oligonucleotide is hybridized to genomic DNA as template. The nucleotide sequence at the genomic position adjacent to the region matching the oligonucleotide is known and therefore the particular nucleotide which will be incorporated (A, C, G, T or U) is known. Co-dominant scoring is achieved using paired, i.e. two or parallel, i.e. three, flanking oligonucleotide sequences. The results obtained are recorded as full, empty, failure or null alleles and can be used to distinguish between heterozygous and/or homozygous genotypes. Optional post-hybridization treatments, including washing and digestion, are provided in order to remove sample DNA not fully hybridized to the solid support-attached oligonucleotide sequences, for example before and after labelling. The presence or absence of hybridization is recorded using a method allowing the recording of the hybridization state, typically on a computer readable medium.

B. Breeding Programs

*Stevia* is typically an outcrossing species, although self-pollination is occasionally observed. Thus, a *Stevia* plant breeding program typically involves the use of one or more of: recurrent selection mass selection, bulk selection, and intercrossing. These techniques can be used alone or in combination with one or more other techniques in a breeding program. See, Yadav et al., *Can. J. Plant Sci.* 91:1-27 (2011). Each identified plant can be crossed to a different plant to produce seed, which is then germinated to form progeny plants. Seed from one or more progeny plants possessing the desired phenotype(s) and desired polymorphism(s) is composited and then randomly mated to form a subsequent progeny generation. The breeding program can repeat these steps for an additional 0 to 5 generations as appropriate in order to achieve the desired stability in the resulting plant population, which retains the polymorphic allele(s). In most breeding programs, analysis for the particular polymorphic allele will be carried out in each generation, although analysis can be carried out in alternate generations if desired. Selfing of progeny plants may be carried out for those *stevia* lines and populations in which selfing is feasible.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are self pollinated or cross pollinated with each other to form progeny for another population. This population is planted and again superior plants are selected to self pollinate or cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties. The number of parental plant varieties, populations, wild accessions, ecotypes, etc., that are used to generate a synthetic can vary from as little as 10 to as much as 500. Typically, about 100 to 300 varieties, populations, etc., are used a parents for the synthetic variety. Seed from the parental seed production plot of a synthetic variety can be sold to the farmer. Alternatively, seed from the parental seed production plot can subsequently undergo one or two generations of multiplication, depending on the amount of seed produced in the parental plot and the demand for seed.

Mass selection is a useful technique when used in conjunction with molecular marker-assisted selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Thus, in some embodiments, a method of making a *Stevia* plant line or population involves identifying one or more plants in the line or population in which the presence of a polymorphism at a locus having nucleotide sequence encoding a polypeptide that is at least 90% identical to SEQ ID NOs: 1, 3, 5, or 7 is associated with variation in a trait of interest. The identified plant(s) is then crossed with itself or a different *stevia* plant to produce seed, and at least one progeny plant grown from the seed is again crossed with itself or a different *stevia* plant for an additional 0-5 generations to make a line or population that possesses the polymorphism.

In some cases, selection for other useful traits is also carried out, e.g., selection for disease resistance. Selection for such other traits can be carried out before, during or after identification of individual plants that possess the desired polymorphic allele.

Marker-assisted breeding techniques may be used in addition to, or as an alternative to, other sorts of identification techniques.

The invention will be further described in the following examples, which do not limit the scope of the invention described in the claims.

VI. EXAMPLES

Example 1—Construction of Kaurene Biosynthesis Pathway Genes

A nucleotide sequence encoding a truncated baker's yeast HMG CoA reductase was cloned into a yeast high copy episomal plasmid vector such that the coding sequence was operably linked to and under the transcriptional control of a promoter which can be repressed by the amino acid methionine. See, U.S. Pat. Nos. 5,460,949 and 5,306,862.

Nucleotide sequences encoding the GGPPS enzymes shown in Table 1 were modified for expression in yeast (see SEQ ID NOs: 18-25) and cloned into an E. coli vector such that the coding sequence was operably linked to and under the transcriptional control of a yeast promoter which can be repressed by the amino acid methionine. The name for each expression cassette-containing plasmid ("entry vector") is also shown in Table 1. The nucleotide sequences from the source organisms from which the polypeptides were originally identified are set forth in SEQ ID NOs: 26-33. Other entry vectors were constructed using GGPPS enzymes expressed by an unmodified nucleotide sequence from Catharanthus roseus designated EV270, an unmodified nucleotide sequence from Aspergillus nidulans designated C301 and an unmodified nucleotide sequence from Xanthophyllomyces dendrorhous designated C413.

TABLE 1

GGPPS Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Stevia rebaudiana | 90289577 | ABD92926 | pMUS14 | MM-1 | 1086 | 18 | 121 |
| Gibberella fujikuroi | 3549881 | CAA75568 | pMUS15 | MM-2 | 1029 | 19 | 122 |
| Mus musculus | 47124116 | AAH69913 | pMUS16 | MM-3 | 903 | 20 | 123 |
| Thalassiosira pseudonana | 223997332 | XP_002288339 | pMUS17 | MM-4 | 1020 | 21 | 124 |
| Streptomyces clavuligerus | 254389342 | ZP_05004570 | pMUS18 | MM-5 | 1068 | 22 | 125 |
| Sulfolobus acidocaldarius | 506371 | BAA43200 | pMUS19 | MM-6 | 993 | 23 | 126 |
| Synechococcus sp. | 86553638 | ABC98596 | pMUS20 | MM-7 | 894 | 24 | 127 |
| Arabidopsis thaliana | 15234534 | NP_195399 | pMUS21 | MM-8 | 1113 | 25 | 128 |

Nucleotide sequences encoding the CDPS enzymes shown in Table 2 were modified for expression in yeast (see SEQ ID NOs: 34-36) and cloned into yeast entry vectors. The nucleotide sequences from the source organisms from which the polypeptides were originally identified are set forth in SEQ ID NOs: 37-39. Other entry vectors were constructed using CDPS enzymes expressed by an unmodified nucleotide sequence from Arabidopsis thaliana designated EV64, an unmodified nucleotide sequence from Zea mays designated EV65 and an unmodified nucleotide sequence from Lycopersicon esculentum designated EV66.

TABLE 2

CDPS Clones

| Enzyme Source Organism | gi Number | Accession Number | Plasmid Name | Construct Name | Length (nts) | SEQ ID: (DNA) | SEQ ID (protein) |
|---|---|---|---|---|---|---|---|
| Stevia rebaudiana | 2642661 | AAB87091 | pMUS22 | MM-9 | 2364 | 34 | 129 |
| Streptomyces clavuligerus | 197705855 | EDY51667 | pMUS23 | MM-10 | 1584 | 35 | 130 |
| Bradyrhizobium japonicum | 529968 | AAC28895.1 | pMUS24 | MM-11 | 1551 | 36 | 131 |

Nucleotide sequences encoding the KS enzymes shown in Table 3 were modified for expression in yeast (see SEQ ID NOs: 40-43) and cloned into yeast entry vectors. The nucleotide sequences from the source organisms from which the polypeptides were originally identified are set forth in SEQ ID NOs: 44-47. Other entry vectors were constructed using KS enzymes expressed by an unmodified nucleotide sequence from Arabidopsis thaliana designated EV70, an unmodified nucleotide sequence from Cucurbita maxima designated EV71 and an unmodified nucleotide sequence from Cucumis sativus designated EV72.

TABLE 3

KS Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Stevia rebaudiana | 4959241 | AAD34295 | pMUS25 | MM-12 | 2355 | 40 | 132 |
| Stevia rebaudiana | 4959239 | AAD34294 | pMUS26 | MM-13 | 2355 | 41 | 133 |
| Zea mays | 162458963 | NP_001105097 | pMUS27 | MM-14 | 1773 | 42 | 134 |
| Populus trichocarpa | 224098838 | XP_002311286 | pMUS28 | MM-15 | 2232 | 43 | 135 |

Nucleotide sequences encoding the CDPS-KS fusion enzymes shown in Table 4 were modified for expression in yeast (see SEQ ID NOs: 48 and 49) and cloned into yeast entry vectors. The nucleotide sequences from the source organisms from which the polypeptides were originally identified are set forth in SEQ ID NOs: 50 and 51.

TABLE 4

CDPS-KS Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Phomopsis amygdali | 186704306 | BAG30962 | pMUS29 | MM-16 | 2952 | 48 | 136 |
| Physcomitrella patens | 146325986 | BAF61135 | pMUS30 | MM-17 | 2646 | 49 | 137 |

Nucleotide sequences encoding the KO enzymes shown in Table 5 were modified for expression in yeast (see SEQ ID NOs: 52-55) and cloned into yeast entry vectors. The nucleotide sequences from the source organisms from which the polypeptides were originally identified are set forth in SEQ ID NOs: 56-59.

TABLE 5

KO Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Stevia rebaudiana | 76446107 | ABA42921 | pMUS31 | MM-18 | 1542 | 52 | 138 |
| Arabidopsis thaliana | 3342249 | AAC39505 | pMUS32 | MM-19 | 1530 | 53 | 139 |
| Gibberella fujikoroi | 4127832 | CAA76703 | pMUS33 | MM-20 | 1578 | 54 | 140 |
| Trametes versicolor | 14278967 | BAB59027 | pMUS34 | MM-21 | 1500 | 55 | 141 |

Nucleotide sequences encoding the KAH enzymes shown in Table 6 were modified for expression in yeast (see SEQ ID NOs: 60-64) and cloned into yeast entry vectors. The nucleotide sequences from the source organisms from which the polypeptides were originally identified are set forth in SEQ ID NOs: 65-69.

TABLE 6

KAH Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Stevia rebaudiana | | —* | pMUS35 | MM-22 | 1578 | 60 | 142 |
| Stevia rebaudiana | 189418962 | ACD93722 | pMUS36 | MM-23 | 1431 | 61 | 143 |
| Arabidopsis thaliana | 15238644 | NP_197872 | pMUS37 | MM-24 | 1578 | 62 | 144 |
| Vitis vinifera | 225458454 | XP_002282091 | pMUS38 | MM-25 | 1590 | 63 | 145 |
| Medicago truncatula | 84514135 | ABC59076 | pMUS39 | MM-26 | 1440 | 64 | 146 |

*= Sequence is shown in U.S. Patent Publication No. 2008-0064063.

Nucleotide sequences encoding the CPR enzymes shown in Table 7 were modified for expression in yeast (see SEQ ID NOs: 70-72) and cloned into yeast entry vectors. The nucleotide sequences from the source organisms from which the polypeptides were originally identified are set forth in SEQ ID NOs: 73-75.

TABLE 7

CPR Clones

| Enzyme Source Organism | Accession gi Number Number | | Plasmid Name | Construct Name | Length (nts) | SEQ ID (DNA) | SEQ ID (protein) |
|---|---|---|---|---|---|---|---|
| Stevia rebaudiana | 93211213 | ABB88839 | pMUS40 | MM-27 | 2133 | 70 | 147 |
| Arabidopsis thaliana | 15233853 | NP_194183 | pMUS41 | MM-28 | 2079 | 71 | 148 |
| Giberella fujikuroi | 32562989 | CAE09055 | pMUS42 | MM-29 | 2142 | 72 | 149 |

Example 2—Construction of Steviol Glycoside Pathway Genes

Integration vectors containing nucleotide sequences encoding the UGT85C2 and UGT74G1 enzymes listed in Table 8 were transformed into yeast. Transformants were obtained that contained UGT85C2, or UGT85C2 and UGT74G1, integrated into the genome.

TABLE 8

UGT Clones

| Source Organism | UGT No. | gi Number | Accession Number | Type | Plasmid Name | Length (nucleotides) | SEQ ID |
|---|---|---|---|---|---|---|---|
| Stevia rebaudiana | UGT85C2 | 37993660 | AY345978.1 | Integration vector | pMUS11 | 1446 | 4 |
| Stevia rebaudiana | UGT74G1 | 37993668 | AY345982 | Integration vector | pMUS12 | 1383 | 2 |
| Stevia rebaudiana | UGT76G1 | 37993652 | AY345974 | Integration vector | pMUS13 | 1377 | 8 |
| Ipomoea purpurea | IP3GGT | 62857205 | AB192315.1 | High copy vector | pMUS10 | 1380 | 77 |
| Bellis perennis | UGT94B1 R25S mutant (wild type) | 56550538 (wild type) | AB190262.1 (wild type) | High copy vector | pEF1156 | 1317 (wild type) | 79 |
| Arabidopsis thaliana | UGT79B3 | 28951020 | BT005370.1 | High copy vector | pEF1153 | 1362 | 151 |

Nucleotide sequences encoding the IP3GGT and UGT94B1 R25S enzymes were modified for expression in yeast (see SEQ ID NOs: 77 and 79) and cloned into yeast entry vectors. Amino acid sequences for IP3GGT and UGT94B1 R25S are set forth in SEQ ID NOs: 76 and 78, respectively. The high copy episomal vector containing a modified IP3GGT nucleotide sequence was designated pEF1155. The high copy episomal vector containing a modified UGT94B1 R25S nucleotide sequence was designated pEF1156.

Example 3—Construction of Yeast Strains

A yeast strain designated EFSC301 was modified by replacing the endogenous ERG9 promoter with the copper inducible CUP1 promoter. Strain EFSC301 is a derivative of EUROSCARF collection yeast strain BY4742. See, the world wide web at uni-frankfurt.de/fb15/mikro/euroscarf/data/by.html. In standard yeast growth medium, the ERG9 gene is transcribed at very low levels, since the concentration of copper in such medium is low. The decrease in ergosterol production in this strain results in increased amounts of isoprene units available for steviol biosynthesis.

The yeast strain was also modified by genomically integrating the Stevia UGT85C2 and UGT74G1 genes, each under the transcriptional control of the strong constitutive GPD1 promoter. See Table 8. The strain has one copy of each of the Stevia UGT85C2 and UGT74G1 genes integrated in the MUS1241 strain genome.

Example 4—Analysis of Steviol Glycoside Pathway Gene Expression in Yeast

Figure 5:
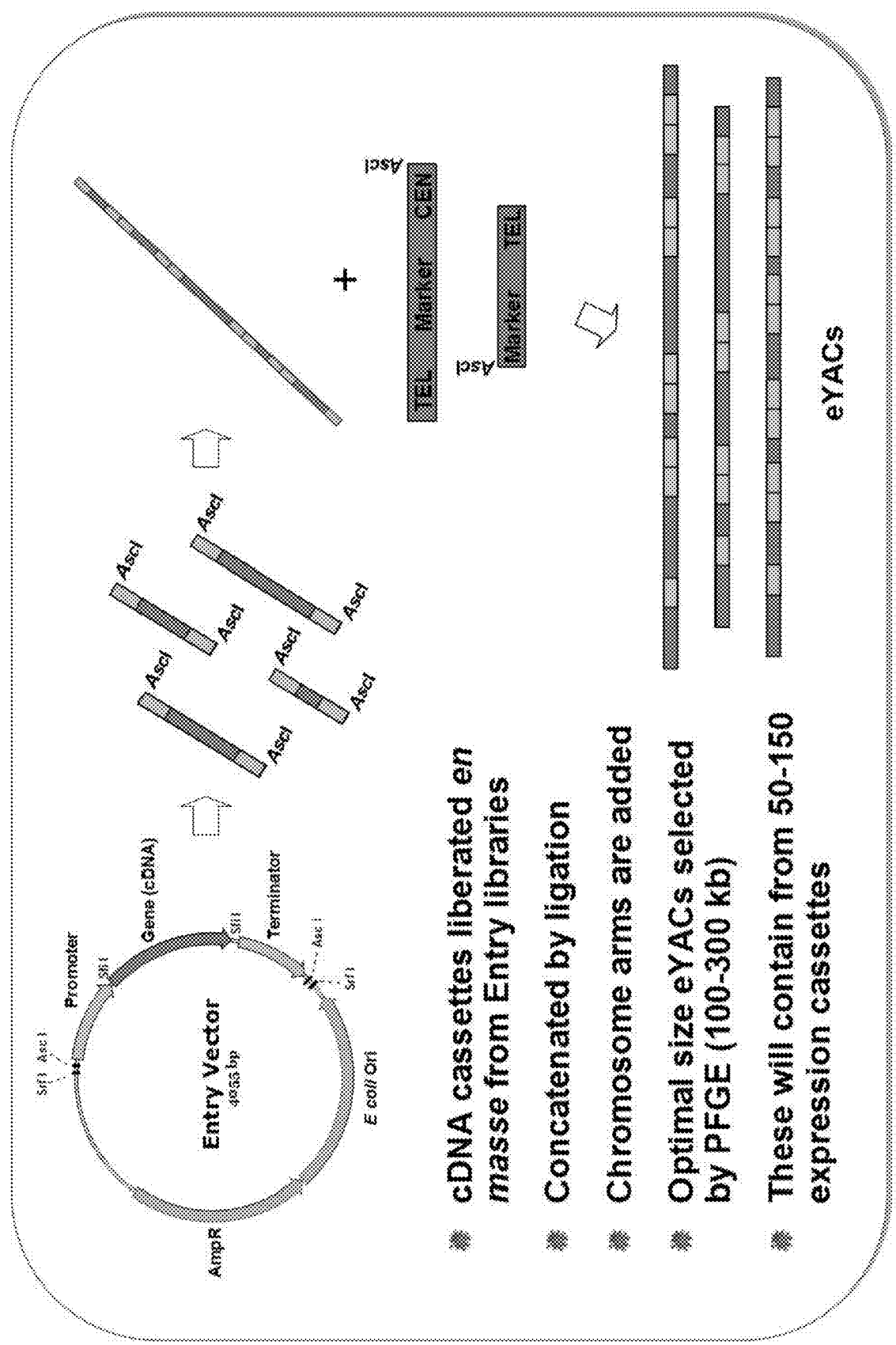
FIG. 5 is a schematic representation of the concatenation of genes to form eYACs.

To examine steviol glycoside biosynthesis in yeast, the expression cassettes of the 36 entry vectors of Tables 1-7 and Example 1 were randomly concatenated in ligation reactions to create artificial yeast chromosomes ("eYACs"). The process is shown schematically in FIG. 5.

Two different sets of ligations were carried out. Ligation set A included all genes listed in Tables 1-7, except that no bi-functional CDPS-KS genes (Table 4) were included. Ligation set B included all genes listed in Tables 1-7 except that no mono-functional CDPS and KS genes (Tables 2-3) were included.

From 30 to 200 μg of DNA was prepared from each of the cassette-containing entry vectors. The gene expression cassettes were released from each vector by digestion with the restriction enzyme AscI. The cassettes were then randomly concatenated into eYACs by ligation with T4 ligase in a 3 hour reaction. The success of the concatenation reaction was assessed by the viscosity of the reaction mixture, since concatenated DNA is highly viscous. DNA fragments ("arms") containing a centromere, two telomeres and the LEU2 and TRP1 selection markers were added to the end of the concatenated expression cassettes, thereby creating functional eYACs.

The eYACs were transformed into spheroplasts of the competent yeast strain MUS1243 by zymolyase digestion of the yeast cell wall, followed by treatment with a $CaCl_2$)/PEG buffer, making the spheroplasts permeable to large molecules such as eYACs.

After transformation, the yeast spheroplasts were embedded in a noble agar based solid growth medium, in which regeneration of the cell wall can take place. Colonies appeared from 4-8 days after inoculation. The regeneration medium lacked the amino acids leucine and tryptophan, thus selecting for the presence of double-armed eYACs in the yeast cells.

About 3,000 transformants were obtained for each set. Each transformant was re-streaked and tested for yeast strain markers and the genetic presence of both arms of the eYAC, i.e., the LEU2 and TRP1 markers. More than 97% of the transformants had the correct genotype. Each transformant was given a CEY designation number.

Initially, 24 CEYs from each set were grown for 24 hours in 2 ml of Synthetic Complete medium (SC), without methionine, so as to induce gene expression from the eYACs. After 24 hours, the supernatant from each culture was collected and subjected to LC-MS (Liquid Chromatography-coupled Mass Spectrometry (Triple Quadrupole)) analysis for the presence of rubusoside. Since the Stevia UGT74G1 and UGT85C2 genes are co-expressed in each CEY transformant, the expected end product when steviol is produced is rubusoside (steviol-(13-β-D-glucopyranosyloxy)-β-D-glucopyranosyl ester).

None of the CEYs from set B produced detectable levels of rubusoside, whereas 7 of the CEYs from set A did. Strain CEY19 was the top producer. CEY19 produced a compound with a mass of 665.2, which could correspond to a sodium adduct of rubusoside. A compound with a mass of 643.2 also was seen, and probably corresponds to protonated rubusoside. MS-MS-based molecular fractionation of the 665.2 mass compound resulted in a break down mass of 503.2, which corresponds to steviol monoside as a sodium adduct. Since the mass, the fractionation pattern, the HPLC spectrum, and the retention standard of this compound corresponded exactly to that of a rubusoside standard produced in vitro by the glucosylation of steviol using Stevia enzymes 85C2 and 74G1, the compound produced by CEY was determined to be rubusoside.

Additional Screening for Rubusoside Production

An additional 95 clones from set A and 95 clones from set B were grown in 96 deep-well trays in 1 ml SC medium without methionine. Supernatants from each of these cultures were combined in pools of two clones, analyzed by LC-MS, and the MS signal/noise ratio determined. The MS s/n ratio is an approximate measure of the relative rubusoside content. When a pool of 2 CEYs was found to produce rubusoside, each clone in that pool was analyzed separately. The results showed that no set B CEYs produced rubusoside, while at least 28 CEYs from set A produced detectable levels of rubusoside.

Identification of Genes Present in Rubusoside Producing CEY Clones

To correlate the gene content of eYACs to rubusoside production, a PCR protocol was developed in which similar sized fragments (0.5 kb) of all the possible eYAC-borne genes could be amplified. Internal primers of 20-25 nt were placed so that a similar annealing temperature could be used to amplify all genes. Genomic DNA, which includes eYAC DNA, was prepared from 4 CEYs with no rubusoside production, 4 with low rubusoside production and 6 with high to very high rubusoside production. Using equimolar amounts of these 14 DNA preparations, analytical PCR was performed for all 37 genes for these 14 CEYs, as well as positive and negative controls. All genes were amplified except one, apparently due to primer failure.

The genes present in the six high rubusoside-producing CEY strains are shown in Table 9. The genes present in the eight low or no rubusoside-producing CEY strains are shown in Table 10.

TABLE 9

Genes Present in High Rubusoside-Producing CEY Strains

| | HIGH production | | | VERY high production | | |
|---|---|---|---|---|---|---|
| Gene | CEY50 | CEY176 | CEY19 | CEY173 | CEY191 | CEY213 |
| tHMG1 | + | + | + | + | − | + |
| MM-1 | − | + | + | + | + | − |
| MM-2 | − | + | + | + | + | − |
| MM-3 | + | + | + | + | + | + |
| MM-4 | + | + | + | − | + | + |
| MM-5 | + | + | + | + | + | + |
| MM-6 | + | + | + | + | + | + |
| MM-7 | − | + | − | + | + | − |
| MM-8 | + | + | + | + | − | + |
| EV270 | + | + | − | + | + | + |
| C301 | + | + | + | + | + | + |
| C413 | + | + | − | + | + | + |
| MM-9 | + | + | + | + | + | + |
| MM-10 | + | − | − | + | + | + |
| MM-11 | + | + | − | + | + | + |
| EV64 | + | + | + | + | + | + |
| EV65 | − | − | + | + | + | + |
| EV66 | + | + | + | + | + | + |
| MM-12 | + | − | − | + | + | + |
| MM-13 | + | + | + | + | + | + |
| MM-14 | + | + | + | + | + | + |
| MM-15 | − | − | − | − | + | − |
| EV70 | − | + | + | + | − | − |
| EV71 | | | Primers failed | | | |
| EV72 | + | + | + | + | + | + |
| MM-18 | + | + | + | + | + | − |
| MM-19 | + | − | + | − | + | + |
| MM-20 | + | + | + | + | + | + |

TABLE 9-continued

Genes Present in High Rubusoside-Producing CEY Strains

| | HIGH production | | | VERY high production | | |
|---|---|---|---|---|---|---|
| Gene | CEY50 | CEY176 | CEY19 | CEY173 | CEY191 | CEY213 |
| MM-21 | − | − | + | + | − | + |
| MM-22 | + | + | + | + | + | + |
| MM-23 | + | − | + | + | − | + |
| MM-24 | + | + | + | + | + | + |
| MM-25 | + | + | + | + | + | + |
| MM-26 | + | + | + | + | + | + |
| MM-27 | + | + | + | + | + | + |
| MM-28 | − | − | − | − | − | − |
| MM-29 | + | + | + | + | + | + |

TABLE 10

Genes Present in CEY Strains Producing Low or No Rubusoside

| | NO rubusoside production | | | | LOW production | | | |
|---|---|---|---|---|---|---|---|---|
| Gene | CEY162 | CEY169 | CEY171 | CEY188 | CEY75 | CEY147 | CEY214 | CEY87 |
| tHMG1 | − | − | − | − | − | − | + | + |
| MM-1 | + | + | + | + | − | + | − | − |
| MM-2 | + | − | + | + | + | + | + | + |
| MM-3 | + | + | + | + | + | + | + | + |
| MM-4 | − | − | + | − | − | + | − | + |
| MM-5 | + | + | + | + | + | + | + | + |
| MM-6 | + | + | + | − | + | + | + | + |
| MM-7 | + | − | + | + | + | + | + | + |
| MM-8 | + | + | + | + | + | + | + | + |
| EV270 | + | + | + | + | + | + | + | + |
| C301 | + | + | + | + | + | + | + | + |
| C413 | + | + | + | + | + | + | + | + |
| MM-9 | + | + | + | + | − | + | + | + |
| MM-10 | + | + | + | + | − | + | + | + |
| MM-11 | + | + | + | + | + | + | + | − |
| EV64 | + | + | + | + | − | + | + | + |
| EV65 | + | − | − | − | + | − | + | − |
| EV66 | + | + | + | + | + | + | + | + |
| MM-12 | + | + | + | + | + | + | + | + |
| MM-13 | + | + | + | + | + | + | + | + |
| MM-14 | + | + | + | + | + | + | + | + |
| MM-15 | + | − | + | − | + | + | − | + |
| EV70 | + | + | + | + | + | + | + | + |
| EV71 | | | | Primers failed | | | | |
| EV72 | + | + | + | + | + | + | + | + |
| MM-18 | + | + | + | + | + | + | + | + |
| MM-19 | + | + | + | + | + | + | + | + |
| MM-20 | + | + | + | + | + | + | + | + |
| MM-21 | − | + | − | − | − | + | − | + |
| MM-22 | + | + | + | + | + | − | + | + |
| MM-23 | + | − | + | − | + | + | − | + |
| MM-24 | + | − | + | + | + | + | + | + |
| MM-25 | + | − | + | + | + | + | + | + |
| MM-26 | + | + | + | + | + | − | + | + |
| MM-27 | + | + | + | + | + | + | + | + |
| MM-28 | − | − | + | − | − | − | − | + |
| MM-29 | + | + | + | + | − | + | + | + |

Example 5—Modification of Yeast Culture Conditions

Experiments were carried out with strain CEY213 in order to determine culture conditions conducive to maximum rubusoside production. The starting material was a glycerol freezer stock (−80° C.) of CEY213. Frozen cells originally came from an agar plate containing SC yeast medium without tryptophan, leucine and histidine (SC-TLH), and containing 2 mM methionine. Five ml of liquid SC-TLH medium containing 2 mM methionine was inoculated with a loop-full of freeze stock CEY213 yeast cells. eYAC expression in CEY213 is repressed under these conditions. The cells were grown overnight at 30° C. with slow shaking (170 rpm) and were designated as "pre-cultures."

The CEY 213 pre-cultures were used to inoculate 25-50 ml of SC media without methionine, in which the parameters indicated below were varied. Rubusoside production under each of the growth conditions was measured by centrifuging 500 μl of each culture medium, transferring 250 μl of the supernatant to a new tube, adding 250 μl methanol, shaking thoroughly and centrifuging for 10 minutes at maximum speed. An aliquot of the supernatant was analyzed for rubusoside production by LC-MS.

Copper Levels

CEY213 precultures were grown in SC medium to which 50 µM bathocuproinedisulfonic acid was added. Bathocuproinedisulfonic acid chelates copper in the growth medium. The ERG9 gene in CEY213 has been modified so that expression is controlled by the CUP1 promoter. A decrease in copper levels in the medium will further decrease ERG9 activity and thereby increase the amount of isoprene units available for steviol biosynthesis.

Chelation of copper ions in the growth medium had a detrimental effect on growth of the yeast culture and rubusoside production was decreased proportionally. These results suggested that even without copper chelation, strain CEY213 is at its minimum rate of ergosterol biosynthesis, and no more isoprene units can be diverted from ergosterol biosynthesis towards steviol glycoside production.

Glucose

Doubling the available glucose from 2 to 4% had a marginal effect on rubusoside production, about a 5-10% increase in rubusoside production.

Limiting Available Nitrogen

CEY213 pre-cultures were grown under conditions of limited available nitrogen. Limiting nitrogen during growth of yeast in culture is known to increase production of ergosterol. When the concentration of $NH_4SO_4$ was decreased from 4 g/l to 2, 1 or 0.4 g/l, the growth rate of CEY213 decreased in proportion to the amount of nitrogen. Rubusoside production decreased proportionally with the decrease in growth.

Aeration of Cultures

CEY213 was grown in Ehrlenmeyer flasks with or without baffles. The results indicated that there was at best a marginal effect of increased aeration via the use of baffles. If anything, the lack of aeration via the lack of baffles increased production.

Optical Density at Initiation, Fermentation Time and Growth Temperature

Cultures were initiated at two different optical densities, $OD_{600}=0.1$ or $OD_{600}=1.0$ of pre-cultured CEY213. Fermentation was then carried out for 24, 48, 72 or 144 hours at a temperature of 20, 25 or 30° C.

Figure 6:
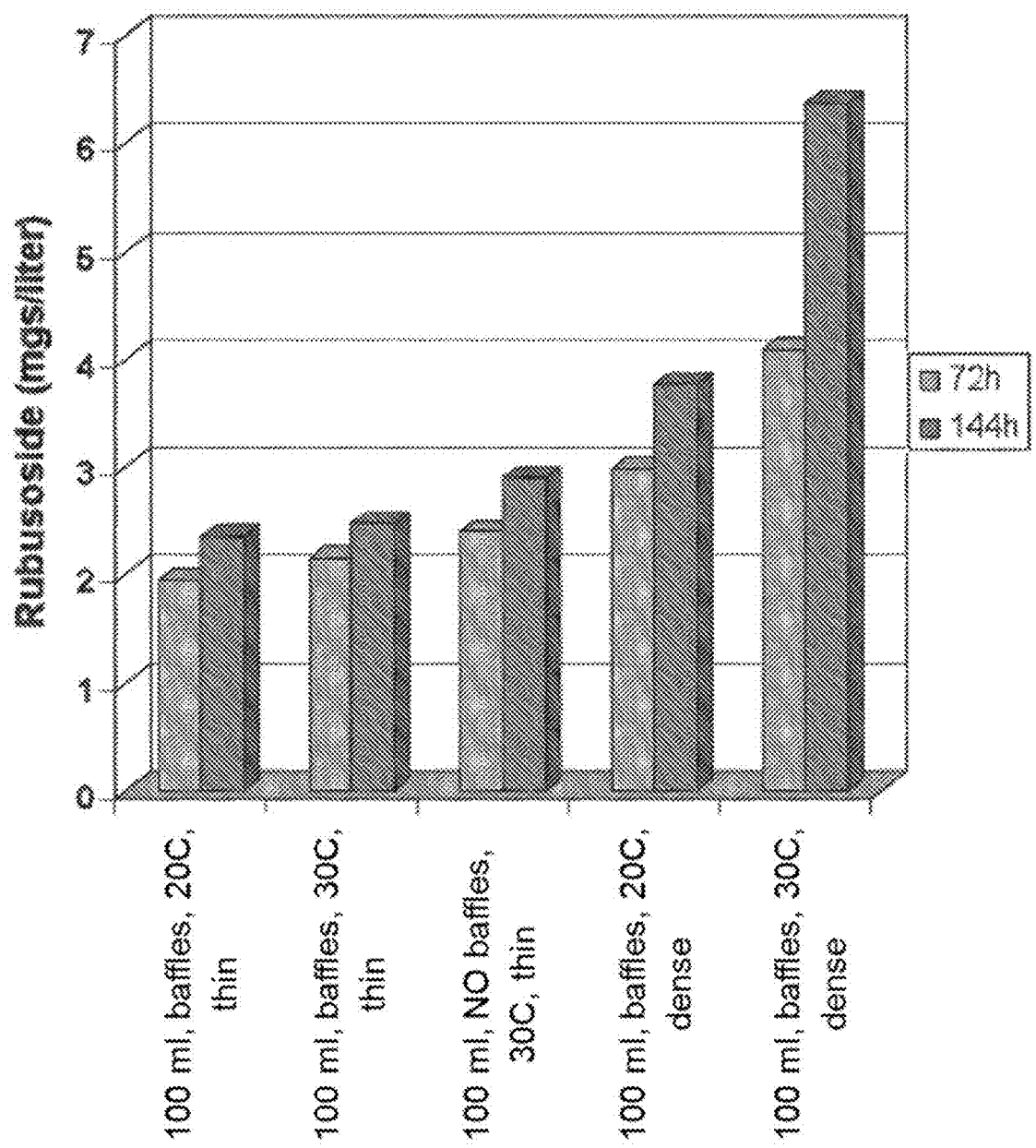
FIG. 6 shows rubusoside production by yeast strain CEY13 under various culture conditions.

As shown in FIG. 6, the density of the batch culture at fermentation start, the culture temperature and the length of time in fermentation, in combination, had a significant effect on the amount of rubusoside produced by CEY213. Thus, 144 hours growth of a culture with a starting density of $OD_{600}=1.0$, at 30° C., resulted in the production of no less than 8.5 mgs/liter of rubusoside.

Example 6—Large Scale Production of Rubusoside

A series of fermentation experiments with CEY213 were performed using 3 kinds of yeast medium (rich medium and two types of synthetic medium), varying inoculation density, and changing timing of eYAC gene cassette expression.

Batch Fermentation Conditions

Batch fermentation was carried out by centrifuging a CEY213 pre-culture, discarding the supernatant and re-suspending the cells in 6 liters of SC-TLH medium containing 100 µM methionine and 4% glucose. The $OD_{600}$ was adjusted to 1.0 in a 100 ml Ehrlenmeyer flask without baffles and the cells were allowed to grow for 144 hours at 30° C. with slow shaking.

Recovery of Rubusoside

After fermentation, the culture was centrifuged and the supernatant was mixed with an equal volume of methanol, shaken thoroughly, and centrifuged to remove precipitated material. The resulting supernatant was purified by flash C18-silica column chromatography with methanol as the eluent, followed by preparative HPLC to obtain one major compound, with one additional minor compound detected.

Figure 7:
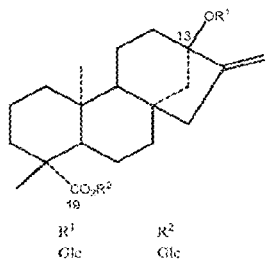
FIG. 7 shows data obtained from $^1$H and $^{13}$C NMR analysis of the compound produced by yeast strain CEY213, compared to literature values for rubusoside.

The purified compound was analyzed by $^1H$ and $^{13}C$ NMR, and the data are shown in FIG. 7. The compound was confirmed to be rubusoside based on comparison to $^1H$ and $^{13}C$ NMR literature values for rubusoside. Quantitative analysis indicated that CEY213 fermentation produced 12.8 mgs/liter of rubusoside.

Example 7—IP3GGT Activity 1. Enzymatic Activity of *Ipomoea purpurea* 3GGT glycosyltransferase in vitro The enzymatic activity of *Ipomoea purpurea* 3GGT glycosyltransferase (IP3GGT) using steviol as a substrate was determined in vitro. Genes for *Stevia rebaudiana* UGT85C2 and IP3GGT glycosyltransferase were each expressed in *E. coli* and each enzyme was purified.

The enzymatic reaction was performed in two steps. First, 0.5 mM steviol (9.55 mgs total) was incubated with ca. 0.5 µg UGT85C2 enzyme for 16 hours at 30° C. in a reaction buffer (containing 1 mM UDP-glucose, 100 mM Tris-HCl (pH 8.0), 5 mM $MgCl_2$, 1 mM KCl, 0.1 U/ul calf intestine phosphatase). Then ca. 0.5 µg IP3GGT enzyme was added and the reaction mixture incubated for an additional 20 hours at 30° C.

Analysis of the reaction products indicated about 100% conversion of steviol to steviol-13-O-monoside, 25% of which was further glycosylated into steviol-13-O-1,2-bioside. The theoretical steviol-13-O-1,2-bioside yield was about 4.8 mg. The reaction mixture was then subjected to preparative HPLC, which yielded 2.5 mg steviol-13-O-1,2-bioside (52% purification yield). Using LC-MS, the mass of the purified compound had a different retention time than rubusoside and steviol-13-O-1,3-bioside. The purified compound was subjected to 1H NMR, heteronuclear single quantum coherence (HSQC)-NMR and heteronuclear multiple bond correlation (HMBC)-NMR analysis, which confirmed that the compound was steviol-13-O-1,2-bioside.

2. In Vivo Expression of IP3GGT in Steviol- or Steviol Monoside-Fed Yeast

To determine whether the IP3GGT was active in yeast, the 2µ high copy (episomal) plasmid, pMUS10, containing an unmodified IP3GGT coding sequence operably linked to a strong GPD1 promoter was transformed into the yeast strain MUS1245. MUS1245 contains a genomically integrated UGT85C2 expression cassette. The resulting yeast strain was grown in SC medium without histidine to select for the continued presence of the IP3GGT expression plasmid, at a starting density of $OD_{600}=0.2$. Steviol or steviol monoside was added to the medium at 3 mM. After growth for 72 hours at 30° C., culture supernatants were assayed for the presence of steviol and steviol glucosides by HPLC.

LC-MS analysis indicated that no 1,2-glucosylated steviol-13-O-glucoside was detected after feeding with steviol, although steviol-13-O-monoside could be detected. In contrast, low but detectable amounts of the steviol 1,2-bioside were produced by MUS1245 carrying pMUS10 after feeding with steviol-13-O-monoside. These results show that the native *Ipomoea purpurea* 3GGT coding sequence is expressed in yeast at levels sufficient to obtain detectable in vivo conversion of steviol monoside to steviol 1,2-bioside.

Example 8—Modification of Yeast Strains

EXG1 and EXG2

*S. cerevisiae* may contain enzymes that degrade the 1,2 or 1,3 sugar bonds in steviol 1,2- and steviol 1,3-biosides. To test this possibility, yeast strain CEY213 was grown for 3 days at 30° C. on media containing 0.1 mM of each of the two biosides. LC-MS analysis of the culture showed the level of 1,2-bioside to be stable, whereas the 1,3-bond in the 1,3-bioside appeared to completely hydrolyse within the limits of detection of the assay.

Twenty-five *S. cerevisiae* mutants, each disrupted in one known or putative glycoside hydrolase gene, were examined for their ability to degrade steviol biosides. A culture of each yeast mutant was grown as described above on media containing steviol 1,3-bioside and analyzed by LC-MS. The yeast strain carrying a mutation in the EXG1 (exo-1,3-β-glucanase) gene was found to have lost most of the 1,3-bioside hydrolysing activity. The nucleotide sequence of the yeast EXG1 gene is reported in Vazquez de Aldana et al. *Gene* 97:173-182 (1991). The yeast strain carrying a mutation in the EXG2 gene (another exo-1,3-β-glucanase) showed a small decrease in hydrolysing activity. Correa, et al., *Current Genetics* 22:283-288 (1992).

A double mutant yeast strain (exg1 exg2) was made. When the double mutant strain was grown on media containing steviol 1,3-bioside, no hydrolysis of the bioside was detected.

Example 9—Increased Titer of Steviol Biosynthesis

Individual clones of enzymes from each of the different enzyme classes tested in Example 4 (and Table 11) were examined using eYAC technology to identify particular clones that exhibited the greatest production of steviol from isopentenyl pyrophosphate and farnesyl pyrophosphate. The GGPPS, KO and KAH enzymes have been tested on eYACs, individually or in the case of GGPPS enzymes individually or in pools of two (e.g., *Synechococcus* sp.+*S. acidocaldarius* GGPPS or *Aspergillus nidulans* GGPPS alone), in a *S. cerevisiae* strain expressing all remaining enzymatic steps in the steviol pathway. The results indicated that the *Synechococcus* spp. GGPPS clone MM-7 (encoded by SEQ ID NO:24) was the most efficient. GGPPS clones from *Aspergillus nidulans* and *Sulfulobus acidocaldarius* also were quite active. The results also indicated that among the KO and KAH clones, the *Stevia* KO clone MM-18 (encoded by SEQ ID NO: 52) and the *A. thaliana* KAH clone MM-24 (encoded by SEQ ID NO:62) resulted in the greatest steviol production.

TABLE 11

| Source Organism | Enzyme | gi Number | Accession Number | Coding Sequence | Coding Sequence Length (nucleotides) |
|---|---|---|---|---|---|
| Stevia rebaudiana | GGPPS-1 | 158104429 | ABD92926 | MM-1 | 1086 |
| Gibberella fujikoroi | GGPPS-2 | 3549881 | CAA75568 | MM-2 | 1029 |
| Mus musculus | GGPPS-3 | | BC069913.1 | MM-3 | 903 |
| Thalassiosira pseudonana | GGPPS-4 | 223997332 | XP_002288339 | MM-4 | 1020 |
| Sulfulobus acidocaldarius | GGPPS-6 | 506371 | BAA43200 | MM-6 | 993 |
| Synechococcus sp. | GGPPS-7 | 86553638 | ABC98596 | MM-7 | 894 |
| Cantharanthus roseus | GGPPS-9 | 1063275 | X92893 | EV270 | 1074 |
| Aspergillus nidulans | GGPPS-10 | 29468175 | AF479566 | C301 | 1191 |
| Xanthophyllomyces dendrorhous | GGPPS11 | 63145970 | DQ016502 | C413 | 1131 |
| Stevia rebaudiana | CDPS-1 | 2642661 | AAB87091 | MM-9 | 2364 |
| Streptomyces clavuligerus | CDPS-2 | 197705855 | EDY51667 | MM-10 | 1584 |
| Bradyrhizobium japonicum | CDPS-3 | 529968 | AAC28895.1 | MM-11 | 1551 |
| Arabidopsis thaliana | CDPS-4 | 18412041 | NM_116512 | EV-64 | 2409 |
| Zea mays | CDPS-5 | 50082774 | AY562490 | EV-65 | 2484 |
| Lycopersicon esculentum | CDPS-6 | 6009477 | AB015675 | EV-66 | 2403 |
| Stevia rebaudiana | KS-1 | 4959241 | AAD34295 | MM-12 | 2355 |
| Stevia rebaudiana | KS-2 | 4959239 | AAD34294 | MM-13 | 2355 |
| Zea mays | KS-3 | 162458963 | NP_001105097 | MM-14 | 1773 |
| Populus trichocarpa | KS-4 | 224098838 | XP_002311286 | MM-15 | 2232 |
| Arabidopsis thaliana | KS-5 | 3056724 | AF034774 | EV-70 | 2358 |
| Cucurbita maxima | KS-6 | 1431869 | U43904 | EV-71 | 2370 |
| Cucumis sativus | KS-7 | 21326756 | AB045310 | EV-72 | 2358 |
| Stevia rebaudiana | KO-1 | 76446107 | ABA42921 | MM-18 | 1542 |
| Arabidopsis thaliana | KO-2 | 3342249 | AAC39505 | MM-19 | 1530 |
| Gibberella fujikoroi | KO-3 | 74676162 | O94142 | MM-20 | 1578 |
| Trametes versicolor | KO-4 | 14278966 | AB057426 | MM-21 | 1500 |
| Stevia rebaudiana | KAH-1 | * | | MM-22 | 1578 |
| Stevia rebaudiana | KAH-2 | 189418962 | ACD93722 | MM-23 | 1431 |
| Arabidopsis thaliana | KAH-3 | 15238644 | NM_122399 | MM-24 | 1578 |

TABLE 11-continued

| Source Organism | Enzyme | gi Number | Accession Number | Coding Sequence | Coding Sequence Length (nucleotides) |
|---|---|---|---|---|---|
| Vitis vinifera | KAH4 | 225458453 | XM_002282055 | MM-25 | 1590 |
| Medicago truncatula | KAH5 | 84514134 | DQ335781 | MM-26 | 1440 |
| Stevia rebaudiana | CPR-1 | 189098311 | DQ269454.4 | MM-27 | 2133 |
| Arabidopis thaliana | CPR-2 | 145343899 | NM_118585 | MM-28 | 2079 |
| Gibberella fujikoroi | CPR-3 | 32562988 | AJ576025.1 | MM-29 | 2142 |

* U.S. Patent Publication No. 20080064063

S. cerevisiae strain CEY213, described in Example 4, was transformed with high copy plasmids carrying one of the CDPS or KS genes shown in Table 11, operably linked to the strong GPD1 promoter. Preliminary experiments indicated that overexpression of the Stevia rebaudiana CDPS (CDPS-1, encoded by SEQ ID NO:34) in CEY213 gave an increase in rubusoside production relative to CEY213 that lacked the high copy CDPS-1 overexpressing plasmid. The experiments also indicated that the Stevia rebaudiana KO (KO-1, encoded by SEQ ID NO:52) was the most active KO of the two tested.

To construct a yeast strain with consistently high levels of steviol glycoside production, expression cassettes containing the GGPPS-10 clone, the KO-1 clone (SEQ ID NO: 52) and the KAH-3 clone (SEQ ID NO:62) were stably integrated into the genome of the S. cerevisiae strain CEN.PK 111-61A. Expression of these cassettes was driven by the constitutive GPD1 and TPI1 promoters. In addition, expression cassettes containing KS-1 (SEQ ID NO:40), CDPS-1 (SEQ ID NO:34) and UGT74G1 (SEQ ID NO: 2) were stably integrated into the genome. The resulting yeast strain, EFSC1751, however, did not produce any steviol-19-O-monoside when grown at laboratory scale under the conditions described in Example 6.

To determine the basis for the lack of steviol glycoside production in EFSC1751, CDPS-3, CDPS-4, CDPS-5 and CPR-1 genes, alone or in combination, were expressed in strain EFSC1751. CPR-1 is from Stevia rebaudiana and its sequence can be found at Genbank Accession DQ269454.4. The results showed that CPR-1, when expressed with either CDPS-3, CDPS-4 or CDPS-5, resulted in production of steviol-19-O-monoside in EFSC1751. None of these genes alone in the same strain resulted in any production. These results indicate that the genomically integrated copy of CDPS-1, Stevia enzyme, is non-functional in this yeast construct, whereas the Bradyrhizobium, Arabidopsis or Zea CDPS clones were functional in this construct. In addition, the plant-derived KAH and/or KO genes integrated into the chromosome for this construct appear to require an exogenous CPR for activity. The CPR from Giberella fujikuroi (MM-29) also appears to be able to work with plant-derived KAH and/or KO polypeptides.

The two leading GGPPS candidates, GGPPS-6 (encoded by SEQ ID NO:23) and GGPPS-7 (encoded by SEQ ID NO:24), were further expressed individually in a S. cerevisiae strain that has a functional steviol glycoside pathway (including UGT74G1) but no GGPPS genes. Transformants then were analyzed for the production of 19-SMG by LC-MS analysis of culture samples that had been boiled in 50% DMSO for 5 minutes and centrifuged at 16000 relative centrifugal force (RCF) for 5 minutes. It was found that many transformants containing the GGPPS-6-expressing plasmid did not produce 19-SMG.

Very few transformants were obtained containing GGPPS-7, indicating that GGPPS-7 (Synechococcus sp.) may be the more active of the two enzymes, and that the activity could be high enough to confer toxicity. For example, a dramatic increase in GGPP production could result in a drain on a downstream pathway such as ergosterol production. To test this hypothesis, a UP (2-1 gene was co-expressed with GGPPS-7, and ergosterol feeding of the cells was attempted to see if this would rescue growth of cells. However, cell growth was not rescued.

Cell toxicity also may be due to an accumulation of GGPP or a metabolite of GGPP. To test this hypothesis, CDPS-5 was further overexpressed in the GGPPS-7-expressing yeast strain to see if the toxicity could be alleviated by increased GGPP usage. CDPS5 over-expression did appear to rescue growth to some extent since transformants with a plasmid overexpressing this enzyme along with the GGPPS-7 gave rise to a few colonies. The number of transformants was still low. Over-expression of CDPS-5 in a similar strain but with GGPPS-10 instead of GGPPS-7 resulted in a doubling of steviol glycoside production, and these results together could suggest that CDPS is a limiting bottleneck in the introduced steviol glycoside biosynthesis pathway.

In summary, based upon production of 19-SMG or rubusoside in test tube cell cultures at 30° C. with yeast medium+ 2% glucose, for 24-72 hours, the following conclusions were made with the eYAC constructs: KS-1 (Stevia rebaudiana, encoded by SEQ ID NO:40), KO-1 (S. rebaudiana, encoded by SEQ ID NO:52) and KAH-1 (S. rebaudiana) or KAH-3 (Arabidopsis thaliana, encoded by SEQ ID NO:62) appear to be the best combinations for the steviol pathway. GGPPS-7 (Synechococcus sp.) appears to show the highest amount of activity for this step, but if downstream bottlenecks occur overexpression also could lead to toxicity and overall lower levels of steviol glycosides. All combinations of CDPS and CPR gene analogs were tested and it was found that all 3 CPRs in Table 11 were active, and that combinations of CPR-1 (S. rebaudiana, encoded by SEQ ID NO:70) or CPR-3 (Gibberella fujikuroi, encoded by SEQ ID NO:72) with either CDPS-5 (Zea mays) or CDPS-4 (A. thaliana) were particularly useful. CDPS-5 appears to be the optimal CDPS in the pathway. Combinations can be further tested in a reporter strain with reduced flux to sterol pathways.

To investigate the potential for even higher activity of the CDPS from Zea mays (CDPS-5), this gene was expressed from a 2 micron multicopy plasmid using the GPD promoter, with and without a plastid signal peptide, to determine if activity is higher in the cytoplasm when targeting sequences are removed. The nucleotide sequence and amino acid sequence of the CDPS-5 from Zea mays and containing the chloroplast signal peptide are set forth in SEQ ID NOs: 80 and 81, respectively. The chloroplast signal peptide is encoded by nucleotides 1-150 of SEQ ID NO:80, and corresponds to amino acids 1 to 50 of SEQ ID NO:81. The plasmid was transformed into the stable rubusoside producer strain (EFSC1859) that has GGPPS-10, CDPS-5, KS-1, KO-1, KAH-3, CPR-1 and UGT74G1 (SEQ ID NO:2) integrated into the genome and expressed from the strong constitutive GPD and TPI promoters. Furthermore, in strain EFSC1859, expression of squalene synthase, which is encoded by ERG9, was downregulated by displacement of the endogenous promoter with the CUP1 inducible promoter. In addition to these genes, strain EFSC1859 also expresses UGT85C2 (SEQ ID NO:3) from a 2 micron multicopy vector using a GPD1 promoter. Rubusoside and 19-SMG production were measured by LC-MS to estimate the production level. The removal of the plastid leader sequence did not appear to increase steviol glycoside production as compared to the wild-type sequence. However, this work demonstrates that the leader sequences can be removed without causing a loss of steviol pathway function.

Similarly, plasmids were constructed for CPR-3, KAH-3 and KO-1 without membrane anchoring sequences (i.e., nucleotides 4-63 of SEQ ID NO: 72; nucleotides 4-87 of SEQ ID NO:62; and nucleotides 1-117 of SEQ ID NO:52) and were transformed into strain EFSC1859 with the UGT85C2 integrated on the chromosome rather than on a plasmid. It is expected that these enzymes will be functional without the anchoring sequence.

Example 10-Identification of Steviol-1,3-O-Monoglucoside 1,2-Glucosyltransferase Sequences

*Stevia* EST Analysis

A tBLASTN search of a *Stevia* (*Stevia rebaudiana*) leaf EST (Expressed Sequence Tags) database (Brandle et al., Plant Mol. Biol. 50:613-622, 2002) was carried out using complete *Ipomoea* (*Ipomoea purpurea*) UGT79 type UGT (IP3GGT), *Bellis* (*Bellis perennis*) UGT94B1, *Stevia* UGT79A2, *Stevia* UGT76G1 and *Stevia* UGT91D1 amino acid sequences as queries, thus representing UGTs from all Family 1 glycosyltransferase sub-families known to primarily contain diglycosyltransferases. Partial sequences for 9 previously undescribed UGT genes were identified. One of the partial sequences was from the UGT 79 sub-family ("79-EV1"), one from the UGT 76 sub-family ("76-EV1") and two from the UGT 91 sub-family ("91-EV-1" and "91-EV2"), as well as members of the UGT 71, 72, 78, 84 and 88 sub-families. Seven of the partial sequences were isolated using *Stevia* cDNA or cDNA libraries as the PCR template for isolation. In addition, two *Stevia* members of the UGT 76 sub-family were isolated, GenBank accession ACT33422.1 which is a member of the 76G1 sub-family (Mohankumar), and GenBank accession ACM47734.1 which is a member of the 76G2 (Yang) sub-family.

Pyrosequencing

Additional UGT clones were identified and isolated by performing pyrosequencing with *Stevia* cDNA as follows. *Stevia* mRNA was prepared from *Stevia* leaves, using the Ambion® Micro Poly Purist™ mRNA preparation kit. As a quality control, reverse transcribed mRNA was tested for the presence of the *Stevia* Rebaudioside A pathway UGT genes 85C2, 74G1 and 76G1, by employing analytical PCR with oligonucleotide primers identical to 21 nucleotides at the 5'- and 3'-termini of each sequence. The amplified full length mRNA was then used for pyrosequencing and contig assembly (MOgene, St. Louis, MO USA). About 3.4 million reads of an average length of 393 nucleotides were performed, and the resulting raw sequences used to obtain 25907 sequence contigs. A database was constructed, containing publicly available amino acid sequences of a total of ca. 1,500 UGTs. About 150 of the sequenced UGTs were fully annotated UGTs from a wide variety of sub-families. The remaining sequenced UGTs were partially annotated homologs of these. A BLASTX search was performed (CLC Genomics, Muehltal, Germany), using the 25907 *Stevia* EST contigs as query, to the fabricated UGT database (Genetic code=1, Low complexity=Yes, Expect value=10.0, Word size=3, No of processors=2, Matrix=BLOSUM62, Gap cost (open)=11, Gap cost (extension)=1). The results suggested that sequences for more than 90 previously unknown UGTs from *Stevia* were present in the pyrosequencing database.

No additional members of the UGT 79 sub-family or the UGT 94 sub-family were identified in the pyrosequencing database. However, the analysis showed new members of the UGT 76 and 91 sub-families. For a few of the genes, full length sequence data was immediately available from the pyrosequencing EST data. A previously constructed *Stevia* plasmid cDNA library was used to obtain full-length sequences for those members for which partial sequence data was obtained. An oligonucleotide primer identical to each specific, partial UGT sequence was combined with an oligonucleotide primer identical to the library plasmid vector sequence. These primers were employed in PCR to obtain the full length product, which was subsequently sequenced. Based on the full length sequence, a second PCR was performed using a proof-reading PCR polymerase enzyme for amplification of the full length UGT gene from a *Stevia* cDNA library as the template for the reaction. Using this strategy, five members of the UGT 76 sub-family, six members of the UGT 91 sub-family, as well as ten members of other UGT sub-families were isolated.

Each of the 7 UGTs identified from the *Stevia* EST database, the 2 publicly available *Stevia* UGT 76 sequences, and the 21 UGTs identified from pyrosequencing was cloned into the *E. coli* expression vectors pET30A+ or pETDuet (making use of the HIS-tag for purification purposes) and expressed in the autolysis-prone *E. coli* strains XjA and XjB. For a large number of these UGTs, expression of the UGT protein resulted in the formation of inclusion bodies. In order to overcome formation of those inclusion bodies, some of these UGTs were expressed in the low temperature expression strain "Arctic Express" (Agilent Technologies). For those which failed to express in this system, coupled in vitro transcription-translation of PCR products (TNTXT7 Quick for PCR DNA kit, Promega) was attempted, allowing successful expression of the remaining UGTs. Efficiency of the reaction was ensured by labeling with 35S-methionine, separation on SDS-PAGE and phosphorimaging detection of a protein band of the expected size for the UGT protein in question.

UGT polypeptides from each clone, expressed as described above, were tested for 1,2-glycosylation activity, using steviol-13-O-monoglucoside as substrate. In vitro transcribed/translated protein, corresponding to approximately one fifth of the total protein formed in a 25 μL reaction, was used in an in vitro reaction, using 0.5 mM steviol-13-O-monoglucoside (SMG) as substrate, in a reaction buffer (containing 1 mM UDP-glucose, 100 mM Tris-HCl (pH 8.0), 5 mM $MgCl_2$, 1 mM KCl, 0.1 U/μl calf intestine phosphatase). The reaction mixture was incubated at 30° C. for 20 hours. The reaction mixture was then analyzed by LC-MS analysis for the presence of Steviol-1,2-bioside. LC-MS analyses were performed using an Agilent 1100 Series HPLC system (Agilent Technologies) fitted with a Phenomenex® Synergy Hydro-RP column (250×3 mm, 3 μm particles, 80 Å pore size) and hyphenated to a TSQ Quantum (ThermoFisher Scientific) triple quadrupole mass spectrometer with electrospray ionization. Elution was carried out using a mobile phase (30° C.) containing MeCN (0.01% Formic acid) and H$_2$O (0.01% Formic acid) by applying a gradient composed of 0.6→0.4 ml/min, 5% MeCN for 4 min; 0.4 ml/min, 5→40% MeCN for 2 min; 0.4 ml/min, 40→55% MeCN for 11 min; 0.4→1.0 ml/min, 55→100% MeCN for 3 min. Steviol biosides were detected using SIM (Single Ion Monitoring) on Mw 665.2 [M+Na$^+$]. None of the 30 UGT enzymes tested exhibited detectable steviol-13-O-monoglucoside glycosylation activity.

The nucleotide sequences of the six UGT91 members identified by pyrosequencing were compared to the sequence of *Stevia* UGT91D1 in Genbank Accession No. AY345980. It appeared that the GenBank sequence encoded 12 additional amino acids at the N-terminus, relative to the six sequences identified by pyrosequencing. To re-test UGT91D1 family members for activity, UGT91D1 sequences were re-isolated by PCR amplification of *Stevia* leaf cDNA. The resulting PCR products were cloned into a plasmid vector and enzymatic activity for each product was measured as described above by: GST-tagged expression in *E. coli*, coupled in vitro transcription-translation, and/or in vivo expression in yeast. Steviol 1,2-glucosylation activity was detected from one clone by all three methods. This clone was designated UGT91D2e. The amino acid sequence of UGT91D2e is set forth in SEQ ID NO:5. In contrast, no 1,2-glucosylation activity was detected from a clone having the same sequence as described by Accession No. AY345980 (Protein Accession number AAR06918), but lacking the 12 amino acids of the amino terminus.

Example 11—Analysis of UGT91D2e Sequences

Sequence Variants of UGT91D2e

As evidenced in FIG. 8, a small number of amino acid modifications exist between the active (91D2e) variants and the closest inactive homologs (91D1). The 91D1 genes cloned by Ma et al., *Shi Yan Sheng Wu Xue Baa*. 2003 36 (2): 123-9 (Protein Accession number AAM53963, GI: 21435782) and Brandle et al., supra (Protein Accession number AAR06918, GI: 37993665) did not exhibit the 1,2-glycosylating activity required for RebA biosynthesis. To ascertain which amino acids are required for activity, 21 single site-directed mutants were created such that the amino acid in UGT91D2e (SEQ ID NO:5) was changed to the corresponding amino acid in an inactive homolog. See Table 12. In addition, a site-directed mutation was made such that position 364 (S→P) also was changed. The mutants were made using the QuikChange® II Site-Directed Mutagenesis kit according to manufacturer's protocols (Agilent Technologies, Santa Clara, Calif.), and the pGEX-4TI vectors were transformed into a XJb Autolysis *E. coli* strain (ZymoResearch, Orange, Calif.). A mutant was not made to change residue 162 from a glycine to an aspartic acid.

In order to assess the activity of the mutant enzymes, a substrate-feeding experiment was performed in vitro using protein produced in *E. coli*. Initially, *E. coli* cells were grown overnight at 30° C., followed by induction with 3 mM arabinose and 0.1 mM IPTG, and further incubation at 20° C. For the in vitro assay, cells were induced overnight at 20° C., lysed by a freeze/thaw cycle, and the crude cell extract used for an enzymatic reaction in which the substrates were 0.5 mM steviol-13-O-glucoside and 0.5 mM rubusoside.

The results are shown in Table 12 for the steviol monoglucoside (SMG) and Rubusoside (Rub) substrates. A "+" indicates that diglycosylation activity was detected, a "−" indicates activity was not detected, and "NA" indicates the assay was not performed. The noted mutations are based on the numbering of the 91D2e sequence (SEQ ID NO:5).

As some of the genes have a tendency to express in inclusion bodies in *E. coli*, the coding sequences that did not show activity in the *E. coli* experiments also were produced by coupled in vitro transcription-translation of PCR products (TNT® T7 Quick for PCR DNA kit, Promega) as above in Example 10. Briefly, 2 μL of DNA from the PCR amplification of the five single mutants and the wild type enzyme were incubated for 90 minutes at 30° C. with the kit master mix and 1 μL L-[$^{35}$S]-Methionine, in a total of 25 μL reaction. For each sample, a volume of 2 μL final reaction was run on a SDS-PAGE gel. All six proteins showed similar levels of soluble recombinant protein as judged by visual observation of the SDS-PAGE gel. The results for the in vitro-translated proteins are shown on the right side of Table 12. The percentages in this table indicate the approximate amount of conversion of substrate to product based on relative peak areas of substrate and product.

TABLE 12

| Mutation | E. coli protein SMG | E. coli protein Rub | in vitro protein SMG | in vitro protein Rub |
| --- | --- | --- | --- | --- |
| Y30→F | + | + | NA | NA |
| P93→Q | + | + | NA | NA |
| S99→V | + | + | NA | NA |
| Y122→F | + | + | NA | NA |
| H→140Y | + | + | NA | NA |
| S142→C | + | + | NA | NA |
| T144→I | − | − | 5.9% | 0.05% |
| A148→T | + | + | NA | NA |
| M152→L | − | − | 25.1% | 0.85% |
| G153→A | + | + | NA | NA |
| A156→S | + | + | NA | NA |
| L195→M | + | + | NA | NA |
| V196→E | + | + | NA | NA |
| K199→E | + | + | NA | NA |
| L211→M | + | + | NA | NA |
| L213→F | − | − | 29.4% | 1.59% |
| S221→F | + | + | NA | NA |
| V286→A | + | + | NA | NA |
| S364→P | − | − | 4.1% | 0.4% |
| G384→C | − | − | 14.1% | 1.28% |
| K427→N | + | + | NA | NA |
| E438→A | + | + | NA | NA |

The approximate amount of diglycosylation activity as compared to UGT91D2e (SEQ ID NO:5) was found to be: 6.1% for T144S, 26.2% for M152L, 30.7% for L213F, 4.3% for S364P, and 14.7% for G384C using 13-SMG as substrate. For rubusoside, the approximate amount of diglycosylation activity as compared to UGT91D2e was 1.4%, 23.4%, 43.7%, 10.9% and 35.2% for T144S, M152L, L213F, S364P, and G384C, respectively.

These results indicate that 5 of the 22 amino acid mutations were noticeably deleterious for activity when done in isolation. It is also possible that combinations of the other 17 mutations also could result in inactivity or loss of activity.

By aligning the 91D2e sequences and the variants described above with proteins termed At72B1, Mt85H2, VvGT1 and Mt71G1 (Osmani et al (2009) *Phytochemistry* 70, 325-347), and analyzing predicted tertiary structures (alpha helices, beta-sheets, and coil regions), regions can be identified where mutations are likely to result in loss of diglycosylation activity. The first three mutations that are deleterious are found in the N-terminal domain, in regions that are thought to be loops. The N-terminal domain (amino acid residues 1-240), in particular the predicted loop regions of the N-terminal domain (amino acids 20-26, 39-43, 88-95, 121-124, 142-158, 185-198, and 203-214), are thought to be primarily responsible for binding of the glucose acceptor molecule substrate. The fourth mutation that appears to be deleterious for activity is found in the C-terminal domain, in a region that is believed to be the C5 loop (corresponding to amino acids 381-386). This loop is also thought to be important for glucose acceptor substrate specificity. Nineteen of the twenty-two mutations that separate the inactive versus the active rubusoside diglycosylase enzymes are located within five amino acids of the predicted acceptor substrate binding regions of 91D2e. Therefore it is likely that the published 91D1 enzymes catalyze a glycosyl transferase reaction between UDP-glucose and an alternative acceptor substrate.

Example 12—Production of Rebaudioside A in Yeast

Production of Rebaudioside A in Steviol-Fed Yeast

The yeast strain EFSC1580, which contains a genomically integrated UGT74G1 expression cassette, was transformed with three different 2μ high copy (episomal) plasmids for co-expression of Stevia UGTs 91D2e (SEQ ID NO:5), 85C2 (SEQ ID NO: 3), and 76G1 (SEQ ID NO:7). The three plasmids, designated pMUS44, pMUS7 and pMUS9, contain coding sequences for UGT91D2e, UGT85C2 and UGT76G1, respectively, operably linked to the strong GPD1 promoter. The resulting yeast strain was grown in SC medium without uracil, histidine, and leucine to select for the continued presence of the pMUS44, pMUS7 and pMUS9 expression plasmids. Steviol was added to the medium to a final concentration of 250 μM, and the strain was cultured at 30° C. At 18 hours and 72 hours of culture, aliquots of the supernatants and cell pellets were analyzed for the presence of Rebaudioside A by LC-MS. LC-MS analyses were performed using an Agilent 1100 Series HPLC system (Agilent Technologies, Wilmington, DE, USA) fitted with a Phenomenex® Synergy Hydro-RP column (250×3 mm, 3 μm particles, 80 Å pore size) and hyphenated to a TSQ Quantum (ThermoFisher Scientific) triple quadrupole mass spectrometer with electrospray ionization. Elution was carried out using a mobile phase (30° C.) containing MeCN (0.01% Formic acid) and $H_2O$ (0.01% Formic acid) by applying a gradient composed of 0.6→0.4 ml/min, 5% MeCN for 4 min; 0.4 ml/min, 5→40% MeCN for 2 min; 0.4 ml/min, 40→55% MeCN for 11 min; 0.4→1.0 ml/min, 55→100% MeCN for 3 min. Steviol biosides were detected using SIM (Single Ion Monitoring).

LC-MS results showed that detectable amounts of Rebaudioside A were found in the supernatant at 18 and 72 hours of culture when strain EFSC1580 containing pMUS44, pMUS7 and pMUS9 was grown in the presence of steviol. The product co-eluted with a Rebaudioside A standard and the expected mass was confirmed as the $[M+Na]^+=989$. By comparing the absorbance of the product to the absorbance of a 10 μM Rebaudioside A standard, the accumulation in the supernatant of the cell culture was estimated to be more than 6 mg/L at 18 hours, and more than 15 mg/L at 72 hours.

Production of Rebaudioside A and Rebaudioside D in Glucose-Fed Yeast

Yeast strain CEY213, described in Example 4, contains steviol biosynthetic pathway genes expressed from eYACs as well as genomically integrated UGT74G1 and UGT85C2 expression cassettes. Strain CEY213 produces rubusoside, as described in Example 6.

Strain CEY213 was transformed with a 2μ high copy (episomal) dual expression plasmid, pMUS47, for simultaneous expression of UGT91D2e (SEQ ID NO:5) and UGT76G1 (SEQ ID NO:7). The pMUS47 plasmid contains two expression cassettes, one having the coding sequence of UGT91D2e and the other having the coding sequence of UGT76G1. Both coding sequences are operably linked to the strong constitutive GPD1 promoter. The resulting yeast strain was pre-cultured overnight at 30° C. in SC medium without histidine, leucine and tryptophan in order to maintain selection for the presence of eYACs, without uracil in order to maintain selection for the presence pMUS47, and finally with methionine (2 mM) in order to suppress promoters present on the eYACs. The next day, the cells were washed and transferred to an identical medium, but without methionine, for induction of the eYAC promoters. Samples were collected after 24 hours and 99 hours of incubation, and supernatants and cell pellets analyzed for the presence of Rebaudioside A and Rebaudioside D, using LC-MS as described above.

Figure 9:
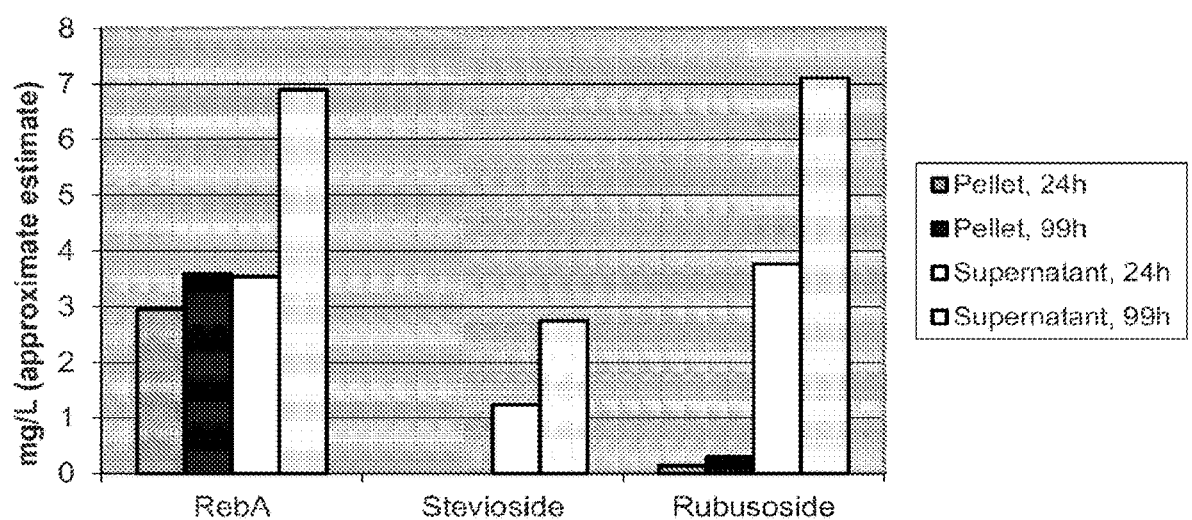
FIG. 9 shows Rebaudioside A, stevioside, and rubusoside production by yeast CEY213 containing plasmid pMUS47 after 24 and 99 hours of culture.

The results showed that detectable amounts of Rebaudioside A were found in the supernatants at both 24 and 99 hours. The product co-eluted with a Rebaudioside A standard and the expected mass was confirmed as the $[M+Na]^+=989$. By comparing the absorbance of the product to a 10 μM Rebaudioside A standard, the accumulation of Rebaudioside A in the supernatant was estimated to be more than 3 mg/L at 24 hours and more than 6 mg/L at 99 hours. See FIG. 9. The results also indicated that small amounts of stevioside and rubusoside were present in the yeast cell pellet and that detectable amounts of stevioside and rubusoside were present in the culture supernatant. See FIG. 9.

The results also showed that small but detectable amounts of Rebaudioside D were produced, suggesting that UGT91D2e is capable of conjugating an additional glucose to the 19-O glucose of either stevioside producing Rebaudioside E or directly to the 19-O glucose of Rebaudioside A. These results also suggest that UGT76G1 may be capable of accepting Rebaudioside E as a substrate to produce Rebaudioside D. See FIG. 2C.

Example 13—Production of Rebaudioside A with Codon Optimized Sequences for UGT Sequences Optimal coding sequences for UGT 91d2e, 74G1, 76G1, and 85C2 were designed and synthesized for yeast expression using two methodologies, supplied by GeneArt (Regensburg, Germany) (SEQ ID NOs: 6, 2, 8, and 4, respectively) or DNA 2.0 (Menlo Park, CA) (SEQ ID NOs: 84, 83, 85, and 82, respectively). The amino acid sequences of UGT 91d2e, 74G1, 76G1, and 85C2 (SEQ ID NOs: 5, 1, 7, and 3, respectively) were not changed.

High copy number plasmids containing expression cassettes with all four optimized UGTs were constructed and expressed, and their activity compared to expression products of similar constructs containing wild-type sequences. The plasmids were transformed into the universal Watchmaker strain, EFSC301 (described in Example 3). UGTs were inserted in high copy (2μ) vectors and expressed from a strong constitutive promoter (GPD1) (vectors P423-GPD, P424-GPD, P425-GPD, and P426-GPD). After overnight growth and re-inoculation in fresh media at an $OD_{600}$ of 0.25, the culture medium (SC-leu-trp-ura-his) was supplemented with 25 μM steviol (final concentration), and production of Rubusoside (Rub), 19-SMG (19SMG) and RebA (RebA) was measured in the media after 24 h. The experiment was repeated, in part due to the fact that 19-SMG was undetectable in one of the first samples.

The results from the two separate studies, shown in Table 13 below, indicate that all eight of the codon-optimized UGTs were active. However, enzyme expression for at least one of the codon-optimized UGTs in each strategy was reduced by the new codon optimization algorithm used to make the constructs. It appears that in the GeneArt modified constructs (SEQ ID NOs: 6, 2, 8, and 4), a bottleneck was potentially created between rubusoside and RebA. It is expected that individual enzyme activity assays and expression analyses of these coding sequences expressed in the yeast strains will allow for the optimal combination of UGT genes in the pathway.

TABLE 13

|  | RebA (μM) | 19SMG (μM) | Rub (μM) |
|---|---|---|---|
| Wild-type | 3.2 | 17.2 | 4.9 |
|  | 1.7 | 14.0 | 3.2 |
| DNA2.0 | 4.4 | 12.4 | 4.6 |
|  | 1.7 | 10.8 | 3.1 |
| GeneArt | 1.2 | nd | 4.6 |
|  | 0.8 | 11.1 | 4.5 | nd = below detection limit

Example 14—Production of Rebaudioside a Using UGTs with Sequence Tags

Fusions of small peptides or protein binding domains with the UGT proteins 85C2, 91D2e, 74G1, and 76G1 can promote interactions between the UGTs (channeling) or aid in targeting/anchoring the UGTs to specific components of the yeast cells.

To assess if scaffolding of the UGTs in the RebA pathway could result in active pathway enzymes, the DNA 2.0 codon-optimized UGTs 85C2 and 74G1 were fused in-frame to a string of 4 high-affinity, short (also known as PMI) peptides that resemble the p53 protein motif. The p53 protein motif interacts with the MDM2 protein in humans (see Li et al., *J Mol Biol.* 2010, 398 (2): 200-13). DNA 2.0 codon-optimized UGTs 85C2, 91D2e, 74G1 and 76G1 (SEQ ID NOs: 82, 84, 83, and 85, respectively) were fused in-frame to the first 158 amino acids of the human protein MDM2 (gene accession number ABT17086). A small GS-rich linker region also was fused just prior to the N-terminal methionine of the UGTs. Unfused, the affinity of PMI/MDM2 binding is in the low nM range representing a high-affinity binding. Yeast cells transformed with the above constructs are expected to produce a UGT scaffold around the 4×PMI (P53-like) peptide repeat fused N-terminally to the 85C2 protein (designated 85C2_P53) scaffold.

Figure 10A:
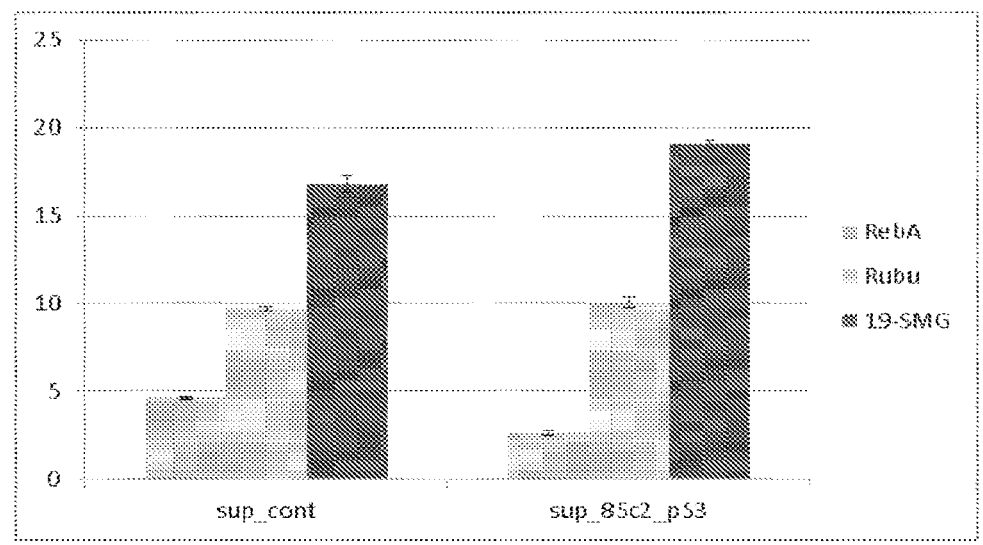
FIG. 10A is a graph illustrating the concentrations of RebA, rubusoside and 19-SMG in supernatants.
Figure 10B:
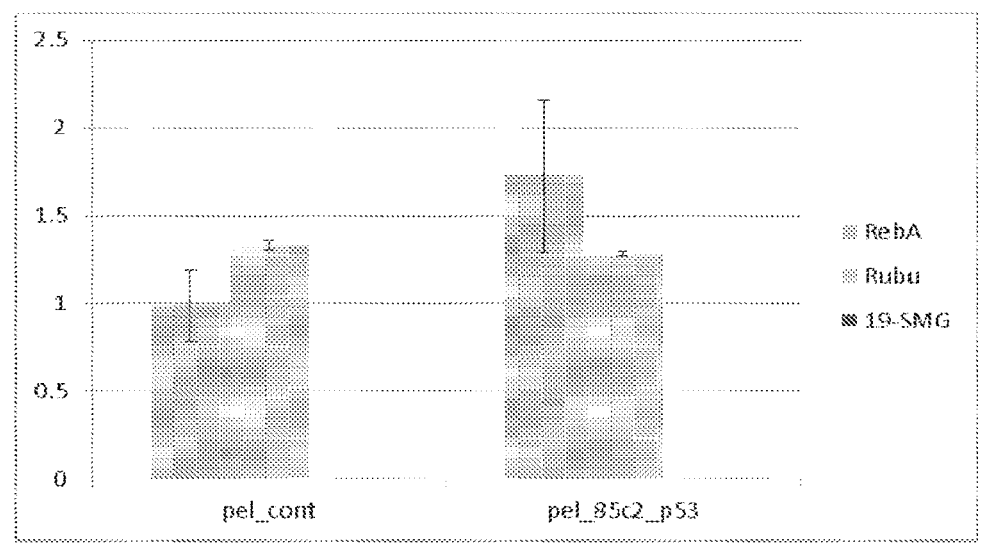
FIG. 10B is a graph of the concentrations of RebA, rubusoside and 19-SMG measured in cell pellets, for experiments where yeast cells were fed with 100 μM steviol. In both graphs, the first set of bars represents the untagged control strains; the second set of bars represents the strain containing the UGT74G1, UGT76G1, and UGT91D2e fusion proteins in which the N-terminal 158 amino acids of the MDM2 protein are fused to each UGT, and a UGT85C2 fusion protein in which four repeats of the synthetic PMI peptide is fused in-frame to the N-terminus of 85C2. The y-axis is concentration in micromolar units.

The laboratory yeast strain BY4741, deleted for TRP1, was transformed with expression plasmids p423-426 GPD (Mumberg et al, *Gene*, 156 (1995), 119-122) expressing *Stevia rebaudiana* UGTs 74G1,76G1 and 91D2e with N-terminal, in-frame fusions of the first 158 amino acids of human MDM2 protein, and expressing *Stevia rebaudiana* UGT85C2 with an N-terminal in-frame fusion of 4 repeats of the synthetic PMI peptide (4×TSFAEYWNLLSP, SEQ ID NO:86). See SEQ ID NOs: 88, 90, 92, and 94 for the amino acid sequences of the 85C2, 74G1, 91D2e, and 76G1 fusion proteins, respectively; see SEQ ID NOs: 89, 92, 93, and 95 for the nucleotide sequences encoding the fusion proteins. This yeast strain and a control strain (expressing the four UGT's without any fusions) were grown overnight in synthetic yeast medium selecting for the presence of plasmids and then transferred the next day to a 96 deep-well tray containing synthetic yeast medium to a cell density giving an $OD_{600}$ of 1. A final concentration of 100 μM steviol was added. After 72 hours, samples were taken and analysed by LC-MS, as described in Example 12. As indicated in FIGS. 10A and 10B, the UGTs are active in yeast when expressed with the various fusion tags.

Example 15—UGT91D2e Activity

Additional sub-family 91 UGTs were cloned using cDNA/library preparations made from 3 *Stevia* sources of different genetic backgrounds. Oligonucleotide primers identical to UGT91D1/91D2e were used for PCR amplification of the cDNA preparations, and the resulting PCR products of correct size were cloned into appropriate plasmid vectors. Numerous clones from each experiment were sequenced, and the sequencing results showed that UGT91D nucleic acids with slight variations in sequence could be amplified. The twenty UGT91D variants with the greatest differences in sequence relative to UGT91D2e were expressed by in vitro transcription-translation followed by enzymatic testing for steviol-13-O-monoglucoside-1,2-glucosylating activity. One of the variants showed weak 1,2-bioside glucosylation activity, while the reminder showed no detectable glucosylation activity. It therefore appears that UGT91D2 polypeptides are the primary steviol-13-O-monoglucoside-1,2-glucosylating enzymes in *Stevia*.

Enzymatic Activity of UGT91D2e

UGT91D2e (SEQ ID NO:5), made by coupled in vitro transcription-translation, was tested for the ability to xylosylate and rhamnosylate steviol-13-O-monoglucoside in an in vitro enzyme assay, using UDP-xylose or UDP-rhamnose as the sugar donors rather than UDP-glucose.

The xylosylation assay was performed as follows: 3 mM UDP-glucuronic acid was mixed with ca. 1 μg *Arabidopsis thaliana*-encoded UDP-glucuronic acid decarboxylase UXS3 (produced in *E. coli* and then purified), 100 mM Tris-HCl (pH 8.0), 1 mM DTT, 6 μg BSA, 1 mM $MgCl_2$, and 1% calf intestine phosphatase. The reaction mixture was incubated for 30 minutes at 30° C., in order for UDP-glucuronic acid to be turned into UDP-xylose. Then 1.5 mM steviol-13-O-monoglucoside substrate and ca. 0.5 μg UGT91D2e enzyme made as described in Example 9 was added to the mixture, which was allowed to incubate at 30° C. for an additional 20 hours.

The rhamnosylation assay was performed in the following way: 3 mM UDP-glucose was mixed with 0.6 μg of each of the N-terminal and C-terminal parts of *Arabidopsis thaliana*-encoded RHM2 rhamnose synthetase (produced in *E. coli* and then purified), 100 mM Tris-HCl (pH 8.0), 1 mM DTT, 1.5 mM NADPH, 1.5 mM NAD+, 6 μg BSA, 1 mM $MgCl_2$, and 1% calf intestine phosphatase. The reaction mixture was incubated for 30 minutes at 30° C., in order for UDP-glucose to be turned into UDP-rhamnose. Then 1.5 mM steviol-13-O-monoglucoside substrate and ca. 0.5 μg UGT91D2e enzyme was added to the mixture, which was allowed to incubate at 30° C. for an additional 20 hours.

The results indicated that UGT91D2e was capable of carrying out xylosylation of the steviol-13-O-monoglucoside substrate at about one half to one third the rate observed with UDP-glucose, forming 1,2-xylosylated steviol-13-O-monoside, which is a precursor to Rebaudioside F. UGT91D2e was capable of carrying out rhamnosylation of the steviol-13-O-monoglucoside substrate at about the same rate as the rate observed with UDP-glucose, forming 1,2-rhamnosylated steviol-13-O-monoside, which is a precursor for Rebaudioside C (Dulcoside B). These results indicate that synthesis of appropriate precursor molecules and expression of appropriate UGTs in vivo should result in the production of Rebaudioside F and C in vivo. See FIGS. 2B and 2D.

that were isolated. The numbering of the amino acids in Table 14 is based on the amino acid sequence of UGT91D2e set forth in SEQ ID NO:5.

TABLE 14

| Clone | Mutations as compared to UGT91D2e (SEQ ID NO: 5) |
|---|---|
| 1 | +1 frameshift between residues 119-145 in the nucleotide sequence, G165V, I367V, L388P |
| 2 | 27 bp deletion starting at nucleotide 728, K214R |
| 3 | D205G, V286A, Y443C |
| 4 | L28P, Y30F, P93Q, S99V, E111Q, I118V, Y122F, H140Y, S142C, T144I, A148T, M152L, G153A, A156S, G162D, L195M, V196E, K199E, L211M, L213F, S221F, L411S, V425A |
| 5 | G206R, Y207C, W343R |
| 6 | Q13R, F46S, S99P, D395G |
| 7 | Y30F, S364P, G384C, K427N, E438A |
| 8 | Y94C, A132V, Y224C, G384C, K427N, E438A, Q455R |
| 9 | K222E, T341M, G384C |
| 10 | Y94C, A132V, Y224C, K313N, R334C, G384C |
| 11 | Y30F, K222E, V286A, G384C, K427N, E438A |
| 12 | Y30F, P93Q, S99V, Y122F, H140Y, S142C, T144I, T145N, A148T, M152L, G153A, A156S, G162D, L195M, V196E, K199E, L211M, L213F, S221F, V286A S289R, R334C, G384C, K427N, E438A |
| 13 | V44A, I136V, G374D, V457I, N463S |
| 14 | I60S, K97R, Q103R, F181S, L411S |
| 15 | V244A, F307L |
| 16 | H140Y, S142C, T144I, A148T, M152L, G153A, A156S |
| 17 | L195M, V196E, K199E, L211M, L213F, S221F, V286A, R334C, G384C, K427N, E438A |
| 18 | V169A, R334C, G384C, K427N, E438A |
| 19 | G25D, Y30F, P93Q, S99V, Y122F, H140Y, S142C, T144I, A148T, M152L, G153A, A156S, G162D, L195M, V196E, K199E, L211M, L213F, S221F, V286A, G384C |
| 20 | I64T, V323A, V330A, G384C, K427N, E438A |

UGT91D2e also was tested for its ability to 1,2-glucosylate substrates other than steviol-13-O-monoglucoside in vitro, i.e., rubusoside, steviol-1,3-bioside and 1,3-stevioside. The results indicated that UGT 91D2e was not active when a 1,3-bound glucose was present (e.g., steviol 1,3-bioside and 1,3-stevioside), while UGT 91D2e was active regardless of primary glucosylation at the 19-O position. These results suggest that steviol 1,3-bioside and 1,3-stevioside are likely not present in the in vivo Stevia pathway for rebA formation. See FIG. 2A and FIG. 3.

Example 16—UGT91D Homologs

Different ecotypes of S. rebaudiana are genetically diverse. Investigation of 96 clones of 91Ds from different Stevia RNA accessions revealed many amino acid changes between six investigated ecotypes (e.g., at nucleotide 74 (resulting in an amino acid change of G to D), 89 (Y to F), 131 (V to A), 137 (F to S), 278 (P to Q), 295 (S to V or P), 331 (E to Q), 365 (Y to F), 395 (A to V), 418 (H to Y), 425 (S to G), 431 (T to I), 442 (A to T), 454 (M to L), 458 (G to A), 466 (A to S), 485 (G to D), 583 (L to M), 587 (V to E), 595 (K to E), 614 (D to G), 616 (G to R), 631 (L to M), 637 (L to F), 662 (S to F), 664 (K to E), 671 (Y to C), 857 (V to A), 867 (S to R), 919 (F to L), 989 (V to A), 1000 (R to C), 1090 (S to P), 1150 (G to C), 1232 (L to S), 1281 (K to N), 1313 (E to A), 1354 (Q to R), and 1369 (V to I)), as numbered with respect to the nucleotide sequence of 91D2e set forth in SEQ ID NO:9. Some additional variation from these polymorphisms was noted, which is likely due to sequencing or PCR errors, particularly if the polymorphisms were found only once. Twenty coding regions were chosen for further analysis. See Table 14 for descriptions of clones All of the clones in Table 14 were tested for activity using 13-SMG as a substrate. Clone 5 had weak 1,2-glycosylating activity whereas the remaining nineteen did not appear to have activity under the conditions tested. The sequence of clone 5 is set forth in SEQ ID NO:95 and has the following mutations with respect to wild-type UGT92D2e (SEQ ID NO:5): G206R, Y207C, and W343R.

Example 17—UGT85C Homologs

The genetic diversity of UGT85Cs from six different S. rebaudiana ecotypes was examined to identify homologs that have the same or enhanced activity in pathways for steviol glycoside production. PCR primers were designed that were specific for UGT85C genes, and PCR reactions were carried out on cDNA (some were done on cDNA libraries, some were done on cDNA preparations). The resulting PCR products were cloned and 96 clones were sequenced. Amino acid polymorphisms were mapped and 16 UGT 85C clones were chosen with varying common polymorphism representation. See Table 15. Additional modifications were also noted for some clones, but could be due to PCR errors or were not common polymorphisms. Polymorphisms are described with respect to the nucleotide and amino acid numbering of the wild-type S. rebaudiana UGT85C nucleotide sequence set forth in Accession No. AY345978.1 (see Table 8).

The clones were expressed through coupled in vitro transcription-translation of PCR products (TNT® T7 Quick for PCR DNA kit, Promega) and assayed for glycosylation activity on the substrates steviol and steviol-19-O-glucoside (0.5 mM), as described in previous examples. The UGT85Cs produced from clones 1, 4, 16, 17, 19, 20, 21, 26, 29, 30, 31, 37, and 39 were soluble and were able to convert 19-SMG to rubusoside in a 90 min assay. The UGT85C produced from clone 27 was considered insoluble. Although UGT85Cs produced from clones 2 and 33 were considered insoluble, trace amounts of rubusoside were produced despite the protein band not being visible. These experiments were independently performed three times. The experiments showed that the following amino acid mutations did not result in a loss of activity: V13F, F15L, H60D, A65S, E71Q, 187F, K220T, R243W, T270M, T270R, Q289H, L334S, A389V, I394V, P397S, E418V, G440D, and H441N. Additional mutations that were seen in active clones include K9E in clone 37, K10R in clone 26, Q21H in clone 2, M27V in clone 30, L91P in clone 4, Y298C in clone 31, K350T in clone 37, H368R in clone 1, G420R in clone 19, L431P in clone 4, R444G in clone 16, and M471T in clone 30.

The only common polymorphisms that were not tested were T270A and 1336T, which are both fairly conservative substitutions. Clone 17 had the most changes incorporated as compared to UGT85C, 6/480 amino acids. The 17-20 amino acids that appear to be changeable represent approximately a 4% difference at the amino acid level.

Generally, there is low genetic diversity among the 85Cs and it is likely that all of the 85C homologs with the common polymorphisms set forth in Table 15 will be active.

Example 18—UGT76G Homologs

The genetic diversity of UGT76Gs from six different *S. rebaudiana* ecotypes was examined to identify homologs that have the same or enhanced activity in pathways for steviol glycoside production. PCR primers were designed that were specific for UGT76G, and PCR reactions were carried out on preparations of cDNA (cDNA libraries or cDNA preparations). The resulting PCR fragments were cloned and 96 clones were sequenced. Common amino acid polymorphisms were mapped and sixteen UGT76G clones chosen, with varying polymorphism representation, including (amino acid numbering): R10S, I16L, F22V, M29I, K52S, V74K/E, P80S, L85A, V87S/G, L91P, 192F, 193F, H96Y, G97R, L108V, E113D, G116E, A123T, Q125A, 1126L, Y128H, T130A, L142I, V145M, S147N, N151T, F152I, H153L, H155Y, V156D, Q160L, E163D, L167F, P169L, K188N, K191Q, C192S/F, S193G/A, F194Y, M196N, K198Q, K199 (I, V, Q), Y200 (L, A, G), Y203I, F204L, E205G, N206K, I207M, T208I, V217I/F, E226Q, S228P, L230V, V233I, 1234T, E236D, 1237F, S253P, P266Q, S273P, R274S, G284T/A, T285S, 287-3 bp deletion, R298H, P326A, L330V, G331A, P341L, L346I, S376L, D377A, G379A, L380F, S438P, and K441N. Generally, there was very high diversity among the 76Gs.

The clones were expressed through in vitro translation and assayed for glycosylation activity using 0.5 mM steviol-13-O-glucoside and 0.5 mM stevioside as substrates, as described in previous examples. Reactions were carried out for 90 min at 30° C. The native 76G1 activity was found in three new 76Gs designated 76G_C4, 76G_G7 and 76G_H12, by formation of 1,3-bioside when steviol-13-O-glucoside was used as substrate. Activity in this case was determined comparatively to the positive control, the functional 76G1. Clones 76G_G7 and 76G_H12 produced slightly higher levels of Reb A than the control but 76G_C4 had slightly less Reb A than the control. The number of changes in these clones represents a difference of about 7% at the amino acid level, from the control enzyme. SEQ ID NOs: 98, 100, and 102 set forth the amino acid sequence of 76G_C4, 76G_G7, and 76G_H12, respectively. SEQ ID NOs: 97, 99, and 101 set forth the nucleotide sequences encoding 76G_C4, 76G_G7, and 76G_H12, respectively. SEQ ID NOs: 98, 100, and 102 set forth the amino acid sequence of 76G_C4, 76G_G7, and 76G_H12, respectively. SEQ ID NOs: 97, 99, and 101 set forth the nucleotide sequences encoding 76G_C4, 76G_G7, and 76G_H12, respectively.

Table 16 summarizes the amino acid changes of the 76G clones that had activity, as compared to the wildtype enzyme. There are a large number of overlapping polymorphisms in the active clones, thus it is expected that these polymorphisms do not cause a loss of activity for the enzyme. It appears that certain mutations are frequent in inactive clones, such as the P→S mutation at position 80 or the F→V mutation at position 22.

TABLE 16

| Clone | Mutations |
| --- | --- |
| 76G_G7 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion, L330V, G331A, L346I |
| 76G_H12 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion |
| 76G_C4 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I |

Example 19—Expression of Truncated Yeast HMG-COA Reductase and Other HMG-CoA Reductases In *S. cerevisiae*, the mevalonate pathway is heavily regulated, for example, at the level of the enzyme 3-Hydroxy-3-methylglutaryl-coenzyme A (HMG-COA) reductase. Expressing a truncated HMG-COA reductase (tHMG1, encoding an enzyme stabilized from degradation) is one method in which flux towards PPP production can be increased in yeast. For example, expression of tHMG1 in yeast has led to dramatic overproduction of β-carotene. See, Verwaal et al., 2007, *Appl. Environ. Microbiol.* 73:4342. Interestingly, such yeast did not show a darker orange coloration on solid growth medium as was expected, but rather a stronger yellow color, likely due to even higher over-production of the intermediate phytoene.

To determine if expression of HMG-COA reductase could be used to improve flux to the steviol and steviol glycoside pathways, a yeast reporter strain for testing isoprenoid flux was prepared by substituting the inherent promoter of the ERG9 gene with a CUP1 promoter. See, U.S. Patent Application No. 61/346,853, filed May 20, 2010.

The genes used to produce the yeast strain are shown in Table 17. The genes from the source organisms were codon optimized according to DNA 2.0 Inc™. For the purpose of monitoring the cellular prenyl phosphate availability, a construct was produced which had a high copy number plasmid containing gene expression cassettes (methionine-repressible promoters) with the genes for the three enzymes needed to turn prenyl phosphates into β-carotene (GGPP synthase from *Xanthophyllomyces dendrorhous*, phytoene synthase and beta carotene synthase from *X. dendrorhous*, and zeta carotene synthase and delta carotene synthase from *Neurospora crassa*). See, Verwaal et al., 2007 supra; and U.S. Patent Application No. 61/346,853.

increased steviol glycoside production using the HMG reductase genes and other mevalonate pathway genes found to be beneficial to beta-carotene production.

Example 20—Production of RebC In Vivo

The synthesis of a precursor molecule to Rebaudioside C, steviol-13-O-glucopyranosyl-1,2-rhamnoside, was shown in vitro in Example 15. In that example steviol-13-O-monoglucoside was used as a substrate, along with UDP-glucose and the *Arabidopsis thaliana* RHM2 enzyme (locus tag AT1G53500) and UGT91D2e. To further demonstrate the pathway shown in FIG. 2B, production of Rebaudioside C from steviol was accomplished in vivo.

TABLE 17

Sources of HMG CoA Reductases and other Mevalonate Genes

| Accession# | Organism | Enzyme | Size (nt) | Gene name | SEQ ID (codon optimized) | SEQ ID (protein) |
| --- | --- | --- | --- | --- | --- | --- |
| XM_001467423 | *Leishmania infantum* | Acetyl-CoA C-acetyltransferase | 1323 | MEV-4 | 103 | 104 |
| YML075C | *Saccharomyces cerevisiae* | Truncated HMG (tHMG1) | 1584 | tHMG1 | 105 | 106 |
| EU263989 | *Ganoderma lucidum* | 3-HMG-CoA reductase | 3681 | MEV-11 | 107 | 108 |
| BC153262 | *Bos taurus* | 3-HMG-CoA reductase | 2667 | MEV-12 | 109 | 110 |
| AAD47596 | *Artemisia annua* | 3-HMG-CoA reductase | 1704 | MEV-13 | 111 | 112 |
| AAB62280 | *Trypanosoma cruzi* | 3-HMG-CoA reductase | 1308 | MEV-14 | 113 | 114 |
| CAG41604 | *Staph aureus* | 3-HMG-CoA reductase | 1281 | MEV-15 | 115 | 116 |
| DNA2.0 sequence | *Archaeoglobus fulgidus* | 3-HMG-CoA reductase | 1311 | HMG reductase | 117 | 118 |
| DNA2.0 sequence | *Pseudomonas mevalonii* | 3-HMG-CoA reductase | 1287 | HMG reductase | 119 | 120 |

The yeast tHMG1 was expressed in the CEN.PK-based yeast strain that produces β-carotene, resulting in a color change from orange to light yellow. Interestingly, expression of the full length HMGs from *Artemisia annua, Trypanosoma cruzi* and *Staphylococcus aureus*, as well as the NADH-dependent HMG's from *Pseudomonas mevalonii* and *Archaeoglobus fulgidus* produced a similar result, indicating these genes also improve the flux through the mevalonate pathway in yeast (similar overexpression of *Bos taurus* HMG had no such effect). Finally, the same color change was seen after over-expression of *Leishmania infantum* acetyl-CoA C-acetyltransferase (first enzyme of mevalonate pathway, described in Table 17) or native *S. cerevisiae* (CAB1, YDR531W) or *B. subtilis*, (acc. No. YP004204141) pantothenate kinases (known to result in increased acetyl-CoA production).

To test if the color change in these experiments were indeed due to higher GGPP availability, the yeast tHMG1, P. mevalonii or *S. aureus* HMGs, or *B. subtilis* pantothenate kinase were expressed in a stable 19-SMG producer strain. None of these constructs appeared to produce an increase in 19-SMG or rubusoside production (UGT85C2 co-expressed) under the conditions tested. Mevalonate feeding to the yeast reporter strain also did not result in increased rubusoside production. The rubusoside reporter strain, however, has not been genetically modified to reduce the ERG9-encoded flux towards ergosterol biosynthesis. It is expected that control of flux to ergosterol production would result in A yeast strain capable of producing Rebaudioside C was constructed, and production of rebaudioside C and rebaudioside A was assayed by LC-MS. A modified *Saccharomyces cerevisiae* strain BY4742 was constructed and designated EYS583-7A. The use of BY4742 has been described by Naesby et al., *Microb Cell Fact.* 8:45 (2009) All four UGTs (91D2d, 76G1, 74G1, and 85C2) were constitutively expressed iin plasmids with GPD promoters. This type of strain has been described by Naesby et. al, *Microb Cell Fact.* 8:45 (2009). UGT85C2 was inserted in plasmid P423 GPD (ATCC #87355), UGT74G1 was cloned into P424 GPD (ATCC #87357) and both UGT91D2e and UGT76G1 were cloned into P425-GPD (ATCC #87359) with 91D2e in the original multiple cloning site (MCS), and 76G1 inserted with an additional GPD promoter and a CYC terminator. The resulting strain was transformed with plasmid P426 GPD (ATCC #87361) containing the RHM2 gene expressed from the GPD promoter. The strain was grown on SC medium lacking histidine, leucine, tryptophan and uracil for 24 hours. The culture was then re-inoculated to an OD$_{600}$ of 0.4 in fresh media containing 25 μM steviol, and the yeast was allowed to grow for 72 more hours before detecting if Rebaudioside C was present in the supernatant and the cell pellets. Rebaudioside C was quantified using an authentic Rebaudioside C standard (Chromadex, Irvine CA). A total of 1.27 μM±0.36 μM of RebC was detected in the supernatant. Similarly, 3.17 μM±1.09 UM RebA was detected in the cell pellet One of skill in the art will recognize that different ratios of RebC to RebA can be obtained by modulation of the activity of the RHM2 enzyme and/or by usage of UGT91D2e or UGT76G1-like enzymes with higher activity for the UDP-rhamnose reactions. The alternative UGTs can be mutagenized versions of the wildtype enzymes or unique enzymes that are obtained through discovery initiatives.

One of skill in the art will recognize that a yeast strain capable of production of Rebaudioside A from glucose, such as strain CEY213 transformed with a plasmid containing UGT91D2e and UGT76G1 in Example 12 would produce Rebaudioside C with the addition of the RHM2 gene either via a vector or integrated into the chromosome.

Example 21—Production of Steviol Glycosides Using UGTs Expressed in *Escherichia coli*

Activity of UGT Enzymes in Gram Negative Bacteria

The wildtype genes for UGTs 91D2e, 74G1, 76G1, and 85C2 were cloned individually into *E. coli* XjB-autolysis BL21 (DE3) cells using the pET30 vector system from Novagen (EMD4 Biosciences, Madison, WI), except for UGT91D2e, which was cloned into a pGEX 4T-1 (GE Healthcare, Uppsala, Sweden) vector. Similar cloning was described in Examples 7 and 10. All vectors use an IPTG-inducible promoter. Plasmid DNA was transformed into chemically competent cells as described by the vendor.

Transformants displaying the desired antibiotic resistance were grown overnight at 30° C. in 2 mL cultures using NZCYM-media and antibiotic. For in vivo feedings, 5 cultures were grown: UGT 91d2e, 74G1, 76G1, and 85C2 individually, and a mix of all 4 clones. The following day, the cultures were induced to a final concentration of 0.3 mM IPTG and 3 mM arabinose, and grown 2 days at 20° C. in the presence of 50 µM steviol (UGT74G1, UGT85C2 and the quadruple mix) or 50 µM rubusoside (UGT91D2e and UGT76G1). The temperature was raised to 30° C. and the cells were grown for one more day. The cells were then harvested by centrifugation at 4000 rpm for 5 min., and the supernatants were removed for LC-MS analysis. The cells were resuspended in 50% DMSO, lysed at 80° C. for 5 min and the lysates were analyzed by LC-MS.

For in vitro assays, transformants displaying the desired antibiotic resistance were grown overnight at 30° C. in 2 mL cultures using NZCYM-media and antibiotic. The following day, the cultures were induced to a final concentration of 0.3 mM IPTG and 3 mM arabinose, and grown for 24 h at 20° C. The cells were then harvested by centrifugation at 4000 rpm for 5 min and resuspended in 200 µL GT-buffer (RBC Bioscience) and 3 tablets/100 ml of Complete mini, protease inhibitor (Roche), transferred to Eppendorf tubes, vortexed and frozen at −80° C. for 1.5 hour. Cells were thawed on ice, and left at room temperature for 3 minutes. When approximately half-way thawed, 15 µl of 0.14 mg/ml $H_2O$ DNase solution+30 µl 0.05M $MgCl_2$ was added to each tube and the samples were incubated for approximately 5 minutes at room temperature. The cells were centrifuged at maximum speed for 5 minutes. One-hundred µL of supernatant (lysate) was transferred to fresh microfuge tubes, and 100 µL of glycerol was added.

Enzyme assays were performed by adding 15.15 µL $H_2O$, 7.5 µL 4× Buffer (400 mM Tris, 20 mM $MgCl_2$, 4 mM KCl), 0.3 µL FastAP™ (1 u/µL) from Fermentas, 0.45 µL of a 100 mM stock of UDP-glucose, 0.6 µL of substrate (steviol or rubusoside) and 6 µL of the crude enzyme preparations described above. UGT74G1, UGT85C2, as well as all four UGTs mixed were incubated with steviol. UGT 76G1 and 85C2 were incubated with rubusoside. The enzyme assays were incubated overnight at 37° C. Following centrifugation at 4000 rpm for 5 minutes, 30 µL samples were transferred to a fresh 96 well plate and 30 µL of DMSO was added. The samples were then subjected to LC-MS analysis. Similar in vitro experiments were also done using steviol 1,2-bioside (for UGT76G1 and UGT74G1) or Rebaudioside B (for UGT74G1) as substrates.

No activity was detected in the in vivo feedings. Table 18 illustrates the results for the in vitro assays.

TABLE 18

| Tube | UGT Clone(s) | Substrate fed | Product detected |
|---|---|---|---|
| 1 | 74G1 | Steviol | 19-SMG, low levels of rubusoside |
| 2 | 85G1 | Steviol | 13-SMG, low levels of rubusoside |
| 3 | 76G1 | Rubusoside | 1,3-stevioside, an unknown tetra-glycoside |
| 4 | 91D2c | Rubusoside | stevioside |
| 5 | Mix of 4 crude UGT preparations | Steviol | Rubusoside, 1,3-stevioside, trace RebA (no mono sides) |
| 6 | 76G1 | Steviol 1,2-bioside | Rebaudioside B |
| 7 | 74G1 | Steviol 1,2-bioside | Stevioside |
| 8 | 74G1 | Rebaudioside B | Rebaudioside A |

These results indicate that the UGT enzymes are all active in *E. coli* cells. However, the substrates may not be readily imported into the cytoplasm. It is expected that if the steviol were produced in *E. coli* from precursor pathways, the production of the various steviol glycoside products would be feasible from glucose. It is unexpected that the 74G1 and 85G1 UGTs, which have slightly overlapping substrate specificities, can produce rubusoside from steviol singly. The mix of the four crude enzyme preparations gave very low levels of the monosides, which indicates that the conversion to di- and tri-glycosides was efficient. With respect to UGT91D2e, the preparation that was used had lost some of its original activity after long-term storage. It is expected that a fresh preparation of the enzyme would have yielded higher levels of Rebaudioside A.

Example 22—Production of Steviol Glycosides in *Physcomitrella patens*

Feeding Experiments in Moss Cells

The genes for UGT 91d2e, 74G1, 76G1, and 85C2 were cloned into *Physcomitrella patens* using the pTHUbi: Gateway vector system described in U.S. Patent Publication No. 20100297722. This vector uses a strong maize Ubiquitin promoter. PCR primers were designed to amplify the coding regions in previous examples (native sequences) with the addition of "CACC" upstream of the start codon. Plasmid DNA was digested with SwaI and used for transformation into protoplasts (generally around 0.5×10⁶ protoplasts). Transformants displaying the desired resistance were grown 1 day in 10 mL cultures and then fed either steviol, rubusoside, or buffer+DMSO as indicated by Table 19. One-half mL of buffer containing substrate was added per 10 mL of culture, and final concentrations of 0.1% DMSO, 50 µM steviol or rubusoside, and 0.125 mM phosphate buffer were added to the cultures. A positive control was done where the YFP (yellow fluorescent protein) was expressed in the presence of steviol or just buffer and DMSO. Cultures were grown 2 more days prior to separation of cells and freezing in liquid nitrogen until further analysis. In some cases multiple UGT-containing plasmids were transformed into the same protoplast cells, to illustrate conversion of multiple steps within the moss cells.

TABLE 19

| Tube | UGT Gene(s) | Substrate fed |
|---|---|---|
| 1 | YFP (control) | none |
| 2 | YFP | Steviol (50 µM) |
| 3 | 74G1 | none |
| 4 | 76G1 | none |
| 5 | 85C2 | none |
| 6 | 91D2E | none |
| 7 | 74G1 | Steviol (50 µM) |
| 8 | 76G1 | Steviol (50 µM) |
| 9 | 85C2 | Steviol (50 µM) |
| 10 | 91D2E | Steviol (50 µM) |
| 11 | 74G1/85C2 | none |
| 12 | 74G1/85C2 | Steviol (50 µM) |
| 13 | 74G1/85C2/91D2E | none |
| 14 | 74G1/85C2/91D2E | Steviol (50 µM) |
| 15 | 76G1 | Rubusoside (50 µM) |
| 16 | 91D2E | Rubusoside (50 µM) |
| 17 | 76G1/91D2E | none |
| 18 | 76G1/91D2E | Rubusoside (50 µM) |

Expression was positive in the controls (tubes 1 and 2) as measured by fluorescent signal observation. The supernatants from the experiments were analyzed by LC-MS; 200 µL of each supernatant sample was mixed with an equal volume of 50 percent DMSO. The samples were spun (15,700 relative centrifugal force, 10 minutes) and 100 microliters of the resulting supernatant was analyzed by LC-MS.

Protoplast pellets were thawed on ice and 10 mM Tris-HCl pH 8 containing 3 tablets/100 ml of Complete Mini Protease Inhibitor (Roche) was added to reach a final volume of 150 µL. The solutions were divided in two: 75 µL was transferred to a new tube and protoplasts were pelleted (15,700 relative centrifugal force, 1 minute). Pellets were washed with 75 µL Milli-Q water before resuspension in 150 µL DMSO (50 percent). Samples were then heated (80 degrees Celsius, 10 minutes), vortexed and centrifuged (15,700 relative centrifugal force, 10 minutes). Fifty µL of the resulting supernatant was analyzed by LC-MS.

No steviol glycoside production was detectable in supernatants or pellets. It is unknown if the steviol and rubusoside can be transported into moss cells.

In Vitro Feeding of Pellet Extracts

In vitro feeding experiments were conducted with samples 1, 3, 4, 5, 6, 11, 13 and 17). Glass beads (425-600 microns) were added to the remaining 75 µL of the original resuspensions and protoplasts were mechanically lysed by vortexing 3 times, 2 minutes each time, at 4 degrees Celsius and storage on ice in between vortexing. The samples were spun (15,700 relative centrifugal force, 10 minutes, 4 degrees Celsius) and 6 µL of resulting supernatants was used in in vitro enzyme reactions. For the enzyme reactions FastAP™ phosphatase (Fermentas) was used (0.3 U/reaction) and the UDP-glucose:substrate ratio was 5. The samples were fed either steviol or rubusoside according to Table 20.

TABLE 20

| Cell extract from tube | UGT Gene(s) | Substrate fed |
|---|---|---|
| 1 | YFP | None |
| 1 | YFP | 0.5 mM steviol |
| 1 | YFP | 0.5 mM rubusoside |
| 3 | 74G1 | 0.5 mM steviol |
| 4 | 76G1 | 0.5 mM rubusoside |
| 5 | 85C2 | 0.5 mM steviol |
| 6 | 91D2E | 0.5 mM rubusoside |
| 11 | 74G1/85C2 | 0.5 mM steviol |
| 13 | 74G1/85C2/91D2E | 0.5 mM steviol |
| 17 | 76G1/91D2E | 0.5 mM rubusoside |

Reactions were incubated at 30° C. overnight. After incubation, an equal amount of DMSO (100 percent) was added to the samples and mixed, then the sample was spun (15,700 relative centrifugal force, 10 minutes) and 30 µL of the resulting supernatant was analyzed by LC-MS.

LC-MS analysis showed conversion of rubusoside to 1,3-stevioside by UGT76G1. None of the other steviol glycosides were detectable. It is unknown if soluble expression of the UGTs occurred in *Physcomitrella*. It is expected if one UGT is active in the moss cells, the others would also be active if expression occurred. In addition, the cloning was done in a transient manner. Stable integration of the genes is expected to produce additional clones that are active for UGT activity when tested.

Methods are known to those with skill in the art for increasing soluble expression of recombinant proteins. Alternative promoters, ribosome binding sites, codon usage, co-expression with chaperones, and change in temperature are non-limiting examples of methods for increasing soluble expression of recombinant proteins.

Example 23—Production of Steviol Glycosides in *Aspergillus nidulans* Activity of UGT Enzymes in Fungal Cells The native genes for UGT 91D2e, 74G1, 76G1, and 85C2 were cloned into *Aspergillus nidulans* using a PCR-fabricated expression cassette and the USER vector system. Cloning methods are described in Hansen et al., *Appl. Environ. Microbiol.* 77:3044-3051 (2011). Briefly, a nucleotide sequence encoding each UGT was inserted between the constitutive PgpdA promoter and the TtrpC terminator, in a vector containing additionally two targeting sequences for genomic integration and argB as selection marker. Plasmid DNA was transformed into *A. nidulans* protoplasts according to Nielsen et al., *Fungal Genet. Biol.* 43:54-64 (2006) and Johnstone et al., *EMBO J.* 4:1307-1311 (1985). Transformants displaying the desired resistance were grown for 48 hours in 150 mL cultures using minimal media (1% Glucose; 10 mM NaNO₃; mineral mix).

Cell lysates prepared by disruption of the mycelia with glass beads were used to determine the activities of the individual UGTs in in vitro. The cell lysates of strains expressing 74G1 and 85C2 were incubated with 0.5 mM steviol and the strains expressing 76G1 and 91D2e were incubated with 0.5 mM steviol-13-O-glucoside for 24 hours, and the supernatants further analyzed using LC/MS. No steviol glycosides were detected.

It is unknown whether soluble expression of the UGT enzymes was achieved as these products are not typically visible on SDS-PAGE. Since *Aspergillus* and *Saccharomyces* are both fungi, it is expected that additional experimentation would result in active clones. Methods are known to those with skill in the art for increasing soluble expression of recombinant proteins. Alternative promoters, inducer levels, ribosome binding sites, codon usage, co-expression with chaperones, and change in temperature are non-limiting examples of methods for increasing soluble expression of recombinant proteins.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for transferring an additional sugar moiety to a C2' position of a glucose in a steviol glycoside, comprising contacting the steviol glycoside with a recombinant polypeptide capable of beta 1,2 glycosylation of the C2' of the 13-O-glucose, 19-O-glucose, or both 13-O-glucose and 19-O-glucose of a steviol glycoside and having at least 95% sequence identity to the amino acid sequence set forth in SEQ ID NO: 5 and a sugar moiety donor under suitable reaction conditions for the transfer of the additional sugar moiety to the steviol glycoside, wherein the steviol glycoside is steviol-13-O-glucoside, rubusoside, stevioside or rebaudioside A, and wherein a stevioside, rebaudioside E, rebaudioside D, steviol-1,2 bioside, steviol-1,2-xylobioside, steviol-1, 2-rhamnobioside, an isomer thereof, and/or a steviol glycoside composition thereof is produced upon transfer of the additional sugar moiety.

2. The method of claim 1, wherein:
(a) the steviol glycoside is rubusoside, wherein the additional sugar moiety is glucose, and stevioside is produced upon transfer of the additional glucose moiety;
(b) the steviol glycoside is stevioside, the additional sugar moiety is glucose, and rebaudioside E is produced upon transfer of the additional glucose moiety;
(c) the steviol glycoside is stevioside, the additional sugar moiety is glucose, the stevioside is contacted with the polypeptide capable of beta 1,2 glycosylation of the C2' of the 13-O-glucose, 19-O-glucose, or both 13-O-glucose and 19-O-glucose of a steviol glycoside and a polypeptide capable of beta 1,3 glycosylation of the C3' of the 13-O-glucose of a steviol glycoside, and rebaudioside D is produced upon transfer of the additional glucose moiety;
(d) the steviol glycoside is steviol-13-O-glucoside, the additional sugar moiety is glucose, and steviol-1,2 bioside is produced upon transfer of the additional glucose moiety;
(e) the steviol glycoside is steviol-13-O-glucoside, the additional sugar moiety is xylose, and steviol-1,2-xylobioside is produced upon transfer of the additional sugar moiety;
(f) the steviol glycoside is steviol-13-O-glucoside, the additional sugar moiety is rhamnose, and steviol-1,2-rhamnobioside is produced upon transfer of the additional sugar moiety;
(g) the steviol glycoside is rebaudioside A, the additional sugar moiety is glucose, and rebaudioside D is produced upon transfer of the additional glucose moiety; or
(h) the precursor steviol glycoside is rubusoside, the additional sugar moiety is xylose, and 1,2-stevioxyloside is produced upon transfer of the sugar moiety.

3. The method of claim 1, wherein the polypeptide capable of beta 1,2 glycosylation of the C2' of the 13-O-glucose, 19-O-glucose, or both 13-O-glucose and 19-O-glucose of a steviol glycoside comprises a polypeptide having:
(a) at least 95% identity to the amino acid sequence set forth in SEQ ID NO: 5 and having at least one amino acid substitution at residues 1-19, 27-38, 44-87, 96-120, 125-141, 159-184, 199-202, 215-380, or 387-473 of SEQ ID NO:5;
(b) at least 95% identity to the amino acid sequence set forth in SEQ ID NO: 5 and having an amino acid substitution at one or more residues selected from the group consisting of residues 30, 93, 99, 122, 140, 142, 144, 148, 152, 153, 156, 195, 196, 199, 206, 207, 211, 213, 221, 286, 343, 364, 384, 427, and 438 of SEQ ID NO:5;
(c) at least 95% identity to the amino acid sequence set forth in SEQ ID NO: 5 and having an arginine at residue 206, a cysteine at residue 207, and an arginine at residue 343 relative to SEQ ID NO:5; or
(d) at least 95% identity to the amino acid sequence set forth in SEQ ID NO: 5 and having a tyrosine or phenylalanine at residue 30, a proline or glutamine at residue 93, a serine or valine at residue 99, a tyrosine or phenylalanine at residue 122, a histidine or tyrosine at residue 140, a serine or cysteine at residue 142, an alanine or threonine at residue 148, a methionine at residue 152, an alanine at residue 153, an alanine or serine at residue 156, a glycine at residue 162, a leucine or methionine at residue 195, a glutamic acid at residue 196, a lysine or glutamic acid at residue 199, a leucine or methionine at residue 211, a leucine at residue 213, a serine or phenylalanine at residue 221, a valine or isoleucine at residue 253, a valine or alanine at residue 286, an asparagine or lysine at residue 427, or an alanine at residue 438 and an alanine or threonine at residue 462 relative to SEQ ID NO:5.

4. The method of claim 2, wherein the polypeptide capable of beta 1,3 glycosylation of the C3' of the 13-O-glucose of a steviol glycoside comprises a polypeptide having at least 95% identity to the amino acid sequence set forth in SEQ ID NO: 7.

5. The method of claim 2, wherein the polypeptide capable of beta 1,3 glycosylation of the C3' of the 13-O-glucose of a steviol glycoside comprises one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 of SEQ ID NO:7.

6. The method of claim 1, wherein the method is an in vitro method, further comprising supplying the sugar moiety donor or a cell-free system for regeneration of the sugar moiety donor.

7. The method of claim 6, wherein the sugar moiety donor comprises ADP-sugar, CDP-sugar, GDP-sugar, and/or UDP-sugar.

8. The method of claim 6, wherein the in vitro method is enzymatic in vitro method.

9. The method of claim 1, further comprising use of a phosphatase, wherein the phosphatase improves yield of the steviol glycoside and removes secondary products.

10. A method of producing a steviol glycoside composition by transferring an additional sugar moiety from a sugar moiety donor to the C2' of a glucose in a steviol glycoside with a recombinant polypeptide capable of beta 1,2 glycosylation of the C2' of the 13-O-glucose, 19-O-glucose, or both 13-O-glucose and 19-O-glucose of a steviol glycoside and having at least 95% sequence identity to the amino acid sequence set forth in SEQ ID NO:5, in a whole cell of yeast S. cerevisiae;

wherein the steviol glycoside is steviol-13-O-glucoside, rubusoside, stevioside or rebaudioside A; and wherein the steviol glycoside composition comprises stevioside, rebaudioside E, rebaudioside D, steviol-1,2 bioside, steviol-1,2-xylobioside, and/or steviol-1,2-rhamnobioside.

11. The method of claim 1, wherein the steviol glycoside composition is produced in a cell culture broth, the method comprising growing a recombinant host cell comprising (i) a gene encoding a polypeptide capable of beta 1,2 glycosylation of the C2' of the 13-O-glucose of a steviol glycoside, (ii) a gene encoding a polypeptide capable of beta 1,2 glycosylation of the C2' of the 19-O glucose of a steviol glycoside, and/or (iii) a gene encoding a polypeptide capable of beta 1,2 glycosylation of the C2' of the 13-O-glucose and the 19-O glucose of a steviol glycoside, wherein the polypeptide capable of beta 1,2 glycosylation of the C2' of the 13-O-glucose of a steviol glycoside, the polypeptide capable of beta 1,2 glycosylation of the C2' of the 19-O glucose of a steviol glycoside, and/or polypeptide capable of beta 1,2 glycosylation of the C2' of the 13-O-glucose and the 19-O glucose of a steviol glycoside has at least 95% sequence identity to the amino acid sequence set forth in SEQ ID NO: 5;

wherein at least one of the genes is a recombinant gene, under conditions in which one or more of the genes are expressed; and wherein contacting the steviol glycoside with the recombinant polypeptide comprises contacting the steviol glycoside with at least one of the polypeptides produced by the recombinant host.

12. The method of claim 11, wherein the recombinant host cell is a yeast cell, a plant cell, a fungal cell, or a bacterial cell.

13. The method of claim 11, wherein the recombinant host cell belongs to the species *Saccharomyces cerevisiae*, *Escherichia coli*, *Yarrowia lipolytica*, or *Pichia pastoris*.

14. The method of claim 11, wherein the steviol glycoside is contacted with the recombinant polypeptide and the sugar moiety donor in vivo in the recombinant host cell.

15. The method of claim 11, wherein the steviol glycoside is contacted with the recombinant polypeptide and the sugar moiety donor in vitro.

16. The method of claim 11, further comprising isolating (i) the polypeptide capable of beta 1,2 glycosylation of the C2' of the 13-O-glucose of a steviol glycoside, (ii) the polypeptide capable of beta 1,2 glycosylation of the C2' of the 19-0 glucose, and/or (iii) the polypeptide capable of beta 1,2 glycosylation of the C2' of the 13-O-glucose and the 19-O glucose of a steviol glycoside from the recombinant host cell;

wherein contacting the steviol glycoside with at least one of the polypeptides produced by the recombinant host comprises contacting the steviol glycoside with at least one of the isolated polypeptides in vitro.

17. The method of claim 11, wherein the steviol glycoside composition comprises at least 1 mg of rebaudioside D per liter of cell culture broth.

18. The method of claim 11, wherein growing can include inducing expression of one or more of the genes or constitutively expressing one or more of the genes.

19. The method of claim 11, wherein:
(a) the steviol glycoside is rubusoside, wherein the additional sugar moiety is glucose, and stevioside is produced upon transfer of the additional glucose moiety;
(b) the steviol glycoside is stevioside, the additional sugar moiety is glucose, and rebaudioside E is produced upon transfer of the additional glucose moiety;
(c) the steviol glycoside is stevioside, the additional sugar moiety is glucose, the stevioside is contacted with the polypeptide capable of beta 1,2 glycosylation of the C2' of the 13-O-glucose, 19-O-glucose, or both 13-O-glucose and 19-O-glucose of a steviol glycoside and a polypeptide capable of beta 1,3 glycosylation of the C3' of the 13-O-glucose of a steviol glycoside, and rebaudioside D is produced upon transfer of the additional glucose moiety;
(d) the steviol glycoside is steviol-13-O-glucoside, the additional sugar moiety is glucose, and steviol-1,2 bioside is produced upon transfer of the additional glucose moiety;
(e) the steviol glycoside is steviol-13-O-glucoside, the additional sugar moiety is xylose, and steviol-1,2-xylobioside is produced upon transfer of the additional sugar moiety;
(f) the steviol glycoside is steviol-13-O-glucoside, the additional sugar moiety is rhamnose, and steviol-1,2-rhamnobioside is produced upon transfer of the additional sugar moiety;
(g) the steviol glycoside is rebaudioside A, the additional sugar moiety is glucose, and rebaudioside D is produced upon transfer of the additional glucose moiety; or
(h) the precursor steviol glycoside is rubusoside, the additional sugar moiety is xylose, and 1,2-stevioxyloside is produced upon transfer of the sugar moiety.

20. The method of claim 11, wherein the polypeptide capable of beta 1,2 glycosylation of the C2' of the 13-O-glucose, 19-O-glucose, or both 13-O-glucose and 19-O-glucose of a steviol glycoside comprises a polypeptide having:
(a) at least 95% identity to the amino acid sequence set forth in SEQ ID NO: 5 and having at least one amino acid substitution at residues 1-19, 27-38, 44-87, 96-120, 125-141, 159-184, 199-202, 215-380, or 387-473 of SEQ ID NO:5;
(b) at least 95% identity to the amino acid sequence set forth in SEQ ID NO: 5 and having an amino acid substitution at one or more residues selected from the group consisting of residues 30, 93, 99, 122, 140, 142, 144, 148, 152, 153, 156, 195, 196, 199, 206, 207, 211, 213, 221, 286, 343, 364, 384, 427, and 438 of SEQ ID NO:5;
(c) at least 95% identity to the amino acid sequence set forth in SEQ ID NO: 5 and having an arginine at residue 206, a cysteine at residue 207, and an arginine at residue 343 relative to SEQ ID NO:5; or
(d) at least 95% identity to the amino acid sequence set forth in SEQ ID NO: 5 and having a tyrosine or phenylalanine at residue 30, a proline or glutamine at residue 93, a serine or valine at residue 99, a tyrosine or phenylalanine at residue 122, a histidine or tyrosine at residue 140, a serine or cysteine at residue 142, an alanine or threonine at residue 148, a methionine at residue 152, an alanine at residue 153, an alanine or serine at residue 156, a glycine at residue 162, a leucine or methionine at residue 195, a glutamic acid at residue 196, a lysine or glutamic acid at residue 199, a leucine or methionine at residue 211, a leucine at residue 213, a serine or phenylalanine at residue 221, a valine or isoleucine at residue 253, a valine or alanine at residue 286, an asparagine or lysine at residue 427, or an alanine at residue 438 and an alanine or threonine at residue 462 relative to SEQ ID NO:5.

21. The method of claim 19, wherein the polypeptide capable of beta 1,3 glycosylation of the C3' of the 13-O-glucose of a steviol glycoside comprises a polypeptide having at least 95% identity to the amino acid sequence set forth in SEQ ID NO: 7.

22. The method of claim 19, wherein the polypeptide capable of beta 1,3 glycosylation of the C3' of the 13-O-glucose of a steviol glycoside comprises one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 of SEQ ID NO:7.

23. The method of claim 11, further comprising isolating the Rebaudioside D, alone or together with at least one other steviol glycoside from the cell culture broth.

24. The method of claim 11, further comprising recovering Rebaudioside D, alone or together with at least one other steviol glycoside, from the cell culture broth.

* * * * *

UNITED STATES PATENT AND TRADEMARK OFFICE
CERTIFICATE OF CORRECTION

PATENT NO. : 12,428,628 B2  
APPLICATION NO. : 18/756786  
DATED : September 30, 2025  
INVENTOR(S) : Ganesh M. Kishore et al.

Page 1 of 1

It is certified that error appears in the above-identified patent and that said Letters Patent is hereby corrected as shown below:

In the Claims

In Claim 16 (Column 187, Line 38), the text "19-0 glucose" should be corrected to read "19-O glucose".

Signed and Sealed this  
Thirtieth Day of December, 2025

John A. Squires  
*Director of the United States Patent and Trademark Office*

```
                         SEQUENCE LISTING

Sequence total quantity: 151
SEQ ID NO: 1            moltype = AA   length = 460
FEATURE                 Location/Qualifiers
source                  1..460
                        mol_type = protein
                        organism = Stevia rebaudiana
SEQUENCE: 1
MAEQQKIKKS PHVLLIPFPL QGHINPFIQF GKRLISKGVK TTLVTTIHTL NSTLNHSNTT    60
TTSIEIQAIS DGCDEGGFMS AGESYLETFK QVGSKSLADL IKKLQSEGTT IDAIIYDSMT   120
EWVLDVAIEF GIDGGSFFTQ ACVVNSLYYH VHKGLISLPL GETVSVPGFP VLQRWETPLI   180
LQNHEQIQSP WSQMLFGQFA NIDQARWVFT NSFYKLEEEV IEWTRKIWNL KVIGPTLPSM   240
YLDKRLDDDK DNGFNLYKAN HHECMNWLDD KPKESVVYVA FGSLVKHGPE QVEEITRALI   300
DSDVNFLWVI KHKEEGKLPE NLSEVIKTGK GLIVAWCKQL DVLAHESVGC FVTHCGFNST   360
LEAISLGVPV VAMPQFSDQT TNAKLLDEIL GVGVRVKADE NGIVRRGNLA SCIKMIMEEE   420
RGVIIRKNAV KWKDLAKVAV HEGGSSDNDI VEFVSELIKA                         460

SEQ ID NO: 2            moltype = DNA  length = 1383
FEATURE                 Location/Qualifiers
source                  1..1383
                        mol_type = genomic DNA
                        organism = Stevia rebaudiana
SEQUENCE: 2
atggcagagc aacaaaagat caaaaagtca cctcacgtct tacttattcc atttcctctg     60
caaggacata tcaacccatt catacaattt gggaaaagat tgattagtaa gggtgtaaag    120
acaacactgg taaccactat ccacactttg aattctactc tgaaccactc aaatactact    180
actacaagta tagaaattca agctatatca gacggatgcg atgagggtgg ctttatgtct    240
gccggtgaat cttacttgga aacattcaag caagtgggat ccaagtctct ggccgatcta    300
atcaaaaagt tacagagtga aggcaccaca attgacgcca taatctacga ttctatgaca    360
gagtgggttt tagacgttgc tatcgaattt ggtattgatg gaggttcctt tttcacacaa    420
gcatgtgttg tgaattctct atactaccat gtgcataaag ggttaatctc tttaccattg    480
ggtgaaactg tttcagttcc aggttttcca gtgttacaac gttgggaaac cccattgatc    540
ttacaaaatc atgaacaaat acaatcacct tggtcccaga tgttgtttgg tcaattcgct    600
aacatcgatc aagcaagatg ggtctttact aattcattct ataagttaga ggaagaggta    660
attgaatgga ctaggaagat ctggaatttg aaagtcattg gtccaacatt gccatcaatg    720
tatttggaca aaagacttga tgatgataaa gataatggtt tcaatttgta caaggctaat    780
catcacgaat gtatgaattg gctggatgac aaaccaaagg aatcagttgt atatgttgct    840
ttcggctctc ttgttaaaca tggtccagaa caagttgagg agattacaag agcacttata    900
gactctgacg taaactttt gtgggtcatt aagcacaaag aggagggaa actgccagaa      960
aacctttctg aagtgataaa gaccggaaaa ggtctaatcg ttgcttggtg taaacaattg   1020
gatgttttag ctcatgaatc tgtaggctgt tttgtaacac attgcggatt caactctaca   1080
ctagaagcca tttccttagg cgtacctgtc gttgcaatgc ctcagttctc cgatcagaca   1140
accaacgcta aacttttgga cgaaatacta ggggtgggtg tcagagttaa agcagacgag   1200
aatggtatcg tcagaagagg gaacctagct tcatgtatca aaatgatcat ggaagaggaa   1260
agaggagtta tcataaggaa aaacgcagtt aagtggaagg atcttgcaaa ggttgccgtc   1320
catgaaggcg gctcttcaga taatgatatt gttgaatttg tgtccgaact aatcaaagcc   1380
taa                                                                 1383

SEQ ID NO: 3            moltype = AA   length = 481
FEATURE                 Location/Qualifiers
source                  1..481
                        mol_type = protein
                        organism = Stevia rebaudiana
SEQUENCE: 3
MDAMATTEKK PHVIFIPFPA QSHIKAMLKL AQLLHHKGLQ ITFVNTDFIH NQFLESSGPH    60
CLDGAPGFRF ETIPDGVSHS PEASIPIRES LLRSIETNFL DRFIDLVTKL PDPPTCIISD   120
GFLSVFTIDA AKKLGIPVMM YWTLAACGFM GFYHIHSLIE KGFAPLKDAS YLTNGYLDTV   180
IDWVPGMEGI RLKDFPLDWS TDLNDKVLMF TTEAPQRSHK VSHHIFHTFD ELEPSIIKTL   240
SLRYNHIYTI GPLQLLLDQI PEEKKQTGIT SLHGYSLVKE EPECFQWLQS KEPNSVVYVN   300
FGSTTVMSLE DMTEFGWGLA NSNHYFLWII RSNLVIGENA VLPPELEEHI KKRGFIASWC   360
SQEKVLKHPS VGGFLTHCGW GSTIESLSAG VPMICWPYSW DQLTNCRYIC KEWEVGLEMG   420
TKVKRDEVKR LVQELMGEGG HKMRNKAKDW KEKARIAIAP NGSSSLNIDK MVKEITVLAR   480
N                                                                   481
```

| SEQ ID NO: 4 | moltype = DNA length = 1446 |
|---|---|
| FEATURE | Location/Qualifiers |
| source | 1..1446 |
| | mol_type = genomic DNA |
| | organism = Stevia rebaudiana |

SEQUENCE: 4

```
atggatgcaa tggcaactac tgagaaaaag cctcatgtga tcttcattcc atttcctgca   60
caatctcaca taaaggcaat gctaaagtta gcacaactat tacaccataa gggattacga  120
ataactttcg tgaataccga cttcatccat aatcaatttc tggaatctag tggccctcat  180
tgtttggacg gagccccagg gtttagattc gaaacaattc ctgacggtgt ttcacattcc  240
ccagaggcct ccatcccaat aagagagagt ttactgaggt caatagaaac caacttttg   300
gatcgtttca ttgacttggt cacaaaactt ccagacccac caacttgcat aatctctgat  360
ggctttctgt cagtgtttac tatcgacgct gccaaaaagt gggtatccc  agttatgatg  420
tactggactc ttgctgcatg cggtttcatg ggtttctatc acatccattc tcttatcgaa  480
aagggttttg ctccactgaa agatgcatca tacttaacca acggctacct ggatactgtt  540
attgactggg taccaggtat ggaaggtata agacttaaag attttccttt ggattggtct  600
acagacctta atgataaagt attgatgttt actacagaag ctcccacaag atctcataag  660
gtttcacatc atatctttca caccttgat gaattgcaac catcaatcat caaaacttg   720
tctctaagat acaatcatat ctacactatt ggtccattca atttacttct agatcaaatt  780
cctgaagaga aaaagcaaac tggtattaca tccttacacg gctactcttt agtgaaagag  840
gaaccagaat gtttttcaatg gctacaaagt aaagagccta attctgtggt ctacgtcaac  900
ttcggaagta caacagtcag gtccttggaa gatatgcctta aatttggttg ggccttgca  960
aattcaaatc attacttctct atggattatc aggtccaatt tggtaatagg ggaaaacgcc 1020
gtattacctc cagaattgga ggaacacatc aaaaagagag gttcattgc  ttcctggtgt 1080
tctcaggaaa aggtattgaa acatcccttct gttggtggtt ccttactca ttgcggttgg 1140
ggctctacaa tcgaatcact aagtgcagga gttccaatga tttgttgcc atatttcatg 1200
gaccaactta caaattgtag gtatatctgt aaagagtgg aagttggatt agaaatggga 1260
acaaggtta acgtgatga agtgaaaaga ttggttcagg agttgatggg ggaaggtggc 1320
cacaagatga aaacaaggc caaagattgg aaggaaaaag ccagaattgc tattgctcct 1380
aacgggtcat cctctctaaa cattgataag atggtcaaag agattacagt cttagccaga 1440
aactaa                                                             1446
```

| SEQ ID NO: 5 | moltype = AA length = 473 |
|---|---|
| FEATURE | Location/Qualifiers |
| source | 1..473 |
| | mol_type = protein |
| | organism = Stevia rebaudiana |

SEQUENCE: 5

```
MATSDSIVDD RKQLHVATFP WLAFGHILPY LQLSKLIAEK GHKVSFLSTT RNIQRLSSHI   60
SPLINVVQLT LPRVQELPED AEATTDVHPE DIPYLKKASD GLQPEVTRFL EQHSPDWIIY  120
DYTHYWLPSI AASLGISRAH FSVTTPWAIA YMGPSADAMI NGSDGRTTVE DLTTPPKWFP  180
FPTKVCWRKH DLARLVPYKA PGISDGYRMG LVLKGSDCLL SKCYHEFGTQ WLPLLETLHQ  240
VPVVPVGLLP PEIPGDEKDE TWVSIKKWLD GKQKGSVVYV ALGSEVLVSQ TEVVELALGL  300
ELSGLPFVWA YRKPKGPAKS DSVELPDGFV ERTRDRGLVW TSWAPQLRIL SHESVCGFLT  360
HCGSGSIVEG LMFGHPLIML PIFGDQPLNA RLLEDKQVGI EIPRNEEDGC LTKESVARSL  420
RSVVVEKEGE IYKANARELS KIYNDTKVEK EYVSQFVDYL EKNARAVAID HES         473
```

| SEQ ID NO: 6 | moltype = DNA length = 1422 |
|---|---|
| FEATURE | Location/Qualifiers |
| source | 1..1422 |
| | mol_type = genomic DNA |
| | organism = Stevia rebaudiana |

SEQUENCE: 6

```
atggctacat ctgattctat tgttgatgac aggaagcagt tgcatgtggc tactttccct   60
tggcttgctt tcggtcatat actgccttac ctacaactat caaaactgat agctgaaaaa  120
ggacataaag tgtcattcct ttcaacaact agaaacattc aaagattatc ttcccacata  180
tcaccattga ttaacgtcgt tcaattgaca cttccaagag tacaggaatt accagaagat  240
gctgaagcta aacagatgt gcatcctgaa gatatcccctt acttgaaaaa ggcatccgat  300
ggattacagc ctgaggtcac tagattcctt gagcaacaca gtccagattg gatcatatac  360
gactacactc actattggtt gccttcaatt gcagcatcac taggcatttc tagggcacat  420
ttcagtgtaa ccacccttg  ggccattgct tacatgggtc catccgctga tgctatgatt  480
aacggcagtg atggtagaac taccgttgaa gatttgacaa ccccaccaaa gtggtttcca  540
tttccaacta agtctgttg  gagaaaacac gacttagcaa gactggttcc atacaaggca  600
ccaggaatct cagacggcta tagaatgggt ttagtcctta aaggtctga  ctgcctattg  660
tctaagtgtt accatgagtt tgggacacaa tggctaccac ttttggaaac attacaccaa  720
gttcctgtcg taccagttgg tctattacct cagaaatcc ctggtgatga aggacgag    780
acttgggttt caatcaaaaa gtggttagac gggaagcaaa aaggctcagt ggtatatgtg  840
gcactggggtt ccgaagtttt agtatctcaa acagaagttg tggaacttgc cttaggtttg  900
gaactatctg gattgccatt tgtctgggcc tacagaaaac caaaaggccc tgcaaagtcc  960
gattcagttg aattgccaga cggctttgtc gagagaacta gagatagag  gttggtatgg 1020
acttcatggg ctccacaatt gagaatcctg agtcacgaat ctgtgtgcgg tttcctaaca 1080
cattgtggtt ctggttctat agttgaagga ctgatgtttg gtcatccact tatcatgttg 1140
ccaatctttg gtgaccagcc tttgaatgca cgtctgttag aagataaaca agttggaatt 1200
gaaatcccac gtaatgagga agatggtgt ttaaccaaga gtctgtgc  cagatcatta 1260
cgttccgttg tcgttgaaaa ggaaggcgaa atctacaagg ccaatgcccg tgaactttca 1320
aagatctaca tgacacaaa  agtagagaag gaatatgtt  tcaatttgt agattaccta 1380
gagaaaaacg ctagagccgt agctattgat catgaatcct aa                    1422
```

SEQ ID NO: 7          moltype = AA length = 458

```
FEATURE                 Location/Qualifiers
source                  1..458
                        mol_type = protein
                        organism = Stevia rebaudiana
SEQUENCE: 7
MENKTETTVR RRRRIILFPV PFQGHINPIL QLANVLYSKG FSITIFHTNF NKPKTSNYPH     60
FTFRFILDND PQDERISNLP THGPLAGMRI PIINEHGADE LRRELELLML ASEEDEEVSC    120
LITDALWYFA QSVADSLNLR RLVLMTSSLF NFHAHVSLPQ FDELGYLDPD DKTRLEEQAS    180
GPPMLKVKDI KSAYSNWQIL KEILGKMIKQ TKASSGVIWN SPKELEESEL ETVIREIPAP    240
SFLIPLPKHL TASSSSLLDH DRTVFQWLDQ QPPSSVLYVS FGSTSEVDEK DFLEIARGLV    300
DSKQSFLWVV RPGFVKGSTW VEPLPDGFLG ERGRIVKWVP QQEVLAHGAI GAFWTHSGWN    360
STLESVCEGV PMIFSDFGLD QPLNARYMSD VLKVGVYLEN GWERGEIANA IRRVMVDEEG    420
EYIRQNARVL KQKADVSLMK GGSSYESLES LVSYISSL                           458

SEQ ID NO: 8            moltype = DNA   length = 1377
FEATURE                 Location/Qualifiers
source                  1..1377
                        mol_type = genomic DNA
                        organism = Stevia rebaudiana
SEQUENCE: 8
atggaaaaca agaccgaaac aacagttaga cgtaggcgta gaatcattct gtttccagta     60
ccttttcaag ggcacatcaa tccaatacta caactagcca acgttttgta ctctaaaggt    120
ttttctatta caatctttca caccaatttc aacaaaccaa aaacatccaa ttacccacat    180
ttcacattca gattcatact tgataatgat ccacaagatg aacgtatttc aaacttacct    240
acccacggtc cttagctgg aatgagaatt ccaatcatca atgaacatgg tgccgatgag    300
cttagaagag aattagagtt acttatgttg gcatccgaag aggacgagga agtctccttgt    360
ctgattactg acgctctatg gtactttgcc caatctgtgg ctgatagttt gaatttgagg    420
agattggtac taatgacatc cagtctgttt aactttcacg ctcatgttag tttaccacaa    480
tttgacgaat tgggatactt ggaccctgat acaagacta ggttagagga caggcctct    540
ggttttccta tgttgaaagt caaagatatc aagtctgcct attctaattg gcaaatcttg    600
aaagagatct taggaaagat gatcaaacag acaaaggct catctggagt gatttggaac    660
agtttcaaag agttagaaga gtctgaattg gagactgtaa tcagagaaat tccagcacct    720
tcattcctga taccattacc aaaacatttg actgcttcct cttcctcttt gttggatcat    780
gacagaacag ttttttcaatg gttggaccaa caaccaccta gttctgtttt gtacgtgtca    840
tttggtagta cttcctgaagt cgatgaaaag gacttccttg aaatcgcaag aggcttagtc    900
gatagtaagc agtcattcct tgggtcgtg cgtccaggtt tcgtgaaagg ctcaacatgg    960
gtcgaaccac ttccagatgg ttttctaggc gaaagaggta gaatagtcaa atgggttcct   1020
caacaggaag ttttagctca tggcgctatt ggggcattct ggactcattc cggatggaat   1080
tcaactttag aatcagtatg cgaagggta cctatgatct tcagttgatttt tggtcttgat   1140
caaccactga acgcaagata catgtctgat gttttgaaag tgggtgtata tctagaaaat   1200
ggctgggaaa gggtgaaat agctaatgca ataagacgtg ttatgttga tgaagagggg    1260
gagtatatca gacaaaacgc aagagtgctg aagcaaaagg ccgacgtttc tctaatgaag   1320
ggaggctctt catacgaatc cttagaatct cttgtttcct acatttcatc actgtaa      1377

SEQ ID NO: 9            moltype = DNA   length = 1422
FEATURE                 Location/Qualifiers
source                  1..1422
                        mol_type = genomic DNA
                        organism = Stevia rebaudiana
SEQUENCE: 9
atggctacca gtgactccat agttgacgac cgtaagcagc ttcatgttgc gacgttccca     60
tggcttgctt tcggtcacat cctcccttac cttcagcttt cgaaattgat agctgaaaag    120
ggtcacaaag tctcgtttct ttctaccacc agaaacattc aacgtctctc ttctcatatc    180
tcgccactca taaatgttgt tcaactcaca cttccacgtg tccaagagct gccggaggat    240
gcagaggcga ccactgacgt ccaccctgaa gatattccat atctcaagaa ggcttctgat    300
ggtcttcaac cggaggtcac ccggtttcta gaacaacact ctccggactg gattatttat    360
gattatactc actactggtt gccatccatc gcggctagcc tcggtatctc acgagcccac    420
ttctccgtca ccactccatg ggccattgct tatatgggac cctcagctga cgccatgata    480
aatggttcag atggtcgaac cacggttgag gatctcacga caccgcccaa gtgtttccc    540
tttccgacca aagtatgctg gcggaagcat gatcttgccc gactggtgcc ttacaaagct    600
ccggggatat ctgatggata ccgtatgggg ctggttctta agggatctga ttgtttgctt    660
tccaaatgtt accatgagtt tggaactcaa tggctacctc tttggagac actacaccaa    720
gtaccggtgt tccggtggg attactgcca ccggaaatac ccggagacga gaaagatgaa    780
acatgggtgt caatcaagaa atggctcgat ggtaaacaaa aaggcagtgt ggtgtacgct    840
gcattaggaa gcgaggtttt ggtgagccaa accgaggttg ttgagttagc attgggtctc    900
gagctttctg ggttgccatt tgtttggct tatagaaaac caaaggtcc cgcgaagtca    960
gactcggtgg agttgccaga cgggttcgtg gaacgaactc gtgaccgtgg gttggtctgg   1020
acgagttggg caccctcagtt acgaatactg agccatgagt cggttgtgg tttcttgact   1080
cattgtggtt ctggatcaat tgtggaaggg ctaatgtttg gtcaccctct aatcatgcta   1140
ccgatttttg ggaccaacc tctgaatgct cgattactgg aggacaaaca ggtgggaatc   1200
gagataccaa gaaatgagga agatggttgc ttgaccaagg agtcggttgc tagatcactg   1260
aggtccgttg ttgtggaaaa agaaggggag atctacaagg cgaacgcgag ggagctgagt   1320
aaaatctata cgacactaa ggttgaaaaa gaatatgtaa gccaattcgt agactatttg   1380
gaaaagaatg cgcgtgcggt tgccatcgat catgagagtt aa                     1422

SEQ ID NO: 10           moltype = AA    length = 473
FEATURE                 Location/Qualifiers
source                  1..473
                        mol_type = protein
```

```
                        organism = Stevia rebaudiana
SEQUENCE: 10
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARLVPYKA PGISDGYRMG LVLKGSDCLL SKCYHEFGTQ WLPLLETLHQ   240
VPVVPVGLLP PEVPGDEKDE TWVSIKKWLD GKQKGSVYV  ALGSEVLVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFGDQPLNA RLLEDKQVGI EIPRNEEDGC LTKESVARSL   420
RSVVVEKEGE IYKANARELS KIYNDTKVEK EYVSQFVDYL EKNTRAVAID HES          473

SEQ ID NO: 11           moltype = DNA  length = 1422
FEATURE                 Location/Qualifiers
source                  1..1422
                        mol_type = genomic DNA
                        organism = Stevia rebaudiana
SEQUENCE: 11
atggctacca gtgactccat agttgacgac cgtaagcagc ttcatgttgc gacgttccca    60
tggcttgctt tcggtcacat cctcccttac cttcagcttt cgaaattgat agctgaaaag   120
ggtcacaaag tctcgtttct ttctaccacc agaaacattc aacgtctctc ttctcatatc   180
tcgccactca taaatgttgt tcaactcaca cttccacgtg tccaagagct gccggaggat   240
gcagaggcga ccactgacgt ccaccctgaa gatattgaat atctcaagaa ggcttctgat   300
ggtcttcaac cggaggtcac ccggtttcta gaacaacact ctccggactg gattatttat   360
gattatactc actactggtt gccatccatc gcggctagcc tcggtatctc acgagcccac   420
ttctccgtca ccactccatg ggccattgct tatatgggac cctcagctga cgccatgata   480
aatggttcag atggtcgaac cacggttgag gatctcacga caccgcccaa gtggtttccc   540
tttccgacca agtatgctg  gcggaagcat gatcttgccc gactggtgcc ttacaaagct   600
ccggggatat ctgatggata ccgtatgggg ctggttctta agggatctga ttgtttgctt   660
tccaaatgtt accatgagtt tggaactcaa tggctacctc ttttggagac actacaccaa   720
gtaccggtgg ttccggtggg attactgcca ccggaagtac ccggagacga gaaagatgaa   780
acatgggtgt caatcaagaa atggctcgat ggtaaacaaa aaggcagtgt ggtgtacgtt   840
gcattaggaa gcgaggtttt ggtgagccaa accgaggttg ttgagttagc attgggtctc   900
gagctttctg ggttgccatt tgtttgggct tatagaaaac caaaaggtcc cgcgaagtca   960
gactcggtgg agttgccaga cgggttcgtg aacgaactcc gtgaccgtgg gttggtctgg  1020
acgagttggg cacctcagtt acgaatactg agccatgagt cggtttgtgg tttcttgact  1080
cattgtggtt ctggatcaat tgtggaaggg ctaatgtttg gtcaccctct aatcatgcta  1140
ccgatttttg gggaccaacc tctgaatgct cgattactgg aggacaaaca ggtgggaatc  1200
gagataccaa gaaatgagga gatggttgc  ttgaccaagt agtcggttgc tagatcactg  1260
aggtccgttg ttgtggaaaa agaagggag  atctcaaggc cgaacgcgag ggagctgagt  1320
aaaatctata acgacactaa ggttgaaaaa gaatatgtaa gccaattcgt agactatttg  1380
gaaaagaata cgcgtgcggt tgccatcgat catgagagtt aa                     1422

SEQ ID NO: 12           moltype = AA  length = 473
FEATURE                 Location/Qualifiers
source                  1..473
                        mol_type = protein
                        organism = Stevia rebaudiana
SEQUENCE: 12
MATSDSIVDD RKQLHVATFP WLAFGHILPF LQLSKLIAEK GHKVSFLSTT RNIQRLSSHI    60
SPLINVVQLT LPRVQELPED AEATTDVHPE DIQYLKKAVD GLQPEVTRFL EQHSPDWIIY   120
DFTHYWLPSI AASLGISRAY FCVITPWTIA YLAPSSDAMI NDSDGRTTVE DLTTPPKWFP   180
FPTKVCWRKH DLARMEPYEA PGISDGYRMG MVFKGSDCLL FKCYHEFGTQ WLPLLETLHQ   240
VPVVPVGLLP PEIPGDEKDE TWVSIKKWLD GKQKGSVYV  ALGSEALVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PLFGDQPLNA RLLEDKQVGI EIPRNEEDGC LTKESVARSL   420
RSVVVENEGE IYKANARELS KIYNDTKVEK EYVSQFVDYL EKNARAVAID HES          473

SEQ ID NO: 13           moltype = DNA  length = 1422
FEATURE                 Location/Qualifiers
source                  1..1422
                        mol_type = genomic DNA
                        organism = Stevia rebaudiana
SEQUENCE: 13
atggctacca gtgactccat agttgacgac cgtaagcagc ttcatgttgc gacgttccca    60
tggcttgctt tcggtcacat cctccctttc cttcagcttt cgaaattgat agctgaaaag   120
ggtcacaaag tctcgtttct ttctaccacc agaaacattc aacgtctctc ttctcatatc   180
tcgccactca taaatgttgt tcaactcaca cttccacgtg tccaagagct gccggaggat   240
gcagaggcga ccactgacgt ccaccctgaa gatattcaat atctcaagaa ggctgttgat   300
ggtcttcaac cggaggtcac ccggtttcta gaacaacact ctccggactg gattatttat   360
gattttactc actactggtt gccatccatc gcggctagcc tcggtatctc acgagcctac   420
ttctgcgtca tcactccatg gaccattgct tatttggcac cctcatctga cgccatgata   480
aatgattcag atggtcgaac cacggttgag gatctcacga caccgcccaa gtggtttccc   540
tttccgacca agtatgctg  gcggaagcat gatcttgccc gaatggagcc ttacgaagct   600
ccaggggatat ctgatggata ccgtatgggg atggtttta agggatctga ttgtttgctt   660
ttcaaatgtt accatgagtt tggaactcaa tggctacctc ttttggagac actacaccaa   720
gtaccggtgg ttccggtggg attactgccg ccggaaatac ccggagacga gaaagatgaa   780
acatgggtgt caatcaagaa atggctcgat ggtaaacaaa aaggcagtgt ggtgtacgtt   840
gcattaggaa gcgaggcttt ggtgagccaa accgaggttg ttgagttagc attgggtctc   900
gagctttctg ggttgccatt tgtttgggct tatagaaaac caaaaggtcc cgcgaagtca   960
```

```
gactcggtgg agttgccaga cgggttcgtg gaacgaactc gtgaccgtgg gttggtctgg   1020
acgagttggg cacctcagtt acgaatactg agccatgagt cggtttgtgg tttcttgact   1080
cattgtggtt ctggatcaat tgtggaaggg ctaatgtttg gtcaccctct aatcatgcta   1140
ccgcttttg gggaccaacc tctgaatgct cgattactgg aggacaaaca ggtgggaatc    1200
gagataccaa gaaatgagga agatggttgc ttgaccaagg agtcggttgc tagatcactg   1260
aggtccgttg ttgtgaaaaa cgaagggga atctacaagg cgaacgcgag ggagctgagt    1320
aaaatctata acgacactaa ggtggaaaaa gaatatgtaa gccaattcgt agactatttg   1380
gaaaagaatg cgcgtgcggt tgccatcgat catgagagtt aa                      1422
```

```
SEQ ID NO: 14           moltype = AA   length = 485
FEATURE                 Location/Qualifiers
source                  1..485
                        mol_type = protein
                        organism = Stevia rebaudiana
SEQUENCE: 14
MYNVTYHQNS KAMATSDSIV DDRKQLHVAT FPWLAFGHIL PFLQLSKLIA EKGHKVSFLS    60
TTRNIQRLSS HISPLINVVQ LTLPRVQELP EDAEATTDVH PEDIQYLKKA VDGLQPEVTR   120
FLEQHSPDWI IYDFTHYWLP SIAASLGISR AYFCVITPWT IAYLAPSSDA MINDSDGRTT   180
VEDLTTPPKW FPFPTKVCWR KHDLARMEPY EAPGISDGYR MGMVFKGSDC LLFKCYHEFG   240
TQWLPLLETL HQVPVVPVGL LPPEIPGDEK DETWVSIKKW LDGKQKGSVV YVALGSEALV   300
SQTEVVELAL GLELSGLPFV WAYRKPKGPA KSDSVELPDG FVERTRDRGL VWTSWAPQLR   360
ILSHESVCGF LTHCGSGSIV EGLMFGHPLI MLPIFCDQPL NARLLEDKQV GIEIPRNEED   420
GCLTKESVAR SLRSVVVENE GEIYKANARA LSKIYNDTKV EKEYVSQFVD YLEKNARAVA   480
IDHES                                                               485
```

```
SEQ ID NO: 15           moltype = DNA   length = 1458
FEATURE                 Location/Qualifiers
source                  1..1458
                        mol_type = genomic DNA
                        organism = Stevia rebaudiana
SEQUENCE: 15
atgtacaacg ttacttatca tcaaaattca aaagcaatgg ctaccagtga ctccatagtt     60
gacgaccgta agcagcttca tgttgcgacg ttcccatggc ttgctttcgg tcacatcctc    120
cctttcctc agctttcgaa attgatagct gaaaagggtc acaaagtctc gtttctttct     180
accaccagaa acattcaacg tctctcttct catatctcgc cactcataaa tgttgttcaa    240
ctcacacttc cacgtgtcca agagctgccg gaggatgcag aggcgaccac tgacgtccac    300
cctgaagata ttcaatatct caagaaggct gttgatggtc ttcaaccgga ggtcaccgg     360
tttctagaac aacactctcc ggactggatt attttatgat ttactcacta ctggttgcca    420
tccatcgcgg ctagcctcgg tatctcacga gcctacttct ggtcgtcatc tccatggacc    480
attgcttatt tggcacccte atctgacgcc atgataaatg attcagatgg tcgaaccacg    540
gttgaggatc tcacgacacc gcccaagtgg tttcccttc cgaccaaagt atgctggcgg     600
aagcatgatc ttgcccgaat ggagcctac gaagctccgg ggatatctga tggataccgt     660
atggggatgg ttttaaggg atctgattgt ttgcttttca aatgttacca tgagtttgga    720
actcaatggc tacctctttt ggagacacta caccaagtac cggtggttcc ggtgggatta    780
ctgccgccgg aaatacccgg agacgagaaa gatgaaacat gggtgtcaat caagaaatgg   840
ctcgatggta acaaaaagg cagtgtggtg tacgttcat taggaagcga ggctttggtg     900
agccaaaccg aggttgttga gttagcattg gtctcgaac tttctgggtt gccatttgtt    960
tgggcttata gaaaaccaaa aggtcccgcg aagtcagact cggtcgagtt gccagacggg   1020
ttcgtggaac gaactcgtga ccgtgggttg gtctggacga gttgggcacc tcagttacga   1080
atactgagcc acgagtcagt ttgtggtttc ttgactcatt gtggttctgg atcaattgtg   1140
gaaggctaa tgtttggtca ccctctaatc atgctaccgc ttttttgtga ccaacctctg    1200
aatgctcgat tactgagga caaacaggtg ggaatcgaga taccaagaaa tgaggaagat    1260
ggttgcttga ccaaggagtc ggttgctaga tcactgaggt ccgttgttgt ggaaaacgaa   1320
ggggagatct acaaggcgaa cgcgagggcg ctgagtaaaa tctataacga cactaaggtg   1380
gaaaagaat atgtaagcca attcgtagac tatttggaaa agaatgcgcg tgcggttgcc    1440
atcgatcatg agagttaa                                                 1458
```

```
SEQ ID NO: 16           moltype = AA   length = 473
FEATURE                 Location/Qualifiers
source                  1..473
                        mol_type = protein
                        organism = Stevia rebaudiana
SEQUENCE: 16
MATSDSIVDD RKQLHVATFP WLAFGHILPF LQLSKLIAEK GHKVSFLSTT RNIQRLSSHI    60
SPLINVVQLT LPRVQELPED AEATTDVHPE DIQYLKKAVD GLQPEVTRFL EQHSPDWIIY   120
DFTHYWLPSI AASLGISRAY FCVITPWTIA YLAPSSDAMI NDSDGRTTVE DLTTPPKWFP   180
FPTKVCWRKH DLARMEPYEA PGISDGYRMG MVFKGSDCLL FKCYHEFGTQ WLPLLETHQ    240
VPVVPVGLLP PEIPGDEKDE TWVSIKKWLD GKQKGSVVYV ALGSEALVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFCDQPLNA RLLEDKQVGI EIPRNEEDGC LTKESVARSL   420
RSVVVENEGE IYKANARALS KIYNDTKVEK EYVSQFVDYL EKNARAVAID HES          473
```

```
SEQ ID NO: 17           moltype = DNA   length = 1422
FEATURE                 Location/Qualifiers
source                  1..1422
                        mol_type = genomic DNA
                        organism = Stevia rebaudiana
SEQUENCE: 17
atggctacca gtgactccat agttgacgac cgtaagcagc ttcatgttgc gacgttccca     60
```

```
tggcttgctt tcggtcacat cctcccttc cttcagcttt cgaaattgat agctgaaaag    120
ggtcacaaag tctcgtttct ttctaccacc agaaacattc aacgtctctc ttctcatatc    180
tcgccactca taaatgttgt tcaactcaca cttccacgtg tccaagagct gccggaggat    240
gcagaggcga ccactgacgt ccaccctgaa gatattcaat atctcaagaa ggctgttgat    300
ggtcttcaac cggaggtcac ccggtttcta gaacaacact ctccggactg gattatttat    360
gattttactc actactggtt gccatccatc gcggctagcc tcggtatctc acgagcctac    420
ttctgcgtca tcactccatg gaccattgct tatttggcac cctcatctga cgccatgata    480
aatgattcag atggtcgaac cacgttgag gatctcacga caccgccaa gtggtttccc     540
tttccgacca agtatgctg gcggaagcat gatcttgcc gaatgaagcc ttacgaagct     600
ccggggatat ctgatgggata ccgtatgggg atggttttta agggatctga ttgtttgctt    660
ttcaaatgtt accatgagtt tggaactcaa tggctacctc ttttggagac actacaccaa    720
gtaccggtgt ttccggtggg attactgccg ccggaaatac ccggagacga gaaagatgaa    780
acatgggtgt caatcaagaa atggctcgat ggtaaacaaa aaggcagtgt ggtgtacgtt    840
gcattaggaa gcgaggcttt ggtgagccaa accgaggttg ttgagttagc attgggtctc    900
gagctttctg ggttgccatt tgtttgggct tatagaaaac caaaaggtcc cgcgaagtca    960
gactcggtgg agttgccaga cgggttcgtg aacgaactc gtgaccgtgg ttggtctgg    1020
acgagttggg cacctcagtt acgaatactg agccacgagt cagtttgtgg tttcttgact   1080
cattgtggtt ctggatcaat tgtggaaggg ctaatgtttg gtcaccctct aatcatgcta   1140
ccgatttttt gtgaccaacc tctgaatgct cgattactgg aggacaaaca ggtgggaatc    1200
gagataccaa gaaatgagga agatggttgc ttgaccaagg agtcggttgc tagatcactg    1260
aggtccgttg ttgtggaaaa cgaaggggag atctacaagg cgaacgcgag ggcgctgagt   1320
aaaatctata acgacactaa ggtggaaaaa gaatatgtaa gccaattcgt agactatttg    1380
gaaaagaatg cgcgtgcggt tgccatcgat catgagagtt aa                      1422
SEQ ID NO: 18         moltype = DNA  length = 1086
FEATURE               Location/Qualifiers
misc_feature          1..1086
                      note = Description of Artificial Sequence: Synthetic
                      polynucleotide
source                1..1086
                      mol_type = other DNA
                      organism = synthetic construct
SEQUENCE: 18
atggctttgg taaacccaac cgctctttc tatggtacct ctatcagaac aagacctaca      60
aacttactaa aatccaactca aaagctaaga ccagtttcat catcttcctt accttctttc    120
tcatcagtta gtgcgattct tactgaaaaa catcaatcta atccttctga gaacaacaat    180
ttgcaaactc atctagaaac tcctttcaac tttgatagtt atatgttgga aaagtcaac     240
atggttaacg aggcgcttga tgcatctgtc ccactaaaag acccaatcaa aatccatgaa    300
tccatgagat actctttatt ggcaggcggt aagagaatca gaccaatgat gtgtattgca   360
gcctgcgaaa tagtcggagg taatatcctt aacgccatgc cagccgcatg tgccgtggaa    420
atgattcata ctatgtcttt ggtgcatgac gatcttccat gtatgataa tgatgacttc    480
agaagaggta aacctatttc acacaaggtc tacggggagg aaatggcagt attgaccggc    540
gatgctttac taagtttatc tttcgaacat atagctactg ctacaaaggg tgtatcaaag    600
gatagaatcg tcagagctat aggggagttg gcccgttcag ttggctccga aggtttagtg    660
gctgacaag ttgtagatat cttgtcagag ggtgctgatg ttggattaga tcacctagaa    720
tacattcaca tccacaaaac agcaatgttg cttgagtcct cagtagttat tggcgctatc    780
atgggaggga gatctgatca gcagatcgaa aagttgaaca aattcgctag atctattggt    840
ctactattcc aagttgtgga tgacattttg gatgttacaa aatctaccga agagttgggg    900
aaaacagctg gtaaggattt gttgacagat aagacaactt acccaaagtt gttaggtata    960
gaaaagtcca gagaatttgc cgaaaaactt aacaaggaag cacaagagca attaagtggc   1020
tttgatagac gtaaggcagc tcctttgatc gcgttagcca actacaatgc gtaccgtcaa   1080
aattga                                                              1086
SEQ ID NO: 19         moltype = DNA  length = 1029
FEATURE               Location/Qualifiers
misc_feature          1..1029
                      note = Description of Artificial Sequence: Synthetic
                      polynucleotide
source                1..1029
                      mol_type = other DNA
                      organism = synthetic construct
SEQUENCE: 19
atggctgagc aacaaatatc taacttgctg tctatgtttg atgcttcaca tgctagtcag     60
aaattagaaa ttactgtcca aatgatggac acataccatt agagagaaac gcctccagat    120
tcctcatctt ctgaaggcgg ttcattgtct agatacgacg agagaagagt ctctttgcct    180
ctcagtcata atgctgcctc tccagatatt gtatcacaac tatgtttttc cactgcaatg    240
tcttcagagt tgaatcacag atggaaatct caaagattaa aggtggccga ttctccttac    300
aactatatcc taacattacc atcaaaagga attagaggtc cctttatcga ttccctgaac    360
gtatggttgg aggttccaga ggatgaaaca tcagtcatca aggaagttat tggtatgctc    420
cacaactctt cattaatcat tgatgacttc caagataatt ctccacttag aagaggaaag    480
ccatctaccc atacagtctt cggccctgcc caggctatca atactgctac ttacgttata    540
gttaaagcaa tcgaaaagat acaagacata gtgggacacg atgcattggc agatgttacg    600
ggtactatta caactatttt ccaaggtcag gccatggact tgtggtggac agcaaatgca    660
atcgttccat caatacagga ataccttactt atggtaaacg ataaaacccg tgctctcttt    720
agactgagtt tggagttgtt agctctgaat tccgaagcca gtatttctga ctctgcttta    780
gaaagtttat ctagtgctgt ttccttgcta ggtcaatact tccaaatcag agcgactat    840
atgaacttga tcgataacaa gtatacagat cagaaaggct tctgcgaaga tcttgatgaa    900
ggcaagtact cactaacact tattcatgcc ctccaaactg attcatccga tctactgacc    960
aacatccttt caatgagaag agtgcaagga aagttaacgg cacaaaagag atgttggttc   1020
``` tggaaatga                                                                  1029

SEQ ID NO: 20          moltype = DNA   length = 903
FEATURE                Location/Qualifiers
misc_feature           1..903
                       note = Description of Artificial Sequence: Synthetic
                        polynucleotide
source                 1..903
                       mol_type = other DNA
                       organism = synthetic construct
SEQUENCE: 20
atggaaaaga ctaaggagaa agcagaacgt atcttgctgg agccatacag atacttatta   60
caactaccag gaaagcaagt ccgttctaaa ctatcacaag cgttcaatca ctggttaaaa  120
gttcctgaag ataagttaca aatcattatt gaagtcacag aaatgctaca caatgcttct  180
ttactgatcg atgatataga ggattcttcc aaactgagaa gaggttttcc tgtcgctcat  240
tccatatacg gggtaccaag tgtaatcaac tcagctaatt acgtctactt cttgggattg  300
gaaaaagtat tgacattaga tcatccagac gctgtaaagc tattcaccag acaacttctt  360
gaattgcatc aaggtcaagg tttggatatc tattggagaa acttatac ttgcccaaca  420
gaagaggagt acaaagcaat ggttctacaa aagactggcg gtttgttcgg acttgccgtt  480
ggtctgatgc aacttttctc tgattacaag gaggacttaa agcctctgtt ggataccttg  540
ggcttgtttt ccagattag agatgactac gctaacttac attcaaagga atattcagaa  600
aacaaatcat tctgtgaaga tttgactgaa gggaagttta gttttccaac aatccacgtc  660
atttggtcaa gaccagaatc tactcaagtg caaaacattc tgcgtcagag aacagagaat  720
attgacatca aaaagtattg tgttcagtac ttggaagatg ttggttcttt tgcttacaca  780
agacatacac ttagagaatt agaggcaaaa gcatacaagc aaatagaagc ctgtggaggc  840
aatccttctc tagtggcatt ggttaaacat ttgtccaaaa tgttcaccga ggaaaacaag  900
taa                                                                903

SEQ ID NO: 21          moltype = DNA   length = 1020
FEATURE                Location/Qualifiers
misc_feature           1..1020
                       note = Description of Artificial Sequence: Synthetic
                        polynucleotide
source                 1..1020
                       mol_type = other DNA
                       organism = synthetic construct
SEQUENCE: 21
atggcaagat tctattttct taacgcacta ttgatggtta tctcattaca atcaactaca   60
gccttcactc cagctaaaact tgcttatcca acaacaacaa cagctctaaa tgtcgcctcc  120
gccgaaactt ctttcagtct agatgaatac ttggcctcta gataggacc tatagagtct  180
gccttggaag catcagtcaa atccagaatt ccacagaccg ataagatctg cgaatctatg  240
gcctactctt tgatggcagg aggcaagaga attagaccag tgttgtgtat cgctgcatgt  300
gagatgttcg gtggatccca agatgtcgct atgcctactg ctggcatt agaaatgata  360
cacacaatgt ctttgattca tgatgatttg ccatccatgg ataacgatga cttgagaaga  420
ggtaaaccaa caaaccatgt cgttttcggc gaagatgtag ctattcttgc aggtgactct  480
ttattgtcaa cttccttcga gcacgtcgct agagaaacaa aaggagtgtc agcagaaaag  540
atcgtggttg ttatcgctag attaggcaaa tctgttgctg ccgagggcct tgctggcggt  600
caagttatgg acttagaatg tgaagctaaa ccaggtacca cattagacga cttgaaatgg  660
attcatatcc ataaaaccgc tacattgtta caagttgctg tagcttctgg tgcagttcta  720
ggtggtgcaa ctcctgaaga ggttgctgca tgcgagttgt tgctatgaa ataggtcttt  780
gcctttcaag ttgccgacga tatccttgat gtaaccgctt catcagaaga tttgggtaaa  840
actgcaggca agatgaagc tactgataag acaacttacc caaagttatt aggattagaa  900
gagagtaagg catacgcaag acaactaatg gatgaagcca aggaaagttt ggctcctttt  960
ggagatagag ctgccccttt attggccatt gcagatttca ttattgatag aaagaattga 1020

SEQ ID NO: 22          moltype = DNA   length = 1068
FEATURE                Location/Qualifiers
misc_feature           1..1068
                       note = Description of Artificial Sequence: Synthetic
                        polynucleotide
source                 1..1068
                       mol_type = other DNA
                       organism = synthetic construct
SEQUENCE: 22
atgcacttag caccacgtag agtccctaga ggtagaagat caccacctga cagagttcct   60
gaaagacaag gtgccttggg tagaagacgt ggagctggct ctactggctg tgcccgtgct  120
gctgctggtt tcaccgtag aagaggagga ggcgaggctg atccatcagc tgctgtgcat  180
agaggctggc aagccggtgg tggcaccggt ttgcctgatg aggtggtgtc taccgcagcc  240
gccttagaaa tgtttcatgc ttttgcttta atccatgata atcatgga tgatagtgca  300
actagaagag gctccccaac tgttcacaga gccctagctg atcgtttagg cgctgctctg  360
gacccagatc aggccggtca actaggagtt ctactgcta tcttggttgg agatctggct  420
ttgacatggt ccgatgaatt gttatacgct ccattgactc acatagact ggcagcagta  480
ctaccattgg taacagctat gagagctgaa accgttcatg gccaatatct tgatataact  540
agtgctagaa gacctgggac cgatacttcc cttgcattga gaatagcag atataagaca  600
gcagcttaca caatgaacg tccactgcac attggtgcag ccctggctgg ggcaagacca  660
gaactattag cagggctttc agcatacgcc ttgccagctg agaagcctt ccaattggca  720
gatgacctgc taggcgtctt cggtgatcca agacgtacag gaaacctga cctagatgat  780
cttagaggtg gaaagcatac tgtctagtc gccttggcaa gagaacatgc cactccagaa  840
cagagacaca cattggatac attattgggt acaccaggtc ttgatagaca aggcgcttca  900

```
agactaagat gcgtattggt agcaactggt gcaagagccg aagccgaaag acttattaca    960
gagagaagag atcaagcatt aactgcattg aacgcattaa cactgccacc tcctttagct   1020
gaggcattag caagattgac attagggtct cagctcatc ctgcctaa                 1068
```

```
SEQ ID NO: 23           moltype = DNA   length = 993
FEATURE                 Location/Qualifiers
misc_feature            1..993
                        note = Description of Artificial Sequence: Synthetic
                         polynucleotide
source                  1..993
                        mol_type = other DNA
                        organism = synthetic construct
SEQUENCE: 23
atgtcatatt tcgataacta cttcaatgag atagttaatt ccgtgaacga catcattaag     60
tcttacatct ctggcgacgt accaaaacta tacgaagcct cctacctttt gtttacatca    120
ggaggaaaga gactaagacc attgatcctt acaatttctt ctgatctttt cggtggacag    180
agagaaagag catactatgc tggcgcagca atcgaagttt tgcacacatt cactttggtt    240
cacgatgata tcatggatca agataacatt cgtagaggtc ttcctactgt acatgtcaag    300
tatggcctac ctttggccat tttagctggt gacttattgc atgcaaaagc ctttcaattg    360
ttgactcagg cattgagagg tctaccatct gaaactatca tcaaggcgtt tgatatcttt    420
acaagatcta tcattatcat atcagaaggt caagctgtcg atatggaatt cgaagataga    480
attgatatca aggaacaaga gtatttggat atgatatctc gtaaaaccgc tgccttattc    540
tcagcttctt cttccattgg ggcgttgata gctggagcta atgataacga tgtgagatta    600
atgtccgatt tcggtacaaa tcttgggatc gcatttcaaa ttgtagatga tatacttggt    660
ttaacagctg atgaaaaaga gctaggaaaa cctgttttca gtgatatcag agaaggtaaa    720
aagaccatat tagtcattaa gactttagaa ttgtgtaagg aagacgagaa aaagattgta    780
ttaaaagcgc taggcaacaa gtcagcatca aaggaagagt tgatgagttc tgctgacata    840
atcaaaaagt actcattgga ttacgcctac aacttagctg agaaatacta caaaaacgcc    900
atcgattctc taaatcaagt ttcaagtaaa agtgatattc cagggaaggc attgaaatat    960
cttgctgaat tcaccatcag aagacgtaag taa                                 993
```

```
SEQ ID NO: 24           moltype = DNA   length = 894
FEATURE                 Location/Qualifiers
misc_feature            1..894
                        note = Description of Artificial Sequence: Synthetic
                         polynucleotide
source                  1..894
                        mol_type = other DNA
                        organism = synthetic construct
SEQUENCE: 24
atggtcgcac aaactttcaa cctggatacc tacttatccc aaagacaaca acaagttgaa     60
gaggccctaa gtgctgctct tgtgccagct tatcctgaga gaatatacga agctatgaga    120
tactcctcc tggcaggtgg caaaagatta agacctatct tatgtttagc tgcttgcgaa    180
ttggcaggtg gttctgttga acaagccatg ccaactgcgt gtgcacttga aatgatccat    240
acaatgtcac taattcatga tgacctgcca gccatggata cgatgatttt cagaagagga    300
aagccaacta atcacaaggt gttcggggaa gatatagcca tcttagcggg tgatgcgctt    360
ttagcttacg cttttgaaca tattgcttct caaacaagga gagtaccacc tcaattggtg    420
ctacaagtta ttgctagaat cggacacgcc gttgctgcaa caggcctcgt tggaggccaa    480
gtcgtagacc ttgaatctga aggtaaagct atttccttag aaacattgga gtatattcac    540
tcacataaga ctggagcctt gctggaagca tcagttgtct caggcggtat tctcgcaggg    600
gcagatgaag agcttttggc cagattgtct cattacgcta gagatatagg cttggcttt     660
caaatcgtcg atgatatcct ggatgttact gctacatctg aacagttggg gaaaaccgct    720
ggtaaagacc aggcagccgc aaaggcaact tatccaagtc tattgggttt agaagcctct    780
agacagaaag cggaagagtt gattcaatct gctaaggaag ccttaagacc ttacggttca    840
caagcagagc cactccagc gctggcagac ttcatcacac gtcgtcagca ttaa           894
```

```
SEQ ID NO: 25           moltype = DNA   length = 1116
FEATURE                 Location/Qualifiers
misc_feature            1..1116
                        note = Description of Artificial Sequence: Synthetic
                         polynucleotide
source                  1..1116
                        mol_type = other DNA
                        organism = synthetic construct
SEQUENCE: 25
atggcctctg ttactttggg ttcctggatc gtcgtccacc accataacca tcaccatcca     60
tcatctatcc taactaaatc tcgttcaaga tcctgtccta ttacactaac caaaccaatc    120
tcttttcgtt caaagagaac agtttcctct agtagttcta tcgtgtcctc tagtgtcgtc    180
actaaggaag acaatctgag acagtctgaa ccttcttcct ttgatttcat gtcatatatt    240
attactaagg cagaactagt gaataaggct cttgattcag cagttccatt aagagagcca    300
ttgaaaatcc atgaagcaat gagatactct cttctagctg gcgggaagag agtcagacct    360
gtactctgca tagcagcgtg cgaattagtt ggtggcgagg aatcaaccgc tatgcctgcc    420
gcttgtgctg tagaaatgat tcatacaatg tcactgatac acgatgatt gccatgtatg    480
gataacgatg atctgagaag gggtaagcca actaaccata aggttttcgg cgaagatgtt    540
gccgtcttag ctggtgatgc tttgttatct ttcgcgttcg aacatttggc atccgcaaca    600
tcaagtgatg ttgtgtcacc agtaagagta gttagagcag ttggagaact ggctaaagct    660
attggaactg agggttagt tgcaggtcaa gtcgtcgata tctcttccga aggtcttgat    720
ttgaatgatg taggtcttga acatctcgaa ttcatccatc ttcacaagac agctgcactt    780
ttagaagcca gtgcggttct cggcgcaatt gttggcggag ggagtgatga cgaaattgag    840
```

-continued

```
agattgagga agtttgctag atgtatagga ttactgttcc aagtagtaga cgatatacta    900
gatgtgacaa agtcttccaa agagttggga aaaacagctg gtaaagattt gattgccgac    960
aaattgacct accctaagat tatggggcta gaaaaatcaa gagaatttgc cgagaaactc   1020
aatagagagg cgcgtgatca actgttgggt ttcgattctg ataaagttgc caccactctta  1080
gccttagcca actacatcgc ttacagacaa aactaa                              1116

SEQ ID NO: 26           moltype = DNA   length = 1086
FEATURE                 Location/Qualifiers
source                  1..1086
                        mol_type = genomic DNA
                        organism = Stevia rebaudiana
SEQUENCE: 26
atggctcttg taaatcccac agctttgttc tatggaacct ccataagaac cagacccaca     60
aacttgctca acccgaccca aaaacttcga cccgtttcct cgtcttcttt gccttccttc    120
tcttcagttt ctgcaatctt gacggaaaaa caccaatcaa acccatcaga aaacaataac    180
ttgcaaaccc atctcgaaac accattcaat ttcgactctt acatgctgga gaaagtaaac    240
atggtgaatg aagctctgga cgcctcggtt ccactcaaag acccgataaa gatccatgaa    300
tccatgcggt actcccttct agctggcggg aaacgcatcc gaccgatgat gtgcatcgcc    360
gcttgcgaaa tagtcggagg caacatatta aacgccatgc cagctgcatg cgcggtcgag    420
atgattcaca ccatgtcact agttcatgac gaccttccat gcatggataa cgacgacttc    480
cgacgtggaa aaccaataag ccacaaggtg tacggtgaag aaatggcggt tctaaccggg    540
gacgcgttac tctcattatc cttcgaacat atcgcgaccg gacaaaaagg ctgtatccaa    600
gacaggatcg tccgagccat tggtgaactc gcaaggtccg ttggctcgga gggtttggtc    660
gccggtcagg tggttgatat tttatccgaa ggggctgatg ttgggttaga ccacttggag    720
tatattcata tacacaagac tgcaatgttg cttgagagct cggtcgtgat cggcgcgatc    780
atgggcggtg ggtctgacca acagatcgaa aagttgcgaa agtttgcgag atcgattgtt    840
ttgttgttc aggtggtaga tgatattctt gatgtcacaa agtcgactga ggaattgggg    900
aaaacggcgg gaaaagattt gctgacggac aagacaacgt atccgaagtt gttggggatc    960
gaaaaatcga gagaatttgc ggagaaatta acaaggaag cgcaagaaca attgtcgggg   1020
tttgatcgcc gcaaggcggc tccgttaatt gcccttgcta attacaatgc ttataggcaa   1080
aactga                                                              1086

SEQ ID NO: 27           moltype = DNA   length = 1029
FEATURE                 Location/Qualifiers
source                  1..1029
                        mol_type = genomic DNA
                        organism = Gibberella fujikuroi
SEQUENCE: 27
atggctgaac aacagatctc caaccttctt tcaatgtttg atgcttctca cgcaagccag     60
aagttggaga ttacggttca gatgatggat acctaccatt acagagaaac tcctccagac    120
tcttcctctt cagaaggcgg ttccttatct cgctatgatg agcgacgggt ctcccttccg    180
ctctctcaca atgcagcctc cccagacata gtctcccagt tatgcttctc aacagctatg    240
agctcggagc tcaatcacag gtggaagtca cagcgcctca aggttgctga ctctccctac    300
aactacatcc tgactcttcc atctaaaggt attcgtgggg cttttcattga ctcactgaat    360
gtctggctcg aggtccccga agacgagacc tcggtgatca aagaggtgat tggcatgctc    420
cacaactcgt ctctcataat cgatgacttc caagacaact ccccacttcg gcggggcaag    480
ccatctacac atactgtctt cggtccagca caagcaatca acacagcaac atatgtcatc    540
gtcaaggcca tcgagaaaat acaggatatc gtcggtcacg atgcattggc agatgtaact    600
ggcactataa ccacaatctt ccagggtcag gcaatggatc tgtggtggac tgctaatgcc    660
attgttccgt ctatccaaga atatctcctg atggtcaatg caagactgg tgccctgttc    720
aggttatcgc ttgaactact ggcgctgaac tctgaagcat ccatcagtga cagcgcgctt    780
gaatctctca gcagcgctgt ctcactgctc gggcagtatt tccagataag agatgattac    840
atgaatctca ttgacaacaa gtatactgat cagaaaggat tttgcgagga tctgacgag    900
gggaaatact cgttgactct aatccatgct ctgcagaccg actccagcga ccttctcacc    960
aacatcttat cgatgagaag agtccaagga aaacttacgg cgcagaaaag atgctggttt   1020
tggaagtga                                                           1029

SEQ ID NO: 28           moltype = DNA   length = 903
FEATURE                 Location/Qualifiers
source                  1..903
                        mol_type = genomic DNA
                        organism = Mus musculus
SEQUENCE: 28
atggagaaaa ctaaagagaa agctgagagg attcttctag agccctatag gtacttactt     60
cagttaccag gtaaacaggt gagaagcaaa ctttcacagg catttaatca ctggctgaaa    120
gttccagaag acaagctaca gattatcatt gaagtgactg aaatgttgca taatgccagt    180
ttactcattg atgatattga agacagttca aagctccgac gtggtttccc agtggctcac    240
agcatctatg gtgtcccatc tgtcattaat tctgccaatt acgtctactt ccttggactg    300
gaaaaagtct taacccttga tcacccggat gcggtgaagc ttttcacacg ccagcttctg    360
gaacttcatc agggacaagg cctcgatatt tactggaggg acacctacac ttgtccaact    420
gaagaagaat ataagccat ggtgttcag aagacaggtg gtttgtttgg attagcagta    480
ggtcttatgc agctgttctc tgattacaaa gaagatctaa agccactgct tgacacactt    540
gggctctttt tccagattag agatgattat gccaatctac actccaaaga atacagtgaa    600
aacaaaagtt tctgtgaaga cttgcagaa ggggaagttct cattcccac tatccatgcc    660
atttggtcaa ggccagaaag cacccaggta cagaacatcc tgcgccagag aacagagaat    720
atagatatta aaagtattg tgtcagtac ctggaggatg taggttcttt tgcatacact    780
cgacacactc ttagagagct tgaagctaaa gcctacaaac aaattgaggc ctgtggtggg    840
aacccttcac tagtggcttt agtcaagcac ttaagtaaga tgttcacaga agaaaataaa    900
taa                                                                  903
```

```
SEQ ID NO: 29           moltype = DNA  length = 1020
FEATURE                 Location/Qualifiers
source                  1..1020
                        mol_type = genomic DNA
                        organism = Thalassiosira pseudonana
SEQUENCE: 29
atggctcgtt tctacttcct gaacgctctc ctcatggtga tttctttaca aagcaccacg    60
gcattcaccc cggcaaaact cgcctaccca acaaccacca ctgcattaaa cgttgcctct   120
gccgaaacat cattagcct cgatgaatac ctagcctcca aaatcggacc cattgaatca   180
gctctcgagg catctgtcaa atctcgcatt cctcaaactg acaagatatg cgagtctatg   240
gcatactcac tcatggctgg aggaaagcgt atccgtcccg ttttgtgcat tgctgcttgt   300
gaaatgtttg ggggaagtca agatgtggct atgccgacgg ctgtggcttt ggagatgatt   360
catactatga gtcttattca tgacgatttg ccttcaagtg acaacgatga tctccgacga   420
ggaaagccaa ctaatcatgt tgtctttgga gaggatgttg ctattcttgc tggggattct   480
cttctcagta cgtctttga acatgttgcc cgtgaaacca aggagtgtc agctgaaaag   540
attgtagatg ttatcgctcg cctcgggaag tctgtgggtg cagagggtct tgctggtgga   600
caggttatgg atcttgagtg tgaggcgaag ccaggaacta ccctcgacga tctcaagtgg   660
attcacattc acaaaactgc cactcttctt caagtggcag tggcatcagg tgctgttctt   720
ggaggggcca caccgagga ggttgctgct tgtgaactgt tcgcaatgaa tattggactt   780
gccttccagg tcgctgatga tattttggac gtgacggcat cgagtgagga tcttggcaaa   840
actgctggaa aggatgaagc cacagataag acaaacttatc ctaagcttt ggggattggag   900
gagagtaagg catacgctcg acaactcata gacgaagcaa aggaatcttt ggctcctttc   960
ggtgatcgtg ctgctccatt gttggcaatt gccgacttta tcattgatcg aaagaactag  1020

SEQ ID NO: 30           moltype = DNA  length = 1068
FEATURE                 Location/Qualifiers
source                  1..1068
                        mol_type = genomic DNA
                        organism = Streptomyces clavuligerus
SEQUENCE: 30
atgcacctgg ctccccgccg agtaccgcgc ggcgtcgaa gcccacctga ccgcgttcct    60
gaacgccaag gagcgctcgg ccgccgccgg ggggccggtt ccacaggatg tgcccgcgct   120
gctgcgggag ttcatcggcg ccggggggg ggggaagcgg atccgtccgc tgctgtgcat   180
cgcggctggc aggccggcgg cggaacagga ctgccggacg aggtggtgtc cacagcgggt   240
gcgctggaga tgttccacgc gttcgcgctg atccacgacg acatcatgga tgactccgcg   300
accaggcgcg gcagcccgac ggtgcaccgg gcactcgccg accggctcgg cgccgctctc   360
gaccccgacc aagccggaca actgggggtg agcacggcga tcctcgtcgg ggacctcgcc   420
ctgacctggt cggacgaact gctgtacgct cccctgcacc ctccacggct gccgcggta   480
ctgccctggg tcacgccat gcgcgcgaa acggtccacg gccagtacct ggacatcacc   540
tccgcccgcc ggcccggcac ggacacctca ctggcgctgc gaatcgcgcg ctacaaaacc   600
gctgcttaca ccatggaacg cccctgcac atcgagcag cgctcgccgg cgcacgaccg   660
gaactcctgg caggcgtcag cgcctacgcg ctgccggcgg gcgaggcatt ccagctcgac   720
gacgacctcc tgggagtgtt cggcgatcca cggagaaccg gcaaaccga cctcgacgac   780
ctccgcggcg gcaagcacac cgtcctcgtg gccctcgccc gggaacacgc cacacctgaa   840
cagcggcaca ccctggacac cctgctcggc acaccaggcc tcgaccggca gggcgcgtcc   900
cggctgcgct gcgtcctcgt cgccaccggg gcccgggcgg aagccgaacg cctgatcacc   960
gaacggcgcg accaggccct caccgcgctc aacgccctga cactgccccc accgctcgcc  1020
gaggcactcg cccgcctcac cctcgggagt accgcacacc cggcctga             1068

SEQ ID NO: 31           moltype = DNA  length = 993
FEATURE                 Location/Qualifiers
source                  1..993
                        mol_type = genomic DNA
                        organism = Sulfolobus acidicaldarius
SEQUENCE: 31
atgagttact ttgacaacta ttttaatgag attgttaatt ctgtaaacga cattattaag    60
agctatatat ctggagatgt tcctaaacta tatgaagcct catatcattt gtttacatct   120
ggaggtaaga ggttaagacc attaatctta actatatcat cagatttatt cggaggacag   180
agagaaagag cttattatgc aggtgcagct attgaagttc ttcatacttt tacgcttgtg   240
catgatgata ttatgatca agataatatc agaagagggt tacccacagt ccacgtgaaa   300
tacggcttac ccttagcaat attagctggg gatttactac atgcaaaggc ttttcagctc   360
ttaacccagg ctcttagagg tttgccaagt gaaaccataa ttaaggcttt cgatatttc   420
actcgttcaa taataattat atccgaagga caggcagaca caggacagca tgaggacaga   480
attgatataa aggagcagga ataccttgac atgatctcac gtaagacagc tgcattattc   540
tcggcatcct caagtatagg cgcacttatt gctggtgcta atgataatga tgtaagactg   600
atgtctgatt tcggtacgaa tctaggtatt gcatttcaga ttgttgacga tatcttaggt   660
ctaacagcag acgaaaagga acttggaaag cctgtttta gtgatattag ggagggtaaa   720
aagactatac ttgtaataaa aactactggag ctttgtaaag aggacgagaa gaagattgtc   780
ctaaaggcgt taggtaataa gtcagcctca aaagaagaat taatgagctc agcagatata   840
attaagaaat actctttaga ttatgcatac aatttagcag agaaatatta taaaaatgct   900
atagactctt taaatcaagt ctcctctaag agtgatatac ctggaaaggc tttaaaatat   960
ctagctgaat ttacgataag aaggagaaaa taa                                993

SEQ ID NO: 32           moltype = DNA  length = 894
FEATURE                 Location/Qualifiers
source                  1..894
                        mol_type = genomic DNA
                        organism = Synechococcus sp.
```

```
SEQUENCE: 32
ttggttgccc aaaccttcaa cctggacacc tacttgagcc aacgccagca acaggtggaa    60
gaggcgcttt ctgcggcatt ggttcccgcc tatccgagc gcatttacga ggcgatgcgc    120
tacagcctgc tggcgggggg gaaacgcctg aggccgatcc tctgtctggc ggcctgtgag   180
ttggccggcg gctctgtgga gcaggccatg cccaccgcct gcgccctgga gatgatccac   240
accatgtcgc tgatccacga cgatctgccg gcgatggaca cgacgattt tcgccgcggc    300
aagcccacca atcacaaggt attcggcgag gatatcgcca ttttggcagg agatgccctg   360
ttggcctatg cctttgagca tatcgccagc caaacgcggg gggtgccgcc gcagttggtg   420
ctgcaagtca ttgcccgcat tggccatgct gtggcggcaa ccggcttggt aggggccag    480
gtggtggatc tggagtccga aggcaaagcc atttccctag aaactttgga gtacatccac   540
agtcacaaga cgggtgctct gctggaggcc tcggtggttt cgggagggat cctggcaggg   600
gccgatgagg agctgctggc gcggctgagc cactacgctc gggacatcgg cctgcttt    660
cagatcgtgg acgacatttt ggatgttact gccaccagc agcaactggg caaaacggca    720
ggcaaggatc aagctgccgc caaagccacc taccccagcc tgtttgggcct agaggcttcc   780
cggcagaaag ctgaggaact gatccaatcg gccaaggagg cgttgcgccc ctacggatcc   840
caggccgagc ccctgttggc tctggccgat ttcatcaccc gccgccagca ttga          894

SEQ ID NO: 33           moltype = DNA    length = 1116
FEATURE                 Location/Qualifiers
source                  1..1116
                        mol_type = genomic DNA
                        organism = Arabidopsis thaliana
SEQUENCE: 33
atggcttcag tgactctagg ttcatggatt gttgttcacc accacaatca tcatcatcca    60
tcttcaatcc ttaccaaatc cagatccaga tcttgtccta aactcttac taaacccatc    120
tcctttcgat caaaacgcac cgtttcatca tcttcttcaa tcgtttcttc ttccgttgtt   180
acaaaagaag acaatctacg ccaatctgaa ccatcctctt tcgatttcat gtcgtacatc    240
atcaccaaag ccgaattagt caacaaagct ttagattcag ctgttcctct ccgtgagcca   300
ctcaagatcc acgaagcgat gcgttactct cttctcgccg gtggcaaaag agttagacca   360
gttctctgca tcgctgcttg tgaactcgtc ggaggtgaag aatcaaccgc tatgccagca   420
gcttgcgccg tcgagatgat tcacaccatg tcgttgatcc acgacgatct cccttgtatg   480
gataacgacg atctccgccg tggaaaaccg accaaccaca aagtgtttgg tgaagacgtc   540
gctgttttag ccggagacgc gcttctctct ttcgctttcg agcatttagc ttcggcgacg   600
agttctgatg ttgtttctcc ggtgagagtg gttcgagccg ttggagaatt ggctaaagcg   660
ataggaacag aagggttagt ggcgggtcaa gtcgtcgata ttagtagtga agggttagat   720
ttaaacgacg tcggtttaga gcatttggag tttatccatt tgcataaaac ggcggcgttg   780
cttgaagctt ctgctgtttt gggagctatt gttggtggag aagtgatga tgagattgag   840
aggttaagaa agtttgcgag atgtattggt tgttgtttc aggtggttga tgatatcttg   900
gatgtgacga aatcgtcgaa agagttaggg aaaactgctg ggaaagattt gattgctgat   960
aagttgacgt atcctaagat tatgggttg gagaaatcga gagagtttgc tgagaaattg   1020
aatagagagg ctcgtgatca gcttttaggg tttgattctg ataaggttgc tccttgttg   1080
gctttggcta attacattgc ctatagacag aactga                             1116

SEQ ID NO: 34           moltype = DNA    length = 2364
FEATURE                 Location/Qualifiers
misc_feature            1..2364
                        note = Description of Artificial Sequence: Synthetic
                        polynucleotide
source                  1..2364
                        mol_type = other DNA
                        organism = synthetic construct
SEQUENCE: 34
atgaaaaccg ggtttatctc accagcaaca gtatttcatc acagaatctc accagcgacc    60
actttcagac atcacttatc acctgctact acaaactcta caggcattgt cgccttaaga   120
gacatcaact tcagatgtaa agcagtttct aaagagtact ctgatctgtt gcagaaagat   180
gaggcttctt tcacaaaatg ggacgatgac aaggtgaaag atcatcttga taccaacaaa   240
aacttatacc caaatgatga gattaaggaa tttgttgaat cagtaaaggc tatgttcggt   300
agtatgaatg acggggagat aaacgtctct gcatacgata ctgcatgggt tgctttggtt   360
caagatgtcg atggatcagg tagtcctcag ttcccttcct ctttagaatg gattgccaac   420
aatcaattgt cagatggatc atgggagagt catttgctgt tctcagctca cgatagaatc   480
atcaacacat tagcatgcgt tattgcactt acaagtggaa atgttcatcc ttctaagtgt   540
gaaaaaggtt tgaattttct gagagaaaac atttgcaaat tagaagatga aaacgcagaa   600
catatgccaa ttggttttga agtaacattc ccatcactaa ttgatatcgc gaaaaagttg   660
aacattgaaa tacctgagga tactccagca cttaaagaa tctacgcacg tagagatatc    720
aagttaacta agatcccaat ggaagttctt cacaaggtac ctactacttt gttacattgt   780
ttggaaggaa tgcctgattt ggagtgggaa aaactgttaa agctacaatg taaagatggt   840
agtttcttgt tttccccatc tagtaccgca ttcgccctaa tgcaaacaaa agatgagaaa   900
tgcttacagt atctaacaaa tatcgtcact aagttcaacg gtggcgtgcc taatgtgtac   960
ccagtcgatt tgtttgaaca tatttgggtt gttgatagac tgcagagatt ggggattgcc   1020
agatacttca aatcagagat aaagattgt gtagagtata tcaataagta ctggaccaaa   1080
aatgggattt tgttgggctag aaatactcac gttcaagata tcgatgatac agccatggga   1140
ttcagagtgt tgagagcgca cggttatgac gtcactccag atgttttag acaatttgaa    1200
aaagatggta aattcgtttg ctttgcaggg caatcaacac aagccgtgac aggaatgttt   1260
aacgtttaca gagcctctca aatgttgttc ccaggggaga aatttttgga agtgccaaa    1320
aagttctctt acaattactt aaaggaaaag caaagtacca acgaattgct ggataaatgt   1380
ataatcgcta aagatctacc tggtgaagtt ggttatgctc tggatatccc atggtatgct   1440
tccttaccaa gattggaaac tcgttattac cttgaacaat acggcggtga agatgatgtc   1500
tggataggca agacattata cagaatgggt tacgtgtcca ataacacata tctagaaatg   1560
gcaaagctgg attacaataa ctatgttgca gtccttcaat tagaatggta cacaatacaa   1620
```

```
caatggtacg tcgatattgg tatagagaag ttcgaatctg acaacatcaa gtcagtcctg   1680
gtttcttact acttggctgc ggcttcaata ttcgaacctg agagatctaa ggagagaatc   1740
gcttgggcaa agacaacaat cttagtcgat aagatcacat caattttcga ttcctctcag   1800
tcaagtaagg aagatattac tgcctttatt gacaagtttc gtaacaagtc ctcctctaaa   1860
aagcactcta tcaacggtga accatggcat gaagttatgg tagctttgaa aaagacctta   1920
cacggctttg ctctggatgc tcttatgact cattctcaag atatacatcc acagttacat   1980
caagcctggg aaatgtggtt gactaaacta caagacggcg tagatgttac tgctgagcta   2040
atggtccaaa tgatcaacat gactgctggc agatgggtat caaaggaatt acttactcat   2100
ccacaatatc aaagattgtc tactgtgaca aattctgtgt gtcacgatat taccaaactt   2160
cacaatttca aggagaattc caccacagtg gattcaaagg ttcaggaact agtccagttg   2220
gtttttagtg acacaccaga tgatttggat caagatatga aacaaacatt cctgacagtg   2280
atgaagacat tctactacaa ggcgtggtgt gatccaaaca ctataaacga tcatatatct   2340
aaagtttttcg aaatcgtaat ttga                                         2364
```

SEQ ID NO: 35          moltype = DNA  length = 1584
FEATURE                Location/Qualifiers
misc_feature           1..1584
                       note = Description of Artificial Sequence: Synthetic
                        polynucleotide
source                 1..1584
                       mol_type = other DNA
                       organism = synthetic construct
SEQUENCE: 35

```
atgcctgatg cacacgatgc tccacctcca caaataagac agagaacact agtgagatgag   60
gctacccaac tgctaactga gtccgcagaa gatgcatggg gtgaagtcag tgtgtcagaa   120
tacgaaacag caaggctagt tgcccatgct acatgtatgg gtggacacgc cacaagagtg   180
gccttccttc tggagagaca acacgaagac gggtcatggg gtccaccagg tggatatagg   240
ttagtcccta cattatctgc tgttcacgca ttattgacat gtcttgcctc tcctgctcag   300
gatcatggcg ttcacatga tagactttta agagctgttg acgcaggctt gactgccttg   360
agaagattgg ggacatctga ctccccacct gatactatag cagttgagct ggttatccca   420
tctttgctag agggcattca acacttactg gaccctgctc atcctcatag tagaccagcc   480
ttctctcaac atagaggctc tctgtttgt cctggtggac tagatgggag aactctagga   540
gctttgagat cacacgccgc agcaggtaca ccagtaccag gaaaagtctg gcacgcttcc   600
gagactttgg gcttgagtac cgaagctgct tctcacttgc aaccagccca aggtataatc   660
ggtggctctg ctgctgccac agcaacatgg ctaaccaggg ttgcaccatc tcaacagtca   720
gattctgcca aagatacct tgaggaatta caacacagat actctggccc agttccttcc   780
attaccccta tcacatactt cgaaagagca tggttattga caattttgc agcagccggt   840
gttccttgtg aggctccagc tgctttgttg gattccttag aagcagcact tacaccacaa   900
ggtgctcctg ctgagcagg attgcctcca gatgctgata atacagccgc tgtgttgctt   960
gcattggcaa cacatgggag aggtagaaga ccagaagtac tgatggatta caggactgac   1020
gggtatttcc aatgctttat tggggaaagg actccatcaa tttcaacaaa cgctcacgta   1080
ttggaaacat tagggcatca tgtggcccaa catccacaaa atagagccag atacggatca   1140
gccatggata ccgcatcagc ttggctgctg cagctcaaaa gcaagatgg tcttggtta   1200
gataaatggc atgcctcacc atactacgct actgtttgtt gcacacaagc cctagccgct   1260
catgcaagtc ctgcaactgc accagtaga cagagagctg tcagtgggt tttagccaca   1320
ttacagatct tggccccacc ttctggtggt ggcaatatca cagtccaaca agcacttact   1440
agaggcagag caagattgtg tggagccttg ccactgactc ctttatggca tgataaggat   1500
ttgtatactc cagtaagagt agtcagagct gccagagctg ctgctctgta cactaccaga   1560
gatctattgt taccaccatt gtaa                                           1584
```

SEQ ID NO: 36          moltype = DNA  length = 1551
FEATURE                Location/Qualifiers
misc_feature           1..1551
                       note = Description of Artificial Sequence: Synthetic
                        polynucleotide
source                 1..1551
                       mol_type = other DNA
                       organism = synthetic construct
SEQUENCE: 36

```
atgaacgccc tatccgaaca catttttgtct gaattgagaa gattattgtc tgaaatgagt   60
gatggcggat ctgttggtcc atctgtgtat gatacggccc aggccctaag attccacggt   120
aacgtaacag gtagacaaga tgcatatgct tggttgatcg cccagcaaca agcagatgga   180
ggttggggct ctgccgactt tccactcttt agacatgctc caacatggc tgcacttctc   240
gcattacaaa gagctgatcc acttcctggc gcagcagacg cagttcagac cgcaacaaga   300
ttcttgcaaa gacaaccaga tccatacgct catgccgttc ctgaggatgc ccctatttgt   360
gctgaactga tcttgcctca gttttgtgga gaggctgctt ggtgttggg aggtgtggcc   420
ttccctagac acccagcccct attaccatta agacaggctt gtttagtcaa actgggtgca   480
gtcgccatgt tgcccttcagg acacccattg ctccactctg gggaggcatg gggtacttct   540
ccaacaacag cctgtccaga cgatgatggt tctataggta tctccaccagc agctacagcc   600
gcctggagag cccaggctgt gaccagaggc tcaactcctc aagtgggcag agctgacgca   660
tacttacaaa tggcttcaag agcaacgaga tcaggcatag aaggagtctt ccctaatgtt   720
tggcctataa acgtattcga accatgctgg tcactgtaca ctctccatct tgccggtctg   780
ttcgcccatc cagcactggc tgaggctgta agagttatcg ttgctcaact tgaagcaaga   840
ttggggagtgc atggcctcgg accagctttta cattttgctg ccgacgctga tgatactgca   900
gttgccttat gcgttctgca tttggctggc agagatcctg cagttgacgc attgagacat   960
tttgaaattg tgagctcttt tgttacattc ccaggagaga gaatgctag tgtctctacg   1020
aacattcacg ctcttcatgc ttttgagattg ttagggtaaaac cagctgccgg agcaagtgca   1080
tacgtcgaag caaatagaaa tccacatggt ttgtgggaca cgaaaaatg gcacgtttca   1140
```

```
tggctttatc caactgcaca cgccgttgca gctctagctc aaggcaagcc tcaatggaga  1200
gatgaaagag cactagccgc tctactacaa gctcaaagag atgatggtgg ttggggagct  1260
ggtagaggat ccactttcga ggaaaccgcc tacgctcttt tcgctttaca cgttatggac  1320
ggatctgagg aagccacagg cagaagaaga atcgctcaag tcgtcgcaag agccttagaa  1380
tggatgctag ctagacatgc cgcacatgga ttaccacaaa caccactcgg gattggtaag  1440
gaattgtact gtcctactag agtcgtaaga gtagctgagc tagctggcct gtggttagca  1500
ttaagatggg gtagaagagt attagctgaa ggtgctggtg ctgcacctta a            1551

SEQ ID NO: 37           moltype = DNA   length = 2364
FEATURE                 Location/Qualifiers
source                  1..2364
                        mol_type = genomic DNA
                        organism = Stevia rebaudiana
SEQUENCE: 37
atgaagaccg gcttcatctc tcccgccacc gtcttccacc accgtatttc tccggcaacc   60
accttccgcc accacctttc tccggcgacc accaactcca ctggaattgt agctcttaga  120
gacatcaact tccggtgtaa agcggtatcc aaagagtact ctgatttact acaaaaagat  180
gaggcttcat ttaccaagtg ggacgatgac aaagtgaagg accatttgga cacaaataag  240
aatttgtatc caaacgatga gatcaaggag tttgttgaga gcgtgaaagc aatgtttggt  300
tctatgaatg acggagaaat aaatgtgtca gcgtatgata cggcttgggt tgcactcgtg  360
caagatgttg atgaagtgg ttccctcaa tttccatcga gtttgagtg atcgcgaac     420
aatcaactct cagatgggtc ttggggcgat catttgttat tttcggctca tgataggatc  480
attaacacgt tggcatgtgt tatagcgctt acttcttgga acgtccatcc aagtaaatgt  540
gaaaaaggac tgaattttct tagagaaaac atatgtaaac tcgaagacga gaacgcggaa  600
catatgccaa ttggttttga agtcacgttc ccgtcgctaa tagatatcgc aaagaagcta  660
aatattgaag ttcctgagga tactcctgcc ttaaaagaaa tttatgcaag aagagacata  720
aaactcacaa agataccaat ggaagtattg cacaaagtgc ccacaacttt acttcatagt  780
ttggaaggaa tgccagattt ggaatgggaa aaacttctga aattgcaatg caaagatgga  840
tcatttctgt tttctccatc atctactgct tttgcactca tgcaaacaaa agatgaaaag  900
tgtcttcagt atttgacaaa tgtcgttacc aaattgcatc gtggagttcc gaatgtgtac  960
ccggtggatc tattcgaaca tatttgggta gttgatcgac ttcaacgact tgggattgct 1020
cgttatttca aatcagagat caaagattgc gttgaatata ttaacaagta ttggacaaag 1080
aatgggattt gttgggcaag aaacacgcac gtacaagata ttgatgatac cgcaatggga 1140
tttaggggtt taagacggca tggttatgat gttactccag atgtatttcg acaatttgag 1200
aaggatggta aattcgtatg tttcgctgga cagtcaacac atgccgtcac cggaatgttc 1260
aatgtgtata gagcgtcaca aatgctcttt cccggagaaa gaattcttga agatgcaaag 1320
aaattttcat ataattattt gaaagaaaaa caatcgacaa atgagcttct tgataaatgg 1380
atcatcgcca aagacttacc tggagaggtt ggatatgcgc tagacatacc atggtatgca 1440
agcttaccgc gactcgagac aagatattac ttagagcaat acggggggcg agatgatgtt 1500
tggattggaa aaactctata caggatggga tatgtgagca ataatacgta ccttgaaatg 1560
gccaaattgg actacaataa ctatgtggcc gtgcttcaac tcgaatggta cactatccag 1620
caatggtatg ttgatatcgg tatcgaaaag tttgaaagtg acaatatcaa aagcgtatta 1680
gtgtcgtatt acttggctgc agccagcata ttcgagccgg aaaggtccaa ggaacgaatc 1740
gcgtgggcta aaaccaccat attagttgac aagatcacct caattttttga ttcatcacaa 1800
tcctcaaaag aggacataac agcctttata gacaaattta ggaacaaatc gtcttctaag 1860
aagcattcaa taaatggaga accatggcac gaggtgatgg ttgcactgaa aaagacccta 1920
cacggcttcg ctttggatgc actcatgact catagtcaag acatccaccg gcaactccat 1980
caagcttggg agatgtggtt gacgaaattg caagatggag tagatgtgac agcggaatta 2040
atggtacaaa tgataaatat gacagctggt cgttgggtat ccaaagaact tttaactcat 2100
cctcaatacc aacgcctctc aaccgtcaca aatagtgtgt gtcacgatat aactaagctc 2160
cataacttca aggagaattc cacgacggta gactcgaaag ttcaagaact agtgcaactt 2220
gtgtttagcg acacgcccga tgatcttgat caggatatga aacagacgtt tctaaccgtc 2280
atgaaaacct tctactacaa ggcgtggtgt gatccgaaca cgataaatga ccatatctcc 2340
aaggtgttcg agattgtaat atga                                        2364

SEQ ID NO: 38           moltype = DNA   length = 1584
FEATURE                 Location/Qualifiers
source                  1..1584
                        mol_type = genomic DNA
                        organism = Streptomyces clavuligerus
SEQUENCE: 38
ttgcccgacg cgcatgatgc ccctccgcct cagatacgac agcggaccct tgtcgatgag   60
gcgacgcaac tcctcacgga gtcggccgag gacgcctggg tgaggtgtc cgtgtccgag  120
tacgaaacgg cgcggctggt ggcccacgcc acctggctcg gcggtcacgc cacacggttg  180
gccttcctgc tggagcggca gcatgaggac ggctcgtggg gccgccggg cgggtaccgt  240
ctcgtaccca cgctgagtgc cgtacacgcc ctgctcacct gtctggcgtc tcccgcgcag  300
gaccacgagt gcctcatgga ccggctcctg cgcgcagttg acgcgggcct gacggcactg  360
cgtcgtcttg gacgagcga cagcccgccg gacaccattg cggtcgaact ggtcataccc  420
tcgctccttg agggcatcca gcacctcctg gacccggtgc acccgcattc ccgaccccgt  480
tttttcgcaac accgcggcag cctcgtctgc ccgggggcc tcgacggccg cacgctgggg  540
gccttgcgct cccacgccgc agcggcaca cctgtcccgg gcaaggtgtg gcacgcctcg  600
gaaaccttgg ggtatcgac cgaggcagcc tccaccttc aacccgccca gggcatcatc  660
ggtggctccg ccgccgcgac agcaacatgg ctcaccaggg tcgcccgtc gcaacagagc  720
gacagcgcac ggcgctacct ggaagaactc cagcaccgat acagcggcc gtgcctcc    780
atcacccga tcacctattt cgaacgggcc tggctgctca caacttcgc tgccgcgggg  840
gttccatgcg aggctccggc agcccttctc gacagcctgg aggcagcgct cacaccacag  900
ggcgctccag cgggtgcggg actgccgccg gacgcggatg acaccgccgc cgttctgctg  960
gcgcttgcca cgcacggccg cggcgccgt cccgaggtcc tcatggacta ccgcacggac 1020
ggctacttcc agtgcttcat cggcgaacgc accccttcca tcagcaccaa tgcccatgtc 1080
```

```
ctggagacgc tcggtcacca cgtcgcccaa caccctcagg acagggcccg atacggctca   1140
gccatggaca ccgcatcagc gtggctcctc gcggctcaga agcaggatgg cagctggctc   1200
gacaagtggc acgcctcccc ctactacgcc accgtctgct gcacccaggc actggcagcc   1260
cacgcttccc ctgccaccgc ccccgcacgg cagcgtgctg tgcggtgggt gctggcaaca   1320
caacgctcgg acggcggctg gggcctgtgg cactccacga tcgaggagac ggcctacgcc   1380
ctgcagatcc tcgccccacc ttccggcggc gggaacatcc ccgtgcaaca ggcgctcacc   1440
aggggcgcg cccgcctctg cggcgctttg ccgctgactc ccctatggca tgacaaggac   1500
ctgtacacgc cggtacgtgt cgtccgcgcc gcccgtgccg ccgccctgta caccacccgt   1560
gacctgcttc tgccgcccct gtga                                         1584
```

SEQ ID NO: 39        moltype = DNA   length = 1551
FEATURE                Location/Qualifiers
source                 1..1551
                        mol_type = genomic DNA
                        organism = Bradyrhizobium japonicum
SEQUENCE: 39

```
gtgaacgcgc tgtccgaaca tatcctttcc gaattgcgcc gcctgctgag cgaaatgagc   60
gatggcggca gcgtcggtcc gtccgtctac gacacggcgg aggcgctgcg cttccacggc   120
aacgtcaccg gtcggcagga cgcatacgcg tggctcatcg cgcagcaaca ggccgacggc   180
ggatggggaa gcgcggactt cccgctgttc cgccatgcgc ccacgtgggc ggcgttactg   240
gcattgcagc gtgccgatcc tcttcccgga gctgcggacg cagtccagac tgcaacgagg   300
ttcctccagc gccagcccga tccctacgca catgcggtgc gcaagacgc gccgatcggc   360
gcggagctga tcctgccgca gttttgcggt gaggccgcat ggttgctggg tggcgtagcg   420
tttccgcgcc atcctgcgct gttgccattg cggcaagcgt gcctggtcaa gctggggcg   480
gtggcgatgt tgccgagcgg ccatccgttg ctacactcct gggaagcctg ggggacgtcg   540
ccgaccaccg catgcccgga tgacgacgag agcatccggc tcagtccggc gccaccgcc   600
gcgtggcgtg cccaggccgt gacacggggg agcacgccgc aggtcgggcg cgccgatgcc   660
tatctgcaga tggcatcgcg ggcgacgcgc agcggcatcg aagtgtctt cccaacgtc   720
tggccgatca atgtgttcga gccatgctgg tcgctgtaca ccctgcatct ggccgggctt   780
ttcgcgcatc ccgcgctcgc ggaggcggtt cgcgtgatcg tcgcgcagct cgaggcccgt   840
ctgggcgtgc acggtctggg ccccggcctt gcacttcgcg gctgatgcgga cgacaccgcc   900
gttgcgttgt gcgtcctgca ccttgcaggc cgtgacccgg cggtcgatgc gttgcgccat   960
ttcgaaatcg gcgagctgtt cgtcaccttc cccggcgaac gcaatgcctc ggtgtcgacc   1020
aacattcatg ccctgcatgc gttgcgactg ttgggaaagc ccgccgcggg cgccagcgcg   1080
tacgtcgagg ccaatcgcaa cccgcacggt ctatgcgaca acgaaaaatg gcacgtttcg   1140
tggctgtatc ccaccgcgca tgcggtcgct gcgctggcga aaggcaagcc ccagtggcga   1200
gatgagcgcg cgctggcggc gctgctgcag gcgcagcgcg acgacggtgg ctggggcgcg   1260
ggtcgcgggt ccacgttcga ggaaaccgcc tatgcgctgt tgcgttgca cgtgatggat   1320
gggagcgaag aggcgacagg gcgccggcgc atcgcgcagg tggtggccgg tgcgctggag   1380
tggatgctcg cccgccatgc ggcgcatgga ttgccgcaga cgccgctgtg gatcggcaag   1440
gaactgtatt gccccactcg ggtcgtgcgc gtggccgaac tcgccgggtt gtggctggcg   1500
cttcgttggg ggcggcgcgt cctggccgag ggggcaggag cggcgccatg a           1551
```

SEQ ID NO: 40        moltype = DNA   length = 2355
FEATURE                Location/Qualifiers
misc_feature         1..2355
                        note = Description of Artificial Sequence: Synthetic
                        polynucleotide
source                 1..2355
                        mol_type = other DNA
                        organism = synthetic construct
SEQUENCE: 40

```
atgaatttga gtttgtgtat agcatctcca ctattgacca aatctaatag accagctgct   60
ttatcagcaa ttcatacagc tagtacatcc catggtggcc aaaccaaccc tacgaatctg   120
ataatcgata cgaccaagga gagaatacaa aaacaattca aaaatgttga aatttcagtt   180
tcttcttatg atactgcgtg ggttgccatg gttccatcac ctaattctcc aaagtctcca   240
tgtttcccag aatgtttgaa ttggctgatt aacaaccagt tgaatgatgg atcttggggt   300
ttagtcaatc acacgcacaa tcacaaccat ccacttttga aagattcttt atcctccact   360
ttggcttgca tcgtggccct aaagagatgg aacgtaggtg aggatcagat taacaaggag   420
cttagtttca ttgaatctaa cttggcttcc gcgactgaaa aatctccaac atctccaata   480
ggattcgata tcatctttcc aggtctgtta gagtacgcca aaaatctaga tatcaactta   540
ctgtctaagc aaactgattt ctcactaatg ttacacaaga gagaattaga acaaaagaga   600
tgtcattcaa acgaaatgga tggttaccta gcttatatct ctgaaggtct tggtaatctt   660
tacgatctga atattggtaa atgaaaaatg gctcagtttt caattcccct   720
tctgcaactg cggcagcatt cattaaccat caaaatccag gatgcctgaa ctatttgaat   780
tcactactag acaaattcgg caacgcagtt ccaactgtat accctcacga tttgtttatc   840
agattgagta tggtggatac aattgaaaga cttggtatat cccaccactt tagagtcgag   900
atcaaaaatg ttttggatga gacataccgt tgtttgggtgg agagaatga acaaatcttt   960
atggatgttg tgacgtgcgc gttggccttt agattgttgc gtattaacgg ttacgaagtt   1020
agtccagatc cacttgccga aattacaaac gaattagctt taaaggatga atacgccgct   1080
cttgaaacat atcatgcgtc acatatcctt taccaagagg acttatcatc tggaaaacaa   1140
attcttaaat ctgctgattt cctgaaggaa atcatatcca ctgatagtaa tagactgtcc   1200
aaactgatcc ataaagaggt tgaaaatgca cttaagttcc ctattaacac cggcttagaa   1260
cgtattaaca caagacgtaa catccagctt tacaacgtag acaatactag aatcttccaa   1320
accacttacc attcttccaa catatcaaac actgattacc taagattagc tgttgaagat   1380
ttctacacat gtcagtctat ctatagaaaa gagctgaaag gattagagag atgggtcgtt   1440
gagaataagc tagatcaatt gaaatttgcc agacaaaaga cagcttattg ttacttctca   1500
gttgccgcca ctttatcaag tccagaattg tcagatgcac gtatttcttg ggctaaaaac   1560
ggaatttgaa caactgttgt tgatgatttc tttgatattg cgggacaat cgacgaattg   1620
```

```
acaaacctga ttcaatgcgt tgaaaagtgg aatgtcgatg tcgataaaga ctgttgctca   1680
gaacatgtta gaatactgtt cttggctctg aaagatgcta tctgttggat cggggatgag   1740
gctttcaaat ggcaagctag agatgtgacg tctcacgtca ttcaaacctg gctagaactg   1800
atgaactcta tgttgagaga agcaatttgg actagagatg catacgttcc tacattaaac   1860
gagtatatgg aaaacgctta tgtctccttt gctttgggtc ctatcgttaa gcctgccata   1920
tactttgtag gaccaaagct atccgaggaa atcgtcgaat catcagaata ccataacttg   1980
ttcaagttaa tgtccacaca aggcagatta cttaatgata ttcattcttt caaaagagag   2040
tttaaggaag gaaagttaaa tgctgttgct ctgcatcttt ctaatggcga aagtggtaaa   2100
gtcgaagagg aagtagttga ggaaatgatg atgatgatca aaaacaagag aaaggagttg   2160
atgaaactaa tcttcgaaga gaacggttca attgttccta gagcatgtaa ggatgcagttt   2220
tggaacatgt gtcatgtgct aaactttttc tacgcaaacg acgatggttt tactgggaac   2280
acaatactag atacagtaaa agacatcata tacaacccttt tggtcttagt aaacgaaaac   2340
gaggagcaaa gataa                                                   2355

SEQ ID NO: 41           moltype = DNA   length = 2355
FEATURE                 Location/Qualifiers
misc_feature            1..2355
                        note = Description of Artificial Sequence: Synthetic
                         polynucleotide
source                  1..2355
                        mol_type = other DNA
                        organism = synthetic construct
SEQUENCE: 41
atgaatctgt cccttttgtat agctagtcca ctgttgacaa atcttctag accaactgct   60
cttctgcaa ttcatactgc cagtactagt catggaggtc aaacaaaccc aacaaatttg   120
ataatcgata ctactaagga gagaatccaa aagctattca aaaatgttga aatctcagta   180
tcatcttatg acaccgcatg ggttgcaatg gtgccatcac ctaattcccc aaaaagtcca   240
tgttttccag agtgcttgaa ttggttaatc aataatcagt taacgatgg ttcttggggt   300
ttagtcaacc acactcataa ccacaatcat ccattattga aggactcttt atcatcaaca   360
ttagcctgta ttgttgcatt gaaaagatgg aatgtaggtg aagatcaaat caacaaggt   420
ttatcattca tagaatccaa tctagcttct gctaccgaca atcacaacc atctccaatc   480
gggttcgaca taatcttccc tggtttgctg gagtatgcca aaaacttga tatcaactta   540
ctgtctaaac aaacagattt ctctttgatg ctacacaaaa gagagttaga gcagaaaaga   600
tgccattcta acgaaattga cgggtactta gcatatatct cagaaggttt gggtaatttg   660
tatgactgga acatggtcaa aaagtatcag atgaaaaatg gatccgtatt caattctcct   720
tctgcaactg ccgcagcatt cattaatcat caaaaccctg ggtgtcttaa ctacttgaac   780
tcactattag ataagtttgg aaatgcagtt ccaacagtct atcctttgga cttgtacatc   840
agattatcta tggttgacac tatagagaga ttaggtattt ctcatcattt cagagttgag   900
atcaaaaatg ttttggacga gacatacaga tgttgggtcg aaagagatga gcaaatcttt   960
atggatgtcg tgacctgcgc tctggctttt agattgctaa ggatacacgg atacaaagta   1020
tctcctgatc aactggctga gattacaaac gaactggctt caaagacga atcgccgca   1080
ttagaaacat accatgcatc ccaaatactt taccaggaag acctaagttc aggaaaacaa   1140
atcttgaagt ctgcagattt cctgaaaggc atctgtcta cagatgtaa taggttgtct   1200
aaattgatac acaaggaagt agaaaacgca ctaaagtttc ctattaacac tggtttagag   1260
agaatcaata ctaggagaaa cattcagctg tacaacgtag ataatacaag gattcttaag   1320
accacctacc atagttcaaa catttccaac acctattact taagattagc tgtcgaagac   1380
ttttcacttt gtcaatcaat ctacagaagg gagttaaagg gcctagaaag atgggtagtt   1440
caaaacaagt tggatcaact gaagtttgct agacagaaga cagcatactg ttatttctct   1500
gttgctgcta cccttttcatc cccagaattg tctgatgcca gaataagttg ggccaaaaat   1560
ggtattctta caactgtagt cgatgatttc tttgatattg gaggtactat tgatgaactg   1620
acaaatctta ttcaatgtgt tgaaaagtgg aacgtggatg tagataagga ttgctgcagt   1680
gaacatgtga gaatactttt cctggctcta aaagatgcaa tatgttggat tggcgacgag   1740
gccttcaagt ggcaagctag agatgttaca tctcatgtca tccaaacctg gcttgaactg   1800
atgaactcaa tgctaagaga agcaatctgg acaagagatg catacgttcc aacattgaac   1860
gaatacatgg aaaacgctta cgtctccattt gccttgggtc ctattgttaa gccagccata   1920
tactttgttg ggccaaagtt atccgaagag attgttgagt cttccgaata tcataaccta   1980
ttcaagttaa tgtcaacaca aggcagactt ctgaacgata tccactcctt caaaagagaa   2040
ttcaaggaag gtaagctaaa cgctgttgct ttgcacttgt ctaatggtga atctggcaaa   2100
gtgaagagg aagtcgttga ggaaatgatg atgatgatca aaaacaagag aaaggaattg   2160
atgaaattga ttttcgagga aaatggttca atcgtaccta gagcttgtaa agatgctttt   2220
tggaatatgt gccatgttct taacttcttt tacgctaatg atgatggctt cactggaaat   2280
acaatattgg atacagttaa agatatccatc tacaacccac ttgttttggt caatgagaac   2340
gaggaacaaa gataa                                                   2355

SEQ ID NO: 42           moltype = DNA   length = 1773
FEATURE                 Location/Qualifiers
misc_feature            1..1773
                        note = Description of Artificial Sequence: Synthetic
                         polynucleotide
source                  1..1773
                        mol_type = other DNA
                        organism = synthetic construct
SEQUENCE: 42
atggctatgc cagtgaagct aacacctgcg tcattatcct taaaagctgt gtgctgcaga   60
ttctcatccg gtggccatgc tttgagattc gggagtagtc tgccatgttg gagaaggacc   120
cctacccaaa gatctactc ttcctctact actagaccag ctgccgaagt gtcatcaggt   180
aagagtaaac aacatgatca ggaagctagt gaagcgacta tcagacaaca attcaacttt   240
gtggatgtcc tggagaatat gggaatatcc agacatttg ctgcagagat aaagtgcata   300
ctagacagaa cttacagatc ttggttacaa agacacgagg aaatcatgct ggacactatg   360
```

```
acatgtgcta tggcttttag aatcctaaga ttgaacggat acaacgtttc atcagatgaa    420
ctataccacg ttgtagaggc atctggtctg cataattctt tgggtgggta tcttaacgat    480
accagaacac tacttgaatt acacaaggct tcaacagtta gtatctctga ggatgaatct    540
atcttagatt caattggctc tagatccaga acattgctta gagaacaatt ggagtctggt    600
ggcgcactga gaaagccttc tttattcaaa gaggttgaac atgcactgga tggaccttt    660
tacaccacac ttgatagact tcatcatagg tggaatattg aaaacttcaa cattattgag    720
caacacatgt tggagactcc atacttatct aaccagcata catcaaggga tatcctagca    780
ttgtcaatta gagattttc ctcctcacaa ttcacttatc aacaagagct acagcatctg    840
gagagttggg ttaaggaatg tagattagat caactacagt tcgcaagaca gaaattagcg    900
tacttttacc tatcagccgc aggcaccatg ttttctcctg agctttctga tgcgagaaca    960
ttatgggcca aaaacggggt gttgacaact attgttgatg atttctttga tgttgccggt   1020
tctaaagagg aattggaaaa cttagtcatg ctggtcgaaa tgtgggatga acatcacaaa   1080
gttgaattct attctgagca ggtcgaaatc atcttctctt ccatctacga ttctgtcaac   1140
caattgggtg agaaggcctc tttggttcaa gacagatcaa ttacaaaaca ccttgttgaa   1200
atatggttag acttgttaaa gtccatgatg acggaagttg aatggagact gtcaaaatac   1260
gtgcctacag aaaaggaata catgattaat gcctctctta tcttcggcct aggtccaatc   1320
gttttaccag ctttgtattt cgttggtcca aagatttcag aaagtatagt aaaggaccca   1380
gaatatgatg aattgttcaa actaatgtca acatgtggta ttgttgaa tgacgtgcaa    1440
acgttcgaaa gagaatacaa tgagggtaaa ctgaattctg tcagtctatt ggttcttcac   1500
ggaggcccaa tgtctatttc agacgcaaag aggaaattac aaaagcctat tgatacgtgt   1560
agaagagatc ttctttcttt ggtccttaga gaagagtctg tagtaccaag accatgtaag   1620
gaactattct ggaaaatgtg taaagtgtgc tatttctttt actcaacaac tgatgggttt   1680
tctagtcaag tcgaaagagc aaaagaggta gacgctgtca taaatgagcc actgaagttg   1740
caaggttctc atacactggt atctgatgtt taa                                1773

SEQ ID NO: 43            moltype = DNA  length = 2232
FEATURE                  Location/Qualifiers
misc_feature             1..2232
                         note = Description of Artificial Sequence: Synthetic
                         polynucleotide
source                   1..2232
                         mol_type = other DNA
                         organism = synthetic construct
SEQUENCE: 43
atgcagaact tccatggtac aaaggaaagg atcaaaaaga tgtttgacaa gattgaattg     60
tccgtttctt cttatgatac agcctgggtt gcaatggtcc catcccctga ttgcccagaa    120
acaccttgtt ttccagaatg tactaaatgg atcctagaaa atcagttggg tgatggtagt    180
tggtcacttc ctcatggcaa tccacttcta gttaaagatg cattatcttc cactcttgct    240
tgtattctgg ctcttaaaag atgggaatc ggtgaggaac agattaacaa aggactgaga    300
ttcatagaac tcaactctgc tagtgtaacc gataacgaac aacacaaacc aattggattt    360
gacattatct ttccaggtat gattgaatac gctatagact tagacctgaa tctaccacta    420
aaaccaactg acattaactc catgttgcat cgtagagccc ttgaattgac atcaggtgga    480
ggcaaaaatc tagaaggtag aagagcttac ttggcctacg tctctgaagg aatcggtaag    540
ctgcaagatt gggaaatggc tatgaaatac caacgtaaaa acggatctct gttcaatagt    600
ccatcaacaa ctgcagctgc attcatccat atacaagatg ctgaatgcct ccactatatt    660
cgttctcttc tccagaaatt tggaaacgca gtccctacaa tataccctct cgatatctat    720
gccagactt caatggtaga tgccctggaa cgtcttggta ttgatagaca tttcagaaag    780
gagagaaagt tcgttctgga tgaaacatac agatttggt tgcaaggaga agaggagatt    840
ttctccgata acgcaacctg tgctttggcc ttcagaatat tgagcttaa tggttacgat    900
gtctctcttg aagatcactt ctctaactct ctgggcggtt acttaaagga ctcaggagca    960
gctttagaac tgtacagagc cctccaattg tcttacccag acagtccct cctgaaaaa   1020
caaaattcta gaacttctta cttcttaaaa caaggtttat ccaatgtctc cctctgtggt   1080
gacagattgc gtaaaaacat aattggagag gtgcatgatg ctttaaactt ttccgaccac   1140
gctaacttac aaagattagc tattcgtaga aggattaagc attacgctac tgacgataca   1200
aggattctaa aaacttccta cagatgctca acaatcgatt accaagattt tctaaaactt   1260
gcagtggaag atttcaatat ctgtcaatca atacaaagag aggaattcaa gcatattgaa   1320
agatgggtcg ttgaaaagacg tctagacaag ttaaagttcg ctagacaaaa agaggcctat   1380
tgctatttct cagccgcagc aacattgttt gcccctgaat tgtctgatgc tagaatgtct   1440
tgggccaaaa atggtgtatt gacaactgtg gttgatgatt tcttcgatgt cggaggctct   1500
gaagaggaat tagttaactt gatagaattg atcgagcgtt gggatgtgaa tggcagtgca   1560
gattttgta gtgaggaagt tgagattatc tattctgcta tccactcaac tatctctgaa   1620
ataggtgata agtcatttgg ctggcaaggt agagatgtaa agtctcaagt tatcaagatc   1680
tggctggact tattgaaatc aatgttaact gaagctcaat ggtcttcaaa caagtctgtt   1740
cctaccctag atgagtatat gacaaccgcc catgtttcat tcgcacttgg tccaattgta   1800
cttccagcct tatacttcgt tggcccaaag ttgtcgaaag aggttgcagg tcatcctgaa   1860
ctactaaacc tctacaaagt cacatctact tgtggcagac tactgaatga ttggagaagt   1920
tttaagagag aatccgagga aggtaagctc aacgctatta gttatacat gatccactcc   1980
ggtggtgctt ctacagaaga ggaaacaatc gaacatttca aaggtttgat tgattctcag   2040
agaaggcaac tgttacaatt ggtgttgcaa gagaaggata gtatcatact tagaccatgt   2100
aaagatctat tttggaatat gattaagtta ttacacactt tctacatgaa agatgatggc   2160
ttcacctcaa atgagatgag gaatgtagtt aaggcaatca ttaacgaacc aatctcactg   2220
gatgaattat ga                                                       2232

SEQ ID NO: 44            moltype = DNA  length = 2355
FEATURE                  Location/Qualifiers
source                   1..2355
                         mol_type = genomic DNA
                         organism = Stevia rebaudiana
SEQUENCE: 44
```

```
atgaatcttt cactatgcat cgcgtcccct tgttaacca aatcaaatcg acccgcggct    60
ctgtcagcta ttcatacagc atcaacttca catggtggac aaactaatcc cactaatctg   120
atcattgata caaccaaaga acggatccaa aaacagttta aaaatgtaga aatttctgtt   180
tcttcatatg acacagcatg ggtagccatg gtcccttctc caaactcacc caaatcgcct   240
tgtttccctg agtgtctcaa ttggttaatt aataatcagc ttaatgatgg ttcatggggt   300
cttgttaatc acactcataa tcataatcac ccgttgctta agattctct atccttcaaca   360
ttagcatgta ttgttgcatt aaaaagatgg aatgttgggg aagatcaaat aaataaaggt   420
ctaagtttta ttgagtcaaa tcttgcttca gctactgaaa aaagtcaacc atctcccatt   480
ggttttgaca tcatatttcc tggttttgctt gagtatgcga aaaacttgga cataaacctc   540
cttcaaaac aaacagattt tagtttgatg ctacataaga gggaattgga gcaaaaaga     600
tgccattcaa atgagattga tggatacttg gcgtatatct ctgaaggact cggtaattta   660
tatgattgga atatggtgaa gaaatatcag atgaaaaatg ttctgtttt caactcacca    720
tcagcaacag ctgctgcttt cattaatcat caaaatcctg gttgtcttaa ttatttaaat   780
tcacttttgg acaagtttgg taatgcagtc ccaacagttt atcctcatga tttatttatc   840
cgactttcta tggttgacac aattgaaaga ttaggaattt cacaccattt cagagtggaa   900
attaaaaatg ttttagatga acatacaga tgttgggtgg aacgagatga gcaaatattc   960
atggatgttg taacatgtgc tttagccttt cggttattaa ggatcaatgg gtataagtt   1020
tccccagatc cattggctga aattactaat gaattagctt tgaaagacga atatgcgct   1080
cttgaaacat atcatgcgtc acatatatta taccaagagg atttatcttc tggaaaacaa   1140
atcttgaagt cagctgattt cctcaaagag ataatatcca ctgattcaaa caggctttct   1200
aaaattaattc acaagaggt ggaaaatgct cttaagttcc ctatcaatac cggttgaaa   1260
cgcataaaca ctagacgaaa tatacagctt tacaatgtag acaatacag aattctgaaa   1320
actacatatc actcatcaaa tattagtaac actgattacc taaggttggc tgttgaagat   1380
ttctacacct gccaatctat ttatcgtgaa gaattaaaag gtcttgaaag gtgggtggta   1440
gagaataagt tggaccagct caagtttgct aggcaaaaga ccgcctactg ttattctct   1500
gttgctgcaa cactttcgtc tcccgaatta tcagatgcg gtatttcatg ggccaaaat    1560
ggcatattaa ctacagtagt tgatgacttt tttgatatcg gtgtacaat cgatgaattg   1620
accaacctga ttcaatgtgt tgaaaaatgg aatgtagatg tcgacaagga ttgttgttca   1680
gagcatgttc ggattttatt tttagcatta aaagatgcaa tctgttggat tggagataa    1740
gcttttaaat ggcaagcgcg cgatgtaact agccatgtta ttcaaacttg gttggaacta   1800
atgaatagta tgttgagaga agctatatgg acaagagatg cttatgtgcc aacattaat   1860
gaatatatgg aaaacgctta cgtgtcattt gcattaggcc cgattgtcaa gccggctatt   1920
tactttgtgg ggcccaaatt atcagaggag attgttgaaa gctctgaata tcataatcta   1980
tttaagctaa tgagcacgca gggtcgactt ctaaacgata tccatagctt caagaggaa   2040
tttaaggaag gcaaattaaa cgcggtagca ttgcatttga gtaacggaga aagtgggaaa   2100
gtggaagaag aggttgtgga ggagatgatg atgatgatta aaaacaagag gaaagaatta   2160
atgaaattaaa tttttgaaga aatggtagc attgttccta gagcttgtaa agatgcattt    2220
tggaacatgt gtcacgtgtt gaattttttt tacgcaaacg atgacgggtt tactggaaac   2280
acgattcttg atactgtgaa ggacatcatt tacaacccgt ggtgcttgt gaatgaaaat    2340
gaagaacaaa ggtaa                                                    2355
```

| SEQ ID NO: 45 | moltype = DNA  length = 2355 |
|---|---|
| FEATURE | Location/Qualifiers |
| source | 1..2355 |
|  | mol_type = genomic DNA |
|  | organism = Stevia rebaudiana |

SEQUENCE: 45
```
atgaatcttt cactatgcat tgcgtcccct tgttaacca aatcaagtcg acccacggct    60
ctgtcagcta ttcatacagc atcaacttca catggtggac aaactaatcc cactaatctg   120
atcattgata caaccaaaga acggatccaa aaactgttta aaaatgtaga aatttctgtt   180
tcttcatatg acacagcatg ggtagccatg gtcccttctc caaactcacc caaatcgcct   240
tgtttccctg agtgtctcaa ttggttaatt aataatcagc ttaatgatgg ttcatggggt   300
cttgttaatc acactcataa tcataatcac ccgttgctta agattctct atccttcaaca   360
ttagcatgta ttgttgcatt aaaaagatgg aatgttgggg aagatcaaat aaataaaggt   420
ctaagtttta ttgagtcaaa tcttgcttca gcaactgaca aaagtcaacc atctcccatt   480
ggttttgata tcatatttcc tggttttgctt gagtatgcga aaaacttgga cataaacctc   540
cttcaaaac aaacagattt tagtttgatg ctacataaga gggaattgga gcaaaaaga     600
tgccattcaa atgagattga tggatacttg gcgtatatct ctgaaggact cggtaattta   660
tatgattgga atatggtgaa gaaatatcag atgaaaaatg ttctgtttt caactcacca    720
tcagcaacag cagctgcttt cattaatcat caaaatcccg gttgtcttaa ttatttaaat   780
tcacttttgg acaagtttgg taatgcagtc ccaacagttt atcctcttga tttatatatc   840
cggctttcta tggttgacac aattgaaaga ttaggaattt cacaccattt cagagtggaa   900
attaaaaatg ttttagatga acatacaga tgttgggtgg aacgagatga gcaaatattc    960
atggatgttg taacatgtgc tttagccttt cggttattaa ggatccacg gtataagtt    1020
tccccagatc aattggctga aattactaat gaattagctt tcaaagacga atacgcagct   1080
cttgaaacat atcatgcatc acagatatta taccaagagg atttatcttc tggaaaacaa   1140
atcttgaagt cagctgattt cctcaaaggg atattatcca ctgattcaaa caggctttct   1200
aaaattaattc acaaagaggt ggaaaatgct cttaagttcc ctatcgtag acaatacaag    1260
cgcataaaca ctagacgaaa tatacagctt tacaatgtag acaatacaag aattctgaaa   1320
actacatatc actcatcaaa tattagtaac acttattacc taaggttggc tgttgaagat   1380
ttctacacct gccaatctat ttatcgtgaa gaattaaaag gtcttgaaag gtgggtggta   1440
cagaataagt tggaccagct caagtttgct aggcaaaaga ccgcctactg ttattctct    1500
gttgctgcaa cactttcgtc tcccgaatta tcagatgcg gtatttcatg ggccaaaat    1560
ggcatattaa ctacagtagt tgatgacttt tttgatatcg gtgtacaat cgatgaattg   1620
accaacctga ttcaatgtgt tgaaaaatgg aatgtagatg tcgacaagga ttgttgttca   1680
gagcatgttc ggattttatt tttagcatta aaagatgcaa tctgttggat tggagataa    1740
gcttttaaat ggcaagcgcg cgatgtaact agccatgtta ttcaaacttg gttggaacta   1800
atgaatagta tgttgagaga agctatatgg acaagagatg cttatgtgcc aacattaat   1860
gaatatatgg aaaacgctta cgtgtcattt gcattaggcc cgattgtcaa gccggctatt   1920
```

```
tactttgtgg ggcccaaatt atcagaggag attgttgaaa gctctgaata tcataatcta 1980
tttaagctaa tgagcacgca gggtcgactt ctaaacgata tccatagctt caagagggaa 2040
tttaaggaag gcaaattaaa cgcggtagca ttgcatttga gtaacggaga aagtgggaaa 2100
gtggaagaag aggttgtgga ggagatgatg atgatgatta aaaacaagag gaaagaatta 2160
atgaaattaa tttttgaaga aaatggtagc attgttccta gagcttgtaa agatgcattt 2220
tggaacatgt gtcacgtgtt gaattttttt tacgcaaacg atgacgggtt tactggaaac 2280
acgattcttg atactgtgaa ggacatcatt tacaacccgt tggtgcttgt gaatgaaaat 2340
gaagaacaaa ggtaa                                                  2355

SEQ ID NO: 46           moltype = DNA  length = 1773
FEATURE                 Location/Qualifiers
source                  1..1773
                        mol_type = genomic DNA
                        organism = Zea mays
SEQUENCE: 46
atggccatgc cagtgaagct gactcctgcc tccctctcgc tgaaggcggt ctgctgccgc 60
ttcagctccg gagggcatgc gctgcgcttc ggctcgtcgc taccgtgctg gaggaggacg 120
ccgacgcaac ggagcacgtc gtcgtctacg acgcgccctg cggctgggtt tagctctggc 180
aaaagcaagc agcacgatca agaagcatcg gaggctacga taagacagca gctccagcta 240
gtcgatgtgc ttgagaacat ggggatttct cggcattttg ctgctgaaat caaatgcatc 300
cttgacagga catacagaag ttggttacag agacatgagg aaattatgct ggacacaatg 360
acctgtgcga tggcatttcg tattctaagg ttgaatggat acaatgtctc ttctgatgag 420
ttgtatcatg ttgttgaagc ttccggactc cataattcac ttggaggata tctcaatgat 480
acaagaacct tgttagaatt acacaaggcc tcgacagtta gtatctctga agatgagtct 540
atcctggata gcataggctc aaggtcacgt accttactga gggaacaact agagtctggt 600
ggtgctctac gaaaaccttc actctttaaa gaggtggaac atgctctgga cggtcccttc 660
tacaccacat tggaccgtct cacccatagg tggaacatcg aaaatttcaa tattatagag 720
cagcacatgc tagagacacc atacttgtca aatcaacata ccagtagaga tattctagcg 780
ttgagtatta gagacttcag ttcctctcag tttacttacc agcaagaact tcaacatctt 840
gaaagctggg tgaaagagtg caggttagac cagctacaat ttgcgcgaca gaagttgaca 900
tacttctact tgtctgctgc tggcaccatg ttctctcctg agctgtctga tgctcgaact 960
ttgtgggcca aaaatggtgt gctcacaact attgttgacg acttctttga tgttgcggga 1020
tcaaaagaag aacttgaaaa ccttgtcatg ttggttgaga tgtgggacga gcatcacaaa 1080
gttgagttct actcagaaca agtagagatt atattttctt caattatga ttcagttaac 1140
caacttggtg aaaaggcttc tttggtacaa gaccgcagta ttaccaaaca cctagtagaa 1200
atatggttgg atttgctaaa gtctatgatg acagaggtag agtggcgttt gagcaaatat 1260
gtgccaacag agaaggaata catgataaat gcatctttaa tatttggact aggcccatt 1320
gtattgccag cattatattt tgttgggcca aagatctcag agtctattgt taaagatcca 1380
gaatatgata aattgttcaa actgatgagc acatgtggtc gcctcttgaa tgatgttcag 1440
acttttgaga gggagtacaa cgagggcaag ttgaatagtg tttctctcct cgttcttcat 1500
ggtggcccca tgtccatatc agacgccaaa aggaaattac agaagcccat agacacatgc 1560
agaagagacc tcctaagttt agttcttcgt gaagaaagtg ttgttcctag gccctgcaag 1620
gaattatttt ggaaaatgtg caaggtgtgc tacttcttct actcgacgac ggatgggttt 1680
agctcacaag tggagagggc taagaagtg gatgcggtga tcaatgagcc actaaagcta 1740
caaggaagtc atacgctggt gtctgatgtg tga                              1773

SEQ ID NO: 47           moltype = DNA  length = 2232
FEATURE                 Location/Qualifiers
source                  1..2232
                        mol_type = genomic DNA
                        organism = Populus trichocarpa
SEQUENCE: 47
atgcagaact tcatggaac taaggaaagg atcaagaaga tgtttgataa gattgaattg 60
tcagtgtctt catatgacac tgcttgggtg gcaatggtcc catctccaga ttgtccggaa 120
actccttgtt ttccagagtg cacaaaatgg attttgaaa atcaacttgg tgatggctcc 180
tggagtcttc ctcatggcaa tccattatta gttaaggatg ctctttcatc tacattagcg 240
tgcatccttg cattgaagcg atggggtatc ggtgaagaac aaataaataa aggccttcga 300
tttattgagt tgaattccgc ttcagttacg ataacgagc aacataaacc aattggattt 360
gatataatat ttcctggcat gattgaaatat gccatagatt tggatttgaa cctccctttg 420
aagccgacag atataaattc catgctccac aggagggctt tggagcttac aagtgcgcgt 480
ggcaagaact tggagggaag aagagcctac ttagcatatg tttcggaagg aattggaaaa 540
ttacaggatt gggaaaatgcc catgaaatat caaagaaaga atggatcact gttcaattca 600
ccatccacca cagcagctgc ctttattcat attcaagatg ctgagtgtct ccattatatt 660
cgttcactct tacagaagtt tgggaatgca gttccaacca tttatccttt ggatatatat 720
gctcgtcttt ctatggttga tgctcttgaa aggttgggaa tcgatcggca ttttaggaag 780
gaaagaaaat ttgttttgga cgaaacatac cgatttttgg tgcagggga ggaagagata 840
ttttctgata atgccacttg tgcttgcgca tttaggatat tacgtttgaa cggatatgat 900
gtctctctag aagatcattt ctctaattca ctgggaggat atttgaagga ttcgggagct 960
gccttagagt tgtacagagc tctgcagcta agttatccag atgaatcact tctggaaaaa 1020
caaaattctc ggacaagcta tttcctgaaa cagggattat ccaacgtttc actttgtgga 1080
gataggcttc gtaaaaatat tatcggagag gtgcatgatg ctctcaattt ttctgaccat 1140
gcaaatttga aacgcttagc tatcagaaga gaattaaac attatgctac agatgatacg 1200
aggattttga aaacttcgta tcgttgttcg actattggta ccaggatttt tctcaaattg 1260
gctgtagaag acttcaatat ctgtcaatca atacagcgtg agaaatttaa acatatcgag 1320
aggtgggttg tagagaggag actgacaag ctaaagtttg ctaggcagaa ggaggcctac 1380
tgttacttct ctgctgcagc aactctcttt gctccagaac tatctgatgc acgcatgtca 1440
tgggcaaaaa atggtgtgct tactactgtt gttgatgact cttttgatgt tggtggttct 1500
gaagaagaac tggtaaacct tattgaattg attgagaggt gggatgtcaa tggcagtgct 1560
gattttttgtt ctgaggaagt tgagatcata tattcggcaa ttcacagcac tataagtgag 1620
```

```
ataggagaca aatctttcgg atggcaagga cgcgatgtga aaagtcaggt tatcaagatt   1680
tggttggatt tgctcaaatc catgttgaca gaagcacaat ggtcaagtaa caaatcagtg   1740
ccgacccttg atgaatatat gacaactgca catgtatcgt tcgctctagg gcctattgtt   1800
cttccagctc tgtattttgt ggggcctaag cttttcagagg aggttgctgg acatcctgaa   1860
ttgcttaatc tatacaaggt tacgagcact tgcgggcgtc tgctcaatga ctggagaagc   1920
tttaagagag aatctgaaga agggaaattg aatgccatct cattgtacat gattcacagc   1980
ggtggtgctt caactgaaga agagaccatc gaacatttta aaggattgat cgacagccag   2040
agaagacaat tgcttcaatt agttttgcag gaaaaggata gtataattcc tagaccctgc   2100
aaggatttgt tttggaacat gataaaatta ttgcacacgt tctacatgaa ggatgatgga   2160
ttcacttcaa acgagatgag aaatgttgtc aaggcaataa taaatgaacc catctctcta   2220
gatgaattat aa                                                       2232

SEQ ID NO: 48           moltype = DNA   length = 2952
FEATURE                 Location/Qualifiers
misc_feature            1..2952
                        note = Description of Artificial Sequence: Synthetic
                        polynucleotide
source                  1..2952
                        mol_type = other DNA
                        organism = synthetic construct
SEQUENCE: 48
atggaatttg atgaaccatt ggttgacgaa gcaagatctt tagtgcagcg tactttacaa     60
gattatgatg acagatacgg cttcggtact atgtcatgtg ctgcttatga tacagcctgg   120
gtgtctttag ttacaaaaac agtcgatggg agaaaacaat ggcttttccc agagtgtttt   180
gaatttctac tagaaacaca atctgatgcc ggaggatggg aaatcgggaa ttcagccaca   240
atcgacggta tattgaatac agctgcatcc ttacttgcta taaaacgtca cgttcaaact   300
gagcaaatca tccaacctca acatgaccat aaggatctag caggtagagc tgaacgtgcc   360
gctgcatctt tgagagcaca attggctgca ttggatgtgt ctacaactga acacgtcggt   420
tttgagataa ttgttcctgc aatgctagac ccattagaag ccgaagatcc atctctagtt   480
ttcgattttc cagctaggaa acctttgatg aagattcatg atgctaagat gagtagattc   540
aggccagaat acttgtatgg caaacaacca atgaccgcct tacattcatt agaggctttc   600
ataggcaaaa tcgacttcga taaggtaaga caccaccgta cccatgggtc tatgatgggt   660
tctccttcat ctaccgcagc ctacttaatg cacgcttcac aatgggatgg tgactcagag   720
gcttaccta gacacgtgat taaacacgca gcagggcagg gaactggtgc tgtaccatct   780
gctttcccat caacacattt tgagtcatct tggattctta ccacattgtt tagagctgga   840
ttttcagctt ctcatcttgc ctgtgatgag ttgaacaagt tggtcgagat acttgagggc   900
tcattcgaga aggaaggtgg ggcaatcggt tacgctccag ggtttcaagc agatgttgat   960
gatactgcta aaacaataag tacattagca gtccttggaa gagatgctac accaagacaa  1020
atgatcaagg tatttgaagc taatacacat tttagaacat accctggtga aagagatcct  1080
tctttgacag ctaattgtaa tgctctatca gccttactac accaaccaga tgcagcaatg  1140
tatgcatctc aaattcaaaa gattaccaaa tttgtctgtg actattggtg gaagtctgat  1200
ggtaagatta agataagtg gaacacttgc tacttgtacc catctgtctt attagttgag  1260
gttttggttg atcttgttag tttattggag cagggtaaat tgcctgatgt tttgatcaa  1320
gagcttcaat acagagtcgc catcacattg ttccaagcat gtttaaggcc attactagac  1380
caagatgccg aaggatcatg gaacaagtct atcgaagcca cagcctacgg catccttatc  1440
ctaactgaag ctaggagagt ttgtttcttc gacagattgt ctgagccatt gaatgaggca  1500
atccgtagag gtatcgcttt cgccgactct atgtctggaa gctcagttga aactac  1560
atttggatcg aaaaggttag ttacgcacct gcattattga ctaaatccta tttgttagca  1620
gcaagatggg ctgctaagtc tccttttaggc gcttccgtag gctcttcttt gtggactcca  1680
ccaagagaag gattggataa gcatgtcaga ttattccatc aagctgagtt attcagatcc  1740
cttccagaat gggaattaag agcctccatg attgaagcag ctttgttcac accacttcta  1800
agagcacata gactagacgt tttccctaga caagatgtag gtgaagacaa atatcttgat  1860
gtagttccat tcttttggac tgccgctaac aacagagata gaacttacgc ttccactcta  1920
ttcctttacg atatgtgttt tatcgcaatg ttaaacttcc agttagacga attcatggag  1980
gccacagccg gtatcttatt cagagatcat atggatgatt tgaggcaatt gattcatgat  2040
cttttggcag agaaaacttc cccaaagagt tctggtagaa gtagtcaggg cacaaaagat  2100
gctgactcag gtatagagga agacgtgtca atgtccgatt cagctcaga ttcccaggat  2160
agaagtccag aatacgactt ggttttcagt gcattgagta cctttacaaa acatgtcttg  2220
caacacccat ctatacaaag tgcctctgta tgggataaga aactacttgc tagagagatg  2280
aaggcttact tacttgctca tatccaacaa gcagaagatt caactccatt gtctgaattg  2340
aaagatgtgc ctcaaaagac tgatgtaaca agagtttcta catctactac taccttcttt  2400
aactgggtta gaacaacttc cgcagaccat atatcctgcc catactcctt ccactttgta  2460
gcatgccatc taggcgcagc attgtcacct aaagggtcta acggtgattg ctatccttca  2520
gctggtgaga agttcttggc agctgcagtc tgcagacatt tggccaccat tgtgataatg  2580
tacaacgatc ttggatcagc tgaacgtgat tctgatgaag gtaatttgaa ctccttggca  2640
ttccctgaat tcgccgattc cgcaggaaac ggagggatag aaattcagaa gccgctcta  2700
ttaaggttag ctgagtttga gagagattca tacttagagg cctccgtcg tttacaagat  2760
gaatccaata gagttcacgg tccagccggt ggtgatgaag ccagattgtc cagaaggaga  2820
atggcaatcc ttgaattctt cgcccagcag gtagatttgt acggtcaagt atacgtcatt  2880
agggatattt ccgctcgtat tcctaaaaac gaggttgaga aaagagaaa attggatgat  2940
gctttcaatt ga                                                      2952

SEQ ID NO: 49           moltype = DNA   length = 2646
FEATURE                 Location/Qualifiers
misc_feature            1..2646
                        note = Description of Artificial Sequence: Synthetic
                        polynucleotide
source                  1..2646
                        mol_type = other DNA
```

```
                    organism = synthetic construct
SEQUENCE: 49
atggcttcta gtacacttat ccaaaacaga tcatgtggcg tcacatcatc tatgtcaagt   60
tttcaaatct tcagaggtca accactaaga tttcctggca ctagaacccc agctgcagtt  120
caatgcttga aaaagaggag atgccttagg ccaaccgaat ccgtactaga atcatctcct  180
ggctctggtt catatagaat agtaactggc ccttctggaa ttaaccctag ttctaacgga  240
cacttgcaag agggttcctt gactcacagg ttaccaatac caatggaaaa atctatcgat  300
aacttccaat ctactctata tgtgtcagat atttggtctg aaacactaca gagaactgaa  360
tgtttgctac aagtaactga aaacgtccag atgaatgagt ggattgagga aattagaatg  420
tactttagaa atatgacttt aggtgaaatt tccatgtccc cttacgacac tgcttgggtg  480
gctagagttc cagcgttgga cggttctcat gggcctcaat tccacagatc tttgcaatgg  540
attatcgaca accaattacc agatggggac tggggcgaac cttctctttt cttgggttac  600
gatagagttt gtaatacttt agcctgtgtg attgcgttga aaacatgggg tgttgggca   660
caaaacgttg aaagaggaat tcagttccta caatctaaca tatacaagat ggaggaagat  720
gacgctaatc atatgccaat aggattcgaa atcgtattcc ctgctatgat ggaagatgcc  780
aaaagcattag gtttggattt gccatacgat gctactattt tgcaacagat ttcagccgaa  840
agagagaaaa agatgaaaaa gatcccaatg gcaatggtgt acaaataccc aaccacttta  900
cttcactcct tagaaggctt gcatagagaa gttgattgga ataagttgtt acaattacaa  960
tctgaaaatg gtagttttct ttattcacct gcttcaaccg catgcgcctt aatgtacact 1020
aaggacgtta aatgttttga ttacttaaac cagttgttga tcaagttcga ccacgcatgc 1080
ccaaatgtat atccagtcga tctattcgaa agattatgga tggttgacag attgcagaga 1140
ttagggatct ccagatactt tgaaagagag attagagatt gtttacaata cgtctacaga 1200
tattggaaaa attgtggaat cggatgggct tctaactctt ccgtacaaga tgttgatgat 1260
acagccatgg cgtttagact tttaaggact catggtttcg acgtaaagga agattgcttt 1320
agacagtttt tcaaggacgg agaattcttc tgcttcgcag ccaatcatc tcaagcagtt  1380
acaggcagtt ttaatctttc aagagccagt caaacattgt ttccaggaga atctttattg 1440
aaaaaggcta gaaccttctc tagaaacttc ttgagaacaa agcatgagaa caacgaatgt 1500
ttcgataaat ggatcattac taaagatttg gctggtgaag tcgagtataa cttgaccttc 1560
ccatggtatg cctctttgcc tagattagaa cataggacat acttagatca atatggaatc 1620
gatgatatct ggataggcaa atctttatac aaaatgcctg ctgttaccaa cgaagttttc 1680
ctaaagttgg caaaggcaga ctttaacatg tgtcaagctc tacacaaaaa ggaattggaa 1740
caagtgataa agtggaacgc gtcctgtcaa ttcagagatc ttgaattcgc cagacaaaaa 1800
tcagtagaat gctatttttgc tggtgcagcc acaatgttcg aaccagaaat ggttcaagct 1860
agattagtct gggcaagatg ttgtgtattg acaactgtct tagacgatta ctttgaccac 1920
gggacacctg ttgaggaact tagagtgttt gttcaagctg tcagaacatg gaatccagag 1980
ttgatcaacg gtttgccaga gcaagctaaa atcttgttta tgggcttata caaaacagtt 2040
aacacaattg cagaggaagc attcatggca cagaaaagag acgtccatca tcatttgaaa 2100
cactattggg acaagttgat aacaagtgcc ctaaggagg ccgaatgggc agagtcaggt 2160
tacgtcccaa catttgatga atacatggaa gtagctgaaa tttctgttgc tctagaacca 2220
attgtctgta gtaccttgtt ctttgcgggt catagactag atgaggatgt tctagatagt 2280
tacgattacc atctagttat gcatttggta aacagagtcg gtaagtaatct gaatgataa  2340
caaggcatga agagggaggc ttcacaaggt aagatctcat cagttcaaat ctacatggag 2400
gaacatccat ctgttccatc tgaggccatg gcgatcgctc aaggagttagttgat 2460
aattcaatgc agcaattgac atacgaagtt cttaggttca ctgcggttcc aaaaagttgg 2520
aagagaatcc acttgaatat ggctaaaatc atgcatgcct tctacaagga tactgatgga 2580
ttctcatccc ttactgcaat gacaggattc gtcaaaaagg ttcttttcga acctgtgcct 2640
gagtaa                                                            2646

SEQ ID NO: 50         moltype = DNA  length = 2952
FEATURE               Location/Qualifiers
source                1..2952
                      mol_type = genomic DNA
                      organism = Phomopsis amygdali
SEQUENCE: 50
atggagttcg atgaaccact tgtggacgag gcgaggtcct tggtccaaag aaccctgcaa   60
gattatgacg accgctatgg ctttggcact atgagctgtg cggcctatga cacagcatgg  120
gtatcgctgg tgactaaaac agtcgatggg cgtaaacaat ggttgttccc tgagtgcttc  180
gaatttctcc tagaaacgca gtccgatgct ggcggctggg aaatcggcaa cagcgcaccc  240
atcgatggga tccttaacac tgctgcttca ctgctggcat tgaagcgcac cgtccaaaca  300
gagcagatta ttcagccgca acacgaccat aaagaccctg ccgggcgtgc ggaaagagcg  360
gcggcgtctt tgcgagcaca gttggcggct ctggatgtgt cgacaacgga gcatgtgggc  420
ttcgaaatca tcgtcccggc catgctcgac cctctcgagg ccgaagaccc gtctttggtg  480
ttcgactttc cagcacgcaa accactgatg aagatccacg acgctaagat gtcgcgattc  540
cgaccagagt acctctacgg taaacagccg atgacggcat tgcattcgct cgaggcctt   600
atcgggaaaa tagacttcga caaagtacgg catcacagga cacacggttc gatgatgggg  660
tcgcccctcgt cgacgctgc ataccctgatg catgcttctc agtgggacgg cgactctgag  720
gcctatctac gccatgtcat caagcacgca gctggccagg caccggagc tgttccgagt  780
gcatttcctt cgacgcattt cgagtcttct tggattttga caacattgtt tcgagctggg  840
ttctcagcct ctcatctcca atgcgacgaa ttaaacaagc tggtagaatg cctcgaaggg  900
tcatttgaga aagaagggg agccatcggt tatgctcctg gtttcaagc agatgtggat  960
gataccgcaa agaccatctc cactttggct gtgcttggga gagtgccac tccccggcaa 1020
atgatcaagg tttttgaagc caatacacac tttcggactt accctggtga agagatcca  1080
agcttgactg ccaattgcaa cgcgctctcg gctcttcttc accagccaga cgcagcaatg 1140
tacggcagcc agatccagaa gatcacaaag tttgtttgta actactggtg gaaaagtgac 1200
ggcaaaatca aggacaagtg gaatacctgc tacttgtatc catcggtcct cctcgtcgag 1260
gtgttagtag accttgtgtc cctgttggag caaggaaagc tacccgacgt gctggatcag 1320
gagctgcaat acagggtcgc cattacgtta ttccaggcct gcttgcgacc gctacttgat 1380
caagatgctg aaggttcatg gaacaaatcc attgaagcca cagcctacgg cattctaatc 1440
cttacggagg cgcggcgagt atgctttttt gaccgtctga gtgagcctct gaatgaggct 1500
```

-continued

```
attcgacgcg ggattgcgtt tgcagattcg atgagcggta ctgaagctca gctgaattat 1560
atatggatcg agaaagtgag ctacgcacct gctcttctga ccaaatcata cctcctcgca 1620
gctcggtggg cggcaaagtc cccgcttggc gcttccgttg gatccagcct ttggacgcct 1680
ccaagagaag gcttggataa gcacgtccgt ctattccacc aggcagagct cttcaggtcg 1740
ttgccggagt gggagctgcg cgcgtccatg atcgaggcag ccctgttcac tccttttgctg 1800
cgtgcgcata ggctggatgt atttccacgc caagacgtcg gcgaggacaa gtacctggac 1860
gttgtgccgt tcttctggac ggccgccaat aaccgcgatc gcacgtacgc atccactctg 1920
tttctgtatg acatgtgctt tatcgccatg cttaacttcc agctggatga gttcatggag 1980
gctacagcg gaatcctctt ccgggaccat atggatgatt tgcgccaact catccacgac 2040
ctgcttgccg aaaagacgag ccccaagtca tcgggcagaa gtagccaagg aaccaaagac 2100
gcggactcgg gcatcgaaga agacgtttct atgagcgact cagcgtcaga ctcccaggac 2160
cgcagccctg aatacgacct ggtcttctct gcgctctcta ccttcaccaa acatgtcctg 2220
cagcacccct caatccagtc agccagtgtc tgggatagga aactactcgc tcgcgagatg 2280
aaagcatacc tcctagctca tattcaacag gctgaggaca gcacgccctt gagtgagctc 2340
aaggacgtcc ctcaaaaac tgacgtgaca cgcgtctcaa cgtccacaac gactttcttc 2400
aactgggtac gcacaacatc cgcagaccac atatcctgcc catattcatt ccatttcgtg 2460
gcgtgtcacc tcggcgccgc gctgagcccc aagggcagca acggcgactg ttaccgtca 2520
gccggtgaaa agttcctcgc ggccgccgta tgccgccatt tggccacgat gtgccgcatg 2580
tacaatgact tgggatcggc ggagcgcgac agtgacgagg gaaatttgaa ttcactcgac 2640
tttcccgagt tcgccgactc agcggggaat ggtgggattg agatccagaa agctgccttg 2700
ctcaggctgg ccgagttcga acgcgactcg tatctcgagg cttccggcg acttcaggat 2760
gaaagcaacc gcgttcacgg accggctggt gggatgaag cagactcag caggcggccg 2820
atggccatcc ttgagttctt tgcccagcag gtgacttgt atggccaggt ctacgttatt 2880
cgcgatatct cggccaggat tccaaagaac gaggttgaga agaaaaggaa actagatgat 2940
gctttcaatt ag                                                    2952

SEQ ID NO: 51        moltype = DNA  length = 2646
FEATURE              Location/Qualifiers
source               1..2646
                     mol_type = genomic DNA
                     organism = Physcomitrella patens
SEQUENCE: 51
atggcttcca gcacccttgat acagaatcgc tcttgtggcg ttacgtcaag catgtcttcc 60
tttcagattt ttcgagggca acctctacgt tttccaggca ctagaactcc tgctgcagtt 120
caatgcctaa agaagcgtcg atgtttgcga cctactgaat cagtcctcga gagctctcct 180
ggtagcggat cttacaggat tgtaactgga ccctccggca tcaatccttc ttcaaacggc 240
cacttgcaag aggggtccct tactcacaga cttccgatac ccatggaaaa atccattgat 300
aacttccagt ctactttgta cgtatcgac atatggtcag aaaccttgca aagaacggaa 360
tgtttgttgc aggtgactga gaatgtacag atgaacgagt ggattgagga aatcagaatg 420
tacttccgaa atatgacact gggggaaata tccatgtctc catacgacac agcttggta 480
gcgcgagtgc cagcgctgga tggctcacat ggccctcagt tccatcggtc tttgcagtgg 540
attattgata atcagctccc ggatggcgat tggggtgaac cgtctctttt ccttggatac 600
gatcgcgttt gcaacactct cgcctgtgta attgccctga aaacttgggg tgttggggct 660
cagaacgtag agcgtggaat ccagtttctg caatctaaca tctacaaaat ggaggaagat 720
gacgccaatc atatgccgat tggatttgag attgtcttcc cagcgatgat ggaagatgcc 780
aaggcactgg gactggattt accatacgat gccactatct tgcaacaaat ctcggctgaa 840
agagagaaga aaatgaaaaa gattcctatg gcgatggtgt acaagtaccc cactactttg 900
ctgcattctc tggaaggcct gcaccggaa gtggactgga acaagctcct ccagctacag 960
tccgagaatg gctcctttct gtattcaccc gcatccactg catgcgcact tatgtacaca 1020
aaagatgtga agtgcttcga ctacttgaac cagctcctca tcaagttcga ccacgcttgt 1080
ccaaacgtgt accccgttga tctcttcgag cgtttgtgta tggtagaccg cctacaaagg 1140
ctggaatat cccgctactt cgagcgagaa atcagagact gtctacaata tgtataccga 1200
tactggaagg attgtggtat tggctgggca agcaattcgt ccgtcaggga cgtggacgac 1260
acggccatgg ccttccgcct tctccgcaca cacggattcg acgtcaagga ggactgcttc 1320
agacagtttt tcaaagatgg tgagttcttc tgcttccgcg gccagtccag ccaagccgtc 1380
acgggaatgt tcaacctcag cagagcatcg caaacgctct tcccagggga atcactccta 1440
aaaaaggcca gaacctttc cagaaacttt ttgagaacca agcatgaaaa caatgaatgc 1500
ttcgacaagt ggataatcac gaaggatcta gcgggcgagg tggaatacaa tctcacattc 1560
ccctgtatg ctagccttcc tcgtcttgag catcgcacct acttgacca atatgggatt 1620
gatgatatct ggattggcaa gtcgctctac aaaatgccgg ccgtcaccaa cgaagtgttt 1680
ctcaaattgg ccaaagccga cttcaacatg tgccaagctc ttcacaagaa ggaactcgag 1740
caggtcatca aatggaatgc cagctgccaa tttagagacc tcgagtttgc tagacagaaa 1800
tccgtggagt gctacttcgc aggcgctgca accatgtttg agcccgaaat ggtgcaggcg 1860
aggctcgttt gggcacgctg ttgctgctc accaccgttc tagacgatta cttcgatcac 1920
ggtacacctg tggaagagct tcgggttttt gtgcaggccg taaggacttg aatcccgag 1980
ctcatcaacg gactacctga gcaagccaag atttctcttta tgggactgta caagactgtg 2040
aacactatcg ccgaggaggc attcatggca cagaaacgag acgtacatca tcatctcaag 2100
cattactggg acaaattgat cacttcagct ttgaaagaag ccgaatgggc agagtccggc 2160
tacgtcccca ccttcgacga gtatatgaa gtcgctgaaa tctccgtcgc actagagcc 2220
attgtatgta gcactctctt cttcgccggc cataggctcg atgaggatgt gcttgacagt 2280
tatgactacc atcttgtcat gcatctcgtc aaccgcgtag gtcgcatcct caacgacatc 2340
caaggaatga gagggaagc cagccaaggg aagatatcga gcgtgcagat ctacatggag 2400
gagcatccaa gtgtgccttc agaggccatg gccatcgctc atctgcagga attggtcgac 2460
aactcatcga acagctgac atacgaagtg ctgcagtcca ctgcagttcc gaagtcctgt 2520
aagagaatcc atttaaacat ggcgaagatc atgcacgctt tctacaagga cactgatggg 2580
ttttcgtcac tgacagccat gacagggttt gtgaagaagg tgctcttcga gccagtacct 2640
gaatag                                                           2646

SEQ ID NO: 52        moltype = DNA  length = 1542
```

| FEATURE | Location/Qualifiers |
|---|---|
| misc_feature | 1..1542 |
| | note = Description of Artificial Sequence: Synthetic polynucleotide |
| source | 1..1542 |
| | mol_type = other DNA |
| | organism = synthetic construct |

SEQUENCE: 52

```
atggatgctg tgacgggttt gttaactgtc ccagcaaccg ctataactat tggtggaact   60
gctgtagcat tggcggtagc gctaatcttt tggtacctga aatcctacac atcagctaga  120
agatcccaat caaatcatct tccaagagtg cctgaagtcc caggtgttcc attgttagga  180
aatctgttac aattgaagga gaaaaagcca tacatgactt ttacgagatg ggcagcgaca  240
tatggaccta tctatagtat caaaactggg gctacaagta tggttgtggt atcatctaat  300
gagatagcca aggaggcatt ggtgaccaga ttccaatcca tatctacaag gaacttatct  360
aaagccctga agtacttac agcagataag acaatggtcg caatgtcaga ttatgatgat  420
tatcataaaa cagttaagag acacatactg accgccgtct tgggtcctaa tgcacagaaa  480
aagcatagaa ttcacagaga tatcatgatg gataacatat ctactcaact tcatgaattc  540
gtgaaaaaca acccagaaca ggaagaggta gaccttagaa aaatctttca atctgagtta  600
ttcggcttag ctatgagaca agccttagga aaggatgttg aaagtttgta cgttgaagac  660
ctgaaaatca ctatgaatag agacgaaatc tttcaagtcc ttgttgttga tccaatgatg  720
ggagcaatca atgttgattg gagagacttc tttccatacc taagtgggt cccaaacaaa  780
aagttcgaaa atactattca acaaatgtat atcagaagga agcgttat gaaatcttta  840
atcaaagagc acaaaaagag aatagcgtca ggcgaaaagc taaatagtta tatcgattac  900
cttttatctg aagctcaaac tttaaccgat cagcaactat tgatgtcctt gtgggaacca  960
atcattgaat cttcagatac aacaatggtc acaacagaat gggcaatgta cgaattagct 1020
aaaaaaccta aattgcaaga taggttgtac agagacatta agtccgtctg tggatctgaa 1080
aagataaccg aagagcatct atcacagctg ccttacatta cagctatttt ccacgaaaca 1140
ctgagaagac actcaccagt tcctatcatt cctctaagac atgtacatga agatacccgtt 1200
ctaggcggct accatgttcc tgctggcaca gaacttgccg ttaacatcta cggttgcaac 1260
atggacaaaa acgtttggga aaatccagag gaatggaacc cagaaagatt catgaaagag 1320
aatgagacaa ttgatttca aaagacgatg gccttcggtg gtggtaagag agtttgtgct 1380
ggttccttgc aagccctttt aactgcatct attgggattg ggagaatggt tcaagagttc 1440
gaatggaaac tgaaggatat gactcaagag gaagtgaaca cgataggcct aactacacaa 1500
atgttaagac cattgagagc tattatcaaa cctaggatct aa                    1542
```

| SEQ ID NO: 53 | moltype = DNA length = 1530 |
|---|---|
| FEATURE | Location/Qualifiers |
| misc_feature | 1..1530 |
| | note = Description of Artificial Sequence: Synthetic polynucleotide |
| source | 1..1530 |
| | mol_type = other DNA |
| | organism = synthetic construct |

SEQUENCE: 53

```
atggcatttt tctctatgat ttcaattttg ttgggatttg ttatttcttc tttcatcttc   60
atcttttttct tcaaaaagtt acttagtttt agtaggaaaa acatgtcaga agtttctact  120
tgccaagtg ttccagtagt gcctggtttt ccagttgttg ggaatttgtt gcaactaaag  180
gagaaaaagc ctcataaaac tttcactaga tggtcagaga tatatggacc tatctactct  240
ataaagatgg gttcttcatc tcttattgta ttgaacagta cagaaactgc taaggaagca  300
atggtcacta gattttcatc aatatctacc agaaaattgt caaacgccct aacagttcta  360
acctgcgata agtctatggt cgccacttct gattatgatg acttccacaa attagttaga  420
agatgtttgc taaatggact tcttggtgct aatgctcaaa agagaaaaag cactacaga  480
gatgctttga ttgaaaatgt gagttccaag ctacatgcac acgctagaga tcatccacaa  540
gagccagtta actttagagc aattttcgaa cacgaattgt ttggtgtagc attaaagcaa  600
gccttcggta aagacgtaga atccatatac gtcaaggagt taggcgtaac attatcaaaa  660
gatgaaatct ttaaggtgct tgtacatgat atgatggagg gtgcaattga tgtagattga  720
agagatttct tcccatattt gaatggatc cctaataagt cttttgaagc taggatacaa  780
caaaagcaca agaagagact agctgttatg aacgcactta caggacag ttgaagcaa  840
aatgggtctg atcagatga tgattgttac cttaacttct taatgtctga ggctaaaaca  900
ttgactaagg aacagatcgc aatccttgtc tgggaaacaa tcattgaaac agcagatact  960
accttagtca caactgaatg ggccatatac gagctagcca acatccatc tgtgcaagat 1020
aggttgtgta aggagatcca aacgtgtgt ggtggagaga aattcaagga agagcagttg 1080
tcacaagttc cttaccttaa cggcgttttc catgaaacct tgagaaaata ctcacctgca 1140
ccattagttc ctattagata cgcccacgaa gatacacaaa tcggtggcta ccatgttcca 1200
gctgggtccg aaattgctat aaacatctac gggtgcaaca tggacaaaaa gagatgggaa 1260
agaccagaag attggtggcc agaaagattc ttagatgatg caaatgatga acatctgat 1320
ttgcataaaa caatggcttt cggagctggc aaaagagtgt gtgccggtgc tctacaagcc 1380
tccctaatgg ctggtatcgc tattggtaga ttggtccaag agttcgaatg gaaacttaga 1440
gatggtgaag aggaaaatgt cgatacttat gggttaacat ctcaaaagtt atacccacta 1500
atggcaatca tcaatcctag aagatcctaa                                   1530
```

| SEQ ID NO: 54 | moltype = DNA length = 1578 |
|---|---|
| FEATURE | Location/Qualifiers |
| misc_feature | 1..1578 |
| | note = Description of Artificial Sequence: Synthetic polynucleotide |
| source | 1..1578 |
| | mol_type = other DNA |
| | organism = synthetic construct |

```
SEQUENCE: 54
atgagtaagt ctaatagtat gaattctaca tcacacgaaa ccctttttca acaattggtc    60
ttgggtttgg accgtatgcc attgatggat gttcactggt tgatctacgt tgctttcggc   120
gcatggttat gttcttatgt gatacatgtt ttatcatctt cctctacagt aaaagtgcca   180
gttgttggat acaggtctgt attcgaacct acatggttgc ttagacttag attcgtctgg   240
gaaggtggct ctatcatagg tcaagggtac aataagttta aagactctat tttccaagtt   300
aggaaattgg gaactgatat tgtcattata ccacctaact atattgatga agtgagaaaa   360
ttgtcacagg acaagactag atcagttgaa ccttttcatta atgattttgc aggtcaatac   420
acaagaggca tggttttctt gcaatctgac ttacaaaacc gtgttataca acaaagacta   480
actccaaaat tggtttcctt gaccaaggtc atgaaggaag agttggatta tgctttaaca   540
aaagagatgc ctgatatgaa aaatgacgaa tgggtagaag tagatatcag tagtataatg   600
gtgagattga tttccaggat ctccgccaga gtctttctag ggcctgaaca ctgtcgtaac   660
caggaatggt tgactactac agcagaatat tcagaatcac ttttcattac agggtttatc   720
ttaagagttg tacctcatat cttaagacca ttcatcgccc tctcattacc ttcatacagg   780
actctactta gaaacgtttc aagtggtaga agagtcatcg gtgacatcat aagatctcag   840
caaggggatg gtaacgaaga tatactttcc tggatgagaa atgctgccac aggagaggaa   900
aagcaaatcg ataacattgc tcagagaatg ttaattcttt ctttagcatc aatccacact   960
actgcgatga ccatgacaca tgccatgtac gatctatgtg cttgccctga gtacattgaa  1020
ccattaagag atgaagttaa atctgttgtt ggggcttctg gctgggacaa gacagccgtta 1080
aacagatttc ataagttgga ctccttccta aaagagtcac aaagattcaa cccagtattc  1140
ttattgacat tcaatagaat ctaccatcaa tctatgacct tatcagatgg cactaacatt  1200
ccatctggaa cacgttattgc tgttccatca cacgcaatgt tgcaagatct tgcacatgtc 1260
ccaggtccaa ccccacctac tgaatttgat ggattcagat atagtaagat acgttctgat  1320
agtaactacg cacaaaagta cctattctcc atgaccgatt cttcaaacat ggctttcgga  1380
tacggcaagt atgcttgtcc aggtagattt tacgcgtcta tgagatgaa actaacatta   1440
gccattttgt tgctacaatt tgagttcaaa ctaccagatg gtaaaggtcg tcctagaaat   1500
atcactatcg attctgatat gattccagac ccaagagcta gactttgcgt cagaaaaaga  1560
tcacttagag atgaatga                                                 1578

SEQ ID NO: 55           moltype = DNA  length = 1500
FEATURE                 Location/Qualifiers
misc_feature            1..1500
                        note = Description of Artificial Sequence: Synthetic
                        polynucleotide
source                  1..1500
                        mol_type = other DNA
                        organism = synthetic construct
SEQUENCE: 55
atggaagatc ctactgtctt atatgcttgt cttgccattg cagttgcaac tttcgttgtt    60
agatggtaca gagatccatt gagatccatc ccaacagttg gtggttccga tttgcctatt   120
ctatcttaca tcgcgcacct aagatggaca agacgtggca gagagatact tcaagaggga   180
tatgatggct acagaggatc tacattcaaa atcgcgatgt tagaccgttg gatcgtgatc   240
gcaaatggtc ctaaactagc tgatgaagtc agacgtgaag ttaaactt                300
atggacggat taggagcatt cgtccaaact aagtacacct taggtgaagc tattcataac   360
gatccatacc atgtcgatat cataagagaa aaactaacaa gaggccttcc agccgtgctt   420
cctgatgtca ttgaagagtt gacacttgcg gttagacagt acattccaac agaaggtgat   480
gaatgggtgt ccgtaaactg ttcaaaggcc gcaagaata ttgttgctag agcttctaat   540
agagtctttg taggttttgcc tgcttgcaga accaaggtt acttagattt ggcaatagac   600
tttacattgt ctgttgtcaa ggatagagcc atcatcaata tgtttccaga attgttgaag   660
ccaatagttg gcagagttgt aggtaacgcc accagaaatg ttcgtagagc tgttcctttt   720
gttgctccat tggtggaaga aagacgtaga ctttatgaag agtacggtga agactgttct   780
gaaaaaccta atgatatgtt acagtgggata atggatgaag ctgcatccag agtatagttca  840
gtgaaggcaa tcgcagagag attgttaatg gtgaacttcg cggctattca tacctcatca   900
aacactatca ctcatgcttt gtaccacctt gccgaaatgc tgaaactttt gcaaccactt   960
agagaagaga tcgaaccatt agtcaaagag gagggctgca ccaaggctgc tatgggaaaa  1020
atgtggtggt tagattcatt tctaagagaa tctcaaagat acaatggcat taacatcgta  1080
tcttttaacta gaatggctga caaagatatt acattgagtg atggcacatt tttgccaaaa  1140
ggtactctag tggccgttcc agcgtattct actcatagag atgatgctgt ctacgctgat  1200
gccttagtat tcgatccttt cagattctca cgtatgagag cgagagaagg tgaaggtaca  1260
aagcaccagt tcgttaatac ttcagtcgag tacgttccat ttggtcacgg aaagcatgct  1320
tgtccaggaa gattcttcgc cgcaaacgaa ttgaaagcaa tgttggctta cattgttcta  1380
aactatgatg taaagttgcc tggtgacggt aaacgtccat tgaacatgta ttggggtcca  1440
acagttttgc ctgcaccagc aggccaagta ttgttcaaga agacaagt tagtctataa   1500

SEQ ID NO: 56           moltype = DNA  length = 1542
FEATURE                 Location/Qualifiers
source                  1..1542
                        mol_type = genomic DNA
                        organism = Stevia rebaudiana
SEQUENCE: 56
atggatgccg tcaccggttt gctgacagtt ccggcaaccg caataaccat cggcggtacg    60
gccgtcgcac tcgccgtcgc tctgatattc tggtacctca aaagctacac atctgcacgc   120
aggagccaat caaaccatct ccctcgggtt cccgaggtac ctggtgtgcc attattgggg   180
aatttattgc agttgaagga gaagaaacct tacatgagtt ttacaagatg ggcggcaact   240
tatggtccga tttattcgat taaaaccgga gcaacttcta tggtggtcgt cagttcaaat   300
gaaattgcaa aggaggcatt ggttaccaga tttcaatcta tctcaaccag aaacctatca   360
aaggcattaa aggttctcac agcagataaa accatggtgg cgatgagtga ttatgatgat   420
tatcataaga ctgtcaaacg ccatactg accgctgttt tgggaccaaa tgctcagaag   480
aaacaccgca tccataggga catcatgatg gataatatat caacccaact tcatgaattt   540
```

```
gttaaaaata atcctgaaca agaggaagtg gatctaagga aaatattcca atccgaactt      600
tttggattag ctatgagaca agcattggga aaggatgtgg agagcttata tgttgaggat      660
cttaaaatca ccatgaaccg agacgagata tttcaggtat tggttgttga cccgatgatg      720
ggtgcaattg acgtcgactg gagagatttc ttcccgtatc taaagtgggt cccgaataaa      780
aagtttgaaa acacgatcca acaaatgtat atccggaaga agctgtgat gaagtctctt      840
attaaagaac ataaaaaacg tattgcatcc ggagagaaat taaacagcta cattgattac      900
ttgctatcgg aagcacaaac gttaaccgat caacaactac ttatgtctct atgggaacct      960
attattgaat catcagacac cactatggtt acaactgaat gggctatgta tgaacttgca     1020
aaaaaccca aacttcagga tcgtttgtat cgggatatca aaagtgtttg cgggtcagag     1080
aagattacag aagaacactt gtctcaactg ccatacataa ctgccatttt tcatgaaacc     1140
ttgagaaggc atagtccagt tcctataatt ccattaagac acgtgcatga agacacagtg     1200
ttaggagggt accatgtgcc agctggaacc gagctagcgg taaacattta tggatgtaac     1260
atggataaga atgtgtggga gaatcctgaa gaatggaatc cagagagatt catgaaggaa     1320
aatgaaacga tagatttcca gaaaacaatg gcgtttgaa gtggaaagcg cgtatgtgct     1380
ggttcgcttc aagcattgtt gactgcttcc attggaattg gaagaatggt gcaaagagtt     1440
gagtggaaac tgaaagayat gacccaagaa gaagttaata cgattgggct tacgacccag     1500
atgcttcgtc cactgcgggc cataataaag cccaggatat ga                        1542

SEQ ID NO: 57           moltype = DNA   length = 1530
FEATURE                 Location/Qualifiers
source                  1..1530
                        mol_type = genomic DNA
                        organism = Arabidopsis thaliana
SEQUENCE: 57
atggccttct tctccatgat ctccattctc cttggctttg ttatctcctc cttcatcttc       60
atcttcttct tcaagaaact tctctccttc tccagaaaga acatgtctga agtctccact      120
ctcccctctg ttccagtggg accagggttt cctgttattg gaacttgct gcaactaaaa      180
gagaagaaac ctcacaagac tttcactaga tggtcagaga tttatggtcc tatttactct      240
ataaagatgg gttcttcttc tcttattgtc ctcaattcta ctgagactgc caaagaggcc      300
atggtgacgc ggttttcgtc tatctcaacg aggaagttgt caaatgcgtt gacagtcctt      360
acttgtgaca aatctatggt tgctactagt gattatgatg atttccacaa gttggtgaaa      420
cggtgtctct tgaacggtct tttgggtgct aatgcacaga aacgaaaaag acattacaga      480
gatgcactca ttgaaaatgt gtcttccaag ttgcatgccc atgctaggga ccatccacaa      540
gaacctgtaa acttcagagc tatatttgag catgagcttt tcggtgtagc attgaagcaa      600
gcttttggga agatgtggaa atccatttat gttaaagaac tcggtgtgac tttgtcgaaa      660
gacgagatct tcaaggtttt agtacatgac atgatggaag gtgcaattga tgttgattgg      720
agagacttct tcccatactt gaaatggatt ccaaataaaa gttttgaagc aagaatccag      780
caaaagcata aacgtagact cgcggtgatg aatgctctga ttcaagatcg actgaagcag      840
aatggttcag aatcggatga tgattgctat ctcaacttct tcatgtcgga agcgaaaaca      900
ctaaccaagg agcaaattgc tatcttggtt tgggagacga ttatcgagac agctgacact      960
actttggtta caactgaatg ggccatctat gagctcgcta agcatccaag tgtccaagat     1020
cgtctgtgta aagaaatcca aaatgtctgc ggaggagaaa agttcaaaga agagcaattg     1080
tctcaagttc cttatctcaa tggagtattc catgaaacgc ttaggaaata cagtcctgct     1140
cctctagtcc ccattcgcta tgcccacgaa gatacgcaaa tcggaggcta tcatgtccct     1200
gcaggaagtg agattgcaat aaacatctat ggatgcaaca tggataagaa gcgttgggag     1260
agaccagagg actggtggcc ggagcggttt cttgatgatg gcaaatacga aacgtcggat     1320
cttcacaaga caatggcgtt tggagcggga aagaggggtt tgctggtgc tcttcaagca     1380
tctctcatgg caggcattgc cattgggagg ttagtgcaag aattcgagtg gaagcttaga     1440
gacggtgaag aagagaatgt ggatacatat ggcttgacct ctcagaagct ttatcctctt     1500
atggctatta tcaatccaag gcgttcttaa                                      1530

SEQ ID NO: 58           moltype = DNA   length = 1578
FEATURE                 Location/Qualifiers
source                  1..1578
                        mol_type = genomic DNA
                        organism = Gibberella fujikoroi
SEQUENCE: 58
atgagtaagt ccaacagcat gaacagtacc agccatgaaa cgttattcca gcagctcgtc       60
ttaggtcttg acagaatgcc gctaatggac gttcactggc tgatctacgt ggccttttggc     120
gcttggttat gctcttatgt catccatgtc ctatcgtcct cttctacgat caaagtgccc      180
gtcgtaggct accgcagcgt ctttgagcct acatggcttc tccgtttgcg cttttgtttgg     240
gaagggggat ctatcatcgg ccaaggctac aacaaattta aagactctat cttccaggtg      300
cgaaagcttg gtaccgatat cgtcatcatc ccgccaaact acatcgatga ggtcagaaag      360
ctgtcccaag acaagactcg ctcggtcgag cccttcatca atgactttgc gggacagtta      420
acacggggca tggtctttct gcaaagtgat ttgcagaacc gtgtgattca gcagcggttg      480
acgccaaaac tcgtatcgtt gacaaagta atgaaggagg agcttgacta tgccttgacc      540
aaagagatgc ctgacatgaa gaatgatgaa tgggttgaag tcgacatttc ttccatcatg      600
gtcaggctca tatcacgcat ctcagccaga gtgtttctcg gtccagagca ctgccgcaac      660
caagaatggt tgacgaccac tgtcagagtac agcgagagc tgttcataac tggctttatt      720
ctccgcgttg tccccatat tctaagacca ttcatagccc cgctgctacc ctcctacaga      780
acactacttc gcaacgtctc gtcaggtcga agagttattg gagacatcat tcgctcccag      840
caaggtgatg gcaacgagga catcctgtca tggatgaggg atgctgcgac agggggaagaa     900
aagcaaattg acaacattgc ccagcggatg cttatcctga gtctcgcgtc tattcacact      960
acggcaatga tgacgca tgctatgtat gacttatgtg cttgccctga gtacatagag     1020
cctcttagag atgaggtcaa aagtgtcgtt ggcgctagtg gttgggacaa gacggcgttg     1080
aatcgattcc acaaactcga cagctttctc aaagagtcac aacgcttcaa ccccgtgttc     1140
ctcttaacgt tcaatcgcat ttatcaccaa tccatgacac tctcagatgg caccaacatc     1200
ccatcaggca ctcgcatcgc ggttccctct cacgcgatgc ttcaggactc agcgcatgtc     1260
ccaggcccga cgccaccaac cgagtttgat ggatttagat actcaaagat tcgctcagac     1320
```

```
tcaaactatg cacagaaata tctcttctcc atgactgatt ctagtaacat ggcgtttggg   1380
tatgggaaat acgcctgccc agggcggttc tatgcatcta atgagatgaa gctgactttg   1440
gcgatactcc ttttacaatt tgagttcaag ttgccagatg ggaaaggaag accacgaaat   1500
atcactattg atagtgacat gatacctgat ccgagagcta ggctgtgcgt taggaagcga   1560
tcactgagag atgaatga                                                 1578
```

| SEQ ID NO: 59 | moltype = DNA  length = 1500 |
|---|---|
| FEATURE | Location/Qualifiers |
| source | 1..1500 |
| | mol_type = genomic DNA |
| | organism = Trametes versicolor |

SEQUENCE: 59
```
atggaggatc ccaccgtact ctacgcttgc ctcgccatcg ctgtcgctac tttcgttgtc    60
agatggtaca gagacccgct tcggtccatt cctacggttg ggggctctga ccttcccatc   120
ctctcataca tcggggcgct caggtggacc cgccgcggaa gagagatact gcaagaaggt   180
tatgatgggt atcgcggatc cacgttcaag atcgcgatgc tcgaccggtg gatcgtcatc   240
gccaacggcc caaagctcgc cgacgaggtg aggaggcgtc ctgacgaaga gctaaacttc   300
atggacggac tgggagcgtt cgtgcagacg aagtataccc ttggggaagc aatccacaat   360
gacccgtacc acgtggacat tattcgtgag aagctgacgc gagggcctcc ggcagtcctg   420
ccggacgtca tcgaggaact cacgctagcc gttcgccagt acatcccgac ggaaggagat   480
gaatgggtca gcgtgaactg ctccaaagca gcgcgggaca tcgtcgcccg ggcaagcaac   540
cgcgtctttg tcgggttgcc cgcttgccgc aaccaggtgt atctcgacct cgccattgac   600
ttcacccctga gcgttgtcaa agacagggcg atcatcaata tgttcccgga gttgctgaaa   660
cctatcgtcg gacgcgtggt tggaaatgcc actaggaacg tgcgccgcgc ggtcccattc   720
gtagcgccgt tggtggagga acgtcgccgc ctcatggagg agtacggtga ggattggtcg   780
gagaaaccga acgacatgct ccagtggatc atggacgaag cgacctcgcg ggactcctcc   840
gtcaaagcga tcgctgagcg tcttctcatg gtcaactttg ccgcaattca cacgtcgtcg   900
aacaccatca cccacgctct ttaccactcc gccgagatgc cggagaccct acagccgctg   960
cgggaagaga tcgagccgct cgtcaaggaa gaaggctgga cgaaggccgc catgggcaag  1020
atgtggtggc tcgacagctt cctgcgggag tcacagcgct acaatggcat caacatcgtc  1080
tccctgacgc gcatggccga caaggacata acgctcagcg acgacgcgtt cctcccgaag  1140
ggcacgctcg tcgcggtccc cgcgtactcg acgcaccgcg acgacgcggt gtacgcggac  1200
gcgctggtct tcgacccgtt ccgcttctcc cgcatgcgcg cccgcgaggg cgagggcacg  1260
aagcaccagt tcgtcaacac tctccgtgga tacgtgccct tggccacgg gaagcacgcc  1320
tgccccgggc ggttcttcgc ggccaacgag ctgaaggcga tgctcgcgta catcgtgctc  1380
aactacgacg tgaagctgcc cggcgatggc aagcgccccc tgaacatgta ctggggcccg  1440
acggtcttgc ctgctccggc tgggcaggtg ctcttccgca agaggcaggt gtcgctgtag  1500
```

| SEQ ID NO: 60 | moltype = DNA  length = 1578 |
|---|---|
| FEATURE | Location/Qualifiers |
| misc_feature | 1..1578 |
| | note = Description of Artificial Sequence: Synthetic polynucleotide |
| source | 1..1578 |
| | mol_type = other DNA |
| | organism = synthetic construct |

SEQUENCE: 60
```
atgggtttgt tcccattaga ggattcctac gcgctggtct ttgaaggact agcaataaca    60
ctggctttgt actatctact gtctttcatc tacaaaacat ctaaaaagac atgtacacct   120
cctaaagcat ctggtgaaat cattccaatt acaggaatca tattgaatct gctatctggc   180
tcaagtggtc tacctattat cttagcactt gcctctttag cagacagatg tggtcctatc   240
ttcaccatta ggctgggtat taggagagtg ctagtagtag caaattggga aatcgctaag   300
gagattttca ctacccacga tttgatagtt tctaatagac aaaatacttt agccgctaag   360
attcttggtt tcaattatgt ttcattctct ttcgctccat acggcccata ttgggtcgga   420
atcagaaaga ttattgctac aaaactaatg tcttcttcca gacttcagaa gttgcaattt   480
gtaagagttt ttgaactaga aaactctatg aaatctatca gagaatcatg gaaggagaaa   540
aaggatgaag agggaaaggt attagttgag atgaaaagt ggttctggga actgaatatg   600
aacatagtgt taaggacagt tgctggtaaa caatacactg gtacagttga tgatgccgat   660
gcaaagcgta tctccgagtt attcagagaa tggtttcact acactggcag atttgtcgtt   720
ggagacgctt ttcctttct aggttggttg gacctgggcg gatacaaaaa gacaatggaa   780
ttagttgcta gtagattgga ctcaatggtc agtaaatggt tagatgagca tcgtaaaaag   840
caagctaacg atgacaaaaa ggaggatatg gatttcatgg atatcatgat ctccatgaca   900
gaagcaaatt caccacttga aggatacggc actgatacta ttatcaagac cacatgtatg   960
actttgattg tttcaggagt tgatacaacc tcaatcgtac ttacttgggc cttatcactt  1020
ttgttaaaca acagagatac tttgaaaaag gcacaagagg aattagatat gtgcgtaggt  1080
aaaggaagac aagtcaacga gtctgatctt gttaacttga tatacttgga agcagtgctt  1140
aaagaggctt taagacttta cccagcagcg ttcttaggcg gaccaagagc attcttgaa  1200
gattgtactg ttgctggtta taagattcca aagggcacct gcttgttgat taacatgtgg  1260
aaactgcata gagatccaaa catttggagt gatccttgcg aattcaagcc agaaagattt  1320
ttgacaccta tcaaaagga tgttgatgtg atcggtatgg atttcgaatt gataccatttt  1380
ggtgccggca aagatattg tccaggtact agattggctt tacagatgtt gcatatcgta  1440
ttagcgacat tgctgcaaaa cttcgaaatg tcaacaccaa acgatgcgcc agtcgatatg  1500
actgcttctg ttggcatgac aaatgccaaa gcatcacctt tagaagtctt gctatcacct  1560
cgtgttaaat ggtcctaa                                                1578
```

| SEQ ID NO: 61 | moltype = DNA  length = 1431 |
|---|---|
| FEATURE | Location/Qualifiers |
| misc_feature | 1..1431 |
| | note = Description of Artificial Sequence: Synthetic |

```
                        polynucleotide
source                  1..1431
                        mol_type = other DNA
                        organism = synthetic construct
SEQUENCE: 61
atgatacaag ttttaactcc aattctactc ttcctcatct tcttcgtttt ctggaaagtc    60
tacaaacatc aaaagactaa aatcaatcta ccaccaggtt ccttcggctg gccattttttg  120
ggtgaaacct tagccttact tagagcaggc tgggattctg agccagaaag attcgtaaga   180
gagcgtatca aaaagcatgg atctccactt gttttcaaga catcactatt tggagacaga   240
ttcgctgttc tttgcggtcc agctggtaat aagttttttgt tctgcaacga aaacaaatta  300
gtggcatctt ggtggccagt ccctgtaagg aagttgttcg gtaaaagttt actcacaata   360
agaggagatg aagcaaaatg gatgagaaaa atgctattgt cttacttggg tccagatgca   420
tttgccacac attatgccgt tactatggat gttgtaacac gtagacatat tgatgtccat   480
tggagggca aggaggaagt taatgtattt caaacagtta agttgtacgc attcgaatta    540
gcttgtagat tattcatgaa cctagatgac ccaaaccaca tcgcgaaact cggtagtctt   600
ttcaacattt tcctcaaagg gatcatcgag cttcctatag acgttcctgg aactagattt   660
tactccagta aaaaggccgc agctgccatt agaattgaat tgaaaaagct cattaaagct   720
agaaaactcg aattgaagga gggtaaggcg tcttcttcac aggacttgct ttctcatcta   780
ttaacatcac ctgatgagaa tgggatgttc ttgacagaag aggaaatagt cgataacatt   840
ctactttttgt tattcgctgg tcacgatacc tctgcactat caataacact tttgatgaaa   900
accttaggtg aacacagtga tgtgtacgac aaggttttga aggaacaatt agaaatttcc   960
aaaacaaagg aggcttggga atcactaaag tgggaagata tccagaagat gaagtactca  1020
tggtcagtaa tctgtgaagt catgagattg aatcctcctg tcataggggac atacagagag   1080
gcgttggttg atatcgacta tgctggttac actatcccaa aaggatggaa gttgcattgg  1140
tcagctgttt ctactcaaag agacgaagcc aatttcgaag atgtaactag attcgatcca  1200
tccagatttg aaggggcagg ccctactcca ttcacatttg tgcctttcgg tggaggtcct  1260
agaatgtgtt taggcaaaga gtttgccagg ttagaagtgt tagcatttct ccacaacatt  1320
gttaccaact ttaagtggga tcttctaatc cctgatgaga agatcgaata tgatccaatg  1380
gctactccag ctaagggctt gccaattaga cttcatccac accaagtcta a             1431

SEQ ID NO: 62           moltype = DNA  length = 1578
FEATURE                 Location/Qualifiers
misc_feature            1..1578
                        note = Description of Artificial Sequence: Synthetic
                        polynucleotide
source                  1..1578
                        mol_type = other DNA
                        organism = synthetic construct
SEQUENCE: 62
atggagtctt tagtggttca tacagtaaat gctatctggt gtattgtaat cgtcgggatt    60
ttctcagttg gttatcacgt ttacggtaga gctgtggtcg aacaatggag aatgagaaga   120
tcactgaagc tacaaggtgt taaaggccca ccaccatcca tcttcaatgg taacgtctca   180
gaaatgcaac gtatccaatc cgaagctaaa cactgctctg gcgataacat tatctcacat   240
gattattctt cttcattatt cccacacttc gatcactgga gaaaacagta cggcagaatc   300
tacacatact ctactggatt aaagcaacac ttgtacatca atcatccaga aatggtgaag   360
gagctatctc agactaacac attgaacttg ggtagaatca cccatataac caaaagattg   420
aatcctatct taggtaacgg aatcataacc tctaatgatc ccatcagcgt                480
agaattatcg cctacgagtt tactcatgat aagatcaagg gtatggttgg tttgatggtt  540
gagtctgcta tgcctatgtt gaataagtgg gaggagatgg taaagagagg cggagaaatg  600
ggatgcgaca taagagttga tgaggacttg aaagatgttt cagcagatgt gattgcaaaa  660
gcctgtttcg gatcctcatt ttctaaaggt aaggctattt tctctatgat aagagatttg  720
cttacagcta tcacaaagag aagtgttcta ttcagattca acggattcac tgatatggtc  780
tttggggta aaaagcatgg tgacgttgat atagacgctt tagaaatgga attgaaatca   840
tccatttggg aaactgtcaa ggaacgtgaa atagaatgta aagatactca caaaaggat   900
ctgatgcaat tgattttgga aggggcaatg cgttcatgtg acggtaacct ttgggataaa  960
tcagcatata gaagatttgt tgtagataat tgtaaatcta tctacttcgc agggcatgat 1020
agtacagctg tctcagtgtc atggtgttt atgttactgg ccctaaaccc atcatggcaa  1080
gttaagatcc gtgatgaaat tctgtcttct tgcaaaatg gtattccaga tgccgaaagt 1140
atcccaaacc ttaaaacagt gactatggtt attcaagaga caatgagatt ataccctcca  1200
gcaccaatcg tcgggagaga agcctctaaa gatatcgat tgggcgatct agttgttcct  1260
aaaggcgtct gtatatggac actaatacca gctttacaca gagatcctga gattgggggga  1320
ccagatgcaa acgatttcaa accagaaaga ttttctgaag aatttcaaa ggcttgtaag    1380
tatcctcaaa gttacattcc attttggtctg ggtcctagaa catgcgttgg taaaaacttt 1440
ggcatgatgg aagtaaaggt tcttgtttcc ctgattgtct ccaagttctc tttcactcta  1500
tctcctacct accaacatag tccagtcac aaactttttag tagaaccaca acatggggtg  1560
gtaattagag tggtttaa                                                 1578

SEQ ID NO: 63           moltype = DNA  length = 1590
FEATURE                 Location/Qualifiers
misc_feature            1..1590
                        note = Description of Artificial Sequence: Synthetic
                        polynucleotide
source                  1..1590
                        mol_type = other DNA
                        organism = synthetic construct
SEQUENCE: 63
atgtacttcc tactacaata cctcaacatc acaaccgttg gtgtctttgc cacattgttt    60
ctctcttatt gtttacttct ctggagaagt agagcgggta acaaaagat tgccccgaa    120
gctgccgctg catggcctat tatcggccac ctccacttac ttgcaggtgg atcccatcaa   180
```

```
ctaccacata ttacattggg taacatggca gataagtacg gtcctgtatt cacaatcaga  240
ataggcttgc atagagctgt agttgtctca tcttgggaaa tggcaaagga atgttcaaca  300
gctaatgatc aagtgtcttc ttcaagacct gaactattag cttctaagtt gttgggttat  360
aactacgcca tgtttggttt ttcaccatac ggttcatact ggagagaaat gagaaagatc  420
atctctctcg aattactatc taattccaga ttggaactat tgaaagatgt tagagcctca  480
gaagttgtca catctattaa ggaactatac aaattgtggg cggaaaagaa gaatgagtca  540
ggattggttt ctgtcgagat gaaacaatgg ttcggagatt tgactttaaa cgtgatcttg  600
agaatggtgt ctggtaaaag atacttctcc gcgagtgacg cttcagaaaa caaacaggcc  660
cagcgttgta gaagagtctt cagagaattc ttccatctct ccggcttgtt tgtggttgc   720
gatgctatac cttttcttgg atggctcgat tggggaagac acgagaagac cttgaaaaag  780
accgccatag aaatggattc catcgcccag gagtggcttg aggaacatag acgtagaaaa  840
gattctggag atgataattc tacccaagat ttcatggacg ttatgcaatc tgtgctagat  900
ggcaaaaatc taggcggata cgatgctgat acgattaaca aggctacatg cttaactctt  960
atatcaggtg gcagtgatac tactgtagtt tctttgcat ggctcttag tcttgtgtta  1020
aacaatagag atactttgaa aaaggcacag gaagagttag acatccaagt cggtaaggaa  1080
agattggtta acgagcaaga catcagtaag ttagtttact tgcaagcaat agtaaaagag  1140
acactcagac tttatccacc aggtcctttg ggtggtttga gacaattcac tgaagattgt  1200
acactaggtg gctatcacgt ttcaaaagga actagattaa tcatgaactt atccaagatt  1260
caaaaagatc cacgtatttg gtctgatcct actgaattcc aaccagagag attccttacg  1320
actcataaag atgtcgatcc acgtggtaaa cactttgaat tcattccatt cggtgcagga  1380
agacgtgcat gtcctggtat cacattcgga ttacaagtac tacatctaac attggcatct  1440
ttcttgcatg cgtttgaatt tcaacacca tcaaatgagc aggttaacat gagagaatca  1500
ttaggtctta cgaatatgaa atctaccca ttagaagttt tgatttctcc aagactatcc  1560
cttaattgct tcaaccttat gaaaatttga                                   1590

SEQ ID NO: 64          moltype = DNA  length = 1440
FEATURE                Location/Qualifiers
misc_feature           1..1440
                       note = Description of Artificial Sequence: Synthetic
                       polynucleotide
source                 1..1440
                       mol_type = other DNA
                       organism = synthetic construct
SEQUENCE: 64
atggaaccta actttactt gtcattacta ttgttgttcg tgaccttcat ttctttaagt   60
ctgtttttca tcttttacaa acaaaagtcc ccattgaatt tgccaccagg gaaaatgggt  120
tacccctatca taggtgaaag tttagaattc ctatccacag gctggaaggg acatcctgaa  180
aagttcatat ttgatagaat gcgtaagtac agtagtgagt tattcaagac ttctattgta  240
ggcgaatcca cagttgttg ctgtgggca gctagtaaca aattcctatt ctctaacgaa  300
aacaaactgg taactgcctg gtggccagat tctgttaaca aaatcttccc aacaacttca  360
ctggattcta atttgaagga ggaatctata aagatgagaa agttgctgcc acagttcttc  420
aaaccagaag cacttcaaag atacgtcggc gttatggatg taatcgcaca agacattttt  480
gtcactcact gggacaacaa aaatgagatc acagtttatc cacttgctaa aagatacact  540
ttcttgcttg cgtgtagact gttcatgtct gttgaggat aaaatcatgt ggcgaaattc  600
tcagacccat tccaactaat cgctgcaggc atcatttcac ttcctatcga tcttcctggt  660
actccattca acaaggccat aaaggcttca aatttcatta gaaagagct gataaagatt  720
atcaaacaaa gacgtgttga tctggcagag ggtacagcat ctccaaccca ggatatcttg  780
tcacatatgc tattaacatc tgatgaaaac ggtaaatcta tgaacgagtt gaacattgcc  840
gacaagattc ttggactatt gataggaggc cacgatacag cttcagtagc ttgcacattt  900
ctagtgaagt acttaggaga attaccacat atctacgata aagtctacca agagcaaatg  960
gaaattgcca agtccaaacc tgctgggaaa ttgttgaatt gggatgactt gaaaaagatg 1020
aagtattcat ggaatgtggc atgtgaggta atgagattgt caccaccttt acaaggtggt 1080
tttagagagg ctataactga ctttatgttt aacggtttct ctattccaaa agggtggaag 1140
ttatactggt ccgccaactc tacacacaaa atgcagaatt gtttcccaat gcctgagaaa 1200
ttcgatccta ccagattga aggtaatggt ccagcgcctt atacatttgt accattcggt 1260
ggaggcccta gaatgtgtcc tggaaaggaa tacgctagat tagaaatctt ggttttcatg 1320
cataatctgg tcaaacgttt taagtgggaa aaggttattc agacgaaaa gattattgtc 1380
gatccattcc caatcccagc taagatcctt ccaatccgtt tgtatcctca caagcttaa  1440

SEQ ID NO: 65          moltype = DNA  length = 1572
FEATURE                Location/Qualifiers
source                 1..1572
                       mol_type = genomic DNA
                       organism = Stevia rebaudiana
SEQUENCE: 65
atgggtctct cccttttgga agatagttac gcactcgtct ttgaaggttt agcaataact   60
actctagctc tctactactt attatccttc atctctaaaaa cctctaaaaa gacttgtact  120
ccacctaaag caagcggtga gcaccctata acaggccact taaaccttct tagtggttca  180
tccggtcttc cccatctagc cttagcatct ttggctgacc gatgtgggcc catattcacc  240
atccgacttg gcatacgtag agttttggtg gttagtaatt gggaaattgc taaggagatc  300
ttcactaccc atgatttgat tgtttcaaac cgtcccaaat acctcgctgc aaagattttg  360
ggattcaact atgtgtcctt ttcgtttgct ccatatggcc cctattgggt tggaatccgt  420
aagatcatcg ccacaaaact gatgtcaagt agcaggctcc agaagcttca gtttgtccga  480
gttttcgaac tagaaaactc catgaaaagc atacgcgatt cttgaaaga gaaaaagac  540
gaagaaggta aagtgttggt gggagatgaa aaatgttttt gggaattgaa tatgaatata  600
gttcttagaa ctgttgctgg taaacagtac actggaactg ttgatgatgc ggatgcgaag  660
aggattagtg aattgtttag agaatggttt cattacacag gaaggtttgt tgtgggagat  720
gcttttcctt ttcttgggtg gttggatttg ggtggatata agaagaccat ggaactagtg  780
gcttccagac tagattccat ggtctcaaaa tggttagacg agcatcgcaa aaagcaggct  840
```

```
aacgacgaca aaaaagagga catggatttc atggacatca tgatatcgat gactgaagcc  900
aattccccct tggagggtta tggtacggat acaataatta aaaccacttg catgactctt  960
attgtcagtg gtgtagatac aacctccatc gtgctaactt gggcactctc gttactactg 1020
aacaaccgtg acactcttaa gaaagctcaa gaagagctag acatgtgtgt gggaaaaggt 1080
cgacaagtaa acgaatcaga tctagtaaac ctaatctacc ttgaagccgt attaaaagaa 1140
gcattgcgac tatacccagc agcattcctt ggaggtccta gagcctttt agaagactgc 1200
accgtggcag ggtaccgtat cccaaaaggc acatgtctac ttattaacat gtggaaactt 1260
catcgtgatc aaacatatg gtcagaccca tgtgagttta aaccagagag gttcttaacc 1320
ccaaaccaaa aggacgtaga tgttattgga atggattttg agttaatccc atttggtgcg 1380
ggaagaaggt attgtccagg gacacgtttg gcattacaaa tgttacacat agttctggcc 1440
actctactac aaaactttga gatgtcaact ccaaatgatg cacccgttga tatgaccgcg 1500
agtgttggaa tgacaaatgc gaaggcaagt ccacttgaag ttctactttc gccacgtgtt 1560
aagtggtcat ag                                                     1572

SEQ ID NO: 66          moltype = DNA  length = 1431
FEATURE                Location/Qualifiers
source                 1..1431
                       mol_type = genomic DNA
                       organism = Stevia rebaudiana
SEQUENCE: 66
atgattcaag ttctaacacc gatccttctc ttcctcattt tcttcgtttt ctggaaggtt   60
tacaagcacc agaaaaccaa aatcaatctt ccaccgggaa gcttcggatg gccatttctg  120
ggcgaaactc tggcactcct acgtgcaggt tgggactcag agccggagag atttgttcgt  180
gaacggatca agaaacacgg aagtcctcta gtgtttaaga cgtcgttgtt tggcgaccgt  240
tttgcggtgt tgtgtggacc tgccggaaac aagttcctgt tctgcaacga gaacaagctg  300
gtggcgtcgt ggtggccggt tccggtgagg aagcttttcg gcaagtctct gctcacgatt  360
cgtggtgatg aagctaagtg gatgaggaag atgttgttat cgtatctcgg tcctgatgct  420
ttcgcaactc attatgccgt caccatggac gtcgtcaccc gtcggcatat cgacgttcat  480
tggcgaggga aggaagaggt gaacgtattc caaaccgtta agtatatgc ctttgagctt  540
gcatgtcgtt tattcatgaa cctagacgac ccaaaccaca ttgcaaaact cggttccttg  600
ttcaacattt tcttgaaagg catcattgag cttccaatcg acgtcccagg gacacgtttt  660
tatagctcca aaaagcagc agcagctatc aggattgaac taaaaaaatt gattaaagca  720
agaaaactgg aactgaaaga agggaaggca tcatcttcac aagacctctt atcacatttg  780
cttacatctc cagatgaaaa tggtatgttt ctaaccgaac aagagattgt agacaactga  840
ttgttactac tctttgcggg tcatgatacc tcggctcttt caatcacttt gctcatgaag  900
actcttggcg aacattctga tgtttatgac aaggtgttaa aagagcaact agagatatcg  960
aagacgaaag aagcatggga gtccctgaaa tgggaggaca tacaaaagat gaaatactcc 1020
tggagtgtta tatgtgaagt catgagacta aatccacctg ttataggaac ctatagagag 1080
gcccttgtgg atattgatta tgcgggttat accatcccca aaggatggaa gctgcactgg 1140
agtgctgtat cgacacaaag ggacgaggct aactttgaag acgtaacacg ttttgaccca 1200
tcacggtttt aaggcgcagg accgactcca ttcacctttg ttccgtttgg agggggcct 1260
agaatgtgtt taggaaaga atttgctcga ttggaagtac ttgcgtttct tcacaatatt 1320
gtcaccaatt tcaaatggga cctgttgata cctgatgaga aaatagaata tgatcccatg 1380
gctaccccag caagggggct tccaattcgt cttcatcccc atcaagtttg a          1431

SEQ ID NO: 67          moltype = DNA  length = 1578
FEATURE                Location/Qualifiers
source                 1..1578
                       mol_type = genomic DNA
                       organism = Arabidopsis thaliana
SEQUENCE: 67
atggagagtt tggttgttca tacggtaaat gcaatttggt gcatagttat tgtcggaatc   60
ttcagcgtag gttatcatgt gtatggaaga gcggtggtgg agcagtggag gatgcggagg  120
agtttaaagt tgcaaggcgt gaagggtcct ccaccgtcga tctttaacgg caatgtgtcg  180
gagatgcaac ggattcagtc ggaggctaaa cactgttccg gtgataacat catttctcat  240
gactattctt cttctctatt tcctcatttc gatcactggc gaaaacaata cggaaggatt  300
tacacatact caacgggtt aaagcagcac ctttacataa accacccgga aatggtgaag  360
gagcttagcc aaaccaacac acttaacctt ggtagaatca ctcacatcac caaacgcctt  420
aaccccattc tcggcaatgg catcatcacc tctaatgggc ctcattgggc ccatcaacgt  480
cgtatcattg cctatgagtt tacccacgac aaaatcaagg gaatggttgg tttaatggtt  540
gaatctgcca tgccaatgtt gaacaaatgg aagagatgg tgaaagagg aggagaaatg  600
ggttgtgaca taagagtgga cgaagacctt aaggatgtct cagctgatgt catcgctaag  660
gcttgcttg ggagctcttt tcaaaaggc aaagcaatat tctctatgat tagggatctt  720
ttaaccgcca ttactaaacg aagcgtcctc ttcagattca atggcttcac tgatatggtg  780
tttggaagta agaagcatgg tgatgtggat attgatgcgc ttgagatgga attagaatct  840
tctatatggg aaacggttaa ggagaggaa attgaatgta aggatactca caagaaggat  900
ctaatgcagt tgatactcga gggagcgatg cgaagctgcg atggtaactt gtgggacaag  960
tcagcctata gacggtttgt ggtggacaat tgcaagagca tctatttcgc cggacatgat 1020
tcaaccgcag tctcagtgtc ttggtgcctt atgctcctcg ctctcaatcc tagttggcag 1080
gttaaaattc gcgatgaaat cttgagttct tgcaagaatg cattcccga cgcagaatca 1140
attcctaatc tcaaaacggt gacaatggta atacaagaaa caatgagact atacccacca 1200
gcaccaatcg tgggaagaga agcatccaaa gacataagac ttgagacct tgtggtgcca 1260
aaaggagtgt gcatttggac actcattcct gccttacacc gagaccccga gatctgggga 1320
ccagacgcaa acgacttcaa gccagagagg tttagtgagg gaatctctaa ggcttgcaaa 1380
taccctcagt catacatccc atttggcctt ggaccaagaa catgcgtagg caaaaacttt 1440
ggtatgatga agtgaaagt gcttgtttca cttattgtct caaagttcag ttttactctt 1500
tccccgactt atcagcactc tccaagccat aaactccttg tagagcctca acatggtgtt 1560
gtcattaggg ttgtttga                                               1578
```

```
SEQ ID NO: 68            moltype = DNA   length = 1590
FEATURE                  Location/Qualifiers
source                   1..1590
                         mol_type = genomic DNA
                         organism = Vitis vinifera
SEQUENCE: 68
atgtatttcc ttctccaata cctaaacatc accacggtcg gagtctttgc cacactttc     60
cttcctact gtctattatt atggaggtct agagctggta acaaaaaaat agcacctgaa    120
gctgctgctg catggcccat aatcggtcac ctacaccgt tagctggtgg ttctcatcag    180
cttcccaca taaccttggg aaacatggcc gacaaatatg gaccggtctt cacaattcag    240
attgggttgc atcgagctgt ggtggtaagt tcttgggaga tggctaaaga atgctcgacc    300
gccaatgacc aggtttcatc ctcgcgtccc gaacttttag cctcaaaact tttgggctac    360
aactacgcca tgtttggttt ctctccatac ggttcttact ggcgtgaaat gcgcaagata    420
atcagcctag agctactctc taacagccgc ttagagctgc tgaaggacgt ccgagctca    480
gaagtggtga catccataaa agagctatac aagctctggg cagagaaaaa aaatgaatcg    540
ggccttgtct cggtggagat gaagcagtgg tttggagact tgactctgaa cgtaattctt    600
aggatggtgg cagggaagcg ttatttcagt gcttcagatg caagtgaaaa taaacaggcg    660
cagaggtgcc ggagagtgtt cagggaattc tttcatttgt cagggctctt tgtgctgggca    720
gacgctattc catttcttgg atggctcgac tggggagac atgagaaaac cctaaagaag    780
acagcaatag aaatggacag tattgctcaa gaatggttag aggagcaccg tcggaggaaa    840
gactccggtg atgataatag tacgcaagac ttcatggatg tgatgcagtc agttcttgat    900
ggcaaaaacc ttggtggtta cgacgctgat accatcaata aagccacatg cctgactcta    960
atctccggag gtagcgacac aactgttgtc tctctaacat gggcactctc tcttgtacta   1020
aacaaccgtg acaccttaaa aaaagctcaa gaagaattag acatccaagt tggtaaggaa   1080
agattagtga atgaacaaga tataagtaag ttggtctatc tccaagccat tgttaaagag   1140
acattacgtg tatatccacc aggaccactt ggaggactac gccaatttac cggaggattgc   1200
accttgggtg gataccatgt ctctaaaggc accgcttaa taatgaacct ttcgaagatc   1260
caaaaggatc caagaatttg gtcagatccg acagaattcc aaccagagag gtttctcacc   1320
acccataaag atgttgatcc tcggggaaaa cattttgagt ttataccatt tggagctggt   1380
cgaagagcat gtccaggaat aacttttggt cttcaagtat tacatttaac attggctagt   1440
ttcttacatg cgtttgaatt ttcaactcca tcaaatgaac aggtcaatat gcgcgagagc   1500
cttggactta caaatatgaa atctacccca cttgaagttc tcatttctcc acgcttatca   1560
ttgaattgtt ttaacctaat gaagatataa                                     1590

SEQ ID NO: 69            moltype = DNA   length = 1440
FEATURE                  Location/Qualifiers
source                   1..1440
                         mol_type = genomic DNA
                         organism = Medicago truncatula
SEQUENCE: 69
atggagccta atttctatct ctcccttctc cttctctttg tcactttcat atctctctct     60
cttttttca tattctacaa acagaaatct ccattaaatt tgccacctgg taaaatgggt    120
tacccaatca taggtgaaag ccttgagttc ttatcaacag gatggaaagg acatcctgaa    180
aaattcattt tcgaccgtat gcgtaaatat tcctcagaac tctttaaaac atcaatcgta    240
ggagaatcta cggtggtttg ttgcggagca gcaagtaaca agttttttgtt ttcaaacgag    300
aataaacttg tgactgcatg gtggccagat agtgtaaaca aaatcttccc tactacttct    360
cttgactcta acttgaagga agaatccatc aagtgaagaa aattgcttcc acaattcttt    420
aaacccgaag ctctcaaacg ttatgttggt gtcatggatg ttattgctca aagacatttt    480
gttactcatt gggataataa aaatgaaatc accgtctacc ccttggccaa gaggtacacc    540
ttttttgttag cttgtcggtt gttcatgagc gttgaagacg agaatcatgt agcaaaattt    600
agtgatccat ttcagttaat tgcggccgga atcatatctc taccaattga tttgccaggga    660
acaccattca acaaagctat aaaggcctca aactttataa gaaaggagtt gattaagatc    720
ataaagcaaa ggagggtaga tttgcagaaa gggacagcat caccaacaca agatatattg    780
tctcacatgt tgttgacaag tgatgaaaat ggaaagagta tgaatgaact taatattgct    840
gataagattc ttggccttt gatcggagga catgacactg ctagcgtcgc atgcacttc     900
cttgtcaaat atctccggcga gttacctcac atttatgata aagtctatca agagcaaatg    960
gaaattgcaa aatcgaaacc agcaggagaa ttgttgaatt gggatgacct gaagaaaatg   1020
aaatactctt ggaacgtagc ttgtgaagta atgagacttt cccctccact ccaaggaggt   1080
ttcagggaag ccatcactga cttttatgttc aatgattct caattcctaa gggatggaag   1140
ctttattgga gtgcaaattc aacacataag aacgcagaat gttttcccat gccagagaaa   1200
tttgacccaa caagatttga aggaaatgga ccagctcctt atactttgt tcccttttggt   1260
ggaggaccaa ggatgtgtcc tggaaaagag tatgcaagat tagaaatact tgttttcatg   1320
cacaatttgg tgaaaaggtt taagtgggaa aaggtgattc cagatgagaa gattattgtt   1380
gatccattcc ccatccctgc aaaggatctt ccaattcgcc tttatccaca caagcttaa    1440

SEQ ID NO: 70            moltype = DNA   length = 2133
FEATURE                  Location/Qualifiers
misc_feature             1..2133
                         note = Description of Artificial Sequence: Synthetic
                         polynucleotide
source                   1..2133
                         mol_type = other DNA
                         organism = synthetic construct
SEQUENCE: 70
atgcaatcag attcagtcaa agtctctcca tttgatttgg tttccgctgc tatgaatggc     60
aaggcaatgg aaaagttgaa cgctagtgaa tctgaagatc caacaacatt gcctgcacta    120
aagatgctat tgaaaatag agaattgttg acactgttca caacttcctt cgcagttctt    180
attgggtgtc ttgtatttct aatgtggaga cgttcatcct ctaaaaagct ggtacaagat    240
ccagttccac aagttatcgt tgtaaagaag aaagagaagg agtcagaggt tgatgacggg    300
```

```
aaaaagaaag tttctatttt ctacggcaca caaacaggaa ctgccgaagg ttttgctaaa    360
gcattagtcg aggaagcaaa agtgagatat gaaaagacct ctttcaaggt tatcgatcta    420
gatgactacg ctgcagatga tgatgaatat gaggaaaaac tgaaaaagga atccttagcc    480
ttcttcttct tggccacata cggtgatggt gaacctactg ataatgctgc taacttctac    540
aagtggttca cagaaggcga cgataaaggt gaatggctga aaaagttaca atacggagta    600
tttggtttag gtaacagaca atatgaacat ttcaacaaga tcgctattgt agttgatgat    660
aaacttactg aaatgggagc caaaagatta gtaccagtag gattagggga tgatgatcag    720
tgtatagaag atgacttcac cgcctggaag gaattggtat ggccagaatt ggatcaactt    780
ttaagggacg aagatgatac ttctgtgact accccataca ctgcagccgt attggagtac    840
agagtggttt accatgataa accagcagac tcatatgctg aagatcaaac ccatacaaac    900
ggtcatgttg ttcatgatgc acagcatcct tcaagatcta atgtggcttt caaaaaggaa    960
ctacacacct ctcaatcaga taggtcttgt actcacttag aattcgatat ttctcacaca   1020
ggactgtctt acgaaactgg cgatcacgtt ggcgtttatt ccgaaacttg tccgaagtt    1080
gtcgatgaag cactaaaact gttagggtta tcaccagaca catacttctc agtccatgct   1140
gataaggagg atgggacacc tatcggtggt gcttcactac caccaccttt tcctccttgc   1200
acattgagag acgctctaac cagatacgca gatgtcttat cctcacctaa aaaggtagct   1260
ttgctggcat tggctgctca tgctagtgat cctagtgaag ccgataggtt aaagttcctg   1320
gcttcaccag ccggaaaaga tgaatatgca caatggatcg tgccaaacca acgttctttg   1380
ctagaagtga tgcaaagttt tccatctgcc aagcctccat taggtgtgtt cttcgcagca   1440
gtagctccac gtttacaacc aagatactac tctatcagtt catctcctaa gatgtctcct   1500
aacagaatac atgttacatg tgctttggtg tacgagacta ctccagcagg cagaattcac   1560
agaggattgt gttcaacctg gatgaaaaat gctgtccctt taacagagtc acctgattgc   1620
tctcaagcat ccattttcgt tagaacatca aatttcagac ttccagtgga tccaaaagtt   1680
ccagtcatta tgataggacc aggcactggt cttgccccat tcaggggctt tcttcaagag   1740
agattggcct tgaaggaatc tggtacagaa ttgggttctt ctatcttttt ctttggttgc   1800
cgtaataaga aagttgactt tatctacgag gacgagctta acatttttgt tgagacagga   1860
gcattgtcag aattgatcgt cgcattttca agagaaggga ctgccaaaga gtacgttcag   1920
cacaagatga gtcaaaaagc ctccgatata tggaaacttc taagtgaagg tgcctatctt   1980
tatgtctgtg gcgatgcaaa gggcatggcc aaggatgtcc atagaactct gcatacaatt   2040
gttcaggaac aagggagtct ggattcttcc aaggctgaat tgtacgtcaa aaacttacag   2100
atgtctggaa gatacttaag agatgtttgg taa                                2133

SEQ ID NO: 71           moltype = DNA  length = 2079
FEATURE                 Location/Qualifiers
misc_feature            1..2079
                        note = Description of Artificial Sequence: Synthetic
                        polynucleotide
source                  1..2079
                        mol_type = other DNA
                        organism = synthetic construct
SEQUENCE: 71
atgacttctg cactttatgc ctccgatctt ttcaaacaat tgaaaagtat catgggaacg     60
gattctttgt ccgatgatgt tgtattagtt attgctacaa cttctctctg actgtttgct   120
ggtttcgttg tctattgtg gaaaaagacc acggcagatc gttccggcga gctaaagcca    180
ctaatgatcc ctaagtctct gatggcgaaa gatgaggatg atgacttaga tctaggttct    240
ggaaaaacga gagtctctat cttcttcggc acacaaaccg gaacagccga aggattcgct    300
aaagcacttt cagaagagat caaagcaaga tacgaaaagg cggctgtaaa agtaatcgat    360
ttggatgatt acgctgccga tgatgaccaa tatgaggaaa agttgaaaaa ggaaacattg    420
gcttctttt gtgtagccac gtatggtgat ggtgaaccaa ccgataacgc cgcaagattc    480
tacaagtggt ttactgaaga gaacgaaaga gatatcaagt gcagcaact tgcttacggc    540
gttttgcct taggtaacag acaatacgag cactttaaca agataggtat tgtcttagat    600
gaagagttat gcaaaagggg tgcgaagaga ttgattgaag tcggtttagg agatgatgat    660
caatctatcg aggatgactt taatgcatgg aaggaatctt tgtggtctga attagataag    720
ttacttaagg acgaagatga taaatccgtt gccactccat acacagccgt cattccagaa    780
tatagagtag ttactcatga tccaagattc acaacacaga aatcaatgga aagtaatgtg    840
gctaatggta atactaccat cgatattcat catccatgta gagtagacgt tgcagttcaa    900
aaggaattgc acactcatga atcagacaga tcttgcatac atcttgaatt tgatatatca    960
cgtactggta tcacttacga aacaggtgat cacgtgggtg tctacgctga aaaccatgtt   1020
gaaattgtag aggaagctgg aaagttgttg ggccatagtt tagatcttgt tttctcaatt   1080
catgccgata aagaggatgg ctcaccacta gaaagtgcag tgcctccacc atttccagga   1140
ccatgcaccc taggtaccgg tttagctcgt tacgcggatc tgttaaatcc tccacgtaaa   1200
tcagctctag tggccttggc tgcgtacgcc acagaacctt ctgaggcaga aaaactgaaa   1260
catctaactt caccagatgg taaggatgaa tactcacaat ggatagtagc tagtcaacgt   1320
tctttactag aagttatggc tgcttttcca tccgctaaact ccctttggg tgttttcttg   1380
gccgcaatag cgcctagact gcaaccaaga tactattcaa tttcatcctc acctagactg   1440
gcaccatcaa gagttcatgt cacatccgct ttagtgtacg gtccaactcc tactggtaga   1500
atccataagg gcgtttgttc aacatggatg aaaaacgcgg ttccagcaga gaagtctcac   1560
gaatgttctg gtgctccaat ctttatcaga gcctccaact tcaaactgcc ttccaatcct   1620
tctactccta ttgtcatggt cggtcctggt acaggtcttg ctccattcag aggtttctta   1680
caagagagaa tggccttaaa ggaggatggt gaagagttgg gatcttcttt gttgtttttc   1740
ggctgtagaa acagacaaat ggatttcatc tacgaagatg aactgaataa ctttgtagat   1800
caaggagtta tttcagagtt gataatggct ttttctagag aaggtgctca gaaggagtac   1860
gtccaacaca aaatgatgga aaaggccgca caagtttggg acttaatcaa agaggaaggc   1920
tatctatatg tctgtggtga tgcaaagggt atggcaagga tgttcacag aacacttcat   1980
actatagtcc aggaacagga aggcgttagt tcttctgaag cggaagcaat tgtgaaaaag   2040
ttacaaacag agggaagata cttgagagat gtgtggtaa                          2079

SEQ ID NO: 72           moltype = DNA  length = 2142
FEATURE                 Location/Qualifiers
```

```
misc_feature            1..2142
                        note = Description of Artificial Sequence: Synthetic
                        polynucleotide
source                  1..2142
                        mol_type = other DNA
                        organism = synthetic construct
SEQUENCE: 72
atggcagaat tagatacact tgatatagta gtattaggtg ttatcttttt gggtactgtg    60
gcatacttta ctaagggtaa attgtggggt gttaccaagg atccatacgc taacggattc   120
gctgcaggtg gtgcttccaa gcctggcaga actagaaaca tcgtcgaagc tatggaggaa   180
tcaggtaaaa actgtgttgt tttctacgga agtcaaacag gtacagcgga ggattacgca   240
tcaagacttg caaaggaagg aaagtccaga ttcggtttga acactatgat cgccgatcta   300
gaagattatg acttcgataa cttagacact gttccatctg ataacatcgt tatgtttgta   360
ttggctactt acggtgaagg cgaaccaaca gataacgccg tggatttcta tgagttcatt   420
actggcgaag atgcctcttt caatgagggc aacgatcctc cactaggtaa cttgaattac   480
gttgcgttcg gtctgggcaa caatacctac gaacactaca actcaatggt caggaacgtt   540
aacaaggctc tagaaaagtt aggagctcat agaattggag aagcaggtga gggtgacgac   600
ggagctggaa ctatggaaga ggacttttta gcttggaaag atccaatgtg ggaagccttg   660
gctaaaaaga tgggcttgga ggaaagagaa gctgtatatg aacctatttt cgctatcaat   720
gagagagatg atttgacccc tgaagcgaat gaggtatact tgggagaacc taataagcta   780
cacttggaag gtacagcgaa aggtccattc aactcccaca acccatatat cgcaccaatt   840
gcagaatcat acgaactttt ctcagctaag gatagaaatt gtcgcatat ggaaattgat   900
atttctggta gtaatctaaa tgatgaaaca ggcgaccata tcgcgatctg gcctaccaac   960
ccaggtgaag aggtcaacaa atttcttgac attctagatc tgtctggtaa gcaacattcc  1020
gtcgtaacag tgaaagcctt agaacctaca gccaaagttc cttttccaaa tccaactacc  1080
tacgatgcta tattgagata ccatctggaa atatgcgctc cagtttctag acagtttgtc  1140
tcaactttag cagcattcgc ccctaatgat gatatcaaag ctgagatgaa ccgtttggga  1200
tcagacaaag attacttcca cgaaaagaca ggaccacatt actacaatat cgctagattt  1260
ttggcctcag tctctaaagg tgaaaatgg acaaagatac cattttctgc tttcatgaa   1320
ggccttacaa aactacaacc aagatactat tctatctcct cctctagttt agttcagcct  1380
aaaaagatta gtattactgc tgttgtcgaa tctcagcaaa ttccaggtag agatgaccca  1440
ttcagaggtg tagcgactaa ctacttgttc gctttgaagc agaaacaaaa cggtgatcca  1500
aatccagctc cttttggcca atcatacgag ttgacaggac caaggaataa gtgatgatggt  1560
atacatgttc cagtccatgt aagacattct aactttaagc taccatctga tccaggcaaa  1620
cctattatca tgatcggtcc aggtaccggt gttgcccctt ttagaggctt cgtccaagag  1680
agggcaaaac aagccagaga tggtgtagaa gttggtaaaa cactgctgtt ctttggatgt  1740
agaaagagta cagaagattt catgtatcaa aaagagtggc aagagtacaa ggaagctctt  1800
ggcgacaaat tcgaaatgat tacagctttt tcaagagaag gatctaaaaa ggtttatgtt  1860
caaccagac tgaaggaaag atcaaaggaa gttttctgatc ttctatccca aaaagcatac  1920
ttctacgttt gcggagacgc cgcacatatg gcacgtgaag tgaacactgt gttagcacag  1980
atcatagcag aaggccgtgg tgtatcagaa gccaagggtg aggaaattgt caaaaacatg  2040
agatcagcaa atcaatacca agtgtgttct gatttcgtaa cttacactg taaagagaca  2100
acatacgcga attcagaatt gcaagaggat gtctggagtt aa                     2142

SEQ ID NO: 73           moltype = DNA  length = 2133
FEATURE                 Location/Qualifiers
source                  1..2133
                        mol_type = genomic DNA
                        organism = Stevia rebaudiana
SEQUENCE: 73
atgcaatcag attccgtaaa agtgtcgccg ttcgatctcg tatctgcagc tatgaacgga    60
aaagcaatgg agaaattgaa cgcatcggaa tcggaagatc cgacgacgct accggcgttg   120
aagatgctgg tggagaatcg cgagctgctg acactgttta cgacgtcgtt tgctgtattg   180
atcggatgtc tcgtgttttt gatgtggcgg agatcgtcct cgaagaaact ggttcaggat   240
ccggtgccgc aggtaatcgt tgttaagaag aaagagaagg agtctgaggt tgatgatgcg   300
aagaagaaag tttcgatatt ctacggaact caaacaggaa ccgctgaagg ttttgccaag   360
gcacttgtag aggaagctaa agttcgatat gaaaagacat cctttaaagt tattgatctg   420
gatgattatg ctgctgatga cgatgagtat gaggagaagc ttaagaaaga atctttggcg   480
ttttctttt tggcaacgta tggagatggt gaaccaacag ataatgcagc caatttttac   540
aaatggttta cagagggaga tgacaaaggc gaatgctga agaaacttca atatggcgtg   600
tttggcctcg gtaacagaca atatgagcat ttcaataaga ttgcaatagt ggttgatgac   660
aaactcacga aaatgggcgc aaaacgcctt gttcctgtgg gtcttggaga tgacgatcaa   720
tgtatagaag atgactttac agcatggaaa gagttagtgt ggcccgagtt ggatcaattg   780
ttgcgtgatg aggatgacac gagtgttacg actcctttaca ctgctgcggt tttgaatac   840
cgagttgtat atcatgataa acctgcagac tcgtatgcag aagatcaaac tcatacaaat   900
ggtcatgttg ttcatgatgc tcaacatcca tctagatcca atgtggcatt taaaaggaa   960
ttgcacacct ctcaatctga ccggtcttgc actcatttgg aatttgatat ctctcacacc  1020
gggctatcat acgagacggg ggatcatgtt ggtgtctaca gtgagaatct aagtgaagtt  1080
gtagatgaga cttaaaaatt actcggtttg tcacccgaca cttatttctc agtccatgcn  1140
gacaaggaag acggaacacc tattggcggc gcctccttgc cgccaccttt ccctccatgc  1200
acttaagag atgcattaac gcgctacgca gatgttttga gttctcctaa aaaggttgct  1260
ttgcttgctc tggctgctca tgcttctgat cctagcgaag ccgatcgatt aaaatttcta  1320
gcatctccgg ctggcaagga tgaatatgct caatggatag ttgcaaacca aagagtctt  1380
cttgaagtta tgcagtcatt tccgtcagct aaaccgccac ttgggtttct cttcgcagct  1440
gtcgcccac gtttacaacc tcgatattac tcgatttctt cttctccaaa gatgtcacca  1500
aacagaattc atgtgacttg tgcattagtt tatgagacaa cacctgcagg acgtattcac  1560
agaggattgt gttcaacatg gatgaagaat gctgtgcctt gaccgaaag tccagattgt  1620
agtcaggcgt cgatttttgt tagaacgtct aacttccgac ttccggttga cccgaaagtc  1680
ccggtcatca tgatcggtcc cgggactggg ttagcccctt tcagaggttt tcttcaagaa  1740
```

```
cggttagctt tgaaggaatc tggaaccgaa ctcgggtcat ctattttctt tttcggatgc  1800
agaaaccgca aagtggattt tatatacgaa gacgaactaa acaactttgt ggagaccggt  1860
gctttatcgg agcttattgt tgcattctcc cgtgaaggaa ccgcaaagga gtatgtgcaa  1920
cataaaatga gccagaaggc ttcagatatc tggaagttgc tttcagaggg agcatattta  1980
tatgtatgtg gtgatgctaa aggcatggct aaagatgtac acagaaccct tcacacaatt  2040
gtacaagaac agggatctct agattcttcc aaggcagaat tgtatgtaaa gaacctacaa  2100
atgtcgggaa gatatcttcg tgatgtttgg taa                              2133

SEQ ID NO: 74        moltype = DNA  length = 2079
FEATURE              Location/Qualifiers
source               1..2079
                     mol_type = genomic DNA
                     organism = Arabidopsis thaliana
SEQUENCE: 74
atgacttctg ctttgtatgc ttccgatttg tttaagcagc tcaagtcaat tatggggaca    60
gattcgttat ccgacgatgt tgtacttgtg attgcaacga cgtctttggc actagtagct   120
ggatttgtgg tgttgttatg gaagaaaacg acggcggatc ggagcgggga gctgaagcct   180
ttgatgatcc ctaagtctct tatggctaag gacgaggatg atgattttgga tttgggatcc   240
gggaagacta gagtctctat cttcttcggt acgcagactg gaacagctga gggatttgct   300
aaggcattat ccgaagaaat caaagcgaga tatgaaaaag cagcagtcaa agtcattgac   360
ttggatgact atgctgccga tgatgaccag tatgaagaga aattgaagaa ggaaactttg   420
gcattttct gtgttgctac ttatggagat ggagagccta ctgacaatgc tgccagattt   480
tacaaatggt ttacggagga aaatgaacgg gatataaagc ttcaacaact agcatatggt   540
gtgtttgctc ttggtaatcg ccaatatgaa catttaata agatcgggat agttcttgat   600
gaagagttat gtaagaaagg tgcaaagcgt cttattgaag tcggtctagg agatgatgat   660
cagagcattg aggatgattt taatgcctag aaagaatcac tatggtctga gctagacaag   720
ctcctcaaag acgaggatga taaaagtgtg gcaactcctt atacagctgt tattcctgaa   780
taccgggtgg tgactcatga tcctcggttt acaactcaaa aatcaatgga atcaaatgtg   840
gccaatggaa atactactat tgacattcat catccctgca gagttgatgt tgctgtgcag   900
aaggagctctc acacacatga atctgatcgg tcttgcattc atctcgagtt cgacatatcc   960
aggacgggta ttacatatga aacaggtgac catgtaggtg tatatgctga aaatcatgtt  1020
gaaatagttg aagaagctgg aaaattgctt ggccactctt tagatttagt attttccata  1080
catgctgaca aggaagatgg ctccccattg gaaagcgcag tgccgcctcc tttccctggt  1140
ccatgcacac ttgggactgg tttggcaaga tacgcgaatg ttttgaaccc tcctcgaaag  1200
tctgcgttag ttgccttggc ggcctatgcc actgaaccaa gtgaagccga gaaacttaag  1260
cacctgacat cacctgatgg aaaggatgag tactcacaat ggattgttgc aagtcagaga  1320
agtcttttag aggtgatggc tgcttttcca tctgcaaaac ccccactagg tgtattttt  1380
gctgcaatag ctcctcgtct acaacctcgt tactactcca tctcatcctc gccaagattg  1440
gcgccaagta gagttcatgt tacatccgca ctagtatatg gtccaactcc tactggtaga  1500
atccacaagg gtgtgtgttc tacgtggatg aagaatgcag ttcctgcgga gaaaagtcat  1560
gaatgtagtg gagcccccaat ctttattcga gcatctaatt tcaagttacc atccaaccct  1620
tcaactccaa tcgttatggt gggacctggg actgggctgg cacctttag aggttttctg  1680
caggaaaagga tggcactaaa agaagatgga gaagaactag gttcatcttt gctcttcttt  1740
gggtgtagaa atcgacagat ggactttata tacgaggatg agctcaataa ttttgttgat  1800
caaggcgtaa tatctgagct catcatggca ttctcccgtg aaggagctca gaaggagtat  1860
gttcaacata gatgatgga gaaggcagca caagtttggg atctaataaa ggaagaagga  1920
tatctctatg tatgcggtga tgctaagggc atggcgaagg acgtccaccg aactctacac  1980
accattgttc aggagcagga aggtgtgagt tcgtcagagg cagaggctat agttaagaaa  2040
cttcaaaccg aaggaagata cctcagagat gtctggtga                         2079

SEQ ID NO: 75        moltype = DNA  length = 2142
FEATURE              Location/Qualifiers
source               1..2142
                     mol_type = genomic DNA
                     organism = Giberella fujikuroi
SEQUENCE: 75
atggctgaac tcgacactct ggacatcgtc gtcctcggcg ttatcttcct cggaacggtt    60
gcatacttta caaagggcaa gctatggggt gttaccaagg atccctacgc gaatggcttc   120
gctgccggcg gcgcttctaa gccgggtcgc acgaggaaca tcgtcgaggc aatggaagaa   180
tccggcaaga actgtgttgt cttctatggt gtactagctga agattatgct   240
tctcgcctcg ccaaggaggg taagagtcga ttcggactaa acaccatgat tgccgatctt   300
gaggactacg atttcgacaa cctggatacc gttcccagtg acaacattgt catgttcgtt   360
ctcgcaactt atggtgaagg tgagcctacc gataacgcg tcgacttcta tgaattcatt   420
accggcgaaga atgccagctt caatgagggc aatgatcctc cgctgggcaa cctcaactac   480
gttgcttttcg gtctcggaaa caacacgtac gagcactaca actctatggt ccgcaatgtt   540
aacaaggctc tcgagaagct tggcgctcac cgcatcggtg aagctggtga gggtgatgat   600
ggtgctggta ccatggaaga ggacttcttg gcctggaagg atcccatgtg gaagccctc   660
gctaagaaaa tgggactgga gagcgtgaa gcagtctacg agctatttt tgccattaac   720
gaacgcgacg acctgactcc tgaagccaat gaagttgtatc tcggtgagcc caacaagtac   780
catctcgaag gcaccgccaa gggaccattc aactctcaca accccttacat tgcccctatc   840
gctgaatctt atgagttgtt ctccgccaag gacagaaact gcctccacat ggaaattgac   900
atcagcggtt ctaaccttcaa gtacgaaact ggagaccata ttgctatctg gcctaccaac   960
cctggtgagg aggtcaacaa attcctggat attctcgacc tctctggaaa gcagcacagc  1020
gttgtcactg tcaaggctct gcagccttacg ccccaaggttc ctttccccaa ccttcacaac  1080
tacgatgcca ttctgcgata ccacctcgag atctcgcgct ctgtttcacg tcaattcgtc  1140
tctactctcg ccgcatttgc tcccaacgat gatatcaagg ctgagatgaa ccgcttggc   1200
agcgataagg attatttcca cgagaagact ggccgcatt actacaacat tgcccgtttc  1260
cttgccagcg tcagcaaggg cgagaagtgg accaaaatcc cgttctctgc cttcatcgag  1320
ggtctcacca agctccagcc ccgttactac tccatttctt cctcgtctct ggttcagccc  1380
```

-continued

```
aagaaaatct cgatcactgc cgtcgttgaa tcccagcaga ttcctggccg ggatgatcct    1440
ttccgtggtg ttgctacaaa ctatcttttt gccctaaagc aaaagcagaa cggtgacccc    1500
aaccctgcac cttttggtca gagctacgag cttacaggcc cccgcaataa gtatgatggc    1560
atccacgttc ctgtccatgt tcgtcactcc aacttcaagc tccctcgga ccccggtaag     1620
cccatcatca tgattggtcc tggtactggt gtcgctcctc tccgcggttt cgtgcaggag    1680
cgtgctaagc aagcccgtga tggtgttgag gttggaaaga cactcttgtt ctttggttgc    1740
cgaaagtcaa ccgaggattt catgtaccaa aaggagtggc aggaatacaa ggaggctctt    1800
ggcgataagt ttgaaatgat caccgccttt tctcgagagg gctccaagaa ggtttatgtt    1860
cagcaccgac ttaaggagcg atctaaggag gtcagcgatc tgctctccca gaaggcttat    1920
ttctatgtct gcggtgatgc agcccacatg gcccgcgagg tcaataccgt cttggcacaa    1980
atcattgccg agggacgtgg ggtgtctgag gccaagggcg aggagatcgt gaagaacatg    2040
agatcagcga accaatacca ggtatgtagt gactttgtta ctcttcactg caaagaaacc    2100
acatatgcta actcagaatt acaggaggat gtttggtcat ag                      2142

SEQ ID NO: 76              moltype = AA  length = 459
FEATURE                    Location/Qualifiers
source                     1..459
                           mol_type = protein
                           organism = Ipomoea purpurea
SEQUENCE: 76
MGSQATTYHM AMYPWFGVGH LTGFFRLANK LAGKGHRISF LIPKNTQSKL ESFNLHPHLI    60
SFVPIVVPSI PGLPPGAETT SDVPFPSTHL LMEAMDKTQN DIEIILKDLK VDVVFYDFTH   120
WLPSLARKIG IKSVFYSTIS PLMHGYALSP ERRVVGKQLT EADMMKAPAS FPDPSIKLHA   180
HEARGFTART VMKFGGDITF FDRIFTAVSE SDGLAYSTCR EIEGQFCDYI ETQFQKPVLL   240
AGPALPVPSK STMEQKWSDW LGKFKEGSVI YCAFGSECTL RKDKFQELLW GLELTGMPFF   300
AALKPPFETE SVEAAIPEEL KEKIQGRGIV HGEWVQQQLF LQHPSVGCFV SHCGWASLSE   360
ALVNDCQIVL LPQVGDQIIN ARIMSVSLKV GVEVEKGEED GVFSRESVCK AVKAVMDEKS   420
EIGREVRGNH DKLRGFLMNA DLDSKYMDSF NQKLQDLLG                          459

SEQ ID NO: 77              moltype = DNA  length = 1380
FEATURE                    Location/Qualifiers
source                     1..1380
                           mol_type = genomic DNA
                           organism = Ipomoea purpurea
SEQUENCE: 77
atgggttctc aagctacaac ttaccatatg gccatgtatc catggtttgg ggttggacat     60
ttgactggtt tcttccgttt ggcaaacaaa ttagctggca aaggacatag aatctccattt   120
ctaattccta aaaacactca atctaagtta gaatctttca accttcatcc acacttaatc   180
tcttttgtgc ctatcgttgt cccaagtata ccaggcctgc cacctggtgc agagactaca   240
tcagatgttc ctttcccaag tacacatttg ctaatggaag caatggacaa gactcaaaac   300
gatatagaga ttatcctgaa ggatcttaaa gtagatgttg ttttctatga ttttactcac   360
tggttgcctt ctctggccag aaagattggc attaagagtg tcttttactc caccatttct   420
cctttaagtc atggatatgc tttatcacca gaaagacgta tagttggtaa gcaattgaca   480
gaggcagata tgatgaaggc cccagcttct ttcccagacc catccattaa gctacatgca   540
catgaagcta gggttttac agccagaacc gttatgaaat tcggtggtga catcaccttt    600
ttcgataaa tattcacagc agtttccgaa agtgatggcc tggcctactc tacttgtaga    660
gagatcgaag gacaattctg tgattacatt gaaacacaat tccagaagcc tgtcttgtta   720
gccggtccag ctttgccagt cccatccaaa tccactatgg aacaaaagtg gtcagattgc   780
ttggggaaat tcaaggaagg ctccgtcatc tactgtgctt tcgggtctga atgtacattg   840
agaaaggaca aatttcagga actttttatgg ggtttgaat tgacaggaat gcctttcttc   900
gctgctctga agccacctt tgagactgag tctgttgagg ctgctatccc tgaggaacta   960
aaggaaaaga ttcagggaag aggtatagta catggagaat gggtacaaca acaattgttt  1020
cttcaacacc catctgtcgg gtgcttcgtt tctcactgcg gctgggcaag tttatctgaa  1080
gcccttgtta atgattgtca aatcgttgta cttccacaag ttggcgatca gattatcaac  1140
gccagaataa tgtcagtatc acttaaagtg ggcgtggaa ttgaaaaggg tgaggaggac   1200
ggtgtctttt caagagaatc tgtgtgcaag gctgttaaag cagtaatgga tgaaaaatct  1260
gaaatcggta gagaagtcag aggtaatcat gataaactga ggggtttctt gatgaatgca  1320
gacttagatt caaagtacat ggattcattc aatcaaaagc tacaagattt gctaggttaa  1380

SEQ ID NO: 78              moltype = AA  length = 438
FEATURE                    Location/Qualifiers
source                     1..438
                           mol_type = protein
                           organism = Bellis perennis
SEQUENCE: 78
MDSKIDSKTF RVVMLPWLAY SHISSFLVFA KRLTNHNFHI YICSSQTNMQ YLKNNLTSQY    60
SKSIQLIELN LPSSSELPLQ YHTTHGLPPH LTKTLSDDYQ KSGPDFETIL IKLNPHLVIY   120
DFNQLWAPEV ASTLHIPSIQ LLSGCVALYA LDAHLYTKPL DENLAKFPFP EIYPKNRDIP   180
KGGSKYIERF VDCMRRSCEI ILVRSTMELE GKYIDYLSKT LGKKVLPVGP LVQEASLLQD   240
DHIWIMKWLD KKEESVVFV CFGSEYILSD NEIEDIAYGL ELSQVSFVWA IRAKTSALNG    300
FIDRVGDKGL VIDKWVPQAN ILSHSSTGGF ISHCGWSSTM ESIRYGVPII AMPMQFDQPY   360
NARLMETVGA GIEVGRDGEG RLKREEIAAV VRKVVVEDSG ESIREKAKEL GEIMKKNMEA   420
EVDGIVIENL VKLCEMNN                                                 438

SEQ ID NO: 79              moltype = DNA  length = 1317
FEATURE                    Location/Qualifiers
source                     1..1317
                           mol_type = genomic DNA
                           organism = Bellis perennis
```

```
SEQUENCE: 79
atggattcta aaatcgattc aaagacattc agagtcgtta tgttgccttg gcttgcatac    60
tcacacattt catcattcct agtgtttgcc aagagactaa caaatcataa cttccacatc   120
tacatttgtt cctctcaaac aaatatgcaa tacctgaaaa acaacttgac gtctcagtat   180
tcaaaatcta tacaactgat tgagttgaat cttccatcta gttccgaatt gcctctgcag   240
tatcatacta ctcacggact accaccacac cttacgaaaa cattgtctga tgattatcaa   300
aagtccggac ctgactttga aaccattttg atcaaattga acccacatct ggtaatctac   360
gactttaatc aactttgggc tccagaggtt gctagtacac ttcatattcc atccatacag   420
ttactgtctg gttgcgtcgc cttatatgcc ttagacgaac atctgtacac aaagccacta   480
gacgaaaact tggctaagtt tcctttccca gaaatctatc ctaaaaacag agatattcct   540
aagggaggta gtaaatacat cgaaaggttc gtagactgta tgagaagatc ttgtgaaatc   600
atattagtca gaagtaccat ggaacttgaa ggaaaataca ttgattactt gtctaagaca   660
ttagggaaaa aggtgttgcc agtagggcct ctggtgcaag aggcttcttt gttgcaagat   720
gatcatatat ggattatgaa gtggttagac aaaaaggagg agtcatccgt cgtgtttgtt   780
tgttttggtt ctgagtacat cttatcagac aacgaaatag aagatattgc ttatggccta   840
gagttgtccc aagtaagttt cgtttgggca ataagagcta agcttctgc cttaaatggc   900
ttcattgata gagtgggtga taaaggctta gtcatcgata aatgggttcc acaggctaac   960
atcttatctc actcttctac tggtggattc attagtcatt ggcggttggtc atcaacaatg  1020
gaatctatta gatatggggt tcctattatc gccatgccaa tgcaattcga tcaaccttac  1080
aatgctaggt tgatggaaac tgttggtgca ggtatcgaag ttggcagaga tggcgaaggt  1140
agattgaaaa gagaagagat tgctgccgtg gttagaaagg tcgttgttga agattctggg  1200
gaatccataa gggagaaggc aaaggaattg ggagaaatca tgaaaaaaa catggaggcc  1260
gaagtagatg gtatagtgat tgaaaatcta gttaagctat gtgagatgaa caattaa    1317

SEQ ID NO: 80           moltype = DNA  length = 2490
FEATURE                 Location/Qualifiers
source                  1..2490
                        mol_type = genomic DNA
                        organism = Zea mays
SEQUENCE: 80
atggttttgt cttcttcttg tactacagta ccacacttat cttcattagc tgtcgtgcaa    60
cttggtcctt ggagcagtag gattaaaaag aaaaccgata ctgttgcagt accagccgct   120
gcaggaaggt ggagaagggc cttggctaga gcacagcaca catcagaatc cgcagctgtc   180
gcaaagggca gcagtttgac ccctatagtg agaactgacg ctgagtcaag gagaacaaga   240
tggccaaccg atgacgatga cgccgaacct ttagtgacag agatcaggga aatgcttact   300
tccatgtctg atggtgacat ttccgtgagc gcatacgata cagcctgggt cggattggtt   360
ccaagattag acgcggtga aggtcctcaa tttccagcag ctgtgagatg gataagaaat   420
aaccagttgc ctgacggaag ttggggcgat gccgcatat tctctgccta tgacaggctt   480
atcaatacce ttgcctgcgt tgtaacttg acaaggtggt ccctagaacc agagatgaga   540
ggtagaggac tatctttttt gggtaggaac atgtggaaat tagcaactga agatgaagag   600
tcaatgccta ttggcttcga attagcattt ccatctttga tagagcttgc taagagccta   660
ggtgtccatg acttccctta tgatcaccag gccctacaag aatctactc ttcaagagag   720
atcaaaatga agaggattcc aaaagaagtg atgcataccg ttccaacatc aatattgaca   780
agtttggagg gtatgcctgg cctagattgg gctaaactac ttaaactaca gagcagcgac   840
ggaagttttt tgttctcacc agctgccact gcatatgctt taatgaatac cggagatgac   900
aggtgttta gctacatcga tagaacagta agaaattca acggcggcgt ccctaatgtt   960
tatccagtgg atctatttga acatatttgg gccgttagta gacttgaaag attaggaatc  1020
tccaggtact tccaaaagga gatcgaacaa tgcatggatt atgtaaacag gcattggact  1080
gaggacggta tttgttgggc aaggaactct gatgtcaaag aggtgacga cacagctatg  1140
gcctttagac ttcttaggtt gcacggctac agcgtcagtc ctgatgtgtt taaaaacttc  1200
gaaaaggacg gtgaattttt cgcatttgtc ggacagtcta atcaagctgt taccggtatg  1260
tacaacttaa acagagcaag ccagatatcc ttcccaggcg aggatgtgct tcatagagct  1320
ggtgccttct catatgagtt cttgaggaga aaagaagcag agggagcttt gagggacaag  1380
tggatcattt ctaaagatct acctggtgaa gttgtgtata ctttgatttt tccatggtac  1440
ggcaacttac ctagagtcga ggccagagac tacctagagc aatacggagg tggtgatgac  1500
gtttggattg gcaagacatt gtataggatg ccacttgtaa acaatgatgt atatttggaa  1560
ttggcaagaa tggatttcaa ccactgccag gctttgcatc agttagagtg gaaggacta  1620
aaaagatggt atactgaaaa taggttgatg gactttggtg tcgccaagaa gatgcccttc  1680
agagcttatt ttcttgcagc cgcatctgtt tacgagcctt gtagagctgc cgagaaggctt  1740
gcatgggcta gagccgcaat actagctaac gccgtgagca cccacttaag aaaatagccca  1800
tcattcagag aaaggttaga gcattctctt aggtgtagac ctagtgaaga gacagatggc  1860
tcctggttta actcctcaag tggctctgat gcagttttag taaaggctgt cttaagactt  1920
actgattcat tagccaggga agcacagcca atccatggag gtgacccaga agatattata  1980
cacaagttgt taagatctgc ttgggccgag tgggttaggg aaaaggcaga cgctgccgat  2040
agcgtgtgca atggtagttc tgcagtagaa caagagggat caagaatggt ccatgataaa  2100
cagacctgtc tattattggc tagaatgatc gaaaattctg ccggtagggc agctggtgaa  2160
gcagccagtg aggacggcga tagaagaata ttcaattaa caggctccat ctgcgacagt  2220
cttaagcaaa aaatgctagt ttcacaggac cctgaaaaaa atgaagagat gatgtctcac  2280
gtggatgacg aattgaagtt gaggattaga gagttcgttc aatatttgct tagactaggt  2340
gaaaaaaaga ctggatctag cgaaaccagg caaacatttt taagtatagt gaaatcatgt  2400
tactatgctg ctcattgccc acctcatgtc gttgatagac acattagtag agtgattttc  2460
gagccagtaa gtgccgcaaa gtaaccgcgg                                    2490

SEQ ID NO: 81           moltype = AA  length = 827
FEATURE                 Location/Qualifiers
source                  1..827
                        mol_type = protein
                        organism = Zea mays
SEQUENCE: 81
```

```
MVLSSSCTTV PHLSSLAVVQ LGPWSSRIKK KTDTVAVPAA AGRWRRALAR AQHTSESAAV    60
AKGSSLTPIV RTDAESRRTR WPTDDDDAEP LVDEIRAMLT SMSDGDISVS AYDTAWVGLV   120
PRLDGGEGPQ FPAAVRWIRN NQLPDGSWGD AALFSAYDRL INTLACVVTL TRWSLEPEMR   180
GRGLSFLGRN MWKLATEDEE SMPIGFELAF PSLIELAKSL GVHDFPYDHQ ALQGIYSSRE   240
IKMKRIPKEV MHTVPTSILH SLEGMPGLDW AKLLKLQSSD GSFLFSPAAT AYALMNTGDD   300
RCFSYIDRTV KKFNGGVPNV YPVDLFEHIW AVDRLERLGI SRYFQKEIEQ CMDYVNRHWT   360
EDGICWARNS DVKEVDDTAM AFRLLRLHGY SVSPDVFKNF EKDGEFFAFV GQSNQAVTGM   420
YNLNRASQIS FPGEDVLHRA GAFSYEFLRR KEAEGALRDK WIISKDLPGE VVYTLDFPWY   480
GNLPRVEARD YLEQYGGGDD VWIGKTLYRM PLVNNDVYLE LARMDFNHCQ ALHQLEWQGL   540
KRWYTENRLM DFGVAQEDAL RAYFLAAASV YEPCRAAERL AWARAAILAN AVSTHLRNSP   600
SFRERLEHSL RCRPSEETDG SWFNSSSGSD AVLVKAVLRL TDSLAREAQP IHGGDPEDII   660
HKLLRSAWAE WVREKADAAD SVCNGSSAVE QEGSRMVHDK QTCLLLARMI EISAGRAAGE   720
AASEDGDRRI IQLTGSICDS LKQKMLVSQD PEKNEEMMSH VDDELKLRIR EFVQYLLRLG   780
EKKTGSSETR QTFLSIVKSC YYAAHCPPHV VDRHISRVIF EPVSAAK                827

SEQ ID NO: 82           moltype = DNA  length = 1461
FEATURE                 Location/Qualifiers
misc_feature            1..1461
                        note = Description of Artificial Sequence: Synthetic
                        polynucleotide
source                  1..1461
                        mol_type = other DNA
                        organism = synthetic construct
SEQUENCE: 82
actagtaaaa tggatgcaat ggcaactact gagaaaaagc tcatgtgat cttcattcca     60
tttcctgcac aatctcacat aaaggcaatg ctaaagttag cacaactatt acaccataag   120
ggattacaga taactttcgt gaataccgac ttcatccata atcaatttct ggaatcagt    180
ggccctcatt gtttggacgg agccccaggg tttagattcg aaacaattcc tgacggtgtt   240
tcacattccc cagaggcctc catcccaata agagagagtt tactgaggtc aatagaaacc   300
aactttttgg atcgtttcat tgacttggtc acaaaacttc cagacccacc aacttgacta   360
atctctgatg gctttctgtc agtgtttact atcgacgctg ccaaaaagtt gggtatccca   420
gttatgatgt actggactct tgctgcatgc ggtttcatgg gtttctatca catccattct   480
cttatcgaaa agggttttgc tccactgaaa gatgcatcat acttaaccaa cggctacctg   540
gatactgtta ttgactgggt accaggtatg gaaggtataa gacttaaaga ttttcctttg   600
gattggtcta cagaccttaa tgataaagta ttgatgttta ctacagaagc tccacaaaga   660
tctcataagg tttcacatca tatctttcac acctttgatg aattggaacc atcaatcatc   720
aaaaccttgt ctctaagata caatcatatc tacactattg gtccattaca attacttcta   780
gatcaaattc ctgaagagaa aaagcaaact ggtattacat ccctacacgg ctactcttta   840
gtgaaagagg aaccagaatg ttttcaatgg ctacaaagta aagagcctaa ttctgtggtt   900
tacgtcaact tcggaagtac aacagtcatg tccttggaag atatgactga atttggttgg   960
ggccttgcta attcaaatca ttactttcta tggattatca ggtccaattt ggtaataggg   1020
gaaaacgccg tattacctcc agaattggag gaacacatca aaagagagg tttcattgct   1080
tcctggtgtt ctcaggaaaa ggtattgaaa catccttctg ttggtggttt cctactcat   1140
tgcggttggg gctctacaat cgaatcacta agtgcaggag ttccaatgat tgttggcca   1200
tattcatggg accaacttac aaattgtagg tatatctgta aagagtggga agttggatta   1260
gaaatgggaa caaaggttaa acgtgatgaa gtgaaagat tggttcagga gttgatgggg    1320
gaaggtggcc acaagatgag aaacaaggcc aaagattgga aggaaaaagc cagaattgct   1380
attgctccta acgggtcatc ctctctaaac attgataaga tggtcaaaga gattacagtc   1440
ttagccagaa actaagtcga c                                            1461

SEQ ID NO: 83           moltype = DNA  length = 1398
FEATURE                 Location/Qualifiers
misc_feature            1..1398
                        note = Description of Artificial Sequence: Synthetic
                        polynucleotide
source                  1..1398
                        mol_type = other DNA
                        organism = synthetic construct
SEQUENCE: 83
actagtaaaa tggcagagca acaaaagatc aaaaagtcac ctcacgtctt acttattcca    60
tttcctctgc aaggacatat caacccattc atacaatttg ggaaaagatt gattagtaag   120
ggtgtaaaga caacactggt aaccactatc cacactttga attctactct gaaccactca   180
aatactacta ctacaagtat agaaattcaa gctatatcag acggatgcga tgagggtggc   240
tttatgtctg ccggtgaatc ttacttggaa acattcaagc aagtgggagc caagtctctg   300
gccgatctaa tcaaaagtt acagagtgaa ggcaccacaa ttgacgccat aatctacgat   360
tctatgacag agtgggtttt agacgttgct atcgaatttg gtattgatgg aggttccttt   420
tcacacaag catgtgttgt gaattctcta tactaccatg tgcataaagg gttaatctct   480
ttaccattgg gtgaaactgt ttcagttcca ggttttcaag tgttacaacg ttgggaaacc   540
ccattgatct tacaaaatca tgaacaaata caatcccctt ggtcgtcagt gttgtttag   600
caattcgcta acatcgatca agcaagatgg gtctttacta attcattcta taggtttagag   660
gaagaggtaa ttgaatggac taggaagatc tggaattga aagtcattgg tccaacattg   720
ccatcaatgt atttggacaa aagacttgat gatgataaag ataatggttt caatttgtac   780
aaggctaatc atcacgaatg tatgaattgg ctggatgaca aaccaaagga atcagttgta   840
tatgttgctt tcggctctct tgttaaacat ggtccagaac aagttgagga attacaaga    900
gcacttatag actctgacgt aaactttttg tgggtcatta gcacaagag ggagggggaaa   960
ctgccagaaa acctttctga agtgataaag accggaaaag gtcaatcgt tgcttggtgt   1020
aaacaattgg atgtttttagc tcatgaatct gtaggctgtt ttgtaacaca ttgcggattc   1080
aactctacac tagaagccat ttccttaggc gtacctgtcg ttgcaatgcc tcagttcctc   1140
gatcagacaa ccaacgctaa actttgtgac gaaatactag ggtgggtgt cagagtaaa    1200
```

```
gcagacgaga atggtatcgt cagaagaggg aacctagctt catgtatcaa aatgatcatg   1260
gaagaggaaa gaggagttat cataaggaaa aacgcagtta agtggaagga tcttgcaaag   1320
gttgccgtcc atgaaggcgg ctcttcagat aatgatattg ttgaatttgt gtccgaacta   1380
atcaaagcct aagtcgac                                                 1398

SEQ ID NO: 84           moltype = DNA   length = 1437
FEATURE                 Location/Qualifiers
misc_feature            1..1437
                        note = Description of Artificial Sequence: Synthetic
                         polynucleotide
source                  1..1437
                        mol_type = other DNA
                        organism = synthetic construct
SEQUENCE: 84
actagtaaaa tggctacatc tgattctatt gttgatgaca ggaagcagtt gcatgtggct   60
actttccctt ggcttgcttt cggtcatata ctgccttacc tacaactatc aaaactgata   120
gctgaaaaag gacataaagt gtcattcctt tcaacaacta gaaacattca agattatctt   180
tcccacatat caccattgat taacgtcgtt caattgacac ttccaagaat acaggaatta   240
ccagaagatg ctgaagctac aacagatgtg catcctgaag atatccctta cttgaaaaag   300
gcatccgatg gattacagcc tgaggtcact agattccttg agcaacacag tccagattgg   360
atcatatacg actacactca ctattggttg ccttcaattg cagcatcact aggcatttct   420
agggcacatt tcagtgtaac cacaccttgg gccattgctc acatgggtcc atccgctgat   480
gctatgatta acgcagtga tggtagaact accgttgaag atttgacaac cccaccaaag   540
tggtttccat ttccaactaa agtctgttgg agaaaacacg acttagcaag actggttcca   600
tacaaggcac caggaatctc agacggctat agaatgggtt tagtccttaa agggtctgac   660
tgcctattgt ctaagtgtta ccatgagttt gggacacaat ggctaccact tttgaaaaca   720
ttacaccaag ttcctgtcgt accagttggt ctattacctc agaaatccc tggtgatgag   780
aaggacgaga cttgggtttc aatcaaaaag tggttagacg ggaagcaaaa aggctcagtg   840
gtatatgtgg cactgggttc cgaagttta gtatctcaaa cagaagttgt ggaacttgcc   900
ttaggtttgg aactatctgg attgccattt gtctgggcct acagaaaacc aaaaggccct   960
gcaaagtccg attcagttga attgccagac ggctttgtcg agagaactag agatagaggg   1020
ttggtatgga cttcatgggc tccacaattg agaatcctga gtcacgaatc tgtgtgcggt   1080
ttcctaacac attgtggttc tggttctata gttgaaggac tgatgtttgg tcatccactt   1140
atcatgttgc caatctttgg tgaccagcct ttgaatgcac gtcgttaga agataaacaa   1200
gttggaattg aaatcccacg taatgaggaa gatggatgtt taaccaagga gtctgtggcc   1260
agatcattac gttccgttgt cgttgaaaag gaaggcgaaa tctacaaggc caatgcccgt   1320
gaactttcaa agatctacaa tgacacaaaa gtagagaagg aatatgtttc tcaatttgta   1380
gattacctag agaaaaacgc tagagccgta gctattgatc atgaatccta agtcgac     1437

SEQ ID NO: 85           moltype = DNA   length = 1392
FEATURE                 Location/Qualifiers
misc_feature            1..1392
                        note = Description of Artificial Sequence: Synthetic
                         polynucleotide
source                  1..1392
                        mol_type = other DNA
                        organism = synthetic construct
SEQUENCE: 85
actagtaaaa tggaaaacaa gaccgaaaca acagttagac gtaggcgtag aatcattctg   60
tttccagtac cttttcaagg gcacatcaat ccaatactac aactagccaa cgttttgtac   120
tctaaaggtt tttctattac aatctttcac accaatttac acaaaccaaa aacatccaat   180
tacccacatt tcacattcag attcatactt gataatgatc cacaagatga acgtatttca   240
aacttaccta cccacggtcc tttagctgga atgagaattc caatcatcaa tgaacatggt   300
gccgatgagc ttagaagaga attagagtta cttatgttgg catccgaaga ggacgaggaa   360
gtctcttgtc tgattactga cgctctatgg tactttgccc aatctgtggc tgatagtttg   420
aatttgagga gattggtact aatgacatcc agtctgttta actttcacgc tcatgttagt   480
ttaccacaat ttgacgaatt gggatacttg gaccctgatg acaagactag gttagaggaa   540
caggcctctg gttttcctat gttgaaagtc aaagatatca agtctgccta ttctaattgg   600
caaatcttga aagagatctt aggaaagatg atcaaacaga caaaggcttc atctggagtg   660
atttggaaca gtttcaaaga gttagaagag tctgaattgg agactgtaat cagagaaatt   720
ccagcacctt cattcctgat accattacca aaacatttga ctgcttcctc ttcctctttg   780
ttggatcatg acagaacagt ttttcaatgg ttggaccaac aaccacctag ttctgttttg   840
tacgtgtcat ttggtagtac ttctgaagtc gatgaaaagg acttccttga aatcgcaaga   900
ggcttagtcg atagtaagca gtcattcctt tgggtcgtgc caggttttcg tgaaaggc   960
tcaacatggg tcgaaccact tccagatggt tttctaggcg aaagaggtag aatagtcaaa   1020
tgggttcctc aacaggaagt tttagctcat ggcgctattg ggcattctg gactcattcc   1080
ggatggaatt caactttaga atcagtatgc gaaggggtac ctatgatctt ttcagatttt   1140
ggtcttgatc aaccactgaa gcaagatac atgtctgatg ttttgaaagt gggtgtatat   1200
ctagaaaatg gctgggaaag gggtgaaata gctaatgcaa taagacgtgt tatggttgat   1260
gaagagggg agtatatcag acaaaacgca agagtgctga agcaaaaggc cgacgtttct   1320
ctaatgaagg gaggctcttc atacgaatcc ttagaatctc ttgtttccta catttcatca   1380
ctgtaagtcg ac                                                       1392

SEQ ID NO: 86           moltype = AA   length = 12
FEATURE                 Location/Qualifiers
REGION                  1..12
                        note = Description of Artificial Sequence: Synthetic peptide
source                  1..12
                        mol_type = protein
```

```
                        organism = synthetic construct
SEQUENCE: 86
TSFAEYWNLL SP                                                                      12

SEQ ID NO: 87           moltype = DNA  length = 1602
FEATURE                 Location/Qualifiers
misc_feature            1..1602
                        note = Description of Artificial Sequence: Synthetic
                        polynucleotide
source                  1..1602
                        mol_type = other DNA
                        organism = synthetic construct
SEQUENCE: 87
atgaccagct ttgccgagta ttggaatctg ttaagtccca cttcttttgc agaatattgg    60
aaccttctat caccgacgag tttcgcggag tactggaatt tgttttctcc aacatcgttc   120
gctgaatact ggaacttact cagccctgct agtaaaatgg atgcaatggc aactactgag   180
aaaaagcctc atgtgatctt cattccattt cctgcacaat ctcacataaa ggcaatgcta   240
aagttagcac aactattaca ccataaggga ttacagataa ctttcgtgaa taccgacttc   300
atccataatc aatttctgga atctagtggc cctcattgtt tggacggagc cccagggttt   360
agattcgaaa caattcctga cggtgtttca cattccccag aggcctccat cccaataaga   420
gagagtttac tgaggtcaat agaaaccaac tttttggatc gtttcattga cttggtcaca   480
aaacttccag acccaccaac ttgcataatc tctgatgact ttctgtcagt gtttactatc   540
gacgctgcca aaaagttggg tatcccagtt atgatgtact ggactcttgc tgcatgcggt   600
ttcatgggtt tctatcacat ccattctctt atcgaaaagg gttttgctcc actgaaagat   660
gcatcatact taaccaacgg ctacctggat actgttattg actgggtacc aggtatggaa   720
ggtataagac ttaaagattt tccttttgga tggtctacag accttaatga taagtattg    780
atgttactta cagaagctcc acaaagatct cataagggtt tcacatcatat ctttcacacc   840
tttgatgaat tggaaccatc aatcatcaaa accttgtctc taagatacaa tcatatctac   900
actattggtc cattacaatt acttctagat caaattcctg aagagaaaaa gcaaactggt   960
attacatcct tacacggcta ctctttagtg aaagaggaac agaatgttt tcaatggcta  1020
caaagtaaag agcctaattc tgtggtctac gtcaacttcg gaagtacaac agtcatgtcc  1080
ttgaagata tgactgaatt tggttggggc cttgctaatt caaatcatta ctttctatgg   1140
attatcaggt ccaatttggt aataggggaa acgccgtat acctccaga attggaggaa   1200
cacatcaaaa agaggtttt cattgcttcc tggtgttctc aggaaaaggt attgaaacat  1260
ccttctgttg gtggtttcct tactcattgc ggttggggct ctacaatcga atcactaagt  1320
gcaggagttc caatgatttg ttggccatat tcatgggacc aacttacaaa ttgtaggtat  1380
atctgtaaag agtgggaagt tggattagaa atgggaacaa aggttaaacg tgatgaagtg  1440
aaaagattgg ttcaggagtt gatgggggaa ggtggccaca gatgagaaa caaggccaaa  1500
gattggaagg aaaaagccag aattgctatt gctcctaacg ggtcatcctc tctaaacatt  1560
gataagatgg tcaaagagat tacagtctta gccagaaact aa                   1602

SEQ ID NO: 88           moltype = AA  length = 533
FEATURE                 Location/Qualifiers
REGION                  1..533
                        note = Description of Artificial Sequence: Synthetic
                        polypeptide
source                  1..533
                        mol_type = protein
                        organism = synthetic construct
SEQUENCE: 88
MTSFAEYWNL LSPTSFAEYW NLLSPTSFAE YWNLFSPTSF AEYWNLLSPA SKMDAMATTE    60
KKPHVIFIPF PAQSHIKAML KLAQLLHHKG LQITFVNTDF IHNQFLESSG PHCLDGAPGF   120
RFETIPDGVS HSPEASIPIR ESLLRSIETN FLDRFIDLVT KLPDPPTCII SDGFLSVFTI   180
DAAKKLGIPV MMYWTLAACG FMGFYHIHSL IEKGFAPLKD ASYLTNGYLD TVIDWVPGME   240
GIRLKDFPLD WSTDLNDKVL MFTTEAPQRS HKVSHHIPHT FDELEPSIIK TLSLRYNHIY   300
TIGPLQLLLD QIPEEKKQTG ITSLHGYSLV KEEPECFQWL QSKEPNSVVY VNFGSTTVMS   360
LEDMTEFGWG LANSNHYFLW IIRSNLVIGE NAVLPPELEE HIKKRGFIAS WCSQEKVLKH   420
PSVGGFLTHC GWGSTIESLS AGVPMICWPY SWDQLTNCRY ICKEWEVGLE MGTKVKRDEV   480
KRLVQELMGE GGHKMRNKAK DWEKARIAI APNGSSSLNI DKMVKEITVL ARN           533

SEQ ID NO: 89           moltype = DNA  length = 1893
FEATURE                 Location/Qualifiers
misc_feature            1..1893
                        note = Description of Artificial Sequence: Synthetic
                        polynucleotide
source                  1..1893
                        mol_type = other DNA
                        organism = synthetic construct
SEQUENCE: 89
atgtgcaata ccaacatgtc tgtacctact gatggtgctg taaccacctc acagattcca    60
gcttcggaac aagagaccct ggttagacca aagccattgc ttttgaagtt attaaagtct   120
gttggtgcac aaaaagacac ttatactatg aaagaggttc ttttttatct tggcagtat    180
attatgacta acgattata tgatgagaag caacaacata ttgtatattg ttcaaatgat   240
cttctaggag atttgtttgg cgtgccaagc ttctctgtga aagagcacag gaaaatatat   300
accatgatct acaggaactt ggtagtagtc aatcagcagg aatcatcgga ctcaggtaca   360
tctgtgagtg agaacaggtg tcaccttgaa ggtgggagtg atcaaaagga ccttgtacaa   420
gagcttcagg aagagaaacc ttcatcttca catttggttt ctagaccatc taccggtggt   480
agcggatcct ctgaggcag tgctagtaaa atggcagagc aacaaaagat caaaaagtca   540
cctcacgtct tacttattcc atttcctctg caaggacata tcaacccatt catacaattt   600
```

-continued

```
gggaaaagat tgattagtaa gggtgtaaag acaacactgg taaccactat ccacactttg  660
aattctactc tgaaccactc aaatactact actacaagta tagaaattca agctatatca  720
gacggatgcg atgagggtgg ctttatgtct gccggtgaat cttacttgga aacattcaag  780
caagtgggat ccaagtctct ggccgatcta atcaaaaagt tacagagtga aggcaccaca  840
attgacgcca taatctacga ttctatgaca gagtgggttt tagacgttgc tatcgaattt  900
ggtattgatg gaggttcctt tttcacacaa gcatgtgttg tgaattctct atactaccat  960
gtgcataaag ggttaatctc tttaccattg ggtgaaactg tttcagttcc aggttttcca 1020
gtgttacaac gttgggaaac cccattgatc ttacaaaatc atgaacaaat acaatcacct 1080
tggtcccaga tgttgtttgg tcaattcgct aacatcgatc aagcaagatg ggtctttact 1140
aattcattct ataagttaga ggaagaggta attgaatgga ctaggaagat ctggaatttg 1200
aaagtcattg gtccaacatt gccatcaatg tatttggaca aaagacttga tgatgataaa 1260
gataatggtt tcaatttgta caaggctaat catcacgaat gtatgaattg ctgggatgac 1320
aaaccaaagg aatcagttgt atatgttgct ttcggctctc ttgttaaaca tggtccagaa 1380
caagttgagg agattacaag agcacttata gactcgtacg taaactttt gtgggtcatt 1440
aagcacaaag aggaggggaa actgccagaa aaccttctg aagtgataaa gaccggaaaa 1500
ggtctaatcg ttgcttggtg taaacaattg gatgtttag ctcatgaatc tgtaggctgt 1560
tttgtaacac attgcggatt caactctaca ctagaagcca tttccttagg cgtacctgtc 1620
gttgcaatgc ctcagttctc cgatcagaca ccaacgtca aactttgtga cgaaatacta 1680
ggggtgggtg tcagagttaa agcagacgag aatggtatcg tcagaagagg gaacctagct 1740
tcatgtatca aatgatcat ggaagacgaa agaggagtta tcataaggaa aaacgcagtt 1800
aagtggaagg atcttgcaaa ggttgccgtc atgaaggcg gctcttcaga taatgatatt 1860
gttgaatttg tgtccgaact aatcaaagcc taa                              1893
```

SEQ ID NO: 90          moltype = AA   length = 630
FEATURE                Location/Qualifiers
REGION                 1..630
                       note = Description of Artificial Sequence: Synthetic
                       polypeptide
source                 1..630
                       mol_type = protein
                       organism = synthetic construct
SEQUENCE: 90
```
MCNTNMSVPT DGAVTTSQIP ASEQETLVRP KPLLLKLLKS VGAQKDTYTM KEVLFYLGQY  60
IMTKRLYDEK QQHIVYCSND LLGDLFGVPS FSVKEHRKIY TMIYRNLVVV NQQESSDSGT 120
SVSENRCHLE GGSDQKDLVQ ELQEEKPSSS HLVSRPSTGG SGSSGGSASK MAEQQKIKKS 180
PHVLLIPFPL QGHINPFIQF GKRLISKGVK TTLVTTIHTL NSTLNHSNTT TTSIEIQAIS 240
DGCDEGGFMS AGESYLETFK QVGSKSLADL IKKLQSEGTT IDAIIYDSMT EWVLDVAIEF 300
GIDGGSFFTQ ACVVNSLYYH VHKGLISLPL GETVSVPGFP VLQRWETPLI LQNHEQIQSP 360
WSQMLFGQFA NIDQARWVFT NSFYKLEEEV IEWTRKIWNL KVIGPTLPSM YLDKRLDDDK 420
DNGFNLYKAN HHECMNWLDD KPKESVVYVA FGSLVKHGPE QVEEITRALI DSDVNFLWVI 480
KHKEEGKLPE NLSEVIKTGK GLIVAWCKQL DVLAHESVGC FVTHCGFNST LEAISLGVPV 540
VAMPQFSDQT TNAKLLDEIL GVGVRVKADE NGIVRRGNLA SCIKMIMEEE RGVIIRKNAV 600
KWKDLAKVAV HEGGSSDNDI VEFVSELIKA                                 630
```

SEQ ID NO: 91          moltype = DNA   length = 1932
FEATURE                Location/Qualifiers
misc_feature           1..1932
                       note = Description of Artificial Sequence: Synthetic
                       polynucleotide
source                 1..1932
                       mol_type = other DNA
                       organism = synthetic construct
SEQUENCE: 91
```
atgtgcaata ccaacatgtc tgtacctact gatggtgctg taaccacctc acagattcca   60
gcttcggaac aagagaccct ggttagacca aagccattgc ttttgaagtt attaaagtct  120
gttggtgcac aaaaagacac ttatactatg aaagaggttc tttttatct ggccagtgt   180
attatgacta aacgattata tgatgagaag caacaacata ttgtatattg ttcaaatgat  240
cttctaggag atttgtttgg cgtgccaagc ttctctgtga agagcacag gaaatatat   300
accatgatct acaggaactt ggtagtagtc aatcagcagg aatcatcgga ctcaggtaca  360
tctgtgagtg agaacaggtg tcaccttgga ggtgggagtg atcaaaagga ccttgtacaa  420
gagcttcagg aagagaaacc ttcatcttca catttggtt ctagaccatc taccggtggt  480
agcggatcct ctgaggcag tgctagtaaa atggctacat ctgattctat tgttgatgac  540
aggaagcagt tgcatgtggc tactttccct tggcttgctt tcggtcatat actgcctac   600
ctacaactat caaaactgat agctgaaaaa ggacataag tgtcattcct ttcaacaact  660
agaaacattc aaagattatc ttcccacata tcaccattga ttaacgtcgt tcaattgaca  720
cttccaagag tacaggaatt accagaagat gctgaagcta acacagatgt gcatcctgaa  780
gatatcccct acttgaaaaa ggcatccgat ggattacagc tgaggtcac tagattcctt  840
gagcaacaca gtccagattg gatcatatac gactacactc actattggtt gccttcaatt  900
gcagcatcac taggcattc tagggcacat ttcagtgtaa ccacaccttg ggccattgt   960
tacatgggtc catccgctga tgctatgatt aacggcagtg atggtagaac taccgttgaa 1020
gatttgacaa cccaccaaa gtgtttcca tttccaacta agtctgttg gagaaaacac  1080
gacttagcaa gactggttcc atacaaggca ccaggaatct cagacggcta gaatggt    1140
ttagtcctta aagggtctga ctgccattgt tctaagtgtt accatgagtt tgggacacaa 1200
tggctaccac ttttggaaac attcaccaa gttcctgtcg taccagttgg tctattacct 1260
ccagaaatcc ctggtgatga aaggacgag acttggggttt caatcaaaa gtggtagac  1320
gggaagcaaa aaggctcagt ggtatatgtg gcactgggtt ccgaagtttt agtatctaa  1380
acagaagttg tggaacttgc cttaggttg gaactatctg gattgccatt gtctgggcc  1440
tacagaaaac caaaaggccc tgcaaagtcc gattcagttg aattgccaga cggctttgtc 1500
gagagaacta gagatagagg gttggtatgg acttcatggg ctccacaatt gagaatcctg 1560
```

```
agtcacgaat ctgtgtgcgg tttcctaaca cattgtggtt ctggttctat agttgaagga   1620
ctgatgtttg gtcatccact tatcatgttc caatctttg gtgaccagcc tttgaatgca   1680
cgtctgttag aagataaaca agttggaatt gaaatcccac gtaatgagga agatggatgt   1740
ttaaccaagg agtctgtggc cagatcatta cgttccgttg tcgttgaaaa ggaaggcgaa   1800
atctacaagg ccaatgcccg tgaactttca aagatctaca atgcacacaaa agtagagaag   1860
gaatatgttt ctcaatttgt agattaccta gagaaaaacg ctagagccgt agctattgat   1920
catgaatcct aa                                                       1932

SEQ ID NO: 92           moltype = AA   length = 643
FEATURE                 Location/Qualifiers
REGION                  1..643
                        note = Description of Artificial Sequence: Synthetic
                        polypeptide
source                  1..643
                        mol_type = protein
                        organism = synthetic construct
SEQUENCE: 92
MCNTNMSVPT DGAVTTSQIP ASEQETLVRP KPLLLKLLKS VGAQKDTYTM KEVLFYLGQY    60
IMTKRLYDEK QQHIVYCSND LLGDLFGVPS FSVKEHRKIY TMIYRNLVVV NQQESSDSGT   120
SVSENRCHLE GGSDQKDLVQ ELQEEKPSSS HLVSRPSTGG SGSSGGSASK MATSDSIVDD   180
RKQLHVATFP WLAFGHILPY LQLSKLIAEK GHKVSFLSTT RNIQRLSSHI SPLINVVQLT   240
LPRVQELPED AEATTDVHPE DIPYLKKASD GLQPEVTRFL EQHSPDWIIY DYTHYWLPSI   300
AASLGISRAH FSVTTPWAIA YMGPSADAMI NGSDGRTTVE DLTTPPKWFP FPTKVCWRKH   360
DLARLVPYKA PGISDGYRMG LVLKGSDCLL SKCYHEFGTQ WLPLLETLHQ VPVVPVGLLP   420
PEIPGDEKDE TWVSIKKWLD GKQKGSVVYV ALGSEVLVSQ TEVVELALGL ELSGLPFVWA   480
YRKPKGPAKS DSVELPDGFV ERTRDRGLVW TSWAPQLRIL SHESVCGFLT HCGSGSIVEG   540
LMFGHPLIML PIFGDQPLNA RLLEDKQVGI EIPRNEEDGC LTKESVARSL RSVVVEKEGE   600
IYKANARELS KIYNDTKVEK EYVSQFVDYL EKNARAVAID HES                     643

SEQ ID NO: 93           moltype = DNA   length = 1887
FEATURE                 Location/Qualifiers
misc_feature            1..1887
                        note = Description of Artificial Sequence: Synthetic
                        polynucleotide
source                  1..1887
                        mol_type = other DNA
                        organism = synthetic construct
SEQUENCE: 93
atgtgcaata ccaacatgtc tgtacctact gatggtgctg taaccacctc acagattcca     60
gcttcggaac aagagaccct ggttagacca aagccattgc ttttgaagtt attaaagtct    120
gttggtgcac aaaaagacac ttatactatg aagagggttc ttttttatct tggccagtat    180
attatgacta acgattata tgatgagaag caacaacata ttgtatattg ttcaaatgat    240
cttctgggag atttgtttgg cgtgccaagc ttctctgata aagagcacag gaaaatatat    300
accatgatct acaggaactt ggtagtagtc aatcagcagg aatcatcgga ctcaggtaca    360
tctgtgagtg agaacaggtg tcaccttgaa ggtgggagtg atcaaaagga ccttgtacaa    420
gagcttcagg aagagaaacc ttcatcttca catttggttt ctagaccatc taccggtggt    480
agcggatcct ctggaggcag tgctagtaaa atggaaaaca agaccgaaac aacagttaga    540
cgtaggcgta gaatcattct gtttccagta ccttttcaag ggcacatcaa tccaatacta    600
caactagcca acgttttgta ctctaaaggt ttttctatta caatctttca caccaatttc    660
aacaaaccaa aaacatccaa ttaccacat ttcacattca gattcatact tgataatgat    720
ccacaagatg aacgtatttc aaacttacct acccacggtc ctttagctgg aatgagaatt    780
ccaatcatca atgaacatgg tgccgatgag cttagaagag aattagagtt acttatgttg    840
gcatccgaag aggacgagga agtctcttgt ctgattactg acgctctatg gtactttgcc    900
caatctgtgt ctgatagttt gaatttgagg agattggtac taatgacatc cagtctgttt    960
aactttcacg ctcatgttag tttaccacaa tttgacgaat tgggtgtactt ggaccctgat   1020
gacaagacta ggttagagga acaggcctct ggttttccta tgttgaaagt caaagatatc   1080
aagtctgcct attctaattg gcaaatcttg aaagagatct taggaagat gatcaaacag   1140
acaaaggctt catctggagt gatttggaac agtttcaaag agtagaaga gtctgaattg   1200
gagactgtaa tcagagaaat tccagcacct tcattcctga taccattacc aaaacattg   1260
actgcttcct cttcctcttt gttggatcat gacagaacag tttttcaatg gttggaccaa   1320
caaccaccta gttctgtttt gtacgtgtca tttggtagta cttctgaagt cgatgaaaag   1380
gacttccttg aaatcgcaag aggcttagtc gatagtaagc agtcattcct ttgggtcgtg   1440
cgtccaggtt tcgtgaaagg ctcaacatgg gtcgaaccac ttccagatgg ttttctaggc   1500
gaaagaggta gaatagtcaa atgggttcct caacaggaag ttttagctca tggcgctatt   1560
ggggcattct ggactcattc cggatgggaat tcaactttag aatcagtatg cgaagggta   1620
cctatgatct ttcagattt tggtcttgat caaccactga acgaagata catgtctgat   1680
gttttgaaag tgggtgtata tctagaaaat ggctgggaaa ggggtgaaat agctaatgca   1740
ataagacgtg ttatggttga tgaagagggg gagtatatca gacaaaacgc aagagtgctg   1800
aagcaaaagg ccgacgtttc tctaatgaag ggaggctctt catacgaatc cttagaatct   1860
cttgtttcct acatttcatc actgtaa                                       1887

SEQ ID NO: 94           moltype = AA   length = 628
FEATURE                 Location/Qualifiers
REGION                  1..628
                        note = Description of Artificial Sequence: Synthetic
                        polypeptide
source                  1..628
                        mol_type = protein
                        organism = synthetic construct
```

-continued

```
SEQUENCE: 94
MCNTNMSVPT DGAVTTSQIP ASEQETLVRP KPLLLKLLKS VGAQKDTYTM KEVLFYLGQY      60
IMTKRLYDEK QQHIVYCSND LLGDLFGVPS FSVKEHRKIY TMIYRNLVVV NQQESSDSGT     120
SVSENRCHLE GGSDQKDLVQ ELQEEKPSSS HLVSRPSTGG SGSSGGSASK MENKTETTVR     180
RRRRIILFPV PFQGHINPIL QLANVLYSKG FSITIFHTNF NKPKTSNYPH FTFRFILDND     240
PQDERISNLP THGPLAGMRI PIINEHGADE LRRELELLML ASEEDEEVSC LITDALWYFA     300
QSVADSLNLR RLVLMTSSLF NFHAHVSLPQ FDELGYLDPD DKTRLEEQAS GFPMLKVKDI     360
KSAYSNWQIL KEILGKMIKQ TKASSGVIWN SFKELEESEL ETVIREIPAP SFLIPLPKHL     420
TASSSSLLDH DRTVFQWLDQ QPPSSVLYVS FGSTSEVDEK DFLEIARGLV DSKQSFLWVV     480
RPGFVKGSTW VEPLPDGFLG ERGRIVKWVP QQEVLAHGAI GAFWTHSGWN STLESVCEGV     540
PMIFSDFGLD QPLNARYMSD VLKVGVYLEN GWERGEIANA IRRVMVDEEG EYIRQNARVL     600
KQKADVSLMK GGSSYESLES LVSYISSL                                       628

SEQ ID NO: 95           moltype = AA   length = 473
FEATURE                 Location/Qualifiers
source                  1..473
                        mol_type = protein
                        organism = Stevia rebaudiana
SEQUENCE: 95
MATSDSIVDD RKQLHVATFP WLAFGHILPY LQLSKLIAEK GHKVSFLSTT RNIQRLSSHI      60
SPLINVVQLT LPRVQELPED AEATTDVHPE DIPYLKKASD GLQPEVTRFL EQHSPDWIIY     120
DYTHYWLPSI AASLGISRAH FSVTTPWAIA YMGPSADAMI NGSDGRTTVE DLTTPPKWFP     180
FPTKVCWRKH DLARLVPYKA PGISDRCRMG LVLKGSDCLL SKCYHEFGTQ WLPLLETLHQ     240
VPVVPVGLLP PEIPGDEKDE TWVSIKKWLD GKQKGSVVYV ALGSEVLVSQ TEVVELALGL     300
ELSGLPFVWA YRKPKGPAKS DSVELPDGFV ERTRDRGLVW TSRAPQLRIL SHESVCGFLT     360
HCGSGSIVEG LMFGHPLIML PIFGDQPLNA RLLEDKQVGI EIPRNEEDGC LTKESVARSL     420
RSVVVEKEGE IYKANARELS KIYNDTKVEK EYVSQFVDYL EKNARAVAID HES            473

SEQ ID NO: 96           moltype = DNA   length = 1422
FEATURE                 Location/Qualifiers
source                  1..1422
                        mol_type = genomic DNA
                        organism = Stevia rebaudiana
SEQUENCE: 96
atggctacca gtgactccat agttgacgac cgtaagcagc ttcatgttgc gacgttccca      60
tggcttgctt tcggtcacat cctcccttac cttcagcttt cgaaattgat agctgaaaag     120
ggtcacaaag tctcgtttct ttctaccacc agaaacattc aacgtctctc ttctcatatc     180
tcgccactca taaatgttgt tcaactcaca cttccacgtg tccaagagct gccggaggat     240
gcagaggcga ccactgacgt ccaccctgaa gatattccat atctcaagaa ggcttctgat     300
ggtcttcaac cggaggtcac ccggtttcta gaacaacact ctccggactg gattatttat     360
gattatactc actactggtt gccatccatc gcggctagcc tcggtatctc acgagcccac     420
ttctccgtca ccactccatg ggccattgct tatatgggac cctcagctga cgccatgata     480
aatggttcag atggtcgaac cacggttgag gatctcacaa caccgcccaa gtggtttcca     540
tttccgacca agtatgctg gcggaagcat gatcttgccc gactggtgcc ttacaaagct     600
ccggggatat ctgatcgatg ccgtatgggg ctggttctta agggatctga ttgtttgctc     660
tccaaatgtt accatgagtt tggaactcaa tggctacctc tttgagac actacaccaa     720
gtaccggtgg ttccggtggg attactgcca ccggaaatac ccggagacga gaaagatgaa     780
acatgggtgt caatcaagaa atggctcgat ggtaaacaaa aaggcagtgt ggtgtacgtt     840
gcattaggaa gcgaggtttt ggtgagccaa accgagttg ttgagttagc attgggtctc     900
gagctttctg gcttgccatt tgtttgggct tatagaaaac caaaaggtcc cgcgaagtca     960
gactcggtgg agttgccaga cggttcgtg aacgaactc gtgaccgtgg gttggtctg     1020
acgagtcggg cacctcagtt acgaatactg agccatgagt cggtttgtgg gttcttgacg     1080
cattgtggtt ctggatcaat tgtggaaggg ctaatgtttg gtcaccctct aatcatgcta     1140
ccgatttttg gggaccaacc tctgaatgct cgattactgg aggacaaaca ggtgggaatc     1200
gagatacaaa gaaatgagga agatggttgc ttgaccaagg agtcggttgc tagatcactg     1260
aggtccgttg ttgtggaaaa agaaggggag atctacaagg cgaacgcgag ggagctgagt     1320
aaaatctata cgacactaa ggttgaaaga gaatatgtaa gccaattcgt agactatttg     1380
gaaaagaatg cgcgtgcggt tgccatcgat catgagagtt aa                       1422

SEQ ID NO: 97           moltype = DNA   length = 1380
FEATURE                 Location/Qualifiers
source                  1..1380
                        mol_type = genomic DNA
                        organism = Stevia rebaudiana
SEQUENCE: 97
atggaaaata aaacggagac caccgttcgc cggcgccgga gaataatatt attcccggta      60
ccatttcaag gccacattaa cccaattctt cagctagcca atgtgttgta ctctaaagga     120
ttcagtatca ccatctttca caccaacttc aacaaaccca aaacatctaa ttaccctcac     180
ttcactttca gattcatcct cgacaacgac ccacaagacg aacgcattc caatctaccg     240
actcatggtc cgctcgctgg tatgcggatt ccgattatca cgaacacgg agctgacgaa     300
ttacgacgcg aactcgaact gttgatgtta gcttctgaag aagatgaaga ggtatcgtgt     360
ttaatcacgg atgctctttg gtacttcgcg caatctgttg ctgacagtct taacctccga     420
cggcttgttt tgatgacaag cagcttgttt aattttcatg cacatgtttc acttcctcag     480
tttgatgagc ttggttacct cgatcctgat gacaaaaccc gtttggaaga aagcagt     540
gggtttccta tgctaaaagt gaaagacatc aagtctgcgt attcgaactg gcaaatactc     600
aaagagatat agggaagat gataaaacaa acaaaagcat cttcaggagt catctggaac     660
tcatttaagg aactcgaaga gtctgagctc gaaactgtta ccgtgagat cccggctcca     720
agtttcttga taccactccc caagcatttg acagcctctt ccagcagctt actagaccac     780
gatcgaaccg ttttttcatg gttagaccaa caaccgtcac gttcggtact gtatgttagt     840
```

```
tttggtagtg gtactgaagt actggatgag aaagatttct tggaaatagc tcgtgggttg     900
gttgatagca agcagtcgtt tttatgggtg gttcgacctg ggtttgtcaa gggttcgacg     960
tgggtcgaac cgttgccaga tgggttcttg ggtgaaagag gacgtattgt gaaatggggtt   1020
ccacagcaag aagtgctagc tcatggagca ataggcgcat tctggactca tagcggatgg    1080
aactctacgt tggaaagcgt tgtgaaggt gttcctatga ttttctcgga ttttgggctc     1140
gatcaaccgt tgaatgctag atacatgagt gatgttttga aggtaggggt gtatttggaa    1200
aatgggtggg aaagaggaga gatagcaaat gcaataagaa gagttatggt ggatgaagaa    1260
ggagaataca ttagacagaa tgcaagagtt ttgaaacaaa aggcagatgt ttctttgatg    1320
aagggtggtt cgtcttacga atcattagag tctctagttt cttacatttc atcgttgtaa    1380

SEQ ID NO: 98              moltype = AA   length = 459
FEATURE                    Location/Qualifiers
source                     1..459
                           mol_type = protein
                           organism = Stevia rebaudiana
SEQUENCE: 98
MENKTETTVR RRRRIILFPV PFQGHINPIL QLANVLYSKG FSITIFHTNF NKPKTSNYPH      60
FTFRFILDND PQDERISNLP THGPLAGMRI PIINEHGADE LRRELELLML ASEEDEEVSC     120
LITDALWYFA QSVADSLNLR RLVLMTSSLF NFHAHVSLPQ FDELGYLDPD DKTRLEEQAS    180
GFPMLKVKDI KSAYSNWQIL KEILGKMIKQ TKASSGVIWN SFKELEESEL ETVIREIPAP    240
SFLIPLPKHL TASSSSLLDH DRTVFPWLDQ QPSRSVLYVS FGSGTEVLDE KDFLEIARGL    300
VDSKQSFLWV VRPGFVKGST WVEPLPDGFL GERGRIVKEW PQQEVLAHGA IGAFWTHSGW    360
NSTLESVCEG VPMIFSDFGL DQPLNARYMS DVLKVGVYLE NGWERGEIAN AIRRVMVDEE    420
GEYIRQNARV LKQKADVSLM KGGSSYESLE SLVSYISSL                           459

SEQ ID NO: 99              moltype = DNA   length = 1380
FEATURE                    Location/Qualifiers
modified_base              861..863
                           mod_base = OTHER
                           note = a, c, t, g, unknown or other
source                     1..1380
                           mol_type = genomic DNA
                           organism = Stevia rebaudiana
SEQUENCE: 99
atggaaaata aaacggagac caccgttcgc cggcgccgga gaataatatt attcccggta      60
ccatttcaag gccacattaa cccaattctt cagctagcca atgtgttgta ctctaaagga    120
ttcagtatca ccatctttca caccaacttc aacaaaccca aaacatctaa ttaccctcac    180
ttcactttca gattcatcct cgacaacgac ccacaagacg aacgcattc caatctaccg     240
actcagtgtc cgctcgctgg tatgcggatt ccgattatca atgaacacgg agctgacgaa    300
ttacgacgcg aactggaact gttgatgtta gcttctgaag aagatgaaga ggtatcgtgt    360
ttaatcacgg atgctctttg gtacttcgcg caatctgttg ctgacagtct taacctccga    420
cggcttgttt tgatgacaag cagcttgttt aattttcatg cacatgtttc acttcctcag    480
tttgatgaac ttggttacct cgatcctgat gacaaaaccc gtttggaaga acaagcgagt    540
gggtttccta tgctaaaagt gaaagacatc aagtctgcgt attcgaactg gcaaatactc    600
aaagagatat tagggaagat gataaaacaa acaaaagcat cttcaggagt catctggaac    660
tcatttaagg aactcgaaga gtctgagctc gaaactgtta tccgtgagat cccggctcca    720
agtttcttga taccactccc caagcatttg acagcctcct tcagcagctt actgaccac    780
gatcgaaccg tttttcaatg gttagaccaa caaccgccaa gttcggtact gtatgttagt    840
tttggtagta ctagtgaagt nnnggatgag aaagatttct tggaaatagc tcgtgggttg    900
gttgatagca agcagtcgtt tttatgggtg gttcgacctg ggtttgtcaa gggttcgacg    960
tgggtcgaac cgttgccaga tgggttcgtg gccgaaagag ggcgtattgt gaaatggggtt  1020
ccgcaacagg aagtgatagc tcatggagca atcggtgcat tctggactca tagcggatgg   1080
aactctacat tggaaagcgt tgtgaaggt gttcctatga ttttctcgga ttttgggctc    1140
gatcaaccgt tgaatgctag atacatgagt gatgttttga aggtaggggt gtatttggaa    1200
aatgggtggg aaagaggaga gatagcaaat gcaatacgaa gagttatggt ggatgaagaa    1260
ggagaataca ttagacagaa tgcaagagtt ttgaaacaaa aggcagatgt ttctttgatg    1320
aagggtggtt catcttacga atcattagag tctctagttt cttacatttc atcgttgtaa    1380

SEQ ID NO: 100             moltype = AA   length = 459
FEATURE                    Location/Qualifiers
MOD_RES                    288
                           note = Any amino acid
source                     1..459
                           mol_type = protein
                           organism = Stevia rebaudiana
SEQUENCE: 100
MENKTETTVR RRRRIILFPV PFQGHINPIL QLANVLYSKG FSITIFHTNF NKPKTSNYPH      60
FTFRFILDND PQDERISNLP THGPLAGMRI PIINEHGADE LRRELELLML ASEEDEEVSC     120
LITDALWYFA QSVADSLNLR RLVLMTSSLF NFHAHVSLPQ FDELGYLDPD DKTRLEEQAS    180
GFPMLKVKDI KSAYSNWQIL KEILGKMIKQ TKASSGVIWN SFKELEESEL ETVIREIPAP    240
SFLIPLPKHL TASSSSLLDH DRTVFQWLDQ QPPSSVLYVS FGSTSEVXDE KDFLEIARGL    300
VDSKQSFLWV VRPGFVKGST WVEPLPDGFV AERGRIVKWV PQQEVIAHGA IGAFWTHSGW    360
NSTLESVCEG VPMIFSDFGL DQPLNARYMS DVLKVGVYLE NGWERGEIAN AIRRVMVDEE    420
GEYIRQNARV LKQKADVSLM KGGSSYESLE SLVSYISSL                           459

SEQ ID NO: 101             moltype = DNA   length = 1380
FEATURE                    Location/Qualifiers
modified_base              861..863
                           mod_base = OTHER
```

```
                        note = a, c, t, g, unknown or other
source                  1..1380
                        mol_type = genomic DNA
                        organism = Stevia rebaudiana
SEQUENCE: 101
atggaaaata aaacggagac caccgttcgc cggcgccgga gaataatatt attcccggta    60
ccatttcaag gccacattaa cccaattctt cagctagcca atgtgttgta ctctaaagga   120
ttcagtatca ccatctttca caccaacttc aacaaaccca aaacatctaa ttaccctcac   180
ttcactttca gattcatcct cgacaacgac ccacaagacg aacgcatttc aatctaccg    240
actcatggtc cgctcgctgg tatgcggatt ccgattatca acgaacacgg agctgacgaa   300
ttacgacgcg aactggaact gttgatgtta gcttctgaag aagatgaaga ggtatcgtgt   360
ttaatcacga atgctctttg gtacttcgcg caatctgttg ctgacagtct aaacctccga   420
cggcttgttt tgatgacaag cagcttgttt aattttcatg cacatgtttc acttcctcag   480
tttgatgagc ttggttacct cgatcctgat gacaaaaccg gtttgaaaga acaagcggt    540
gggtttccta tgctaaaagt gaaagacatc aagtctgcgt attcgaactg gcaaatactc   600
aaagagatat tagggaagat gataaaacaa acaaaagcat cttcaggagt catctggaac   660
tcatttaagg aactcgaaga gtctgagctc gaaactgtta tccgtgagat cccggctcca   720
agtttcttga taccactccc caagcatttg acagcctcct ccagcagctt actagaccac   780
gatcgaaccg tttttcaatg gttagaccaa caaccgccaa gttcggtact gtatgttagt   840
tttggtagta ctagtgaagt nnnggatgag aaagattcct ggaaatagc tcgtgggttg    900
gttgatagca agcagtcgtt tttatgggtg gttcgacctg ggtttgtcaa gggttcgacg   960
tgggtcgaac cgttgccaga tgggttcttg ggtgaaagag gacgtattgt gaaatgggtt  1020
ccacagcaag aagtgctagc tcatggagca ataggcgcat tctggactca tagcggatgg  1080
aactctacgt tggaaagcgt tgtgaaggt gttcctatga ttttctcgga ttttgggctc    1140
gatcaaccgt tgaatgctag atacatgagt gatgttttga aggtagggt gtatttgaa     1200
aatgggtggg aaagaggaga gatagcaaat gcaataagag ggtattatgt ggatgaagaa  1260
ggagaataca ttagacagaa tgcaagagtt ttgaaacaaa aggcagatgt ttcttttgatg  1320
aagggtggtt cgtcttacga atcattagag tctctagttt cttacatttc atcgttgtaa  1380

SEQ ID NO: 102           moltype = AA   length = 459
FEATURE                  Location/Qualifiers
MOD_RES                  288
                         note = Any amino acid
source                   1..459
                         mol_type = protein
                         organism = Stevia rebaudiana
SEQUENCE: 102
MENKTETTVR RRRRIILFPV PFQGHINPIL QLANVLYSKG FSITIFHTNF NKPKTSNYPH    60
FTFRFILDND PQDERISNLP THGPLAGMRI PIINEHGADE LRRELELLML ASEEDEEVSC   120
LITDALWYFA QSVADSLNLR RLVLMTSSLF NFHAHVSLPQ FDELGYLDPD DKTRLEEQAS   180
GFPMLKVKDI KSAYSNWQIL KEILGKMIKQ TKASSGVIWN SFKELEESEL ETVIREIPAP   240
SFLIPLPKHL TASSSSLLDH DRTVFQWLDQ QPPSSVLYVS FGSTSEVXDE KDFLEIARGL   300
VDSKQSFLWV VRPGFVKGST WVEPLPDGFL GERGRIVKWV PQQEVLAHGA IGAFWTHSGW   360
NSTLESVCEG VPMIFSDFGL DQPLNARYMS DVLKVGVYLE NGWERGEIAN AIRRVMVDEE   420
GEYIRQNARV LKQKADVSLM KGGSSYESLE SLVSYISSL                          459

SEQ ID NO: 103           moltype = DNA   length = 1323
FEATURE                  Location/Qualifiers
misc_feature             1..1323
                         note = Description of Artificial Sequence: Synthetic
                          polynucleotide
source                   1..1323
                         mol_type = other DNA
                         organism = synthetic construct
SEQUENCE: 103
atgcattcta ccagacatat cttaagacaa agggccgtcc tagttacagg cgctagaaca    60
ccattcgtga aatcatttgg ggctcttatg aaagcagata ccttggaatt ggcatcagca   120
tcagtcgctg ggttgctgaa caagacctca ctggaccta gagatatcga tcatatcgtt   180
tggggtaatg ttgtacttca aggatcagct cataactgcg ccagagaaat agttatcgac   240
cttaacatgc ctaaaagat catcggtaat ttgacatcta tggcctgtgc ttcaggctta    300
tcttctttgt cacaagcctg tatgctaata gaggtggtc atgccgatgt cgtcattgct   360
ggcggttctg attcagtctc caacactgaa gtgcctttgc caagatcgt cacttacggt    420
ctaatgatgg cccaaaggaa gggtgttatg gcttctttta aggaagcagg atacaaccca   480
ttcaaatggt ttccaggcgg tattgcttta accgaacgta gtacaggaaa aactatgggt   540
tggcatggag acttaattgc tgagttaaac tctatatcta gagatgacca ggaagccctg   600
gctgtggctt ctcatgcaaa tgctgctaga gcagaaaaag ctgggtactt taaggaggaa   660
attgtacctg tgacaatcga caaaaagggc aaaaagactg agtaacatg tgatgatgtt    720
atgcaaagag atacagaaaa gatgaaggcc aagatgccat cattgaagcc tgttttcaga   780
aaagagggag gtacaataac agcagccact tccagtactc tgactgatgg tggctctgca   840
atgttggtta tgtcagagga aaaggccaaa aagtttgggtt atccaactga tgtctgcgtg   900
aagtcttggt atttcagtgg tatcgatcct tacccacaac ttttgttagc accagttcta   960
ggttggggtc cagcttttaa aaaggccgga ttaaccccta agatatcga tttgtacgaa   1020
attcacgaag catttgctgc acaagttcta gccacaatta gtgtttgaa gtctcaggaa  1080
ttcttcgata gtacgctaa cggtgcaaag ccagtattaa gtgatcttct                1140
aaactaaatg ttaatggcgg ttccttagca cttggccacc cattcgcgc tacaggaggt   1200
agaatcgtaa tctctctagc aaatgagttg agaagatccg gaaagagaca cgggctggtc  1260
agtatttgtg cagctggagg gttaggcgga gtagctatac ttgagcatac agcaagtaag  1320
taa                                                                 1323
```

-continued

```
SEQ ID NO: 104          moltype = AA   length = 440
FEATURE                 Location/Qualifiers
source                  1..440
                        mol_type = protein
                        organism = Leishmania infantum
SEQUENCE: 104
MHSTRHILRQ RAVLVTGART PFVKSFGALM KADTLELASA SVAGLLNKTS LDPRDIDHIV   60
WGNVVLQGSA HNCAREIVID LNMPKKIIGN LTSMACASGL SSLSQACMLI EGGHADVVIA  120
GGSDSVSNTE VPLPRSVTYG LMMAQRKGVM GFFKEAGYNP FKWFPGGIAL TERSTGKTMG  180
WHGDLIAELN SISRDDQEAL AVASHANAAR AEKAGYFKEE IVPVTIDKKG KKTEVTCDDV  240
MQRDTEKMKA KMPSLKPVFR KEGGTITAAT SSTLTDGGSA MLVMSEEKAK KLGYPTDVCV  300
KSWYFSGIDP YPQLLLAPVL GWGPALKKAG LTPKDIDLYE IHEAFAAQVL ATIKCLKSQE  360
FFDRYANGAK PVLTEDIDLS KLNVNGGSLA LGHPFAATGG RIVISLANEL RRSGKRHGLV  420
SICAAGGLGG VAILEHTASK                                             440

SEQ ID NO: 105          moltype = DNA   length = 1584
FEATURE                 Location/Qualifiers
misc_feature            1..1584
                        note = Description of Artificial Sequence: Synthetic
                        polynucleotide
source                  1..1584
                        mol_type = other DNA
                        organism = synthetic construct
SEQUENCE: 105
atggcagctg accaattggt gaaaactgaa gtcaccaaga agtcttttac tgctcctgta    60
caaaaggctt ctacaccagt tttaaccaat aaaaacagta tttctggatc gaaagtcaaa   120
agtttatcat ctgcgcaatc gagctcatca ggaccttcat catctagtga ggaagatgat   180
tcccgcgata ttgaaagctt ggataagaaa atacgtcctt tagaagaatt agaagcatta   240
ttaagtagtg gaaatacaaa acaattgaag aacaaagagg tcgctgcctt ggttattcac   300
ggtaagttac ctttgtacgc tttggagaaa aaattaggtg atactacgag agccggttcg   360
gtacgtagga aggctctttc aattttggca gaagctcctg tattagcatc tgatcgttta   420
ccatataaaa attatgacta cgaccgcgta tttggcgctt gttgtgaaaa tgttataggt   480
tacatgcctt tgcccgttgg tgttataggc cccttggtta tcgatggtac atcttatcat   540
ataccaatgg caactacaga gggttgtttg gtagcttcat ccatgcgtgg ctgtaaggca   600
atcaatgctg gcgtggtgc aacaactgtt ttaactaagg atggtatgac aagaggccca   660
gtagtccgtt tcccaacttt gaaaagatct ggtgcctgta agatatggtt agactcagaa   720
gagggacaaa acgcaattaa aaaagctttt aactctacat caagatttgc acgtctgcaa   780
catattcaaa cttgtctagc aggagattta ctcttcatga gatttagaac aactactggt   840
gacgcaatgg gtatgaatat gatttctaaa ggtgtcgaat actcattaaa gcaaatggta   900
gaagagtatg gctgggaaga tatggaggtt gtctccgttt ctggtaacta ctgtaccgac   960
aaaaaaccag ctgccatcaa ctggatcgaa ggtcgtggta agagtgtcgt cgcagaagct  1020
actattcctg gtgatgttgt cagaaaagtg ttaaaaagtg atgtttccgc attggttgag  1080
ttgaacattg ctaagaattt ggttggatct gcaatggctg ggtctgtttg tggatttaac  1140
gcacatgcag ctaatttagt gacagctgtt ttccttggcat taggacaaga tcctgcacaa  1200
aatgttgaaa gttccaactg tataacattg atgaaagaag tggacggtga tttgagaatt  1260
tccgtatcca tgcatccat cgaagtaggt accatcggtg tggtactgt tctagaacca  1320
caaggtgcca tgtggactt attaggtgta agaggcccgc atgtcaccgc tcctggtacc  1380
aacgcacgtc aattagcaag aatagttgcc tgtgccgtct tggcaggtga attatcctta  1440
tgtgctgccc tagcagccgg ccatttggtt caaagtcata tgaccacaa caggaaacct  1500
gctgaaccaa caaaacctaa caatttggac gccactgata taaatcgttt gaagatggg  1560
tccgtcacct gcattaaatc ctaa                                         1584

SEQ ID NO: 106          moltype = AA   length = 527
FEATURE                 Location/Qualifiers
source                  1..527
                        mol_type = protein
                        organism = Saccharomyces cerevisiae
SEQUENCE: 106
MAADQLVKTE VTKKSFTAPV QKASTPVLTN KTVISGSKVK SLSSAQSSSS GPSSSSEEDD   60
SRDIESLDKK IRPLEELEAL LSSGNTKQLK NKEAVALVIH GKLPLYALEK KLGDTTRAVA  120
VRRKALSILA EAPVLASDRL PYKNYDYDRV FGACCENVIG YMPLPVGVIG PLVIDGTSYH  180
IPMATTEGCL VASAMRGCKA INAGGGATTV LTKDGMTRGP VVRFPTLKRS GACKIWLDSE  240
EGQNAIKKAF NSTSRFARLQ HIQTCLAGDL LFMRFRTTTG DAMGMNMISK GVEYSLKQMV  300
EEYGWEDMEV VSVSGNYCTD KKPAAINWIE GRGKSVVAEA TIPGDVVRKV LKSDVSALVE  360
LNIAKNLVGS AMAGSVGGFN AHAANLVTAV FLALGQDPAQ NVESSNCITL MKEVDGDLRI  420
SVSMPSIEVG TIGGGTVLEP QGAMLDLLGV RGPHATAPGT NARQLARIVA CAVLAGELSL  480
CAALAAGHLV QSHMTHNRKP AEPTKPNNLD ATDINRLKDG SVTCIKS               527

SEQ ID NO: 107          moltype = DNA   length = 3681
FEATURE                 Location/Qualifiers
misc_feature            1..3681
                        note = Description of Artificial Sequence: Synthetic
                        polynucleotide
source                  1..3681
                        mol_type = other DNA
                        organism = synthetic construct
SEQUENCE: 107
atgagagctg tccttagatt gttatcaaca catactgttg tctctcctat tgaaacaatt    60
gtatctgttt tcgtgttagc tacattagct tacttccaca tcttgtccgg aatcaagcac   120
```

-continued

```
tcaagtttct ttgcatcttc tcatcctcct gctatcagac ctgcttttgc acatctgacc  180
aacggggaat gggttgccgt ctcccaacat gattggactg aagcatggaa gcatcctggc  240
ggttcacttg atgcattaga acttcaacaa gtagttttca ctttagatga caagactcaa  300
ccatctgctg tgctagatgc atccgcaatt agtcagcact tagttccaa tgttcctgca   360
ttatctggaa aagcctactc ttcattgtgc caccatccaa atgtatcagg cacctcctgt  420
tttacatcag tttctggtcc aggagcttca ccaatcttga cactgagttt taagcctgga  480
actagagacg attggttagg atcattaagg aaggagaaaa ctatcacact agatggggtt  540
aagtacgacg ttggagccgg aaaaagacaa gagtcaatcg gcgatatgga atcatctaag  600
tgggttgctt atgcattatc agctttggta cttagatttt gggaattaac aaaggcagat  660
tccttagata tactagtggt tctaactggg tacatcctaa tgcacgtaac attcatgaga  720
ttgttcttgg catccagagc acttggcagt aacttttggt tatcagctgg catattctcc  780
tccgcaacaa tttctttcct attcacttta ccaatgtgta gatctatgga tattccactt  840
gatccaattg ccttgacaga agccctgcca ttcttggtgt gtaccgtagg ttttgacaaa  900
ccacttagat tggcaagagc tgtgatggct catcctaata tccttaaacc tcaagatgat  960
ggtaggatga aagctgccgg agatgtcatt cttgaggcac tggacagagt tggtaacatg 1020
atattgagag attacgcttt agagatcgca gttctattcg ttggcgttaa ctccagagtt 1080
ggcggtctta aggaattttg tgctgtagct gcagcattac ttgctatgga cagattaatg 1140
acattcacac tttatacagc agtgttaacc atcatggttg aggtaaggcg tatcaaaaag 1200
gtcagagata tgactaaggc tagatctaga agttcttcta ttaccgccgt tacagccaac 1260
ggcaccgcca taagaggcgt tttgagtaga aaatcttcaa aacaatctgt gacagaacca 1320
gagacaacta aaaacctaag acaaagagcc actgattcag ccatcggtgt taagggttca 1380
ttgctgaaag atgaggcag attgcaggaa gccgaggaga atccaatggc aagattaaag 1440
ctattgttaa tcgcttcctt cttaacacta cacatcttga acttttgtac tactttgact 1500
tcagccacg ctaacgcaag acatcaaaga catccttta gaaccgttca agaggtagta  1560
ccaattccta gagttgacat tactaccca gccatagcca atatcttgtc tcatctagct  1620
gtggctcagg aacctatgtt cactgttgtt ggcagtgaac ctatcgaact tcttgttaaa 1680
gtcgctgctc cagtctacgt ccatgctcta ccattggccc ctgctttaag agcttcaaac 1740
actaatactg gagaagctat tgaaaacttt atgagttcat ggtctagtct ggtaggtgac 1800
ccagttgtta gtaagtggat cgtagcattg ctagctgtct ctgttgcatt gaatggatac 1860
ttgttaaagg gtatagccgc aggttccggg ttggctgcca tgagagctag tagatctcaa 1920
ggtgttcgtt tcagatctag agctagaagt atcgtaaaga tatctgatga acctgagcca 1980
gagccagaac actctatcga cccagccaca gtagtgttct tcgcttccgc agcaccagct 2040
gtagaggccc ctgctccagc tcctgcacct gaaccagaac caccagtcaa cagaccacca 2100
ccattgacta ttttctcaag accactgaac ttagaaacag tggacaaaaa gttacaagat 2160
gctctgccaa taagatcccc accacctgtt gaaccaatca ctccagaatc tagagaagtg 2220
gaaccaaccc aagtagaagt aagatctcta gctgaatgtg tggatgtgtt cgagaatggg 2280
ccaagaccag tctcagtggc tttaaagact ctgaatgatg aggaagttat cctgctttgc 2340
caaacaggta agatgctcc atatgcattg gttaagatgt tggctgattt cgatagggcc 2400
gtacgtgtca gaagagcact tattagtaga gcttcacgta caaaaactt agaaaactca 2460
ctggttccta tgaaagatta tgattacgcc agagtcatgg gtgcctgttg tgaaaacgtt 2520
atcggataca tgccattacc actagggatt gcaggtccat tgaagattga tggcttgatg 2580
tatcctatac aatggcaac cgcagaaggt accttggttg catctacttc tagggctgtg 2640
aaggccttaa atgctggtgg aggggtcaca actgtcttga cagcgatgg catgacaaga 2700
gggccagcta tagactttcc ttccatcgtc agagctgcag aggctaaggc cttcattgaa 2760
tcagaagatg gatacgctac aatcaggag gctttcgagt ctacttctag atttgccaag 2820
ttgcaaaaga tcagtgtgc actagctggt cgtactcttt ttgtcagatt tgctactaga 2880
acaggaggta ccatgggtat gaacatgatt tctaaggcta ccgaaaaggc acttgatgtc 2940
ctgagtcacg agttccctga atggtcgtc cttgctttgt ctggtaacta ctgcacagac 3000
aaaaagcctg cagctatttc atggatcgaa ggtaggggaa aatctattgt agcagaagca 3060
gttattcctg gtaaggtcgt taagtcagtc ctgaaaacaa cagtcgagtc tctttgcaat 3120
gtcaacacta agaaaaacct gattggttca gccatggca gttctgtttgg tggttttcaac 3180
gctcatgccg ccaacatcct aacagctgtg ttcctagcca caggtcagga tcctgctcaa 3240
aatgtcgaat cttctaattg catgacttta atggaaccaa caaacggcgg tgaggatttg 3300
ctaatgacaa tttcaatgcc atgtatagag gtaggaaccg ttggtggagg gacaattctg 3360
gaaccacaag gtgcagtttt ggatttgttg gcgttaaga gggtcaccc tactaatcct 3420
ggtcaaaacg ctcaacagtt agccagaatt atcgcatcg ctgtaatggc aggcgaattg 3480
tctttgataa gtgccttagc cgcaggtcat ttggttagag ctcatcttgc ccacaatcgt 3540
tctcaattga atacaccat gccatccaga ccacatactc ctggcctga ggatgtctca  3600
catgtgcagc agctacctac accatctgca tctgatgata aggtgttac agctcaaggt  3660
tacgttgtcg aagcaaaata a                                           3681
```

```
SEQ ID NO: 108          moltype = AA  length = 1226
FEATURE                 Location/Qualifiers
source                  1..1226
                        mol_type = protein
                        organism = Ganoderma lucidum
SEQUENCE: 108
MRAVLRLLST HTVFSPIETI VSVFVLATLA YFHILSGIKH SSFFASSHPP AIRPAFAHLT   60
NGEWVAVSQH DWTEAWKHPG GSLDALELQQ VVFTLDDKTQ PSAVLDASAI SQHLVSNVPA  120
LSGKAYSSLC HHPNVSGTSC FTSVSGPGAS PILTLSFKPG TRDDWLGSLR KEKTITLDGV  180
KYDVGAGKRQ ESIGDMESSK WVAYALSALV LRFWELTKAD SLDILVVLTG YILMHVTFMR  240
LFLASRALGS NFWLSAGIFS SATISFLFTL PMCRSMDIPL DPIALTEALP FLVCTVGFDK  300
PLRLARAVMA HPNILKPQDD GRMKAAGDVI LEALDRVGNM ILRDYALEIA VLFVGVNSRV  360
GGLKEFCAVA AALLAMDRLM TFTLYTAVLT IMVEVRRIKK VRDMTKARSR SSSITAVTAN  420
GTAIRGVLSR KSSKQSVTEP ETTKNLRQRA TDSAIGVKGS LLKDGGRLQE AEENPMARLK  480
LLLIASFLTL HILNFCTTLT SATANARHQR HPFRTVQEVV PIPRVDITTP AIANILSHLA  540
VAQEPMFTVV GSEPIELLVK VAAPVYVHAL PLAPALRASN TNTGEAIENF MSSWSSLVGD  600
PVVSKWIVAL LAVSVALNGY LLKGIAAGSG LAAMRAVRSQ GVRFRSRARS IVKISDEPEP  660
EPEHSIDPAP VVFFASAAPA VEAPAPAPAP EPEPPVNRPP PLTIFSRPLN LETVDKKLQD  720
```

```
ALPIRSPPPV EPITPESREV EPTQVEVRSL AECVDVFENG PRPVSVALKT LNDEEVILLC   780
QTGKIAPYAL VKMLADFDRA VRVRRALISR ASRTKTLENS LVPMKDYDYA RVMGACCENV   840
IGYMPLPLGI AGPLKIDGLM YPIPMATAEG TLVASTSRGC KALNAGGGVT TVLTADGMTR   900
GPAIDFPSIV RAAEAKAFIE SEDGYATIRE AFESTSRFAK LQKIKCALAG RTLFVRFATR   960
TGDAMGMNMI SKATEKALDV LSHEFPEMVV LALSGNYCTD KKPAAISWIE GRGKSIVAEA  1020
VIPGKVVKSV LKTTVESLCN VNTKKNLIGS AMAGSVGGFN AHAANILTAV FLATGQDPAQ  1080
NVESSNCMTL MEPTNGGEDL LMTISMPCIE VGTVGGGTIL EPQGAVLDLL GVRGAHPTNP  1140
GQNAQQLARI IASAVMAGEL SLISALAAGH LVRAHLAHNR SQLNTPMPSR PHTPGPEDVS  1200
HVQQLPTPSA SDDKGVTAQG YVVEAK                                      1226

SEQ ID NO: 109          moltype = DNA  length = 2667
FEATURE                 Location/Qualifiers
misc_feature            1..2667
                        note = Description of Artificial Sequence: Synthetic
                         polynucleotide
source                  1..2667
                        mol_type = other DNA
                        organism = synthetic construct
SEQUENCE: 109
atgttatcaa gattgttcag aatgcatggt ctatttgttg cttctcaccc ttgggaagta    60
atagttggta ctgtaacatt aacgatctgt atgatgtcta tgaacatgtt taccggaaac   120
aacaagattt gtgttggaa ttatgagtgt cctaagctgg aagaggatgt gttgagttca    180
gacatcatca tacttactat aacaagatgc attgcaatat tgtatatcta cttccaattt   240
caaaacctta gacaattggg tagtaaatac atcctaggca tcgccggatt gttcactatt   300
ttctctagtt ttgttttctc aaccgtcgtt attcactttt tggacaaaga gttaactggt   360
ttgaacgaag ctctaccatt cttcttgctg ctggtattgg tctccagagc ttccgcttta   420
gctaaattcg ctctgtcctc taattctcaa gatgaagtta gagagaatat agcaagggga   480
atggccatac ttgacctac tttcacactt gatgcccttg tcgaatgttt ggttattggg   540
gttggcacaa tgtccggcgt tagacagtta gaaatcatgt gttgttttgg ctgtatgagt   600
gtcttggcta actactttgt cttatgaca ttctttccag cttgcgtttc tttggtattg    660
gagctgtcaa gagaatcaag agaaggcaga ccaatatgag aactatcaca tttcgccaga   720
gtgttagaag aggaggaaaa caaacctaat cctgtcacac agagagtgaa aatgatcatg   780
tctttgggtt tagtcctagt gcatgctcat tctagatgga tcgcagatcc atcccctcag   840
aattctacag ctgataactc taaagttagt ttaggtttag tgaaaatgt aagtaaggag    900
attgaacctt ccgtgtcttt gtggcaattc tacttatcaa aaatgatttc catggatatt   960
gaacaagtga taacgttgtc tttggcttta ttgttagccg ttaagtacat tttctcttgag  1020
caagccgaaa cggaatctac attatcactg aaaaacccaa ttacatcccc agtcgttacc  1080
cagaaaaaga taactgatga ttgctgtaga agagatccag tgttggtcag aatgatcaa   1140
aagttccacg ccatggagga ggaaactagg aaaaacagag aaggaaagt tgaagttatc   1200
aagcctctat tagcagaaaa tgacacttca cataggggcca ctttcgttgt cggcaattca  1260
tctctttttag gtacgtcatt ggagctggaa acacaggaac cagaaatgga actaccagtt  1320
gaaccaagac caaatgagga atgtttgcaa atactagaga acgctgaaaa gggagccaag  1380
ttcctatctg atgccgagat tatccagctg gtcaatgcca agcacattcc tgcctacaag  1440
ttggaaaccc ttatggagac acatgagaga ggtgtgtcta ttaggagaca attactatct  1500
aaaaaagttac ctgaaccaag ttccctacaa tacctgcctt atagagatta caattactcc  1560
ttggtaatgg agcttgttg tgaaaatgtc attgggtaca tgccaattcc agtgggtgtc  1620
gccggtccac tatgtttgga cggtaaggaa tttcaagtac ctatggcaac gactgaaggc  1680
tgcttagttg catctacaaa cagaggttgt agagccattg gattaggtgg cggtgcttct  1740
tcaagagtct tggctgacgg tatgactaga ggtcctgttg tgagatttcc tagggcctgt  1800
gactctgcag aagttaaggc ttggttgaa actccagaag gtttcaccgt aatcaaagag  1860
gcctttgatt ccacatcaag ggtggccaga ttacaaaaac tacacatgtc tgtcgctgtg  1920
agaaatctgt atatcagatt tcaatccaga tccggcgacg caatgggtat gaatatgatt  1980
tcaaaaggga cagaaaaggc tttgtcaaag ctgcaggagt atttcccaga gatgcaaatc  2040
ttggccgtat ctggcaacta ttgcacagac aaaaagcctg ccgccatcaa ctggattgaa  2100
ggaagagcaa aatctgtggt ttgtgaagct gtaattccag ccaaagttgt tagagaagtg  2160
ttaaagacca caacagaagc tatgattgaa gtaaacataa acaaaaactt agtagggtct  2220
gccatggctg gttcaattgg aggatacaac gctcatgctg ccaatattgt aaccgctatc  2280
tacatcgcat gtgacaagaa tgctgcccaa aatgtcggtt cctcaaattg catcacattg  2340
atggaagcat ctggccctac aaacgaggat ttgtatatca gttgcacaat gccatctata  2400
gaaatagggga ctgtgggagg aggaactaac ttacttccac agcaagcctg cttacaaatg  2460
ctgggtgtac aaggagcctg tagagataat ccagggggaga acgctagaca acttgccaga  2520
attgttgtg ggacagttat ggctggtgaa cttagtctaa tggcagcttt ggctgctggg  2580
cacctggtga gatctcatat gattcataat agaagtaaga ttaaccttca agatttgcaa  2640
ggtacgtgta cgaaaaaggc tgcctaa                                      2667

SEQ ID NO: 110          moltype = AA  length = 888
FEATURE                 Location/Qualifiers
source                  1..888
                        mol_type = protein
                        organism = Bos taurus
SEQUENCE: 110
MLSRLFRMHG LFVASHPWEV IVGTVTLTIC MMSMNMFTGN NKICGWNYEC PKLEEDVLSS    60
DIIILTITRC IAILYIYFQF QNLRQLGSKY ILGIAGLFTI FSSFVFSTVV IHFLDKELTG   120
LNEALPFFLL LVDLSRASAL AKFALSSNSQ DEVRENIARG MAILGPTFTL DALVECLVIG   180
VGTMSGVRQL EIMCCFGCMS VLANYFVFMT FFPACVSLVL ELSRESREGR PIWQLSHFAR   240
VLEEEENKPN PVTQRVKMIM SLGLVLVHAH SRWIADPSPQ NSTADNSKVS LGLDENVSKR   300
IEPSVSLWQF YLSKMISMDI EQVITLSLAL LLAVKYIFFE QAETESTLSL KNPITSPVVT   360
QKKITDDCCR RDPVLVRNDQ KFHAMEEETR KNRERKVEVI KPLLAENDTS HRATFVVGNS   420
SLLGTSLELE TQEPEMELPV EPRPNEECLQ ILENAEKGAK FLSDAEIIQL VNAKHIPAYK   480
```

```
LETLMETHER GVSIRRQLLS KKLPEPSSLQ YLPYRDYNYS LVMGACCENV IGYMPIPVGV    540
AGPLCLDGKE FQVPMATTEG CLVASTNRGC RAIGLGGGAS SRVLADGMTR GPVVRFPRAC    600
DSAEVKAWLE TPEGFTVIKE AFDSTSRVAR LQKLHMSVAG RNLYIRFQSR SGDAMGMNMI    660
SKGTEKALSK LQEYFPEMQI LAVSGNYCTD KKPAAINWIE GRGKSVVCEA VIPAKVVREV    720
LKTTTEAMIE VNINKNLVGS AMAGSIGGYN AHAANIVTAI YIACGQDAAQ NVGSSNCITL    780
MEASGPTNED LYISCTMPSI EIGTVGGGTN LLPQQACLQM LGVQGACRDN PGENARQLAR    840
IVCGTVMAGE LSLMAALAAG HLVRSHMIHN RSKINLQDLQ GTCTKKAA                 888

SEQ ID NO: 111           moltype = DNA  length = 1704
FEATURE                  Location/Qualifiers
misc_feature             1..1704
                         note = Description of Artificial Sequence: Synthetic
                         polynucleotide
source                   1..1704
                         mol_type = other DNA
                         organism = synthetic construct
SEQUENCE: 111
atggatttga gaaggaaatt accacctaag cctccatctt caacaacaac aaaacagcca     60
agtcataggt cccattctcc tacgccaatt ccaaaggctt cagatgcatt gcctcttcca    120
ttgtacctga ccaatacgtt tttcttcact cttttctttt ccgtagcata ttacctgttg    180
cataggtgga gagacaagat tagatccgga cacctttac acgttgtgac actgactgaa     240
ctatccgcaa ttgtactgct gattgcttcc ttcatctatc ttttaggctt tttcggtatt    300
gattttgtgc aatctttcac atcaagagaa aatgagcaac taaacaacga tgatcacaac    360
gtcgtgtcaa caaacaatgt tttatctgat agaaggttag tttacgacta tggattcgat    420
gtgacaggag acaacgataa cgataatgat gacgatgtta ttgtgaaaag tgtcgtttct    480
ggggaagtta attcttatag tttggaggct tccctaggag attgttacag agccgcaaag    540
attagaaaga gagccgtcga gagaattgtc gggagagaaa tattaggctt gggtttcgag    600
ggatttgatt atgaatctat cctggggcaa tgttgtgaaa tgcctatcgg gtacgtccaa    660
gtgccagtag gtgtcgctgg accttttattg ttaaatggtg gggaattcat ggttccaatg    720
gctacaactg aaggctgtct tgtagcttcc actaataga gttgtaaagc catatgctta    780
tcaggtggtg ccactgccat attgctaaaa gatggtatga caagagcccc agtagtgaga    840
ttcgccacag ctgagagagc ttcacaacta aagttttact tggaagatgg tgtcaatttc    900
gatacattgt ctgttgtctt taacaaaagt tcaagatttg ccagattgca aaacatccaa    960
tgctcaattg ccggtaaaaa cttgtacatt aggtttactt gctccacagg cgacgccatg   1020
ggtatgaaca tggtttcaaa aggagtacaa aatgtattga acttttaca aaaatgatttt   1080
cctgatatgg acgtaattgg gatctcttgg aagttctgct ctgacaaaaa gccaacagct   1140
gtcaactgga ttgagggcag aggaaagtct gtcgttttcc aggccgtaat taccaaaaag   1200
gtggttagaa agtctgcact gaaccctcaa acttgcacat gtagaacttt gacctgttta   1260
agaccattat tggttctgct acttctggtt ttgcctagtag acttaatgca tatgcttcat   1320
atcgtgtctg ccgtgttcat cgctaccggt caagatccag ctcagaatat cgaattcagt   1380
cactgtatca ctatgatgga ggctgtcaac aatggtaagg atttgcacgt taatgttacg   1440
atgccatcta tagaagttgg cacggtggga ggtggcactc agctagcctc tcaatcagcc   1500
tgtttgaact tgcttggtgt aaagggtgcc tgtatagaat ccccaggatc aaacgcccaa   1560
ttgttagcta gaatcgttgc tggttctgtt ctggcaggcg aattaagttt gatgctcagct   1620
ataagtgctg gcaactagt taaatctcat atgaaataca ataggtctag tagagatatg    1680
tcagcaatag cttctaaggt ctaa                                          1704

SEQ ID NO: 112           moltype = AA  length = 567
FEATURE                  Location/Qualifiers
source                   1..567
                         mol_type = protein
                         organism = Artemisia annua
SEQUENCE: 112
MDLRRKLPPK PPSTTTKQP SHRSHSPTPI PKASDALPLP LYLTNTFFFT LFFSVAYYLL     60
HRWRDKIRSG TPLHVVTLTE LSAIVLLIAS FIYLLGFFGI DFVQSFTSRE NEQLNNDDHN    120
VVSTNNVLSD RRLVYDYGFD VTGDNDNDND DDVIVKSVVS GEVNSYSLEA SLGDCYRAAK    180
IRKRAVERIV GREVLGLGFE GFDYESILGQ CCEMPIGYVQ VPVGVAGPLL LNGGEFMVPM    240
ATTEGCLVAS TNRGCKAICL SGGATAILLK DGMTRAPVVR FATAERASQL KFYLEDGVNF    300
DTLSVVFNKS SRFARLQNIQ CSIAGKNLYI RFTCSTGDAM GMNMVSKGVQ NVLDFLQNDF    360
PDMDVIGISW KFCSDKKPTA VNWIEGRGKS VVFQAVITKK VVRKSALNPQ TCTCRTLTCL    420
RPLLVLLLLV LLVDLMHMLH IVSAVFIATG QDPAQNIESS HCITMMEAVN NGKDLHVNVT    480
MPSIEVGTVG GGTQLASQSA CLNLLGVKGA CIESPGSNAQ LLARIVAGSV LAGELSLMSA    540
ISAGQLVKSH MKYNRSSRDM SAIASKV                                       567

SEQ ID NO: 113           moltype = DNA  length = 1308
FEATURE                  Location/Qualifiers
misc_feature             1..1308
                         note = Description of Artificial Sequence: Synthetic
                         polynucleotide
source                   1..1308
                         mol_type = other DNA
                         organism = synthetic construct
SEQUENCE: 113
atgtttagaa gagctatact gttaggatgc tctgctgcca agacaccatg gtctgagtgt     60
tctaacgctc aattagttga tgcagttaag tctagaaaga tctcattcta cggtcttgaa    120
caagccttgg aaccagatta tagaagggct atcgaagtaa ggagagaggt tgtctctgaa    180
atcgcctcac aacagccaga agcaaaaaag aagcaatccg cattgcacac aataccatt     240
gagaattatg attggaataa ggtcgttggc caaaactgtg aaaacattat tggatacgtc    300
ccaataccac tgggcgttgc tggccctatt ttgattgatg gtaaagagta cccaatacca    360
```

```
atggctacaa cagaaggcgc tttggtcgct agtactcata gaggtgctag agctattaca   420
agatccggag gttgtaagac attgttatta ggtgaaggta tgacaagagc accagtggtt   480
gaattgcctt cattagagga agctgggcgt tgcacaagt actgtaatga aacttctta    540
tctttaaagg aagcatttga atcaactacc caatatggaa aacttaattc tttaaagtgc   600
gtactagctg gtagaaaagc ataccttaga ttcagagcca ctacaggcga tgctatgggc   660
atgaacatga taacaaaggg tgtagacaaa gcactgtctg ttctacagca acatttccct   720
tcaatggaaa tcctagccct aagtggtaat tactgtaccg acaaaaagcc atctgctgta   780
aattggatta tggcagagg taaatcagtg gttgcagaag ccactttatt ggctgatgtt    840
gtcgaagata ctctgaaatg tacagtcgat tctttggtat ccttgaatat cgacaaaaac   900
cttgttgggt cagctatggc tggttctgtt ggaggtttta acgcccaggc tgcaaacgct   960
gtggcagcca ttttcattgc aaccggtcaa gatcctgctc aagtggtaga aagttcaatg  1020
tgtatcacta caatgtccaa ggtaggtaac gatctattga tctctgtgac catgccttct  1080
atcgaggtcg ggtcgtggg aggagggact ggtcttgctg cccaaagagg atgcttagag   1140
ttaataggg gcggaggccc atctaaggag tctcctggta ctaatgccca acttctaagt   1200
agagttgttg cagctggcgt tttatcagcc gaacttcct tgatgtccgg actggcagca   1260
ggtcatctat tgtcagcaca tatgagattg aacagaaaga gaaataa              1308

SEQ ID NO: 114           moltype = AA   length = 435
FEATURE                  Location/Qualifiers
source                   1..435
                         mol_type = protein
                         organism = Trypanosoma cruzi
SEQUENCE: 114
MFRRAILLGC SAAKTPWSEC SNAQLVDAVK SRKISFYGLE QALEPDYRRA IEVRREVVSE    60
IASQQPEAKK KQSALHTIPF ENYDWNKVVG QNCENIIGYV PIPLGVAGPI LIDGKEYPIP   120
MATTEGALVA STHRGARAIT RSGGCKTLLL GEGMTRAPVV ELPSLEEAGR LHKYCNENFL   180
SLKEAFESTT QYGKLNSLKC VLAGRKAYLR FRATTGDAMG MNMITKGVDK ALSVLQQHFP   240
SMEILALSGN YCTDKKPSAV NWIDGRGKSV VAEATLLADV VEDTLKCTVD SLVSLNIDKN   300
LVGSAMAGSV GGFNAQAANA VAAIFIATGQ DPAQVVESSM CITTMSKVGN DLLISVTMPS   360
IEVGVVGGGT GLAAQRGCLE LIGCGGPSKE SPGTNAQLLS RVVAAGVLSA ELSLMSGLAA   420
GHLLSAHMRL NRKKK                                                   435

SEQ ID NO: 115           moltype = DNA   length = 1281
FEATURE                  Location/Qualifiers
misc_feature             1..1281
                         note = Description of Artificial Sequence: Synthetic
                         polynucleotide
source                   1..1281
                         mol_type = other DNA
                         organism = synthetic construct
SEQUENCE: 115
atgcaatccc tggacaaaaa ctttagacac ttatcaagac aacagaagtt acaacagcta    60
gttgataaac aatggctatc agaggaacaa ttcaatattc tacttaacca cccacttatt   120
gatgaagagg tagcaaactc attgatagaa aatgtcatcg cacagggcgc actgcctgtt   180
ggtttactac caaatatcat cgttgatgac aaagcatacg tcgtgccttat gatggtggaa   240
gagccatctg ttgttgccgc tgcttcatac ggcgctaaat tggtaaacca aacaggtggt   300
ttcaaaaccg tgtcctcaga acgtatcatg ataggtcaaa tagtatttga tggagtcgat   360
gataccgaga aactgtctgc agatatcaag gctcttgaaa aacaaatcca tcagattgca   420
gatgaggctt acccttctat taaggccaga ggtggaggct atcaaaggat cgccatcgat   480
acattcccag aacaacagtt gctttcattg aaggttttcg ttgatactaa ggatgctatg   540
ggcgctaata tgttaaacac aatcctagaa gcaatcacag ccttttttga aaacgaattc   600
ccacaatctg atatcttgat gtctatcctt tccaaccacg caacagccag tgttgtcaag   660
gtccagggtg aaatagacgt taaggatttg gcaagaggag aacgtactgg agaagaggtc   720
gctaagagaa tggaaagagc atctgtgtta gctcaagtgg acattcatag agcagcaaca   780
cacaataagg tgttatgaa tggcattcat gctgtagtct tggctacagg taatgatact   840
agaggtgcag aagcctctgc tcacgcttac gcttccaaag acggtcaata tagagggata   900
gctacatgga gatacgatca agagagacaa aggttaatag gaactataga agttccaatg   960
actctgcca ttgttggtgg cggtaccaag gtactgccta ttgctaaggc ctctttagaa  1020
ctgttaaacg tagaaagtgc ccaagagttg ggacatgttg tcgctgccgt tggactagct  1080
caaaacttcg ctgcatgtag agctttggtt tccgaaggta ttcaacaagg gcatatgtct  1140
ttgcaataca gtctttagc catcgtagtc ggggctaagg gcgatgaaat tgctcaggta  1200
gccgaagcac taaagcaaga gccaagagca aacactcaag ttgcagagag aattttgcaa  1260
gatttgagaa gtcaacaata a                                           1281

SEQ ID NO: 116           moltype = AA   length = 426
FEATURE                  Location/Qualifiers
source                   1..426
                         mol_type = protein
                         organism = Staphylococcus aureus
SEQUENCE: 116
MQSLDKNFRH LSRQQKLQQL VDKQWLSEEQ FNILLNHPLI DEEVANSLIE NVIAQGALPV    60
GLLPNIIVDD KAYVVPMMVE EPSVVAAASY GAKLVNQTGG FKTVSSERIM IGQIVFDGVD   120
DTEKLSADIK ALEKQIHQIA DEAYPSIKAR GGGYQRIAID TFPEQQLLSL KVFVDTKDAM   180
GANMLNTILE AITAFLKNEF PQSDILMSIL SNHATASVVK VQGEIDVKDL ARGERTGEEV   240
AKRMERASVL AQVDIHRAAT HNKGVMNGIH AVVLATGNDT RGAEASAHAY ASKDGQYRGI   300
ATWRYDQERQ RLIGTIEVPM TLAIVGGGTK VLPIAKASLE LLNVESAQEL GHVVAAVGLA   360
QNFAACRALV SEGIQQGHMS LQYKSLAIVV GAKGDEIAQV AEALKQEPRA NTQVAERILQ   420
DLRSQQ                                                             426
```

| SEQ ID NO: 117 | moltype = DNA length = 1311 |
|---|---|
| FEATURE | Location/Qualifiers |
| misc_feature | 1..1311 |
| | note = Description of Artificial Sequence: Synthetic polynucleotide |
| source | 1..1311 |
| | mol_type = other DNA |
| | organism = synthetic construct |

SEQUENCE: 117

```
atgcaggtct taagattgga taggagacat tacaaaagtg gcaagattag aagagcaatg    60
agttctagaa ttcctggttt ctacaaattg tcagtcgagg aaagactgaa aaaggttgct   120
gaatttgcag ggttatctga tgaggaagtg aaagctgttt tgtcacaagg tttacctttg   180
gacgtagctg atagaatgat cgaaaatgtg atcggtacat ttgaattacc acttggtata   240
gcaaccaatt tccttattga tggcaaggat tatctaatcc ctatggctat agaggaacca   300
tcagtagttg cagctgcttc taacgcagct agaatggcca gagagtctgg cgggtttaca   360
actgattaca cagggtccct gatgattggt caaattcaag tcacaaaact gttgaatcca   420
aatgcagcta agttcgaagt tctacgtcaa aaagacgaaa tcatagaaag agcaaatgag   480
tgtgatccaa tgttggtgaa tttgggcggt ggatgtaaag atatagaagc aagggtgatc   540
gatacaatca tgggtaagat gctaattgtt catctgatcg ttgatgttaa agacgctatg   600
ggtgcaaatg ctgtcaacac tatgtgtgaa aagttgctc ctttcatcga acgtattact    660
gggggaaagg tctatcttag aatcatttcc aacttggctg catatagact tgctagagca   720
aaggccgttt ttgacaaaga cgttattggc ggagaggagg ttgtagaagg gatcatgctt   780
gcatacgcct tcgctgccgc tgacccattt cgttgcgcca cccacaataa gggtatcatg   840
aatggcatat cagccttaat gatcgctaca ggaaacgact ttagagccat tgaagcagga   900
gctcattcct atgctgcaat aggtggatac aaaccactaa ctacctacga agttgataga   960
aaaggtaatc tagtaggcac aattgaaata cctatgcag taggcgtgat tggtggtgca   1020
accaaagtca acccactagc caagatctct cttaagatac taggagtgaa cactgctgaa  1080
gagttagcca gagtcgcagc cgctctaggt ttggctcaaa actttgctgc cttaagagcc  1140
ttggccacag aaggtatcca aagaggtcac atggaattac atgccaggaa cttagcaatc  1200
atggctggag ctactggaga tgaggttgac agagttgtag agattatggt gagagatggc  1260
aaaatcgat tggactacgc taaggaagta ttggagagac tgcgttccta a            1311
```

| SEQ ID NO: 118 | moltype = AA length = 436 |
|---|---|
| FEATURE | Location/Qualifiers |
| source | 1..436 |
| | mol_type = protein |
| | organism = Archaeoglobus fulgidus |

SEQUENCE: 118

```
MQVLRLDRRH YKSGKIRRAM SSRIPGFYKL SVEERLKKVA EFAGLSDEEV KAVLSQGLPL    60
DVADRMIENV IGTFELPLGI ATNFLIDGKD YLIPMAIEEP SVVAAASNAA RMARESGGFT   120
TDYTGSLMIG QIQVTKLLNP NAAKFEVLRQ KDEIIERANE CDPMLVNLGG GCKDIEARVI   180
DTIMGKMLIV HLIVDVKDAM GANAVNTMCE KVAPFIERIT GGKVYLRIIS NLAAYRLARA   240
KAVFDKDVIG GEEVVEGIML AYAFAAADPF RCATHNKGIM NGISALMIAT GNDFRAIEAG   300
AHSYAAIGGY KPLTTYEVDR KGNLVGTIEI PMAVGVIGGA TKVNPLAKIS LKILGVNTAE   360
ELARVAAALG LAQNFAALRA LATEGIQRGH MELHARNLAI MAGATGDEVD RVVEIMVRDG   420
KIRLDYAKEV LERLRS                                                  436
```

| SEQ ID NO: 119 | moltype = DNA length = 1287 |
|---|---|
| FEATURE | Location/Qualifiers |
| misc_feature | 1..1287 |
| | note = Description of Artificial Sequence: Synthetic polynucleotide |
| source | 1..1287 |
| | mol_type = other DNA |
| | organism = synthetic construct |

SEQUENCE: 119

```
atgtccttag attcaagact gccagctttc agaaatctgt ctccagctgc aagactagat    60
cacattggcc aacttttggg actaagtcat gacgacgttt ccctttagc aaacgccggt    120
gctttaccaa tggatatcgc taatggtatg attgaaaatg taatcgggac ctttgaactg   180
ccatatgcaa tggccagtaa cttttcagatc aatggccgtg acgtcttagt accattagtt   240
gtggaggaac ctagtatcgt tgctgcagcc tcttacatgg caaagttagc tagagccaat   300
ggtgggttca ctcacatcttc atctgctcca ctaatgcatg cacaagtaca aattgtcggc   360
attcaggatc cactaaacgc aagattgtct ttactgcgta gaaaggatga gatcatgaaa   420
ttagccaata ggaaggacca acttctgaat tcattgggcg gtggttgcag agacatgaag   480
gtgcatacat ttgccgatac tccaagagga ccaatgcttg tagcacacct tatttgtgat   540
gtgcgtgatg ccatgggagc taatactgtt aacactatgg ctgaagcagt agcacctctg   600
atggaagcca taacaggtgg ccaggtaaga ttgagaatcc tttccaattt ggctgatctt   660
agattggcca gagcccaagt gagaactcact cctcagcaat tggaaactgc cgaattctca   720
ggtgaggcag taattgaggg tatcttggac gcatatgctt ttgccgctgt ggacccttac   780
agagccgcta cccacaacaa aggcataatg aacggtatcg atcctttgat cgtcgctaca   840
ggaaatgatt tcagagctgt tgaggcagga gctcatgcat acgcttgtag atccggacat   900
tacggttcat taacaacatg gaaaagagat aacaatggac acttggtcgg acattggaa   960
atgcctatgc cagttggttt agttgggggt gctacaaaaa ccatcctct tgctcaattg   1020
tctttgagga tacttggtgt caaaactgct caagcactag ccgaaattgc cgttgctgtt  1080
ggtttggcac aaaacttggg tgcaatgcgt gctttagcta cagaaggcat ccaaagagga  1140
catatgctc tacacgctag aaacattgca gttgttgcag gagccagagg tgatgaggtt  1200
gattgggtgg ctagacaact tgtcgaatat catgatgtca gagcagacag ggctgtggca  1260
ttactgaaac agaagagagg tcaataa                                      1287
```

```
SEQ ID NO: 120           moltype = AA   length = 428
FEATURE                  Location/Qualifiers
source                   1..428
                         mol_type = protein
                         organism = Pseudomonas mevalonii
SEQUENCE: 120
MSLDSRLPAF RNLSPAARLD HIGQLLGLSH DDVSLLANAG ALPMDIANGM IENVIGTFEL    60
PYAVASNFQI NGRDVLVPLV VEEPSIVAAA SYMAKLARAN GGFTTSSSAP LMHAQVQIVG   120
IQDPLNARLS LLRRKDEIIE LANRKDQLLN SLGGGCRDIE VHTFADTPRG PMLVAHLIVD   180
VRDAMGANTV NTMAEAVAPL MEAITGGQVR LRILSNLADL RLARAQVRIT PQQLETAEFS   240
GEAVIEGILD AYAFAAVDPY RAATHNKGIM NGIDPLIVAT GNDWRAVEAG AHAYACRSGH   300
YGSLTTWEKD NNGHLVGTLE MPMPVGLVGG ATKTHPLAQL SLRILGVKTA QALAEIAVAV   360
GLAQNLGAMR ALATEGIQRG HMALHARNIA VVAGARGDEV DWVARQLVEY HDVRADRAVA   420
LLKQKRGQ                                                            428

SEQ ID NO: 121           moltype = AA   length = 361
FEATURE                  Location/Qualifiers
source                   1..361
                         mol_type = protein
                         organism = Stevia rebaudiana
SEQUENCE: 121
MALVNPTALF YGTSIRTRPT NLLNPTQKLR PVSSSSLPSF SSVSAILTEK HQSNPSENNN    60
LQTHLETPFN FDSYMLEKVN MVNEALDASV PLKDPIKIHE SMRYSLLAGG KRIRPMMCIA   120
ACEIVGGNIL NAMPAACAVE MIHTMSLVHD DLPCMDNDDF RRGKPISHKV YGEEMAVLTG   180
DALLSLSFEH IATATKGVSK DRIVRAIGEL ARSVGSEGLV AGQVVDILSE GADVGLDHLE   240
YIHIHKTAML LESSVVIGAI MGGGSDQQIE KLRKFARSIG LLFQVVDDIL DVTKSTEELG   300
KTAGKDLLTD KTTYPKLLGI EKSREFAEKL NKEAQEQLSG FDRRKAAPLI ALANYNAYRQ   360
N                                                                   361

SEQ ID NO: 122           moltype = AA   length = 342
FEATURE                  Location/Qualifiers
source                   1..342
                         mol_type = protein
                         organism = Gibberella fujikuroi
SEQUENCE: 122
MAEQQISNLL SMFDASHASQ KLEITVQMMD TYHYRETPPD SSSSEGGSLS RYDERRVSLP    60
LSHNAASPDI VSQLCFSTAM SSELNHRWKS QRLKVADSPY NYILTLPSKG IRGAFIDSLN   120
VWLEVPEDET SVIKEVIGML HNSSLIIDDF QDNSPLRRGK PSTHTVFGPA QAINTATYVI   180
VKAIEKIQDI VGHDALADVT GTITTIFQGQ AMDLWWTANA IVPSIQEYLL MVNDKTGALF   240
RLSLELLALN SEASISDSAL ESLSSAVSLL GQYFQIRDDY MNLIDNKYTD QKGFCEDLDE   300
GKYSLTLIHA LQTDSSDLLT NILSMRRVQG KLTAQKRCWF WK                      342

SEQ ID NO: 123           moltype = AA   length = 300
FEATURE                  Location/Qualifiers
source                   1..300
                         mol_type = protein
                         organism = Mus musculus
SEQUENCE: 123
MEKTKEKAER ILLEPYRYLL QLPGKQVRSK LSQAFNHWLK VPEDKLQIII EVTEMLHNAS    60
LLIDDIEDSS KLRRGFPVAH SIYGVPSVIN SANYVYFLGL EKVLTDHPD AVKLFTRQLL    120
ELHQGQGLDI YWRDTYTCPT EEEYKAMVLQ KTGGLFGLAV GLMQLFSDYK EDLKPLLDTL   180
GLFFQIRDDY ANLHSKEYSE NKSFCEDLTE GKFSFPTIHA IWSRPESTQV QNILRQRTEN   240
IDIKKYCVQY LEDVGSFAYT RHTLRELEAK AYKQIEACGG NPSLVALVKH LSKMFTEENK   300

SEQ ID NO: 124           moltype = AA   length = 339
FEATURE                  Location/Qualifiers
source                   1..339
                         mol_type = protein
                         organism = Thalassiosira pseudonana
SEQUENCE: 124
MARFYFLNAL LMVISLQSTT AFTPAKLAYP TTTTALNVAS AETSFSLDEY LASKIGPIES    60
ALEASVKSRI PQTDKICESM AYSLMAGGKR IRPVLCIAAC EMFGGSQDVA MPTAVALEMI   120
HTMSLIHDDL PSMDNDDLRR GKPTNHVVFG EDVAILAGDS LLSTSFEHVA RETKGVSAEK   180
IVDVIARLGK SVGAEGLAGG QVMDLECEAK PGTTLDDLKW IHIHKTATLL QVAVASGAVL   240
GGATPEEVAA CELFAMNIGL AFQVADDILD VTASSEDLGK TAGKDEATDK TTYPKLLGLE   300
ESKAYARQLI DEAKESLAPF GDRAAPLLAI ADFIIDRKN                          339

SEQ ID NO: 125           moltype = AA   length = 355
FEATURE                  Location/Qualifiers
source                   1..355
                         mol_type = protein
                         organism = Streptomyces clavuligerus
SEQUENCE: 125
MHLAPRRVPR GRRSPPDRVP ERQGALGRRR GAGSTGCARA AAGVHRRRGG GEADPSAAVH    60
RGWQAGGGTG LPDEVVSTAA ALEMFHAFAL IHDDIMDDSA TRRGSPTVHR ALADRLGAAL   120
DPDQAGQLGV STAILVGDLA LTWSDELLYA PLTPHRLAAV LPLVTAMRAE TVHGQYLDIT   180
SARRPGTDTS LALRIARYKT AAYTMERPLH IGAALAGARP ELLAGLSAYA LPAGEAFQLA   240
DDLLGVFGDP RRTGKPDLDD LRGGKHTVLV ALAREHATPE QRHLDTLLG TPGLDRQGAS    300
RLRCVLVATG ARAEAERLIT ERRDQALTAL NALTLPPPLA EALARLTLGS TAHPA         355
```

```
SEQ ID NO: 126            moltype = AA   length = 330
FEATURE                   Location/Qualifiers
source                    1..330
                          mol_type = protein
                          organism = Sulfulobus acidicaldarius
SEQUENCE: 126
MSYFDNYFNE IVNSVNDIIK SYISGDVPKL YEASYHLFTS GGKRLRPLIL TISSDLFGGQ   60
RERAYYAGAA IEVLHTFTLV HDDIMDQDNI RRGLPTVHVK YGLPLAILAG DLLHAKAFQL  120
LTQALRGLPS ETIIKAFDIF TRSIIIISEG QAVDMEFEDR IDIKEQEYLD MISRKTAALF  180
SASSSIGALI AGANDNDVRL MSDFGTNLGI AFQIVDDILG LTADEKELGK PVFSDIREGK  240
KTILVIKTLE LCKEDEKKIV LKALGNKSAS KEELMSSADI IKKYSLDYAY NLAEKYYKNA  300
IDSLNQVSSK SDIPGKALKY LAEFTIRRRK                                  330

SEQ ID NO: 127            moltype = AA   length = 297
FEATURE                   Location/Qualifiers
source                    1..297
                          mol_type = protein
                          organism = Synechococcus sp.
SEQUENCE: 127
MVAQTFNLDT YLSQRQQQVE EALSAALVPA YPERIYEAMR YSLLAGGKRL RPILCLAACE   60
LAGGSVEQAM PTACALEMIH TMSLIHDDLP AMDNDDFRRG KPTNHKVFGE DIAILAGDAL  120
LAYAFEHIAS QTRGVPPQLV LQVIARIGHA VAATGLVGGQ VVDLESEGKA ISLETLEYIH  180
SHKTGALLEA SVVSGGILAG ADEELLARLS HYARDIGLAF QIVDDILDVT ATSEQLGKTA  240
GKDQAAAKAT YPSLLGLEAS RQKAEELIQS AKEALRPYGS QAEPLLALAD FITRRQH     297

SEQ ID NO: 128            moltype = AA   length = 371
FEATURE                   Location/Qualifiers
source                    1..371
                          mol_type = protein
                          organism = Arabidopsis thaliana
SEQUENCE: 128
MASVTLGSWI VVHHHNHHHP SSILTKSRSR SCPITLTKPI SFRSKRTVSS SSSIVSSSVV   60
TKEDNLRQSE PSSFDPMSYI ITKAELVNKA LDSAVPLREP LKIHEAMRYS LLAGGKRVRP  120
VLCIAACELV GGEESTAMPA ACAVEMIHTM SLIHDDLPCM DNDDLRRGKP TNHKVFGEDV  180
AVLAGDALLS FAFEHLASAT SSDVVSPVRV VRAVGELAKA IGTEGLVAGQ VVDISSEGLD  240
LNDVGLEHLE FIHLHKTAAL LEASAVLGAI VGGGSDDEIE RLRKFARCIG LLFQVVDDIL  300
DVTKSSKELG KTAGKDLIAD KLTYPKIMGL EKSREFAEKL NREARDQLLG FDSDKVAPLL  360
ALANYIAYRQ N                                                      371

SEQ ID NO: 129            moltype = AA   length = 787
FEATURE                   Location/Qualifiers
source                    1..787
                          mol_type = protein
                          organism = Stevia rebaudiana
SEQUENCE: 129
MKTGFISPAT VFHHRISPAT TFRHHLSPAT TNSTGIVALR DINFRCKAVS KEYSDLLQKD   60
EASFTKWDDD KVKDHLDTNK NLYPNDEIKE FVESVKAMFG SMNDGEINVS AYDTAWVALV  120
QDVDGSGSPQ FPSSLEWIAN NQLSDGSWGD HLLFSAHDRI INTLACVIAL TSWNVHPSKC  180
EKGLNFLREN ICKLEDENAE HMPIGFEVTF PSLIDIAKKL NIEVPEDTPA LKEIYARRDI  240
KLTKIPMEVL HKVPTTLLHS LEGMPDLEWE KLLKLQCKDG SFLFSPSSTA FALMQTKDEK  300
CLQYLTNIVT KFNGGVPNVY PVDLFEHIWV VDRLQRLGIA RYFKSEIKDC VEYINKYWTK  360
NGICWARNTH VQDIDDTAMG FRVLRAHGYD VTPDVFRQFE KDGKFVCFAG QSTQAVTGMF  420
NVYRASQMLF PGERILEDAK KFSYNYLKEK QSTNELLDKW IIAKDLPGEV GYALDIPWYA  480
SLPRLETRYY LEQYGGEDDV WIGKTLYRMG YVSNNTYLEM AKLDYNNYVA VLQLEWYTIQ  540
QWYVDIGIEK FESDNIKSVL VSYYLAAASI FEPERSKERI AWAKTTILVD KITSIFDSSQ  600
SSKEDITAFI DKFRNKSSSK KHSINGEPWH EVMVALKKTL HGFALDALMT HSQDIHPQLH  660
QAWEMWLTKL QDGVDVTAEL MVQMINMTAG RWVSKELLTH PQYQRLSTVT NSVCHDITKL  720
HNFKENSTTV DSKVQELVQL VFSDTPDDLD QDMKQTFLTV MKTFYYKAWC DPNTINDHIS  780
KVFEIVI                                                           787

SEQ ID NO: 130            moltype = AA   length = 527
FEATURE                   Location/Qualifiers
source                    1..527
                          mol_type = protein
                          organism = Streptomyces clavuligerus
SEQUENCE: 130
MPDAHDAPPP QIRQRTLVDE ATQLLTESAE DAWGEVSVSE YETARLVAHA TWLGGHATRV   60
AFLLERQHED GSWGPPGGYR LVPTLSAVHA LLTCLASPAQ DHGVPHDRLL RAVDAGLTAL  120
RRLGTSDSPP DTIAVELVIP SLLEGIQHLL DPAHPHSRPA FSQHRGSLVC PGGLDGRTLG  180
ALRSHAAAGT PVPGKVWHAS ETLGLSTEAA SHLQPAQGII GGSAAATATW LTRVAPSQQS  240
DSARRYLEEL QHRYSGPVPS ITPITYFERA WLLNNFAAAG VPCEAPAALL DSLEAALTPQ  300
GAPAGAGLPP DADDTAAVLL ALATHGRGRR PEVLMDYRTD GYFQCFIGER TPSISTNAHV  360
LETLGHHVAQ HPQDRARYGS AMDTASAWLL AAQKQDGSWL DKWHASPYYA TVCCTQALAA  420
HASPATAPAR QRAVRWVLAT QRSDGGWGLW HSTVEETAYA LQILAPPSGG GNIPVQQALT  480
RGRARLCGAL PLTPLWHDKD LYTPVRVVRA ARAAALYTTR DLLLPPL               527

SEQ ID NO: 131            moltype = AA   length = 516
FEATURE                   Location/Qualifiers
```

```
source                  1..516
                        mol_type = protein
                        organism = Bradyrhizobium japonicum
SEQUENCE: 131
MNALSEHILS ELRRLLSEMS DGGSVGPSVY DTAQALRFHG NVTGRQDAYA WLIAQQQADG   60
GWGSADFPLF RHAPTWAALL ALQRADPLPG AADAVQTATR FLQRQPDPYA HAVPEDAPIG  120
AELILPQFCG EAAWLLGGVA FPRHPALLPL RQACLVKLGA VAMLPSGHPL LHSWEAWGTS  180
PTTACPDDDG SIGISPAATA AWRAQAVTRG STPQVGRADA YLQMASRATR SGIEGVFPNV  240
WPINVFEPCW SLYTLHLAGL FAHPALAEAV RVIVAQLEAR LGVHGLGPAL HFAADADDTA  300
VALCVLHLAG RDPAVDALRH FEIGELFVTF PGERNASVST NIHALHALRL LGKPAAGASA  360
YVEANRNPHG LWDNEKWHVS WLYPTAHAVA ALAQGKPQWR DERALAALLQ AQRDDGGWGA  420
GRGSTFEETA YALFALHVMD GSEEATGRRR IAQVVARALE WMLARHAAHG LPQTPLWIGK  480
ELYCPTRVVR VAELAGLWLA LRWGRRVLAE GAGAAP                            516

SEQ ID NO: 132          moltype = AA  length = 784
FEATURE                 Location/Qualifiers
source                  1..784
                        mol_type = protein
                        organism = Stevia rebaudiana
SEQUENCE: 132
MNLSLCIASP LLTKSNRPAA LSAIHTASTS HGGQTNPTNL IIDTTKERIQ KQFKNVEISV   60
SSYDTAWVAM VPSPNSPKSP CFPECLNWLI NNQLNDGSWG LVNHTHNHNH PLLKDSLSST  120
LACIVALKRW NVGEDQINKG LSFIESNLAS ATEKSQPSPI GFDIIFPGLL EYAKNLDINL  180
LSKQTDFSLM LHKRELEQKR CHSNEMDGYL AYISEGLGNL YDWNMVKKYQ MKNGSVFNSP  240
SATAAAFINH QNPGCLNYLN SLLDKFGNAV PTVYPHDLFI RLSMVDTIER LGISHHFRVE  300
IKNVLDETYR CWVERDEQIF MDVVTCALAF RLLRINGYEV SPDPLAEITN ELALKDEYAA  360
LETYHASHIL YQEDLSSGKQ ILKSADFLKE IISTDSNRLS KLIHKEVENA LKFPINTGLE  420
RINTRRNIQL YNVDNTRILK TTYHSSNISN TDYLRLAVED FYTCQSIYRE ELKGLERWVV  480
ENKLDQLKFA RQKTAYCYFS VAATLSSPEL SDARISWAKN GILTTVVDDF FDIGGTIDEL  540
TNLIQCVEKW NVDVDKDCCS EHVRILFLAL KDAICWIGDE AFKWQARDVT SHVIQTWLEL  600
MNSMLREAIW TRDAYVPTLN EYMENAYVSF ALGPIVKPAI YFVGPKLSEE IVESSEYHNL  660
FKLMSTQGRL LNDIHSFKRE FKEGKLNAVA LHLSNGESGK VEEEVVEEMM MMIKNKRKEL  720
MKLIFEENGS IVPRACKDAF WNMCHVLNFF YANDDGFTGN TILDTVKDII YNPLVLVNEN  780
EEQR                                                               784

SEQ ID NO: 133          moltype = AA  length = 784
FEATURE                 Location/Qualifiers
source                  1..784
                        mol_type = protein
                        organism = Stevia rebaudiana
SEQUENCE: 133
MNLSLCIASP LLTKSSRPTA LSAIHTASTS HGGQTNPTNL IIDTTKERIQ KLFKNVEISV   60
SSYDTAWVAM VPSPNSPKSP CFPECLNWLI NNQLNDGSWG LVNHTHNHNH PLLKDSLSST  120
LACIVALKRW NVGEDQINKG LSFIESNLAS ATDKSQPSPI GFDIIFPGLL EYAKNLDINL  180
LSKQTDFSLM LHKRELEQKR CHSNEIDGYL AYISEGLGNL YDWNMVKKYQ MKNGSVFNSP  240
SATAAAFINH QNPGCLNYLN SLLDKFGNAV PTVYPLDLYI RLSMVDTIER LGISHHFRVE  300
IKNVLDETYR CWVERDEQIF MDVVTCALAF RLLRIHGYEV SPDQLAEITN ELAFKDEYAA  360
LETYHASQIL YQEDLSSGKQ ILKSADFLKG ILSTDSNRLS KLIHKEVENA LKFPINTGLE  420
RINTRRNIQL YNVDNTRILK TTYHSSNISN TYYLRLAVED FYTCQSIYRE ELKGLERWVV  480
QNKLDQLKFA RQKTAYCYFS VAATLSSPEL SDARISWAKN GILTTVVDDF FDIGGTIDEL  540
TNLIQCVEKW NVDVDKDCCS EHVRILFLAL KDAICWIGDE AFKWQARDVT SHVIQTWLEL  600
MNSMLREAIW TRDAYVPTLN EYMENAYVSF ALGPIVKPAI YFVGPKLSEE IVESSEYHNL  660
FKLMSTQGRL LNDIHSFKRE FKEGKLNAVA LHLSNGESGK VEEEVVEEMM MMIKNKRKEL  720
MKLIFEENGS IVPRACKDAF WNMCHVLNFF YANDDGFTGN TILDTVKDII YNPLVLVNEN  780
EEQR                                                               784

SEQ ID NO: 134          moltype = AA  length = 590
FEATURE                 Location/Qualifiers
source                  1..590
                        mol_type = protein
                        organism = Zea mays
SEQUENCE: 134
MAMPVKLTPA SLSLKAVCCR FSSGGHALRF GSSLPCWRRT PTQRSTSSST TRPAAEVSSG   60
KSKQHDQEAS EATIRQQLQL VDVLENMGIS RHFAAEIKCI LDRTYRSWLQ RHEEIMLDTM  120
TCAMAFRILR LNGYNVSSDE LYHVVEASGL HNSLGGYLND TRTLLELHKA STVSISEDES  180
ILDSIGSRSR TLLREQLESG GALRKPSLFK EVEHALDGPF YTTLDRLHHR WNIENFNIIE  240
QHMLETPYLS NQHTSRDILA LSIRDFSSSQ FTYQQELQHL ESWVKECRLD QLQFARQKLA  300
YFYLSAAGTM FSPELSDART LWAKNGVLTT IVDDFFDVAG SKEELENLVM LVEMWDEHHK  360
VEFYSEQVEI IFSSIYDSVN QLGEKASLVQ DRSITKHLVE IWLDLLKSMM TEVEWRLSKY  420
VPTEKEYMIN ASLIFGLGPI VLPALYFVGP KISESIVKDP EYDELFKLMS TCGRLLNDVQ  480
TFEREYNEGK LNSVSLLVLH GGPMSISDAK RKLQKPIDTC RRDLLSLVLR EESVVPRPCK  540
ELFWKMCKVC YFFYSTTDGF SSQVERAKEV DAVINEPLKL QGSHTLVSDV              590

SEQ ID NO: 135          moltype = AA  length = 743
FEATURE                 Location/Qualifiers
source                  1..743
                        mol_type = protein
                        organism = Populus trichocarpa
SEQUENCE: 135
```

```
MQNFHGTKER IKKMFDKIEL SVSSYDTAWV AMVPSPDCPE TPCFPECTKW ILENQLGDGS    60
WSLPHGNPLL VKDALSSTLA CILALKRWGI GEEQINKGLR FIELNSASVT DNEQHKPIGF   120
DIIFPGMIEY AIDLDLNLPL KPTDINSMLH RRALELTSGG GKNLEGRRAY LAYVSEGIGK   180
LQDWEMAMKY QRKNGSLFNS PSTTAAAFIH IQDAECLHYI RSLLQKFGNA VPTIYPLDIY   240
ARLSMVDALE RLGIDRHFRK ERKFVLDETY RFWLQGEEEI FSDNATCALA FRILRLNGYD   300
VSLEDHFSNS LGGYLKDSGA ALELYRALQL SYPDESLLEK QNSRTSYFLK QGLSNVSLCG   360
DRLRKNIIGE VHDALNFSDH ANLQRLAIRR RIKHYATDDT RILKTSYRCS TIGNQDFLKL   420
AVEDFNICQS IQREEFKHIE RWVVERRLDK LKFARQKEAY CYFSAAATLF APELSDARMS   480
WAKNGVLTTV VDDFFDVGGS EEELVNLIEL IERWDVNGSA DFCSEEVEII YSAIHSTISE   540
IGDKSFGWQG RDVKSQVIKI WLDLLKSMLT EAQWSSNKSV PTLDEYMTTA HVSFALGPIV   600
LPALYFVGPK LSEEVAGHPE LLNLYKVTST CGRLLNDWRS FKRESEEGKL NAISLYMIHS   660
GGASTEEETI EHFKGLIDSQ RRQLLQLVLQ EKDSIIPRPC KDLFWNMIKL LHTFYMKDDG   720
FTSNEMRNVV KAIINEPISL DEL                                          743

SEQ ID NO: 136           moltype = AA  length = 983
FEATURE                  Location/Qualifiers
source                   1..983
                         mol_type = protein
                         organism = Phomopsis amygdali
SEQUENCE: 136
MEFDEPLVDE ARSLVQRTLQ DYDDRYGFGT MSCAAYDTAW VSLVTKTVDG RKQWLFPECF    60
EFLLETQSDA GGWEIGNSAP IDGILNTAAS LLALKRHVQT EQIIQPQHDH KDLAGRAERA   120
AASLRAQLAA LDVSTTEHVG FEIIVPAMLD PLEAEDPSLV FDFPARKPLM KIHDAKMSRF   180
RPEYLYGKQP MTALHSLEAF IGKIDFDKVR HHRTHGSMMG SPSSTAAYLM HASQWDGDSE   240
AYLRHVIKHA AGQGTGAVPS AFPSTHFESS WILTTLFRAG FSASHLACDE LNKLVEILEG   300
SFEKEGGAIG YAPGFQADVD DTAKTISTLA VLGRDATPRQ MIKVFEANTH FRTYPGERDP   360
SLTANCNALS ALLHQPDAAM YGSQIQKITK FVCDYWWKSD GKIKDKWNTC YLYPSVLLVE   420
VLVDLVSLLE QGKLPDVLDQ ELQYRVAITL FQACLRPLLD QDAEGSWNKS IEATAYGILI   480
LTEARRVCFF DRLSEPLNEA IRRGIAFADS MSGTEAQLNY IWIEKVSYAP ALLTKSYLLA   540
ARWAAKSPLG ASVGSSLWTP PREGLDKHVR LFHQAELFRS LPEWELRASM IEAALFTPLL   600
RAHRLDVFPR QDVGEDKYLD VVPFFWTAAN NRDRTYASTL FLYDMCFIAM LNFQLDEFME   660
ATAGILFRDH MDDLRQLIHD LLAEKTSPKS SGRSSQGTKD ADSGIEEDVS MSDSASDSQD   720
RSPEYDLVFS ALSTFTKHVL QHPSIQSASV WDRKLLAREM KAYLLAHIQQ AEDSTPLSEL   780
KDVPQKTDVT RVSTSTTTFF NWVRTTSADH ISCPYSFHFV ACHLGAALSP KGSNGDCYLS   840
AGEKFLAAAV CRHLATMCRM YNDLGSAERD SDEGNLNSLD FPEFADSAGN GGIEIQKAAL   900
LRLAEFERDS YLEAFRRLQD ESNRVHGPAG GDEARLSRRR MAILEFFAQQ VDLYGQVYVI   960
RDISARIPKN EVEKKRKLDD AFN                                          983

SEQ ID NO: 137           moltype = AA  length = 881
FEATURE                  Location/Qualifiers
source                   1..881
                         mol_type = protein
                         organism = Physcomitrella patens
SEQUENCE: 137
MASSTLIQNR SCGVTSSMSS FQIFRGQPLR FPGTRTPAAV QCLKKRRCLR PTESVLESSP    60
GSGSYRIVTG PSGINPSSNG HLQEGSLTHR LPIPMEKSID NFQSTLYVSD IWSETLQRTE   120
CLLQVTENVQ MNEWIEEIRM YFRNMTLGEI SMSPYDTAWV ARVPALDGSH GPQFHRSLQW   180
IIDNQLPDGD WGEPSLFLGY DRVCNTLACV IALKTWGVGA QNVERGIQFL QSNIYKMEED   240
DANHMPIGFE IVFPAMMEDA KALGLDLPYD ATILQQISAE REKKMKKIPM AMVYKYPTTL   300
LHSLEGLHRE VDWNKLLQLQ SENGSFLYSP ASTACALMYT KDVKCFDYLN QLLIKFDHAC   360
PNVYPVDLFE RLWMVDRLQR LGISRYFERE IRDCLQYVYR YWKDCGIGWA SNSSVQDVDD   420
TAMAFRLLRT HGFDVKEDCF RQFFKDGEFF CFAGQSSQAV TGMFNLSRAS QTLFPGESLL   480
KKARTFSRNF LRTKHENNEC FDKWIITKDL AGEVEYNLTF PWYASLPRLE HRTYLDQYGI   540
DDIWIGKSLY KMPAVTNEVF LKLAKADFNM CQALHKKELE QVIKWNASCQ FRDLEFARQK   600
SVECYFAGAA TMFEPEMVQA RLVWARCCVL TTVLDDYFDH GTPVEELRVF VQAVRTWNPE   660
LINGLPEQAK ILFMGLYKTV NTIAEEEAFMA QKRDVHHHLK HYWDKLITSA LKEAEWAESG   720
YVPTFDEYME VAEISVALEP IVCSTLFFAG HRLDEDVLDS YDYHLVMHLV NRVGRILNDI   780
QGMKREASQG KISSVQIYME EHPSVPSEAM AIAHLQELVD NSMQQLTYEV LRFTAVPKSC   840
KRIHLNMAKI MHAFYKDTDG FSSLTAMTGF VKKVLFEPVP E                      881

SEQ ID NO: 138           moltype = AA  length = 513
FEATURE                  Location/Qualifiers
source                   1..513
                         mol_type = protein
                         organism = Stevia rebaudiana
SEQUENCE: 138
MDAVTGLLTV PATAITIGGT AVALAVALIF WYLKSYTSAR RSQSNHLPRV PEVPGVPLLG    60
NLLQLKEKKP YMTFTRWAAT YGPIYSIKTG ATSMVVVSSN EIAKEALVTR FQSISTRNLS   120
KALKVLTADK TMVAMSDYDD YHKTVKRHIL TAVLGPNAQK KHRIHRDIMM DNISTQLHEF   180
VKNNPEQEEV DLRKIFQSEL FGLAMRQALG KDVESLYVED LKITMNRDEI FQVLVVDPMM   240
GAIDVDWRDF FPYLKWVPNK KFENTIQQMY IRREAVMKSL IKEHKKRIAS GEKLNSYIDY   300
LLSEAQTLTD QQLLMSLWEP IIESSDTTMV TTEWAMYELA KNPKLQDRLY RDIKSVCGSE   360
KITEEHLSQL PYITAIFHET LRRHSPVPII PLRHVHEDTV LGGYHVPAGT ELAVNIYGCN   420
MDKNVWENPE EWNPERFMKE NETIDFQKTM AFGGGKRVCA GSLQALLTAS IGIGRMVQEF   480
EWKLKDMTQE EVNTIGLTTQ MLRPLRAIIK PRI                                513

SEQ ID NO: 139           moltype = AA  length = 509
FEATURE                  Location/Qualifiers
source                   1..509
```

```
                        mol_type = protein
                        organism = Arabidopsis thaliana
SEQUENCE: 139
MAFFSMISIL LGFVISSFIF IFFFKKLLSF SRKNMSEVST LPSVPVVPGF PVIGNLLQLK    60
EKKPHKTFTR WSEIYGPIYS IKMGSSSLIV LNSTETAKEA MVTRFSSIST RKLSNALTVL   120
TCDKSMVATS DYDDFHKLVK RCLLNGLLGA NAQKRKRHYR DALIENVSSK LHAHARDHPQ   180
EPVNFRAIFE HELFGVALKQ AFGKDVESIY VKELGVTLSK DEIFKVLVHD MMEGAIDVDW   240
RDFFPYLKWI PNKSFEARIQ QKHKRRLAVM NALIQDRLKQ NGSESDDDCY LNFLMSEAKT   300
LTKEQIAILV WETIIETADT TLVTTEWAIY ELAKHPSVQD RLCKEIQNVC GGEKFKEEQL   360
SQVPYLNGVF HETLRKYSPA PLVPIRYAHE DTQIGGYHVP AGSEIAINIY GCNMDKKRWE   420
RPEDWWPERF LDDGKYETSD LHKTMAFGAG KRVCAGALQA SLMAGIAIGR LVQEFEWKLR   480
DGEEENVDTY GLTSQKLYPL MAIINPRRS                                    509

SEQ ID NO: 140          moltype = AA  length = 525
FEATURE                 Location/Qualifiers
source                  1..525
                        mol_type = protein
                        organism = Gibberella fujikoroi
SEQUENCE: 140
MSKSNSMNST SHETLFQQLV LGLDRMPLMD VHWLIYVAFG AWLCSYVIHV LSSSSTVKVP    60
VVGYRSVFEP TWLLRLRFVW EGGSIIGQGY NKFKDSIFQV RKLGTDIVII PPNYIDEVRK   120
LSQDKTRSVE PFINDFAGQY TRGMVFLQSD LQNRVIQQRL TPKLVSLTKV MKEELDYALT   180
KEMPDMKNDE WVEVDISSIM VRLISRISAR VFLGPEHCRN QEWLTTTAEY SESLFITGFI   240
LRVVPHILRP FIAPLLPSYR TLLRNVSSGR RVIGDIIRSQ QGDGNEDILS WMRDAATGEE   300
KQIDNIAQRM LILSLASIHT TAMTMTHAMY DLCACPEYIE PLRDEVKSVV GASGWDKTAL   360
NRFHKLDSFL KESQRFNPVF LLTFNRIYHQ SMTLSDGTNI PSGTRIAVPS HAMLQDSAHV   420
PGPTPPTEFD GFRYSKIRSD SNYAQKYLFS MTDSSNMAFG YGKYACPGRF YASNEMKLTL   480
AILLLQFEFK LPDGKGRPRN ITIDSDMIPD PRARLCVRKR SLRDE                  525

SEQ ID NO: 141          moltype = AA  length = 499
FEATURE                 Location/Qualifiers
source                  1..499
                        mol_type = protein
                        organism = Trametes versicolor
SEQUENCE: 141
MEDPTVLYAC LAIAVATFVV RWYRDPLRSI PTVGGSDLPI LSYIGALRWT RRGREILQEG    60
YDGYRGSTFK IAMLDRWIVI ANGPKLADEV RRRPDEELNF MDGLGAFVQT KYTLGEAIHN   120
DPYHVDIIRE KLTRGLPAVL PDVIEELTLA VRQYIPTEGD EWVSVNCSKA ARDIVARASN   180
RVFVGLPACR NQGYLDLAID FTLSVVKDRA IINMFPELLK PIVGRVVGNA TRNVRRAVPF   240
VAPLVEERRR LMEEYGEDWS EKPNDMLQWI MDEAASRDSS VKAIAERLLM VNFAAIHTSS   300
NTITHALYHL AEMPETLQPL REEIEPLVKE EGWTKAAMGK MWWLDSFLRE SQRYNGINIV   360
SLTRMADKDI TLSDGTFLPK GTLVAVPAYS THRDDAVYAD ALVFDPFRFS RMRAREGEGT   420
KHQFVNTSVE YVPFGHGKHA CPGRFFAANE LKAMLAYIVL NYDVKLPGDG KRPLNMYWGP   480
TVLPAPAGQV LFRKRQVSL                                               499

SEQ ID NO: 142          moltype = AA  length = 525
FEATURE                 Location/Qualifiers
source                  1..525
                        mol_type = protein
                        organism = Stevia rebaudiana
SEQUENCE: 142
MGLFPLEDSY ALVFEGLAIT LALYYLLSFI YKTSKKTCTP PKASGEIIPI TGIILNLLSG    60
SSGLPIILAL ASLADRCGPI FTIRLGIRRV LVVSNWEIAK EIFTTHDLIV SNRPKYLAAK   120
ILGFNYVSFS FAPYGPYWVG IRKIIATKLM SSSRLQKLQF VRVFELENSM KSIRESWKEK   180
KDEEGKVLVE MKKWFWELNM NIVLRTVAGK QYTGTVDDAD AKRISELFRE WFHYTGRFVV   240
GDAFPFLGWL DLGGYKKTME LVASRLDSMV SKWLDEHRKK QANDDKKEDM DFMDIMISMT   300
EANSPLEGYG TDTIIKTTCM TLIVSGVDTT SIVLTWALSL LLNNRDTLKK AQEELDMCVG   360
KGRQVNESDL VNLIYLEAVL KEALRLYPAA FLGGPRAFLE DCTVAGYRIP KGTCLLINMW   420
KLHRDPNIWS DPCEFKPERF LTPNQKDVDV IGMDFELIPF GAGRRYCPGT RLALQMLHIV   480
LATLLQNFEM STPNDAPVDM TASVGMTNAK ASPLEVLLSP RVKWS                  525

SEQ ID NO: 143          moltype = AA  length = 476
FEATURE                 Location/Qualifiers
source                  1..476
                        mol_type = protein
                        organism = Stevia rebaudiana
SEQUENCE: 143
MIQVLTPILL FLIFFVFWKV YKHQKTKINL PPGSFGWPFL GETLALLRAG WDSEPERFVR    60
ERIKKHGSPL VFKTSLFGDR FAVLCGPAGN KPLFCNENKL VASWWPVPVR KLFGKSLLTI   120
RGDEAKWMRK MLLSYLGPDA FATHYAVTMD VVTRRHIDVH WRGKEEVNVF QTVKLYAFEL   180
ACRLFMNLDD PNHIAKLGSL FNIFLKGIIE LPIDVPGTRF YSSKKAAAAI RIELKKLIKA   240
RKLELKEGKA SSSQDLLSHL LTSPDENGMF LTEEEIVDNI LLLLFAGHDT SALSITLLMK   300
TLGEHSDVYD KVLKEQLEIS KTKEAWESLK WEDIQKMKYS WSVICEVMRL NPPVIGTYRE   360
ALVDIDYAGY TIPKGWKLHW SAVSTQRDEA NFEDYTRFDP SRFEGAGPTP FTFVPFGGGP   420
RMCLGKEFAR LEVLAFLHNI VTNFKWDLLI PDEKIEYDPM ATPAKGLPIR LHPHQV      476

SEQ ID NO: 144          moltype = AA  length = 525
FEATURE                 Location/Qualifiers
source                  1..525
```

```
                         mol_type = protein
                         organism = Arabidopsis thaliana
SEQUENCE: 144
MESLVVHTVN AIWCIVIVGI FSVGYHVYGR AVVEQWRMRR SLKLQGVKGP PPSIFNGNVS    60
EMQRIQSEAK HCSGDNIISH DYSSSLFPHF DHWRKQYGRI YTYSTGLKQH LYINHPEMVK   120
ELSQTNTLNL GRITHITKRL NPILGNGIIT SNGPHWAHQR RIIAYEFTHD KIKGMVGLMV   180
ESAMPMLNKW EEMVKRGGEM GCDIRVDEDL KDVSADVIAK ACFGSSFSKG KAIFSMIRDL   240
LTAITKRSVL FRFNGFTDMV FGSKKHGDVD IDALEMELES SIWETVKERE IECKDTHKKD   300
LMQLILEGAM RSCDGNLWDK SAYRRFVVDN CKSIYFAGHD STAVSVSWCL MLLALNPSWQ   360
VKIRDEILSS CKNGIPDAES IPNLKTVTMV IQETMRLYPP APIVGREASK DIRLGDLVVP   420
KGVCIWTLIP ALHRDPEIWG PDANDFKPER FSEGISKACK YPQSYIPFGL GPRTCVGKNF   480
GMMEVKVLVS LIVSKFSFTL SPTYQHSPSH KLLVEPQHGV VIRVV                   525

SEQ ID NO: 145           moltype = AA   length = 529
FEATURE                  Location/Qualifiers
source                   1..529
                         mol_type = protein
                         organism = Vitis vinifera
SEQUENCE: 145
MYFLLQYLNI TTVGVFATLF LSYCLLLWRS RAGNKKIAPE AAAAWPIIGH LHLLAGGSHQ    60
LPHITLGNMA DKYGPVFTIR IGLHRAVVVS SWEMAKECST ANDQVSSSRP ELLASKLLGY   120
NYAMFGFSPY GSYWREMRKI ISLELLSNSR LELLKDVRAS EVVTSIKELY KLWAEKKNES   180
GLVSVEMKQW FGDLTLNVIL RMVAGKRYFS ASDASENKQA QRCRRVFREF FHLSGLFVVA   240
DAIPFLGWLD WGRHEKTLKK TAIEMDSIAQ EWLEEHRRRK DSGDDNSTQD FMDVMQSVLD   300
GKNLGGYDAD TINKATCLTL ISGGSDTTVV SLTWALSLVL NNRDTLKKAQ EELDIQVGKE   360
RLVNEQDISK LVYLQAIVKE TLRLYPPGPL GGLRQFTEDC TLGGYHVSKG TRLIMNLSKI   420
QKDPRIWSDP TEFQPERFLT THKDVDPRGK HFEFIPFGAG RRACPGITFG LQVLHLTLAS   480
FLHAFEFSTP SNEQVNMRES LGLTNMKSTP LEVLISPRLS LNCFNLMKI               529

SEQ ID NO: 146           moltype = AA   length = 479
FEATURE                  Location/Qualifiers
source                   1..479
                         mol_type = protein
                         organism = Medicago truncatula
SEQUENCE: 146
MEPNFYLSLL LLFVTFISLS LFFIFYKQKS PLNLPPGKMG YPIIGESLEF LSTGWKGHPE    60
KFIFDRMRKY SSELFKTSIV GESTVVCCGA ASNKFLFSNE NKLVTAWWPD SVNKIFPTTS   120
LDSNLKEESI KMRKLLPQFF KPEALQRYVG VMDVIAQRHF VTHWDNKNEI TVYPLAKRYT   180
FLLACRLFMS VEDENHVAKF SDPFQLIAAG IISLPIDLPG TPFNKAIKAS NFIRKELIKI   240
IKQRRVDLAE GTASPTQDIL SHMLLTSDEN GKSMNELNIA DKILGLLIGG HDTASVACTF   300
LVKYLGELPH IYDKVYQEQM EIAKSKPAGE LLNWDDLKKM KYSWNVACEV MRLSPPLQGG   360
FREAITDFMF NGFSIPKGWK LYWSANSTHK NAECFPMPEK FDPTRFEGNG PAPYTFVPFG   420
GGPRMCPGKE YARLEILVFM HNLVKRFKWE KVIPDEKIIV DPFPIPAKDL PIRLYPHKA   479

SEQ ID NO: 147           moltype = AA   length = 710
FEATURE                  Location/Qualifiers
source                   1..710
                         mol_type = protein
                         organism = Stevia rebaudiana
SEQUENCE: 147
MQSDSVKVSP FDLVSAAMNG KAMEKLNASE SEDPTTLPAL KMLVENRELL TLFTTSFAVL    60
IGCLVFLMWR RSSSKKLVQD PVPQVIVVKK KEKESEVDDG KKKVSIFYGT QTGTAEGFAK   120
ALVEEAKVRY EKTSFKVIDL DDYAADDDEY EEKLKKESLA FFFFLATYGD EPTDNAANFY   180
KWFTEGDDKG EWLKKLQYGV FGLGNRQYEH FNKIAIVVDD KLTEMGAKRL VPVGLGDDDQ   240
CIEDDFTAWK ELVWPELDQL LRDEDDTSVT TPYTAAVLEY RVVHDKPAD SYAEDQTHTN   300
GHVVHDAQHP SRSNVAFKKE LHTSQSDRSC THLEFDISHT GLSYETGDHV GVYSENLSEV   360
VDEALKLLGL SPDTYFSVHA DKEDGTPIGG ASLPPPFPPC TLRDALTRYA DVLSSPKKVA   420
LLALAAHASD PSEADRLKFL ASPAGKDEYA QWIVANQRSL LEVMQSFPSA KPPLGVFFAA   480
VAPRLQPRYY SISSSPKMSP NRIHVTCALV YETTPAGRIH RGLCSTWMKN AVPLTESPDC   540
SQASIFVRTS NFRLPVDPKV PVIMIGPGTG LAPFRGFLQE RLALKESGTE LGSSIFFFGC   600
RNRKVDFIYE DELNNFVETG ALSELIVAFS REGTAKEYVQ HKMSQKASDI WKLLSEGAYL   660
YVCGDAKGMA KDVHRTLHTI VQEQGSLDSS KAELYVKNLQ MSGRYLRDVW               710

SEQ ID NO: 148           moltype = AA   length = 692
FEATURE                  Location/Qualifiers
source                   1..692
                         mol_type = protein
                         organism = Arabidopsis thaliana
SEQUENCE: 148
MTSALYASDL FKQLKSIMGT DSLSDDVVLV IATTSLALVA GFVVLLWKKT TADRSGELKP    60
LMIPKSLMAK DEDDDLDLGS GKTRVSIFFG TQTGTAEGFA KALSEEIKAR YEKAAVKVID   120
LDDYAADDDQ YEEKLKKETL AFFCVATYGD GEPTDNAARF YKWFTEENER DIKLQQLAYG   180
VFALGNRQYE HFNKIGIVLD EELCKKGAKR LIEVGLGDDQ QSIEDDFNAW KESLWSELDK   240
LLKDEDDKSV ATPYTAVIPE YRVVTHDPRF TTQKSMESNV ANGNTTIDIH HPCRVDVAVQ   300
KELHTHESDR SCIHLEFDIS RTGITYETGD HVGVYAENHV EIVEEAGKLL GHSLDLVFSI   360
HADKEDGSPL ESAVPPPFPG PCTLGTGLAR YADLLNPPRK SALVALAAYA TEPSEAEKLK   420
HLTSPDGKDE YSQWIVASQR SLLEVMAAFP SAKPPLGVFF AAIAPRLQPR YYSISSSPRL   480
APSRVHVTSA LVYGPTPTGR IHKGVCSTWM KNAVPAEKSH ECSGAPIFIR ASNFKLPSNP   540
STPIVMVGPG TGLAPFRGFL QERMALKEDG EELGSSLLFF GCRNRQMDFI YEDELNNFVD   600
```

```
QGVISELIMA FSREGAQKEY VQHKMMEKAA QVWDLIKEEG YLYVCGDAKG MARDVHRTLH   660
TIVQEQEGVS SSEAEAIVKK LQTEGRYLRD VW                                692

SEQ ID NO: 149            moltype = AA   length = 713
FEATURE                   Location/Qualifiers
source                    1..713
                          mol_type = protein
                          organism = Giberella fujikuroi
SEQUENCE: 149
MAELDTLDIV VLGVIFLGTV AYFTKGKLWG VTKDPYANGF AAGGASKPGR TRNIVEAMEE   60
SGKNCVVFYG SQTGTAEDYA SRLAKEGKSR FGLNTMIADL EDYDFDNLDT VPSDNIVMFV  120
LATYGEGEPT DNAVDFYEFI TGEDASFNEG NDPPLGNLNY VAFGLGNNTY EHYNSMVRNV  180
NKALEKLGAH RIGEAGEGDD GAGTMEEDFL AWKDPMWEAL AKKMGLEERE AVYEPIFAIN  240
ERDDLTPEAN EVYLGEPNKL HLEGTAKGPF NSHNPYIAPI AESYELFSAK DRNCLHMEID  300
ISGSNLKYET GDHIAIWPTN PGEEVNKFLD ILDLSGKQHS VVTVKALEPT AKVPFPNPTT  360
YDAILRYHLE ICAPVSRQFV STLAAFAPND DIKAEMNRLG SDKDYFHEKT GPHYYNIARF  420
LASVSKGEKW TKIPFSAFIE GLTKLQPRYY SISSSSLVQP KKISITAVVE SQQIPGRDDP  480
FRGVATNYLF ALKQKQNGDP NPAPFGQSYE LTGPRNKYDG IHVPVHVRHS NFKLPSDPGK  540
PIIMIGPGTG VAPFRGFVQE RAKQARDGVE VGKTLLFFGC RKSTEDFMYQ KEWQEYKEAL  600
GDKFEMITAF SREGSKKVYV QHRLKERSKE VSDLLSQKAY FYVCGDAAHM AREVNTVLAQ  660
IIAEGRGVSE AKGEEIVKNM RSANQYQVCS DFVTLHCKET TYANSELQED VWS         713

SEQ ID NO: 150            moltype = AA   length = 453
FEATURE                   Location/Qualifiers
source                    1..453
                          mol_type = protein
                          organism = Arabidopsis thaliana
SEQUENCE: 150
MGGLKFHVLM YPWFATGHMT PFLFLANKLA EKGHTVTFLL PKKSLKQLEH FNLFPHNIVF   60
RSVTVPHVDG LPVGTETASE IPVTSTDLLM SAMDLTRDQV EAVVRAVEPD LIFFDFAHWI  120
PEVARDFGLK TVKYVVVSAS TIASMLVPGG ELGVPPPGYP SSKVLLRKQD AYTMKKLEPT  180
NTIDVGPNLL ERVTTSLMNS DVIAIRTARE IEGNFCDYIE KHCRKKVLLT GPVFPEPDKT  240
RELEERWVKW LSGYEPDSVV FCALGSQVIL EKDQFQELCL GMELTGSPFL VAVKPPRGSS  300
TIQEALPEGF EERVKGRGLV WGGWVQQPLI LSHPSVGCFV SHCGFGSMWE SLLSDCQIVL  360
VPQLGDQVLN TRLLSDELKV SVEVAREETG WFSKESLCDA VNSVMKRDSE LGNLVRKNHT  420
KWRETVASPG LMTGYVDAFV ESLQDLVSGT THD                               453

SEQ ID NO: 151            moltype = DNA   length = 1362
FEATURE                   Location/Qualifiers
source                    1..1362
                          mol_type = genomic DNA
                          organism = Arabidopsis thaliana
SEQUENCE: 151
atgggtggtt tgaagtttca tgtacttatg tatccatggt tcgcaacagg ccatatgacc    60
ccgttccttt ttcttgccaa caaattggct gagaaaggtc atacggtcac tttcttgctt   120
cccaagaaat ctctgaaaca gttggaacat ttcaatctgt ttccacacaa cattgtcttt   180
cgctctgtca ccgtccctca tgtggatggt ctccccgttg gcacagagac agcctctgag   240
atccctgtga catcaactga tcttcttatg tctgctatgg atctcacacg tgatcaagtt   300
gaagctgtgg tccgagccgt tgaaccggac ctgatcttct ttgactttgc tcattggatt   360
ccagaagtag ctagggactt cggccttaag actgaaagt acgtcgtggt gtctgcatcg   420
actatagcta gtatgcttgt cccaggtggt gagttaggtg ttcctccacc gggatatcca   480
tcatcaaagg tgctgcttcg taaacaagat gcttacacta tgaagaaact ggagcctaca   540
aatacaatcg atgtcggacc aaacctcttg gaacgagtca ctacaagtct tatgaactct   600
gatgtcattg cgataaggac agccagagaa atcgaaggaa actttttgcga ctatatagaa   660
aaacattgca ggaaaaaggt tctcttgaca ggtccggtgt tccctgagcc agacaagact   720
agagagctag aggaacgatg ggttaagtgg ctaagtgggt atgaaccaga ctcagtggtg   780
ttttgtgcac tgggctcaca agtcattta gagaaagatc aattccaaga actctgctta   840
ggaatggagc taacaggttc accgtttctt gtagcggtta agcccctag aggctcatca   900
acgattcaag aagcacttcc tgaaggattc gaagagcggg ttaaaggaag aggccttgtt   960
tggggaggat gggttcaaca accattgata ttgtctcatc catcagtcgg gtgctttgtg  1020
agccattgtg ggtttggatc aatgtgggag tctttgctga gtgattgtca gatagtctta  1080
gtaccagagt tgggtgatca agtcctgaac acaagattga gtgagtgacga actcaagttt  1140
tcggttgaag tggcaagaga ggaaacagga tggttctcga agagagcttg tgcgatgct   1200
gtcaatagtc tgatgaaaag ggacagcgag ctcgggaacc tggtgaggaa gaatcacacc  1260
aagtggaggg agacagtagc tagtcctgga ctaatgactg ttatgtcga tgctttcgta   1320
gagtcattgc aggatcttgt ctctgggacc acccatgact ga                     1362
```